US012065458B2

(12) United States Patent
Li et al.

(10) Patent No.: US 12,065,458 B2
(45) Date of Patent: Aug. 20, 2024

(54) TRIALKYNE LINKING AGENTS AND METHODS OF USE

(71) Applicant: Arrowhead Pharmaceuticals, Inc., Pasadena, CA (US)

(72) Inventors: Zhen Li, Westfield, NJ (US); Erich Altenhofer, Madison, WI (US); Jeffrey Carlson, Madison, WI (US); Matthew Fowler-Watters, Madison, WI (US); Bo Chen, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 710 days.

(21) Appl. No.: 16/970,130

(22) PCT Filed: Feb. 15, 2019

(86) PCT No.: PCT/US2019/018232
§ 371 (c)(1),
(2) Date: Aug. 14, 2020

(87) PCT Pub. No.: WO2019/161213
PCT Pub. Date: Aug. 22, 2019

(65) Prior Publication Data

US 2022/0402947 A1 Dec. 22, 2022

Related U.S. Application Data

(60) Provisional application No. 62/790,300, filed on Jan. 9, 2019, provisional application No. 62/633,763, filed on Apr. 27, 2018, provisional application No. 62/646,739, filed on Mar. 22, 2018, provisional application No. 62/631,683, filed on Feb. 17, 2018.

(51) Int. Cl.

| | |
|---|---|
| ***C07F 9/06*** | (2006.01) |
| ***A61K 47/54*** | (2017.01) |
| ***C07C 205/59*** | (2006.01) |
| ***C07C 235/34*** | (2006.01) |
| ***C07D 403/14*** | (2006.01) |
| ***C12N 15/113*** | (2010.01) |

(52) U.S. Cl.

CPC .............. *C07F 9/06* (2013.01); *A61K 47/545* (2017.08); *C07C 205/59* (2013.01); *C07C 235/34* (2013.01); *C07D 403/14* (2013.01); *C12N 15/113* (2013.01); *C12N 2310/14* (2013.01); *C12N 2310/351* (2013.01)

(58) Field of Classification Search

None

See application file for complete search history.

(56) References Cited

U.S. PATENT DOCUMENTS

| | | | |
|---|---|---|---|
| 4,522,811 A | 6/1985 | Eppstein et al. | |
| 2009/0124571 A1 | 5/2009 | Francois et al. | |
| 2016/0024570 A1* | 1/2016 | Ju | C12Q 1/6869 536/28.5 |
| 2016/0185814 A1 | 6/2016 | Field et al. | |
| 2017/0202970 A1 | 7/2017 | Foreman et al. | |
| 2020/0369613 A1 | 11/2020 | Li et al. | |

FOREIGN PATENT DOCUMENTS

| | | |
|---|---|---|
| WO | 2007125429 A2 | 11/2007 |
| WO | 2015107115 A1 | 7/2015 |
| WO | 2018013525 A1 | 1/2018 |
| WO | 2019010274 A1 | 1/2019 |

OTHER PUBLICATIONS

Amarzguioui et al. "An algorithm far selection of functional siRNA sequences" Biochemical and Biophysical Research Communications 2004 vol. 316, p. 1050-1058.
Chalk et al. "Improved and automated prediction of effective siRNA" Biochemical and Biophysical Research Communications 2004 vol. 319, p. 264-274.
Heale et al. "siRNA target site secondary structure predictions using local stable substructures" Nucleic Acids Research (2005) 33(3).
Khvorova et al. "Functional siRNAs and miRNAs Exhibit Strand Bias" Cell 2003 vol. 115, p. 209-216.
Pei et al. "On the art of identifying effective and specific siRNAs" Nature Methods 2006 vol 3(9), p. 670-676.
Reynolds et al. "Targeting the cancer stroma with a fibroblast activation protein-activated promelittin protoxin" Nature Biotechnology 2004.
Schwarz et al. "Asymmetry in the Assembly of the RNAi Enzyme Complex" Cell 2003 vol. 115, p. 199-208.
Ui-Tei et al. "Guidelines for the selection of highly effective siRNA sequences for mammalian and chick RNA Interference" Nucleic Acids Research 2004 vol. 32(3)936-948.
ISR and Written Opinion for corresponding Application No. PCT/US19/18232 dated Apr. 25, 2019.
Jayaprakash et al.; "Non-Nucleoside Building Blocks for Copper-Assisted and Copper-Free Click Chemistry for the Effficient Synthesis of RNA Conjugates"; Organic Lette3rs; vol. 12, No. 23; 5410-5413; 2010.
Farzan, Valentina M. et al.; "Automated Solid-Phase Click Synthesis of Oligonucleotide Conjugates: From Small Molecules to Diverse N-Acetylgalactosamine Clusters"; Bioconjugate Chemistry; vol. 28, No. 10; pp. 2599-2607; 2017.

(Continued)

*Primary Examiner* — Joseph R Kosack
*Assistant Examiner* — Jed A Kucharczk
(74) *Attorney, Agent, or Firm* — Paul VanderVelde; Meibo Chen; Darrin Flanigan

(57) ABSTRACT

Described are improved linking agents that are useful for facilitating the attachment of targeting groups, pharmacokinetic (PK) enhancers or modifiers, or other delivery agents to oligonucleotides. The described linking agents may exhibit improved reaction yields, stability, and biological activity, particularly when used in connection with oligonucleotide-based compounds, such as RNA interference (RNAi) agents.

19 Claims, No Drawings

Specification includes a Sequence Listing.

(56) References Cited

Liang et al.; "Effects of neighboring glycans on antibody-carbohydrate interaction"; Angew Chem Int Ed Engl. Feb. 11, 2011;50(7):1608-12. doi: 10.1002/anie.201003482. Epub Jan. 5, 2011. PMID: 21308915.
Pubmed Compound Summary for CID 122688301, 'BCEDWFWNPLDHRB-UHFFFAOYSAN', 7 U.S. National Library of Medicine, Dec. 8, 2016 (Dec. 8, 2016), p. 1-7; p. 2; (https://pubchem.ncbi.nlm.nih .gov/compound/122688301).
Pubmed Compound Summary for CID 11365294, 'CSVSHCJSKCUINQ-UHFFFAOYSA-N', U.S. 13, 17 National Library of Medicine, Oct. 26, 2006 (Oct. 26, 2006),p. 1-6; (https://pubchem.ncbi.nlm.nih.gov/compound/11365294).
Kiran P, Bhatia S, Lauster D, Aleksić S, Fleck C, Peric N, Maison W, Liese S, Keller BG, Herrmann A, Haag R. Exploring Rigid and Flexible Core Trivalent Sialosides for Influenza Virus Inhibition. Chemistry. Dec. 20, 2018;24 (72):19373-19385. doi: 10.1002/chem.201804826. Epub Nov. 22, 2018. PMID: 30295350; PMCID: PMC6587447.

* cited by examiner

SEQUENCE LISTING

```
<160> NUMBER OF SEQ ID NOS: 13

<210> SEQ ID NO 1
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1

uuucaugaaa ucguuacguu g                                             21


<210> SEQ ID NO 2
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 2

uauuuguucu gguugcacag g                                             21


<210> SEQ ID NO 3
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 3

uauuuguucu gguugcacag g                                             21


<210> SEQ ID NO 4
<211> LENGTH: 21
<212> TYPE: RNA
<213> ORGANISM: Artificial sequence
<220> FEATURE:
<223> OTHER INFORMATION: RNAi agent sense strand modified sequence
```

<400> SEQUENCE: 4
caacguaacg auuucaugaa a 21

<210> SEQ ID NO 5
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 5
caacguaacg auuucaugaa a 21

<210> SEQ ID NO 6
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 6
caacguaacg auuucaugaa a 21

<210> SEQ ID NO 7
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 7
caacguaacg auuucaugaa a 21

<210> SEQ ID NO 8
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 8
caacguaacg auuucaugaa a 21

<210> SEQ ID NO 9
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 9
caacguaacg auuucaugaa a 21

<210> SEQ ID NO 10
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 10
caacguaacg auuucaugaa a 21

<210> SEQ ID NO 11

-continued

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 11
caacguaacg auuucaugaa a 21

<210> SEQ ID NO 12
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 12
ccugugcaac cagaacaaau a 21

<210> SEQ ID NO 13
<211> LENGTH: 21
<212> TYPE: DNA
<213> ORGANISM: Artificial sequence
<220> FEATURE:
<223> OTHER INFORMATION: RNAi agent sense strand modified sequence

<400> SEQUENCE: 13
ccugugcaac cagaacaaau a 21

TRIALKYNE LINKING AGENTS AND METHODS OF USE

CROSS REFERENCE TO RELATED APPLICATIONS

This application claims priority to U.S. Provisional Application Ser. No. 62/631,683, filed Feb. 17, 2018, U.S. Provisional Application Ser. No. 62/646,739, filed Mar. 22, 2018, U.S. Provisional Application Ser. No. 62/663,763, filed Apr. 27, 2018 and U.S. Provisional Application Ser. No. 62/790,300, filed Jan. 9, 2019, all of which are incorporated by reference herein in their entirety.

SEQUENCE LISTING

This application contains a Sequence Listing which has been submitted in ASCII format and is hereby incorporated by reference in its entirety. The ASCII copy is named 30665_SequenceListingWO1.txt, created Feb. 15, 2019, and is 4 kb in size.

FIELD OF THE INVENTION

The present disclosure relates to trialkyne linking agents suitable for use with synthetic oligonucleotides, such as RNA interference (RNAi) agents.

BACKGROUND

Synthetic oligonucleotides, such as antisense compounds, aptamers, ribozymes, and RNA interference (RNAi) agents or molecules, are increasingly used in biomedical research, diagnostics and therapeutics. These synthetic oligonucleotides have been used to inhibit or knock-down expression of a gene in vitro, in situ, and in vivo in a sequence-dependent manner.

It is frequently useful to attach or link targeting ligands or other pharmacological or pharmacokinetic enhancers or modifiers to synthetic oligonucleotides, especially for therapeutic in vivo delivery. To be useful, the linkage chemistry should be modular, so that it is readily adaptable to different synthetic oligonucleotides as well as different targeting ligands and pharmacological modifiers. In addition, the linkage chemistry should have simple reaction conditions, be efficient (i.e. give high chemical yields), not require toxic or other detrimental products, and not produce toxic or other detrimental byproducts. The linkage chemistry should also be stable outside of the target cell, such as in circulation, subcutaneous space, or extracellular space, but be readily cleavable at the final site of action, such as inside the target cell. Further, for oligonucleotide-based therapeutics in particular, linker length and flexibility has been known to substantially impact the efficacy of therapeutic compounds in vivo by, among other things, altering cell uptake in certain instances.

There exists a need for linking agents with suitable properties for linking oligonucleotide-based compounds, such as RNAi agents, to targeting ligands.

SUMMARY

In one aspect the invention provides compounds according to the structure of Formula I:

Formula I

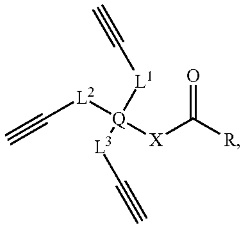

or a pharmaceutically acceptable salt thereof, wherein $L^1$, $L^2$, and $L^3$ are each independently linkers comprising optionally substituted alkylene;

Q is a tetravalent carbon, tetra-substituted phenyl or optionally substituted alkylene;

R comprises a coupling moiety or an RNAi agent; and

X is $NR^x$ or a bond, and $R^x$ is H or optionally substituted $C_1$-$C_6$ alkyl.

In one aspect the invention provides compounds according to the structure of Formula II:

Formula II

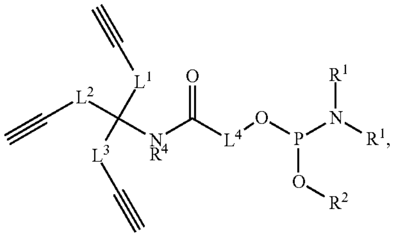

or a pharmaceutically acceptable salt thereof, wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

each instance of $R^1$ is optionally substituted alkyl;

$R^2$ is optionally substituted alkyl; and $R^4$ is H or optionally substituted alkyl.

Another aspect of the invention described herein are compounds according to the structure of Formula III:

Formula III

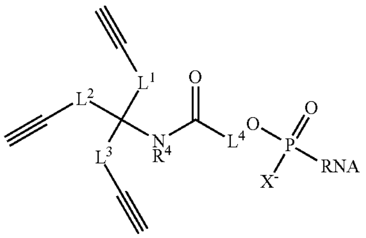

or a pharmaceutically acceptable salt thereof,
wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

$R^4$ is H or optionally substituted alkyl;

X is O or S; and

RNA comprises or consists of an RNAi agent.

In another aspect described herein are compounds according to the structure of Formula IV:

Formula IV

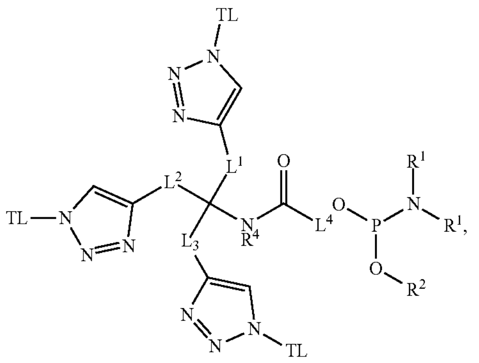

or a pharmaceutically acceptable salt thereof,
wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

$R^1$ and $R^2$ are each independently optionally substituted alkyl;

$R^4$ is H or optionally substituted alkyl; and

TL is a targeting ligand.

Another aspect of the invention described herein are compounds according to the structure of Formula V:

Formula V

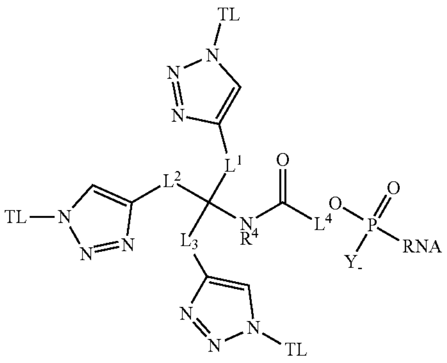

or a pharmaceutically acceptable salt thereof,
wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

$R^4$ is H or optionally substituted alkyl;

TL is a targeting ligand;

Y is O or S; and

RNA comprises or consists of an RNAi agent.

In another aspect described herein are compounds according to the structure of Formula VI:

Formula VI

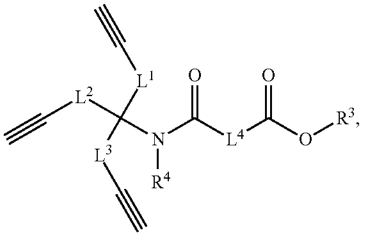

or a pharmaceutically acceptable salt thereof,
wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

$R^3$ is H, optionally substituted alkyl, or optionally substituted aryl; and $R^4$ is H or optionally substituted alkyl.

Another aspect of the invention described herein are compounds according to the structure of Formula VII:

Formula VII

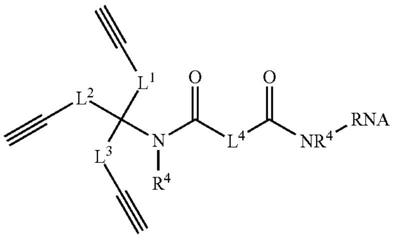

or a pharmaceutically acceptable salt thereof,
wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

each instance of $R^4$ is H or optionally substituted alkyl;

X is O or S; and

RNA comprises or consists of an RNAi agent.

In another aspect described herein are compounds according to the structure of Formula VIII:

Formula VIII

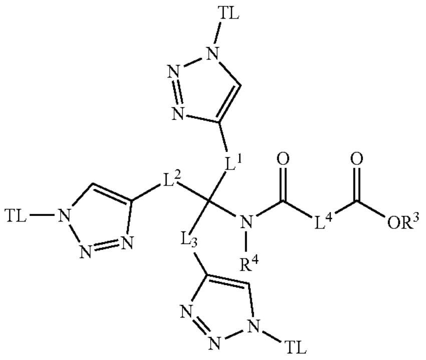

or a pharmaceutically acceptable salt thereof, wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

$R^4$ is H or optionally substituted alkyl; and

TL is a targeting ligand.

Another aspect of the invention described herein are compounds according to the structure of Formula IX:

Formula IX

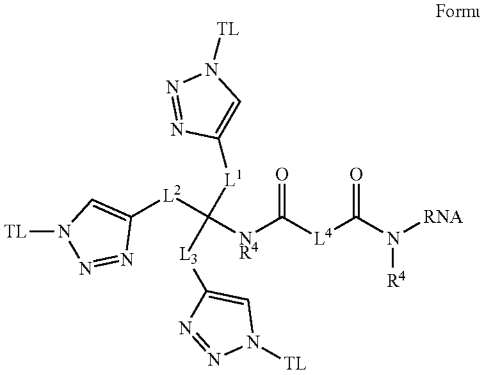

or a pharmaceutically acceptable salt thereof, wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

$R^4$ is H or optionally substituted alkyl;

TL is a targeting ligand;

X is O or S; and

RNA comprises or consists of an RNAi agent.

Another aspect of the invention provides a method of reacting a compound of Formula II:

Formula II

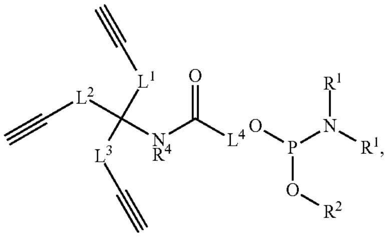

with an RNAi agent to form a compound of Formula III:

Formula III

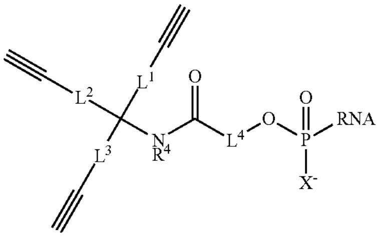

wherein, $L^1$, $L^2$, and $L^3$ are each independently linkers comprising optionally substituted alkylene;

$L^4$ is a linker comprising optionally substituted alkylene, optionally substituted arylene, and optionally substituted cycloalkylene;

each instance of $R^1$ is optionally substituted alkyl;

$R^2$ is optionally substituted alkyl; and $R^4$ is H or optionally substituted alkyl X is O or S; and RNA comprises or consists of an RNAi agent.

Another aspect of the invention provides a method of reacting a compound of Formula VI:

Formula VI

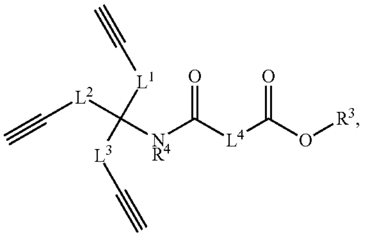

with an RNAi agent comprising a free amine to form a compound of Formula VII:

Formula VII

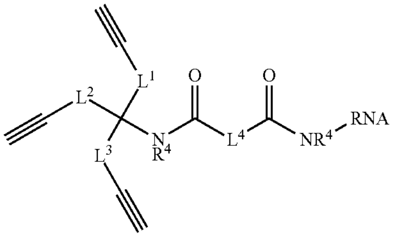

wherein, $L^1$, $L^2$ and $L^3$ are each independently linkers comprising optionally substituted alkylene;

$L^4$ is a linker comprising optionally substituted alkylene, optionally substituted arylene, or optionally substituted cycloalkylene;

$R^3$ is H, optionally substituted alkyl, or optionally substituted aryl; and each instance of $R^4$ is H or optionally substituted alkyl; and RNA comprises or consists of an RNAi agent.

Another aspect of the invention provides a method of reacting a compound of Formula III Formula III

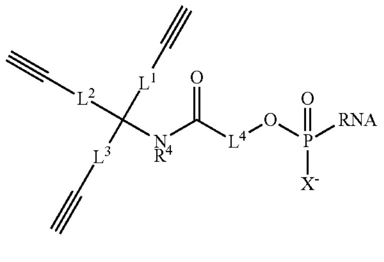

with a targeting ligand comprising an azide to form a compound of Formula V

Formula V

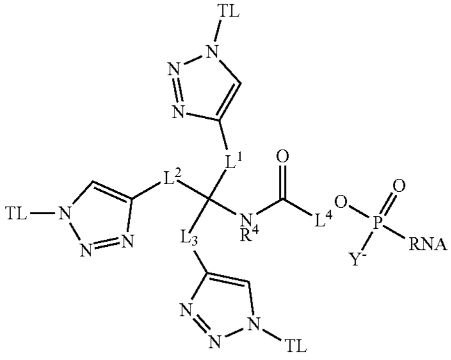

wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

$R^4$ is H or optionally substituted alkyl;

TL is a targeting ligand;

Y is O or S; and

RNA comprises or consists of an RNAi agent.

Another aspect of the invention provides a method of reacting a compound of Formula VII Formula VII

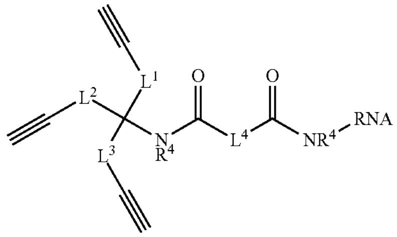

with a targeting ligand comprising an azide to form a compound of Formula IX,

Formula IX

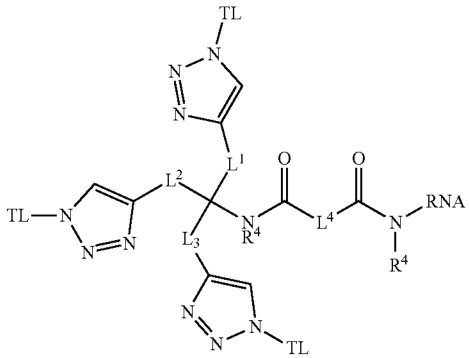

wherein, $L^1$, $L^2$ and $L^3$ are each independently linkers comprising optionally substituted alkylene;

$L^4$ is a linker comprising optionally substituted alkylene, optionally substituted arylene, or optionally substituted cycloalkylene;

each instance of $R^4$ is H or optionally substituted alkyl; and

RNA comprises or consists of a RNAi agent.

DETAILED DESCRIPTION

Novel compounds comprising phosphoramidite tri-alkynes, their synthesis, and methods of use thereof, are disclosed herein. The improved compounds disclosed herein exhibit improved reaction yields, stability, and biological activity when used to conjugate synthetic oligonucleotides such as RNAi agents to targeting ligands or other pharmacokinetic (PK) enhancers or modifiers.

Disclosed herein are trialkyne linking agents, their synthesis, and methods of use thereof. The trialkyne linking agents disclosed herein can be attached to oligonucleotides, and thereafter the oligonucleotides can be readily attached to a compound of interest such as a targeting ligand, lipid, cholesterol, delivery agent (such as an endosomolytic polymer), or pharmacological modifier. The trialkyne linking agents disclosed herein can facilitate the synthesis of oligonucleotide conjugates having improved yields and have fewer impurities than can be done using other known linking agents, while retaining or even in some embodiments improving the efficacy of the oligonucleotide conjugates, such as an RNAi agent linked to one or more targeting ligands and/or pharmacokinetic modifiers.

As used herein, the term "linker" means an organic moiety that connects two parts of a compound. Linkers typically comprise a direct bond or an atom such as oxygen or sulfur, a unit such as $NR^L$ (where $R^L$ is hydrogen, acyl, aliphatic or substituted aliphatic), C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylheterocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylheteroaryl, which one or more methylenes can be interrupted or terminated by O, S, S(O), $SO_2$, $N(R^L)$ (where $R^L$ is hydrogen, acyl, aliphatic or substituted aliphatic), C(O), substituted or unsubstituted aryl, substituted or unsubstituted heteroaryl, substituted or unsubstituted heterocyclic; $-(CH_2)_n-$, $-(CH_2)_nN-$, $-(CH_2)_nO-$, $-(CH_2)_nS-$, $-(CH_2)_n-C(O)-$, $-C(O)-(CH_2)_n-C(O)-NH-(CH_2)_m-C(O)-NH-(CH_2)_x-$, $-C(O)-(CH_2)_n-C(O)-NH-(CH_2)_m-C(O)-(CH_2)_n-C(O)-(CH_2)_m-$, $-C(O)-(CH_2)_n-NH-C(O)-(CH_2)_m-$, $-C(O)-(CH_2)_n-O-(CH_2-CH_2-O)_m-(CH_2)_x-$, $-(O-CH_2-CH_2)_n-$, $-O-(CH_2-CH_2-O)_n-$, $-O-(CH_2-CH_2-O)_n-CH_2-$, $-CH_2-(O-CH_2-CH_2)_n-$, $-CH_2-(O-CH_2-CH_2)_n-O-$, $-CH_2-(O-CH_2-CH_2)_n-O-CH_2-$, $-CH_2-CH_2-(O-CH_2-CH_2)_n-$, $-(CH_2-CH_2-O)_n-$, $-(CH_2-CH_2-O)_n-CH_2-$,

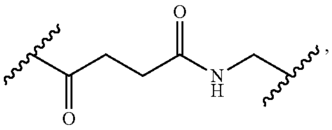,

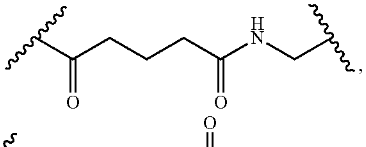,

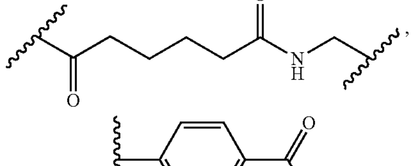, and

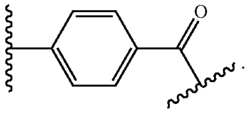.

Reactive groups are those commonly available in the art and include, but are not limited to, activated ester, NHS, TFP, PFP, tetrazine, norbornenes, trans-cy clooctenes, hydrazines (e.g. hynic), aminooxy reagents, and aldehydes (e.g. 4-formyl benzoic acid).

Targeting ligands (which may sometimes be referred to in the art as targeting groups) are used for targeting or improving the delivery of a compound to target cells or tissues, or specific cell types. Targeting ligands enhance the association of molecules to a target cell. Thus, targeting ligands can enhance the pharmacokinetic or biodistribution properties of a conjugate to which they are attached to improve cellular distribution and cellular uptake of the conjugate. Binding of a targeting group to a cell or cell receptor may initiate endocytosis. Targeting groups may be monovalent, divalent, trivalent, tetravalent, or have higher valency. Targeting groups can be, but are not limited to, compounds with affinity to cell surface molecules, cell receptor ligands, antibodies, monoclonal antibodies, antibody fragments, and antibody mimics with affinity to cell surface molecules, hydrophobic groups, cholesterol, cholesteryl groups, or steroids. In some embodiments, a targeting group comprises a cell receptor ligand. A variety of targeting groups have been used to target drugs and genes to cells and to specific cellular receptors. Cell receptor ligands may be, but are not limited to: carbohydrates, glycans, saccharides (including, but not limited to: galactose, galactose derivatives (such as N-acetyl-galactosamine), mannose, and mannose derivatives), haptens, vitamins, folate, biotin, aptamers, and peptides (including, but not limited to: RGD-containing peptides, RGD mimics, insulin, EGF, and transferrin).

As used herein, the term "alkyl" refers to a saturated aliphatic hydrocarbon group, straight chain or branched, having from 1 to 10 carbon atoms unless otherwise specified. For example, "$C_1$-$C_6$ alkyl" includes alkyl groups having 1, 2, 3, 4, 5, or 6 carbons in a linear or branched arrangement. Non-limiting examples of alkyl groups include methyl, ethyl, iso-propyl, tert-butyl, n-hexyl. As used herein, the term "aminoalkyl" refers to an alkyl group as defined above, substituted at any position with one or more amino groups as permitted by normal valency. The amino groups may be unsubstituted, monosubstituted, or di-substituted. Non-limiting examples of aminoalkyl groups include aminomethyl, dimethylaminomethyl, and 2-aminoprop-1-yl.

As used herein, the term "alkylene" refers to a divalent radical of an alkyl group as described herein. Alkylene is a subset of alkyl, referring to the same residues as alkyl, but having two points of substitution. Examples of alkylene are methylene, $-CH_2-$ or

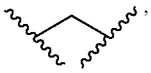, ethylene, $-CH_2CH_2-$ or

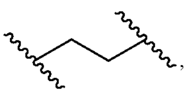 [SMILES: *CC*], and propylene, $-CH_2CH_2CH_2-$

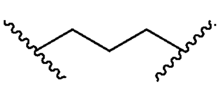 [SMILES: *CCC*].

As used herein, the term "cycloalkyl" means a saturated or unsaturated nonaromatic hydrocarbon ring group having from 3 to 14 carbon atoms, unless otherwise specified. Non-limiting examples of cycloalkyl groups include, but are not limited to, cyclopropyl, methyl-cyclopropyl, 2,2-dimethyl-cyclobutyl, 2-ethyl-cyclopentyl, and cyclohexyl. Cycloalkyls may include multiple spiro- or fused rings. Cycloalkyl groups are optionally mono-, di-, tri-, tetra-, or penta-substituted on any position as permitted by normal valency.

As used herein, the term "cycloalkylene" refers to a divalent radical of a cycloalkyl group as described herein. Cycloalkylene is a subset of cycloalkyl, referring to the same residues as cycloalkyl, but having two points of substitution. Examples of cycloalkylene include cyclopropylene,

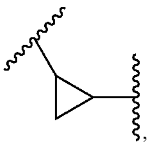

, 1,4-cyclohexylene,

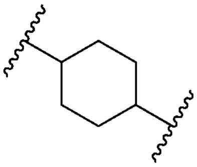

, and 1,5-cyclooxylene

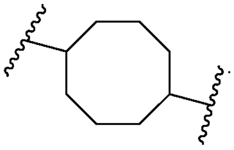 [SMILES: *C1CCCC(*)CCC1]

.

Cycloalkylene groups are optionally mono-, di-, tri-, tetra-, or penta-substituted on any position as permitted by normal valency. Cycloalkylene groups may be mono-, di-, or tricyclic.

As used herein, the term "alkenyl" refers to a non-aromatic hydrocarbon radical, straight, or branched, containing at least one carbon-carbon double bond, and having from 2 to 10 carbon atoms unless otherwise specified. Up to five carbon-carbon double bonds may be present in such groups. For example, "$C_2$-$C_6$" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least one carbon-carbon triple bond. Up to 5 carbon-carbon triple bonds may be present. Thus, "$C_2$-$C_6$ alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may be optionally mono-, di-, tri-, tetra-, or penta-substituted on any position as permitted by normal valency.

As used herein, "alkoxyl" or "alkoxy" refers to —O-alkyl radical having the indicated number of carbon atoms. For example, $C_1$-$C_6$ alkoxy is intended to include $C_1$, $C_2$, $C_3$, $C_4$, $C_5$, and $C_6$ alkoxy groups. For example, $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "keto" refers to any alkyl, alkenyl, alkynyl, cycloalkyl, cycloalkenyl, heterocyclyl, heteroaryl, or aryl group as defined herein attached through a carbonyl bridge. Examples of keto groups include, but are not limited to, alkanoyl (e.g., acetyl, propionyl, butanoyl, pentanoyl, or hexanoyl), alkenoyl (e.g., acryloyl) alkynoyl (e.g., ethynoyl, propynoyl, butynoyl, pentynoyl, or hexynoyl), aryloyl (e.g., benzoyl), heteroaryloyl (e.g., pyrroloyl, imidazoloyl, quinolinoyl, or pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxycarbonyl, benzyloxycarbonyl, or n-pentoxycarbonyl.

As used herein, "aryloxycarbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryloxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxycarbonyl, 4-thiazolyloxycarbonyl, or pyrimidinyloxycarbonyl.

As used herein, "aryl" or "aromatic" means any stable monocyclic or polycyclic carbon ring of up to 6 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency.

As used herein, the term "arylene" refers to a divalent radical of an aryl group as described herein. Arylene is a subset of aryl, referring to the same residues as aryl, but having two points of substitution. Examples of arylene include phenylene, which refers to a divalent phenyl group. Arylene groups are optionally mono-, di-, tri-, tetra-, or penta-substituted on any position as permitted by normal valency.

As used herein, the term "coupling moiety" refers to a chemical moiety that may be used to couple two molecules together. For instance, a "coupling moiety" may refer to a phosphoramidite, which reacts with an alcohol on a separate molecule to form an organophosphate. Further examples of coupling agents may include, but are not limited to, esters, carbonates, carboxylic acids, olefins, alcohols, amines, aldehydes, ketones, alkynes, halogens, Grignard reagents, leaving groups, and any other moieties used for coupling two molecules known in the art.

As used herein, the term "halo" refers to a halogen radical. For instance, "halo" may refer to a fluoro (F), chloro (Cl), bromo (Br), or an iodo (I) radical.

As used herein, the term "heteroaryl" represents a stable monocyclic or polycyclic ring of up to 7 atoms in each ring, wherein at least one ring is aromatic and contains from 1 to 4 heteroatoms selected from the group consisting of O, N, and S. Examples of heteroaryl groups include, but are not limited to, acridinyl, carbazolyl, cinnolinyl, quinoxalinyl, pyrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, and tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, di-, tri-, tetra-, or penta-substituted on any position as permitted by normal valency.

As used herein, the term "heteroarylene" refers to a divalent radical of a heteroaryl group as described herein. Heteroarylene is a subset of heteroaryl, referring to the same residues as heteroaryl, but having two points of substitution. Examples of heteroaryl include pyridinylene, pyrimidinylene, and pyrrolylene. Heteroarylene groups are optionally mono-, di-, tri-, tetra-, or penta-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N, and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyridinonyl, pyrimidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dibydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

As used herein, the term "heterocycloalkyl" means a 3- to 14-membered nonaromatic heterocycle containing from 1 to 4 heteroatoms selected from the group consisting of O, N, and S, including polycyclic groups. Examples of heterocyclyl groups include, but are not limited to, azetidinyl, oxopiperazinyl, oxopyrrolidinyl, oxomorpholinyl, oxetanyl, pyranyl, pyridinonyl, pyrimidinonyl, tetrahydropyranyl, tetrahydrofuranyl, tetrahydrothiopyranyl, tetrahydroisoquinolinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, dioxidothiomorpholinyl, and tetrahydrothienyl, and N-oxides thereof. Attachment of a heterocycloalkyl substituent can occur via a carbon atom or via a heteroatom. Heterocyclyl groups are optionally mono-, di-, tri-, tetra-, or penta-substituted on any position as permitted by normal valency.

As used herein, the term "heterocycloalkylene" refers to a divalent radical of a heterocycloalkyl group as described herein. Heteroycloalkylene is a subset of heterocycloalkyl, referring to the same residues as heterocycloalkyl, but having two points of substitution. Examples of heterocycloalkylene include piperidinylene, azetidinylene, and tetrahydrofuranylene. Heterocycloalkylene groups are optionally mono-, di-, tri-, tetra-, or penta-substituted on any position as permitted by normal valency.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means that delivering the RNAi agent to the cell in a manner that enables the RNAi agent to have the expected biological activity, e.g., sequence-specific inhibition of gene expression.

Unless stated otherwise, use of the symbol

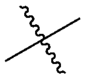

as used herein means that any group or groups may be linked thereto that is in accordance with the scope of the inventions described herein. In some embodiments herein, the symbol

is used multiple times in a structure to describe the points of attachment of a particular variable in a compound of Formula I. Unless otherwise stated, the shown variable may be oriented such that any one of the points of connection on the variable may be connected to any one of the points of connection on the compound of Formula I. For example, the variable $L^1$ has two points of attachment to the compound of Formula I. While one embodiment of $L^1$ may be shown as

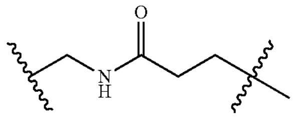
, the embodiment should also be understood to refer to a compound where $L^1$ is

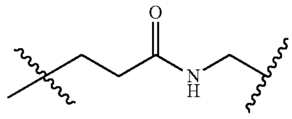
.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereomers," and stereoisomers that are non-superimposable mirror images are termed "enantiomers," or sometimes optical isomers. A carbon atom bonded to four non-identical substituents is termed a "chiral center." When the compounds described herein contain olefinic double bonds or other centers of geometric asymmetry for which the isomeric structure is not specifically defined, it is intended that the compounds can include both E and Z geometric isomers individually or in a mixture. The compounds of Formula I or their pharmaceutically acceptable salts, for example, are meant to include all possible isomers, as well as their racemic and optically pure forms. Likewise, unless expressly stated otherwise, all tautomeric forms are also intended to be included.

As used herein, a linking group is one or more atoms that connects one molecule or portion of a molecule to another to second molecule or second portion of a molecule. In the art, the terms linking group and spacers are sometimes used interchangeably. Similarly, as used in the art, the term scaffold is sometimes used interchangeably with a linking group. In some embodiments, a linking group can include a peptide-cleavable linking group. In some embodiments, a linking group can include or consist of the peptide phenylalanine-citrulline-phenylalanine-proline. In some embodiments, a linking group can include or consist of a PEG group.

As used herein, the term "linked" when referring to the connection between two molecules means that two molecules are joined by a covalent bond or that two molecules are associated via noncovalent bonds (e.g., hydrogen bonds or ionic bonds). In some examples, where the term "linked" refers to the association between two molecules via noncovalent bonds, the association between the two different molecules has a $K_D$ of less than $1\times10^{-4}$ M (e.g., less than $1\times10^{-5}$ M, less than $1\times10^{-6}$ M, or less than $1\times10^{-7}$ M) in physiologically acceptable buffer (e.g., phosphate buffered saline). Unless stated, the term linked as used herein may refer to the connection between a first compound and a second compound either with or without any intervening atoms or groups of atoms.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

Structures may be depicted as having a bond "floating" over a ring structure to indicate binding to any carbon or heteroatom on the ring as permitted by valency. For example, the structure

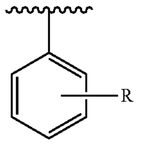

indicates that R may replace any hydrogen atom at any of the five available positions on the ring. "Floating" bonds may also be used in bicyclic structures to indicate a bond to any position on either ring of the bicycle as permitted by valency. In the case of bicycles, the bond will be shown "floating" over both rings, for example,

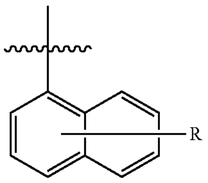

indicates that R may replace any hydrogen atom at any of the seven available positions on the ring.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

As used herein, a "pharmaceutical composition" comprises a pharmacologically effective amount of at least one kind of RNAi agent and one or more a pharmaceutically acceptable excipients. Pharmaceutically acceptable excipients (excipients) are substances other than the Active Pharmaceutical ingredient (API, therapeutic product, e.g., RNAi agent) that have been appropriately evaluated for safety and are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use.

Excipients include, but are not limited to: absorption enhancers, anti-adherents, anti-foaming agents, anti-oxidants, binders, binders, buffering agents, carriers, coating agents, colors, delivery enhancers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents. A pharmaceutically acceptable excipient may or may not be an inert substance.

The pharmaceutical compositions can contain other additional components commonly found in pharmaceutical compositions. The pharmaceutically-active materials may include, but are not limited to: anti-pruritics, astringents, local anesthetics, or anti-inflammatory agents (e.g., antihistamine, diphenhydramine, etc.). It is also envisaged that cells, tissues or isolated organs that express or comprise the herein defined RNAi agents may be used as "pharmaceutical compositions". As used herein, "pharmacologically effective amount," "therapeutically effective amount," or simply "effective amount" refers to that amount of an RNAi agent to produce the intended pharmacological, therapeutic or preventive result.

The term polynucleotide, or polynucleic acid, refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Synthetic oligonucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

The synthetic oligonucleotides of the invention can be chemically modified. The use of chemically modified polynucleotides can improve various properties of the polynucleotide including, but not limited to: resistance to nuclease degradation in vivo, cellular uptake, activity, and sequence-specific hybridization. Non-limiting examples of such chemical modifications include: phosphorothioate internucleotide linkages, 2'-O-methyl ribonucleotides, 2'-deoxy-2'-fluoro ribonucleotides, 2'-deoxyribonucleotides, "universal base" nucleotides, 5-C-methyl nucleotides, 2',3'-seco nucleotide mimics (unlocked nucleobase analogues, represented herein as NUNA or NUNA), and inverted deoxyabasic residue incorporation. These chemical modifications, when used in various polynucleotide constructs, are shown to preserve polynucleotide activity in cells while at the same time, dramatically increasing the serum stability of these compounds.

In some embodiments, a synthetic oligonucleotide of the invention comprises a duplex having two strands, one or both of which can be chemically-modified, wherein each strand is about 19 to about 29 (e.g., about 19, 20, 21, 22, 23, 24, 25, 26, 27, 28, or 29) nucleotides. In some embodiments, a synthetic oligonucleotide of the invention comprises one or more modified nucleotides. A synthetic oligonucleotide of the invention can comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions).

A synthetic oligonucleotide may comprise a 5' or 3' end modification. 3' and 5' end modifications include, but are not limited to: amine-containing groups, alkyl groups, alkyl amine groups, reactive groups, TEC groups, and PEG groups.

An "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. HIF-2 alpha mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

In some embodiments, the RNAi agent comprises at least two sequences that are partially, substantially, or fully complementary to each other. In some embodiments, the two RNAi agent sequences comprise a sense strand comprising a first sequence and an antisense strand comprising a second sequence. In some embodiments, the two RNAi agent sequences comprise two sense strands which together comprise a first sequence and an antisense strand comprising a second sequence, wherein the sense strands and the antisense strand together form a meroduplex. The sense strand may be connected to the antisense strand via a linking molecule, such as a polynucleotide linker or a non-nucleotide linker.

The antisense strand comprises a nucleotide sequence which is complementary to a part of an mRNA encoded by a target gene, and the region of complementarity is most preferably less than 30 nucleotides in length. The RNAi agent sense strands comprise sequences which have an identity of at least 85% to at least a portion of a target mRNA. The RNAi agent, upon delivery to a cell expressing the target gene, inhibits the expression of said target gene in vitro or in vivo.

In some embodiments, the RNAi agent may be comprised of naturally occurring nucleotides or may be comprised of at least one modified nucleotide or nucleotide mimic. The RNAi agent sense and antisense strands of the invention may be synthesized and/or modified by methods well established in the art. RNAi agent nucleosides, or nucleotide bases, may be linked by phosphate-containing (natural) or non-phosphate-containing (non-natural) covalent internucleoside linkages, i.e. the RNAi agent may have natural or non-natural oligonucleotide backbones. In some embodiments, the RNAi agent contains a non-standard (non-phosphate) linkage between to nucleotide bases.

In some embodiments, an RNAi agent may comprise a 5' or 3' end modification. 3' and 5' end modifications include, but are not limited to: amine-containing groups, alkyl groups, alkyl amine groups, reactive groups, TEG groups, and PEG groups.

In some embodiments, the RNAi agent may comprise overhangs, i.e. typically unpaired, overhanging nucleotides which are not directly involved in the double helical structure normally formed by the core sequences of the sense strand and antisense strand.

In some embodiments, the RNAi agent may contain 3' and/or 5' overhangs of 1-5 bases independently on each of the sense strands and antisense strands. In some embodiments, both the sense strand and the antisense strand contain 3' and 5' overhangs. In some embodiments, one or more of the 3' overhang nucleotides of one strand base pairs with one or more 5' overhang nucleotides of the other strand. In some embodiments, the one or more of the 3' overhang nucleotides of one strand do not pair with the one or more 5' overhang nucleotides of the other strand. The sense and antisense strands of an RNAi agent may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In some embodiments, one or more of the nucleotides in the overhang contains a thiophosphate, phosphorothioate, deoxynucleotide inverted (3' to 3' linked) nucleotide, or is a modified ribonucleotide or deoxynucleotide.

Lists of known mRNA sequences can be found in databases maintained by various research organizations, including the database GenBank, which is a database maintained by the National Center for Biotechnology Information, a branch under the National Institutes of Health in the United States, as part of the International Nucleotide Sequence Database Collaboration. Known effective siRNA sequences and cognate binding sites are also well represented in the relevant literature. RNAi agent molecules are readily designed and produced by technologies known in the art. In addition, there are computational tools that may increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

Formula I

Formula I is represented by the structure:

Formula I

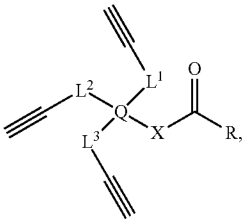

wherein $L^1$, $L^2$, and $L^3$ are each independently linkers comprising optionally substituted alkylene;

Q is a tetravalent carbon atom, tetra-substituted phenyl or optionally substituted alkylene;

R comprises a coupling moiety or an RNAi agent; and

X is $NR^x$ or a bond, and $R^x$ is H or optionally substituted $C_1$-$C_6$ alkyl.

In some embodiments of Formula I, Q is a tetravalent carbon. In other embodiments of Formula I, Q is

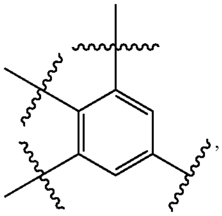 [SMILES: *c1cc(*)c(*)c(*)c1], wherein  indicates the point of attachment. In other embodiments, Q is

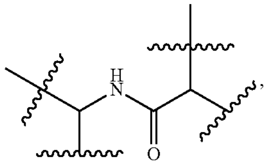 [SMILES: *C(*)NC(=O)C(*)*], wherein  indicates the point of attachment.

In some embodiments of Formula I, $L^1$, $L^2$, and $L^3$ are each

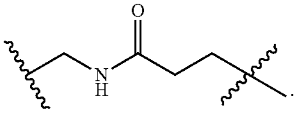 [SMILES: *CCC(=O)NC*].

In some embodiments of Formula I, $L^1$, $L^2$, and $L^3$ are each

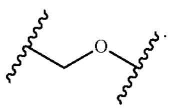 [SMILES: *CO*]

In some embodiments of Formula I, $L^1$ $L^2$, and $L^3$ are each

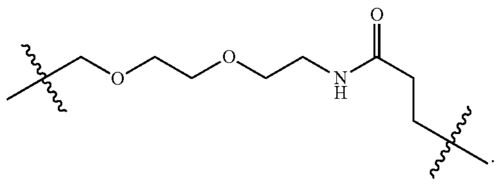 [SMILES: *CCC(=O)NCCOCCOC*]

In some embodiments of Formula I, X is NH.

In some embodiments of Formula I, R comprises a phosphoramidite. In some embodiments of Formula I, R comprises an organophosphate and an RNAi agent. In other embodiments of Formula I, R comprises an ester. In some embodiments of Formula I, R comprises a para-nitro phenol ester. In some embodiments of Formula I, R comprises an amide and an RNAi agent. In other embodiments of Formula I, R comprises a carbonate. In some embodiments, R comprises a carbamate and an RNAi agent.

In some embodiments of Formula I, R is selected from the group consisting of

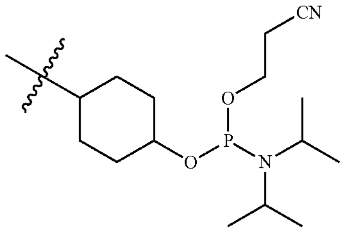

,

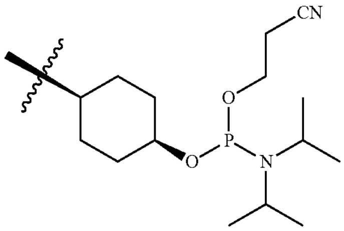

,

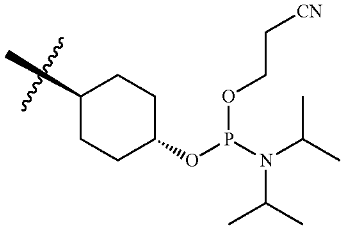

,

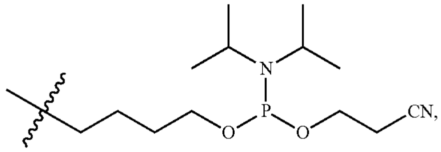

-continued

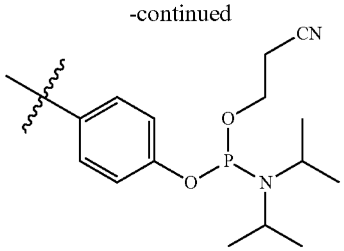

,

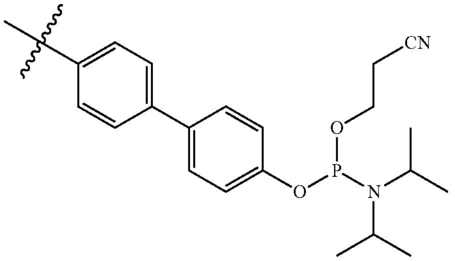

,

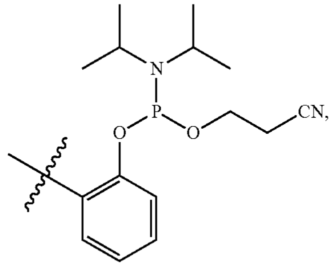

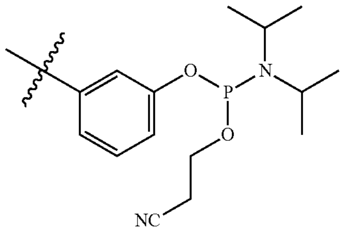

,

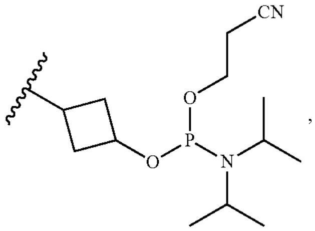

,

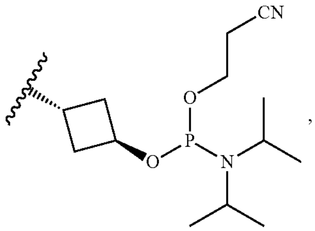

,

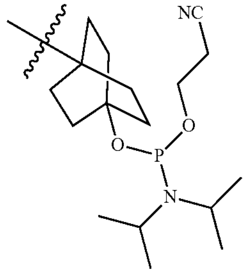

,

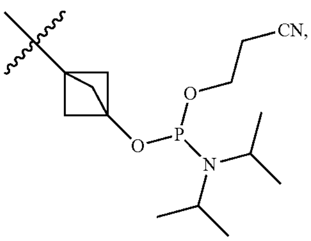

-continued
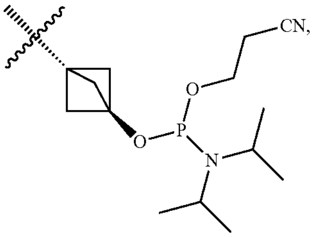
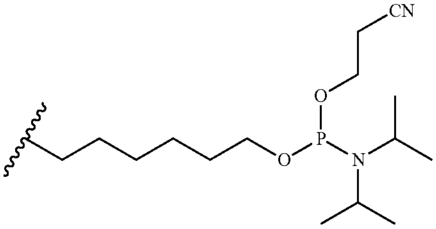
,
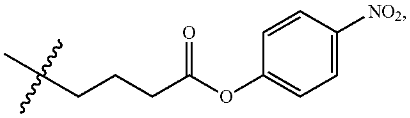
-continued
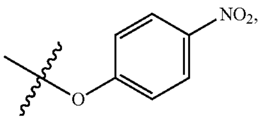
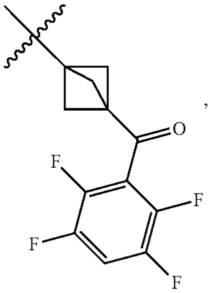
, and
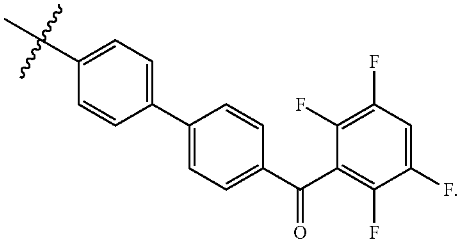
Example compounds of Formula I are shown in Table 1 below:
TABLE 1
| Compounds of Formula I. | |
|---|---|
| Compound No. | Structure |
| 1 | 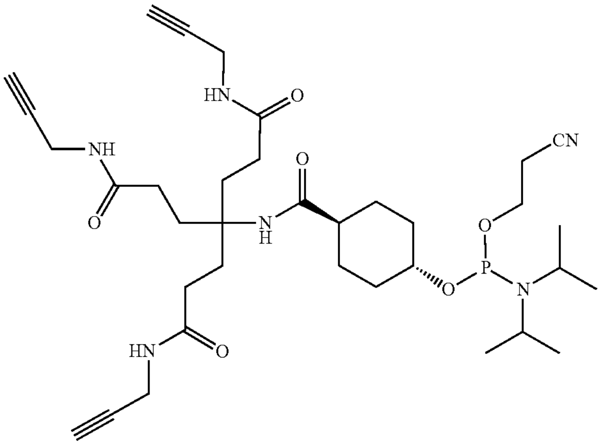 [SMILES: C#CCNC(=O)CCC(CCC(=O)NCC#C)(CCC(=O)NCC#C)NC(=O)[C@H]1CC[C@H](OP(OCCC#N)N(C(C)C)C(C)C)CC1] |
| 2 | 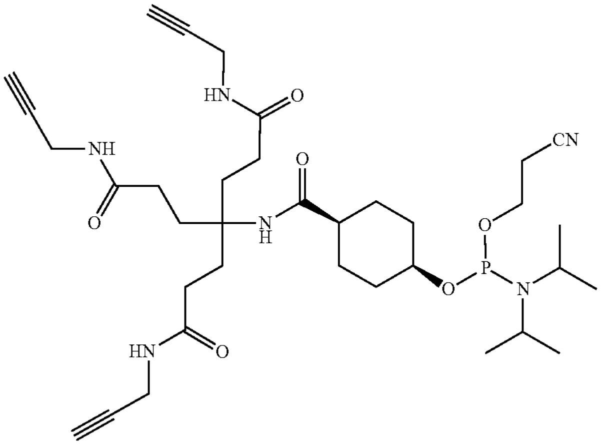 [SMILES: C#CCNC(=O)CCC(CCC(=O)NCC#C)(CCC(=O)NCC#C)NC(=O)[C@H]1CC[C@@H](OP(OCCC#N)N(C(C)C)C(C)C)CC1] |

TABLE 1-continued
| Compounds of Formula I. | |
|---|---|
| Compound No. | Structure |
| 3 | 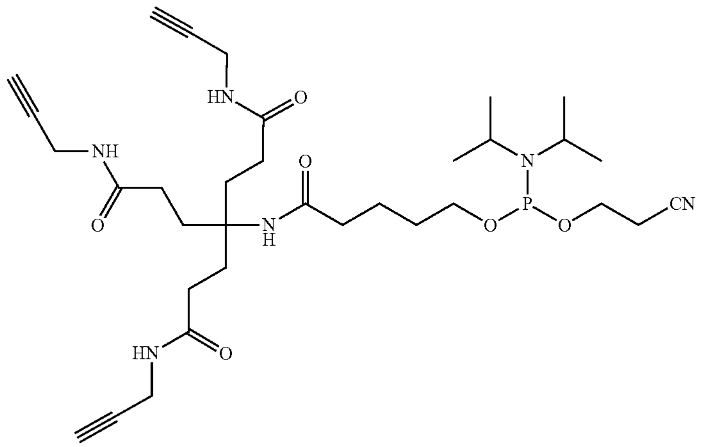 [SMILES: C#CCNC(=O)CCC(CCC(=O)NCC#C)(CCC(=O)NCC#C)NC(=O)CCCCOP(OCCC#N)N(C(C)C)C(C)C] |
| 4 | 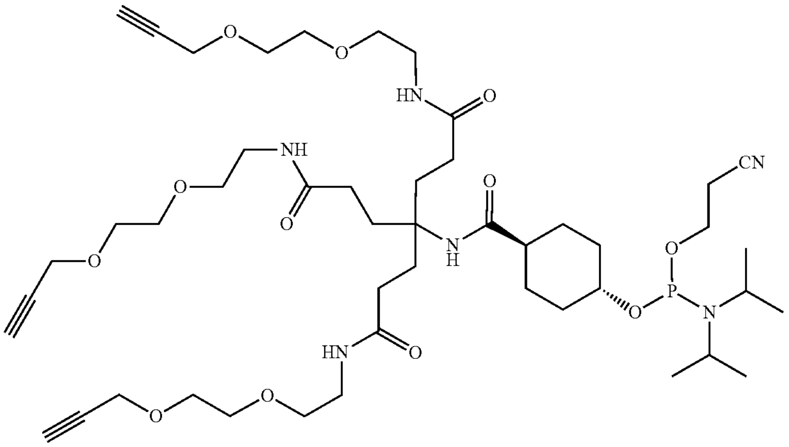 [SMILES: C#CCOCCOCCNC(=O)CCC(CCC(=O)NCCOCCOCC#C)(CCC(=O)NCCOCCOCC#C)NC(=O)[C@H]1CC[C@H](OP(OCCC#N)N(C(C)C)C(C)C)CC1] |
| 5 | 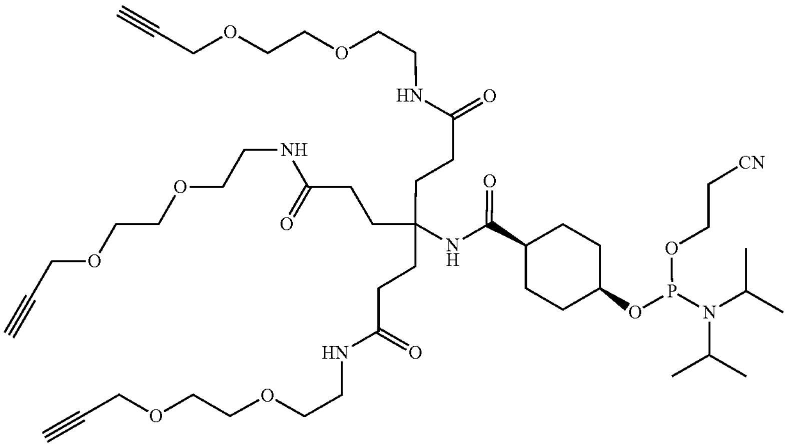 [SMILES: C#CCOCCOCCNC(=O)CCC(CCC(=O)NCCOCCOCC#C)(CCC(=O)NCCOCCOCC#C)NC(=O)[C@H]1CC[C@@H](OP(OCCC#N)N(C(C)C)C(C)C)CC1] |

TABLE 1-continued
| Compounds of Formula I. | |
|---|---|
| Compound No. | Structure |
| 6 | 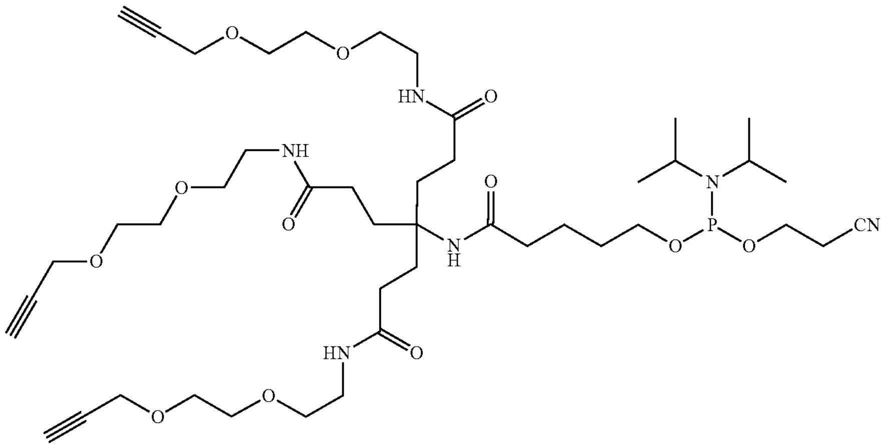 [SMILES: C#CCOCCOCCNC(=O)CCC(CCC(=O)NCCOCCOCC#C)(CCC(=O)NCCOCCOCC#C)NC(=O)CCCCOP(OCCC#N)N(C(C)C)C(C)C] |
| 7 | 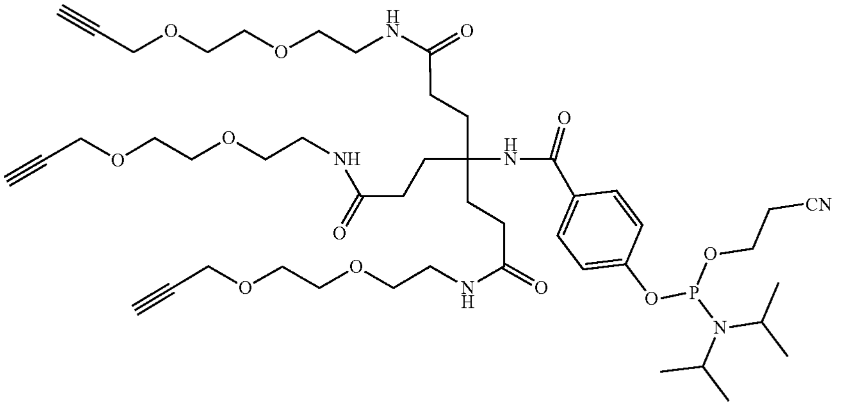 [SMILES: C#CCOCCOCCNC(=O)CCC(CCC(=O)NCCOCCOCC#C)(CCC(=O)NCCOCCOCC#C)NC(=O)c1ccc(OP(OCCC#N)N(C(C)C)C(C)C)cc1] |
| 8 | 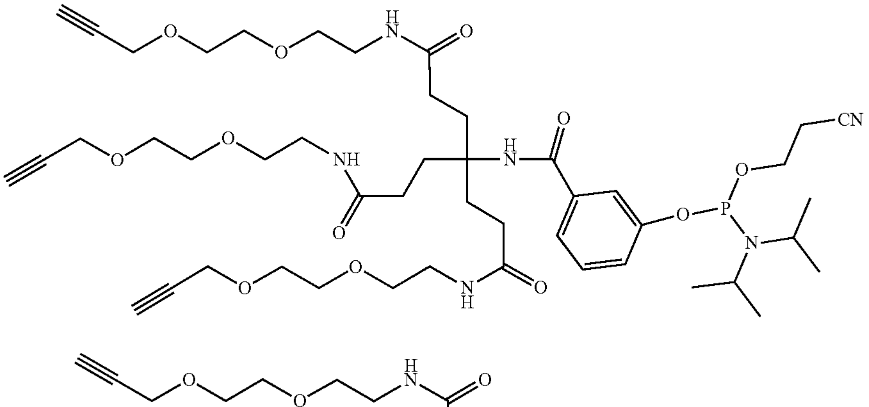 |
| 9 | 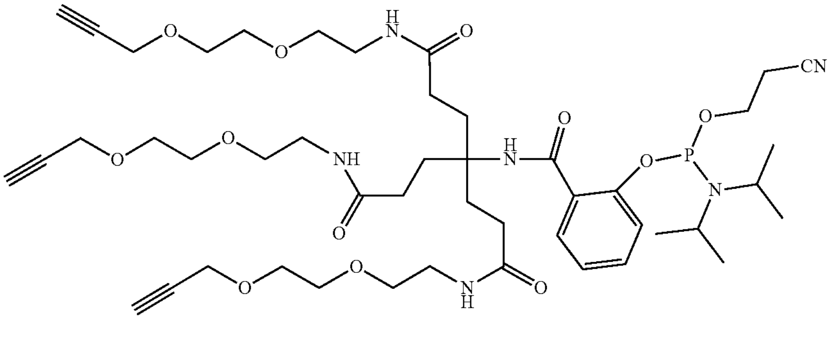 [SMILES: C#CCOCCOCCNC(=O)CCC(CCC(=O)NCCOCCOCC#C)(CCC(=O)NCCOCCOCC#C)NC(=O)c1ccccc1OP(OCCC#N)N(C(C)C)C(C)C] |

TABLE 1-continued
| Compounds of Formula I. | |
|---|---|
| Compound No. | Structure |
| 10 | 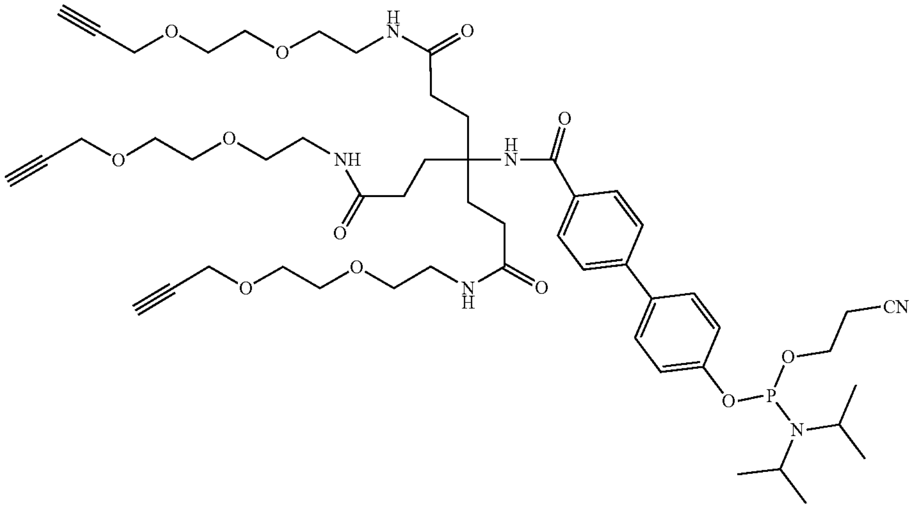 [SMILES: C#CCOCCOCCNC(=O)CCC(CCC(=O)NCCOCCOCC#C)(CCC(=O)NCCOCCOCC#C)NC(=O)c1ccc(-c2ccc(OP(OCCC#N)N(C(C)C)C(C)C)cc2)cc1] |
| 11 | 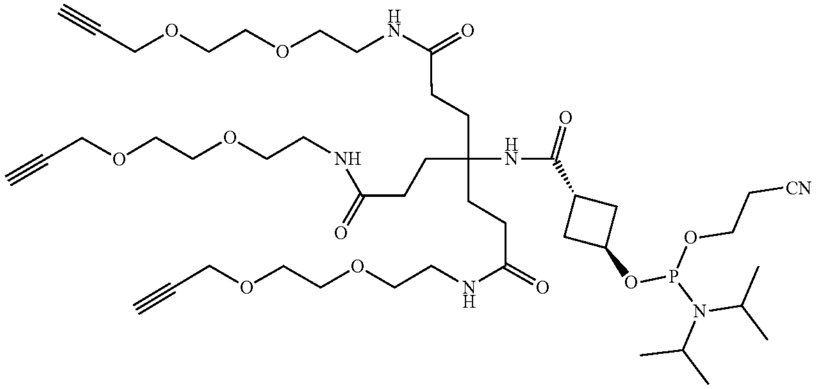 [SMILES: C#CCOCCOCCNC(=O)CCC(CCC(=O)NCCOCCOCC#C)(CCC(=O)NCCOCCOCC#C)NC(=O)[C@H]1C[C@H](OP(OCCC#N)N(C(C)C)C(C)C)C1] |
| 12 | 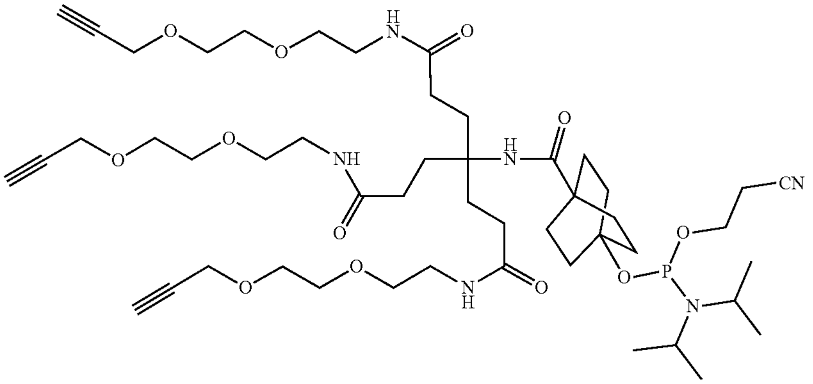 [SMILES: C#CCOCCOCCNC(=O)CCC(CCC(=O)NCCOCCOCC#C)(CCC(=O)NCCOCCOCC#C)NC(=O)C12CCC(OP(OCCC#N)N(C(C)C)C(C)C)(CC1)CC2] |

TABLE 1-continued
| Compounds of Formula I. | |
|---|---|
| Compound No. | Structure |
| 13 | 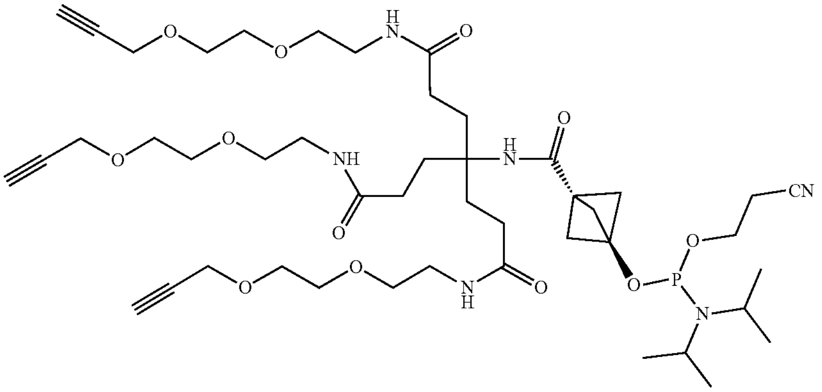 [SMILES: C#CCOCCOCCNC(=O)CCC(CCC(=O)NCCOCCOCC#C)(CCC(=O)NCCOCCOCC#C)NC(=O)[C@]12C[C@@](OP(OCCC#N)N(C(C)C)C(C)C)(C1)C2] |
| 14 | 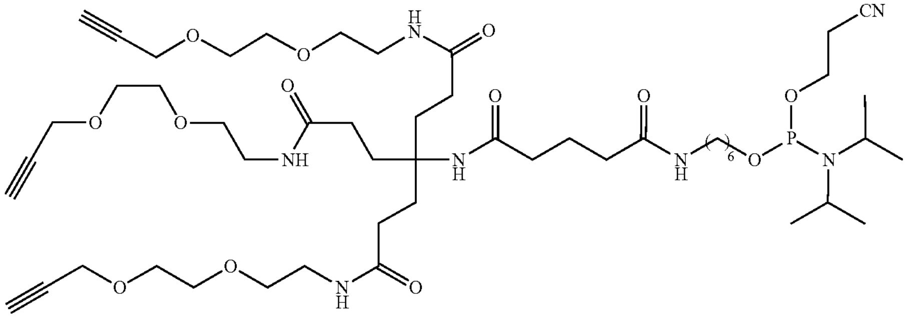 |
| 15 | 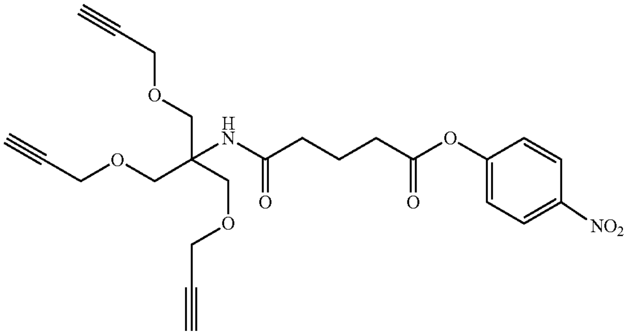 [SMILES: C#CCOCC(COCC#C)(COCC#C)NC(=O)CCCC(=O)Oc1ccc([N+](=O)[O-])cc1] |
| 16 | 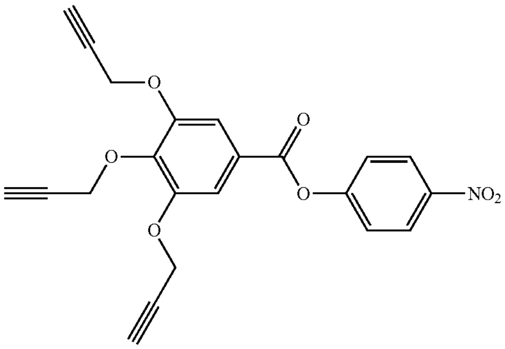 [SMILES: C#CCOc1cc(C(=O)Oc2ccc([N+](=O)[O-])cc2)cc(OCC#C)c1OCC#C] |

TABLE 1-continued
| Compounds of Formula I. | |
|---|---|
| Compound No. | Structure |
| 17 | 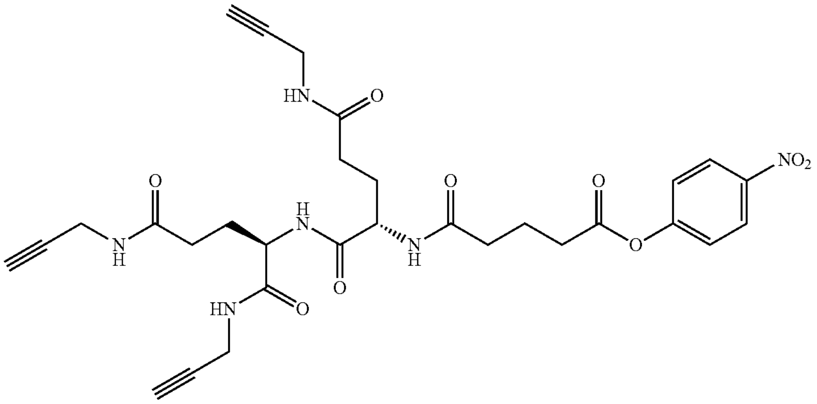 [SMILES: C#CCNC(=O)CC[C@H](NC(=O)CCCC(=O)Oc1ccc([N+](=O)[O-])cc1)C(=O)N[C@H](CCC(=O)NCC#C)C(=O)NCC#C] |
| 18 | 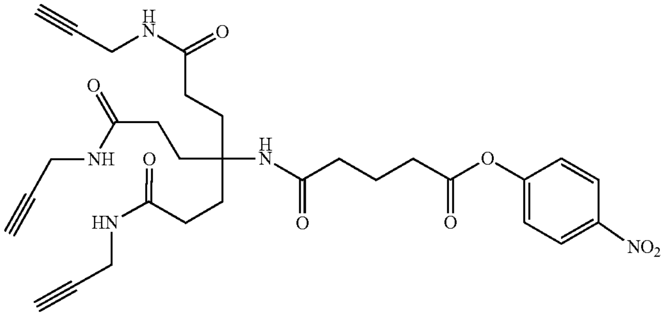 [SMILES: C#CCNC(=O)CCC(CCC(=O)NCC#C)(CCC(=O)NCC#C)NC(=O)CCCC(=O)Oc1ccc([N+](=O)[O-])cc1] |
| 19 | 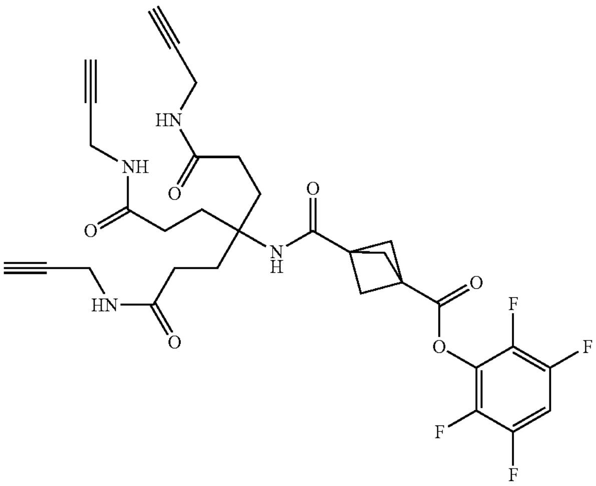 [SMILES: C#CCNC(=O)CCC(CCC(=O)NCC#C)(CCC(=O)NCC#C)NC(=O)C12CC(C(=O)Oc3c(F)c(F)cc(F)c3F)(C1)C2] |

TABLE 1-continued
| Compounds of Formula I. | |
|---|---|
| Compound No. | Structure |
| 20 | 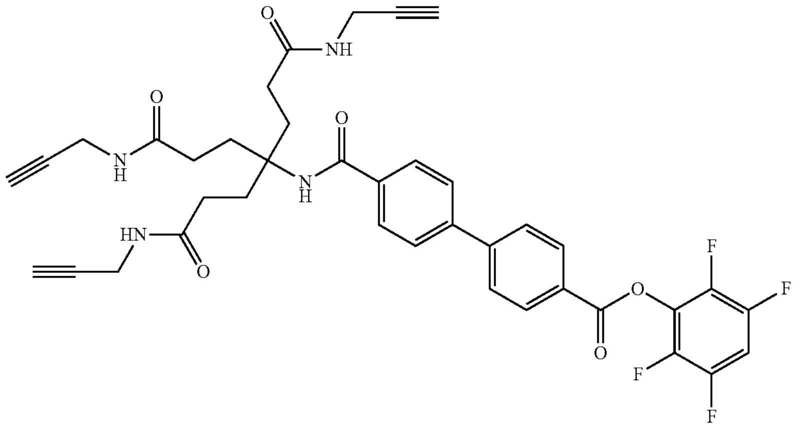 [SMILES: C#CCNC(=O)CCC(CCC(=O)NCC#C)(CCC(=O)NCC#C)NC(=O)c1ccc(-c2ccc(C(=O)Oc3c(F)c(F)cc(F)c3F)cc2)cc1] |
| 21 | 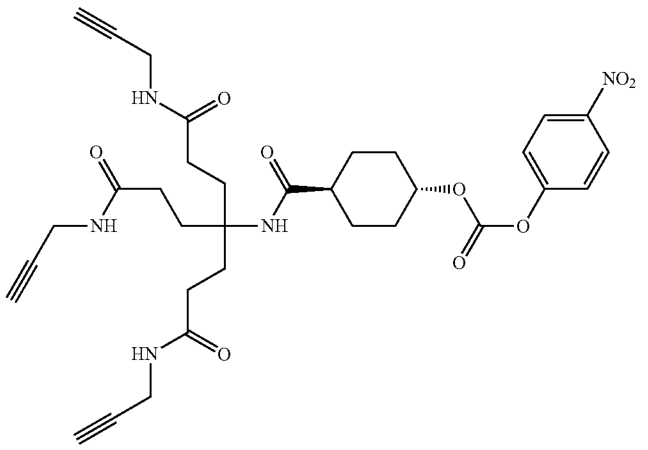 [SMILES: C#CCNC(=O)CCC(CCC(=O)NCC#C)(CCC(=O)NCC#C)NC(=O)[C@H]1CC[C@H](OC(=O)Oc2ccc([N+](=O)[O-])cc2)CC1] |
| 22 | 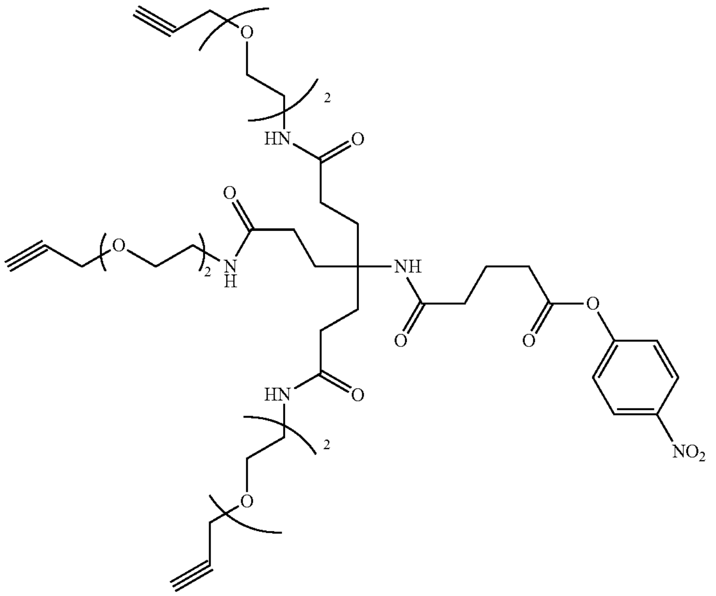 |

Formula II

Formula II is represented by the structure:

Formula II

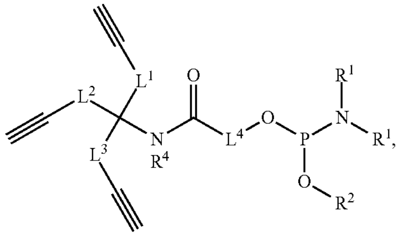

or a pharmaceutically acceptable salt thereof, wherein, $L^1$, $L^2$, and $L^3$ are each independently linkers comprising optionally substituted alkylene;

$L^4$ is a linker comprising optionally substituted alkylene, optionally substituted arylene, and optionally substituted cycloalkylene;

each instance of $R^1$ is optionally substituted alkyl;

$R^2$ is optionally substituted alkyl; and $R^4$ is H or optionally substituted alkyl.

In some embodiments of Formula II, $L^1$, $L^2$ and $L^3$ are each

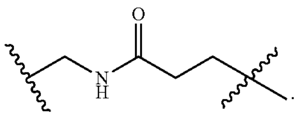 [SMILES: *CCC(=O)NC*]

In some embodiments of Formula II, $L^1$, $L^2$ and $L^3$ are each

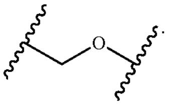 [SMILES: *CO*]

In some embodiments of Formula II, $L^1$, $L^2$ and $L^3$ are each

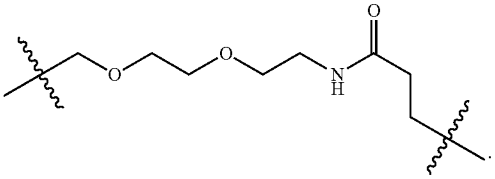 [SMILES: *CCC(=O)NCCOCCOC*]

In some embodiments of Formula II, each instance of $R^1$ is isopropyl.

In some embodiments of Formula II, $R^2$ is

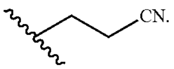 [SMILES: *CCC#N]

In some embodiments of Formula II, $L^4$ selected from the group consisting of:

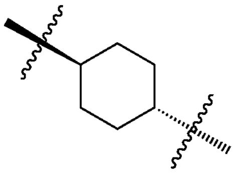 , 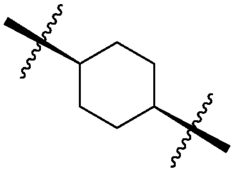 ,

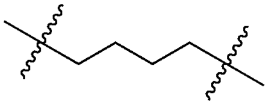 , 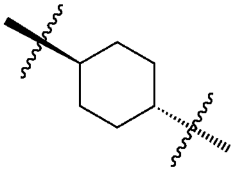 ,

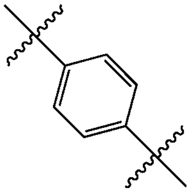 , 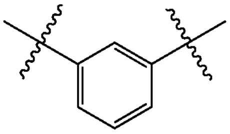 ,

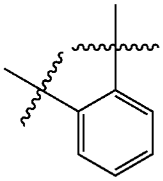 , 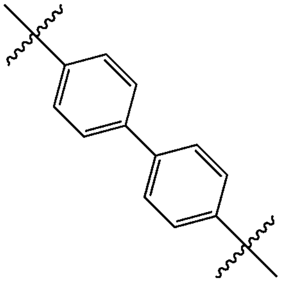 ,

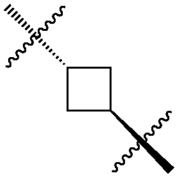 , 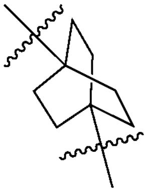 ,

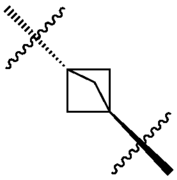 , and

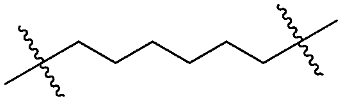 , and wherein  indicates the point of attachment.

Formula III

Formula III is represented by the structure:

Formula III

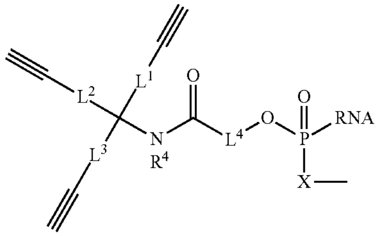

or a pharmaceutically acceptable salt thereof, wherein, $L^1$, $L^2$, and $L^3$ are each independently linkers comprising optionally substituted alkylene;

$L^4$ is a linker comprising optionally substituted alkylene, optionally substituted arylene, and optionally substituted cycloalkylene;

$R^4$ is H or optionally substituted alkyl;

X is O or S; and

RNA comprises or consists of an RNAi agent.

In some embodiments of Formula III, X is O, and the compound of Formula III is an organophosphate. In some embodiments of Formula II, X is S and the compound of Formula III is a phosphorothioate.

In some embodiments of Formula III, $L^1$, $L^2$ and $L^3$ are each

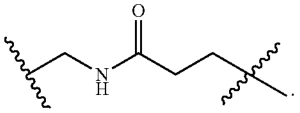 [SMILES: *CCC(=O)NC*]

In some embodiments of Formula III, $L^1$, $L^2$ and $L^3$ are each

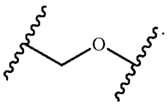 [SMILES: *CO*]

In some embodiments of Formula III, $L^1$, $L^2$ and $L^3$ are each

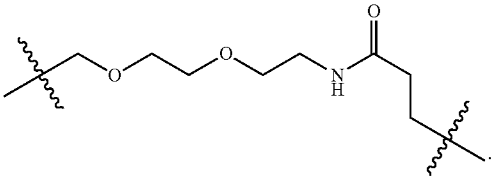 [SMILES: *CCC(=O)NCCOCCOC*]

In some embodiments of Formula III, $L^4$ is selected from the group consisting of:

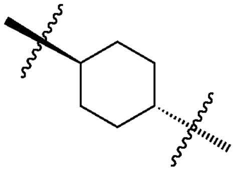 , 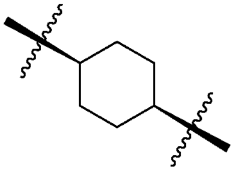 ,

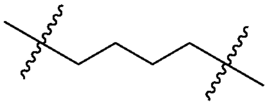 , 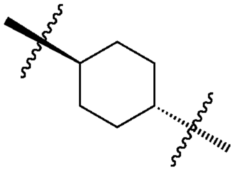 ,

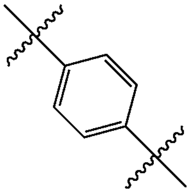 , 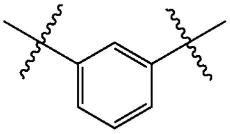 ,

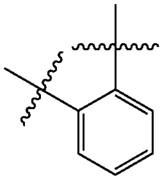 , 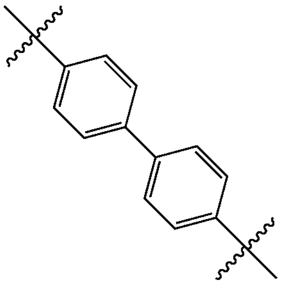 ,

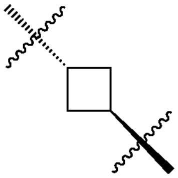 , 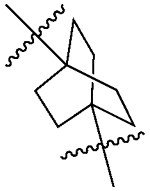 ,

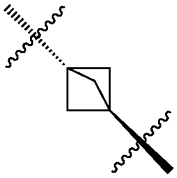 , and

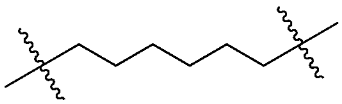 , wherein ⌇ indicates the point of attachment.

Example compounds of Formula III are shown in Table 2 below:
TABLE 2
| Compounds of Formula III. | |
|---|---|
| Compound No. | Structure |
| 1-O-III | 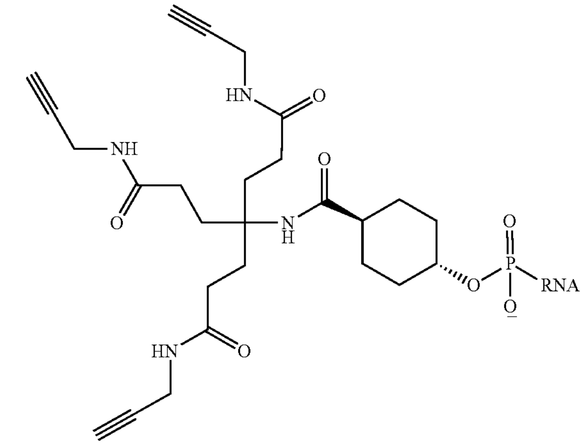 |
| 1-S-III | 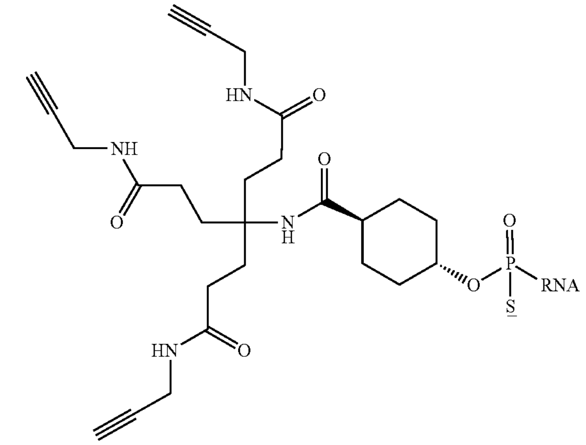 |
| 2-O-III | 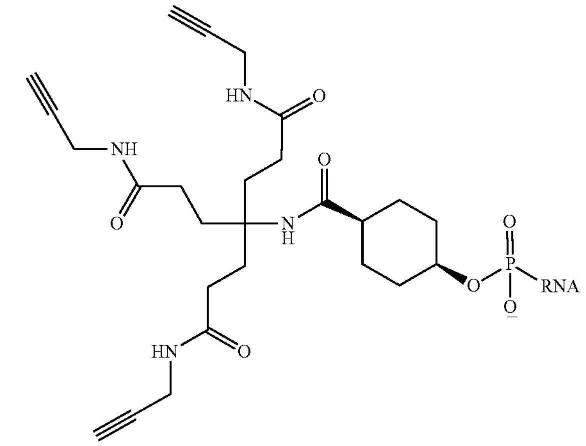 |

TABLE 2-continued
| Compounds of Formula III. | |
|---|---|
| Compound No. | Structure |
| 2-S-III | 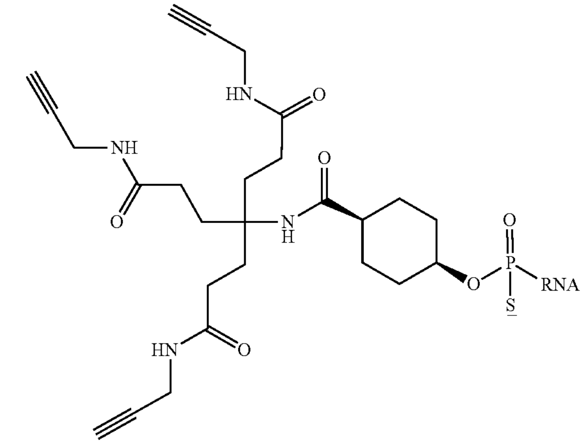 |
| 3-O-III | 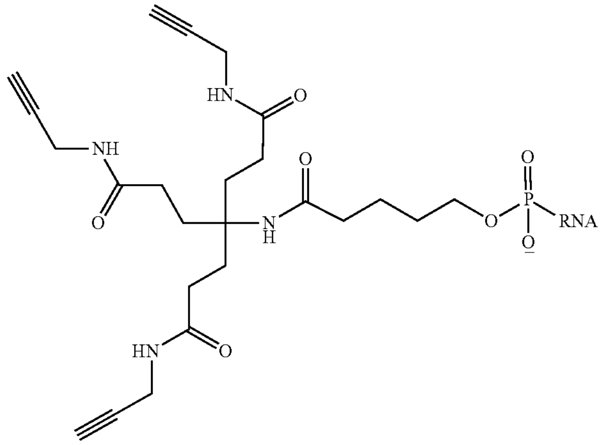 |
| 3-S-III | 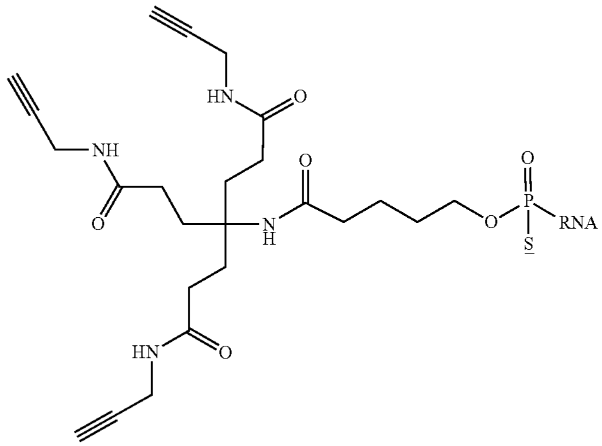 |

TABLE 2-continued
| Compounds of Formula III. | |
|---|---|
| Compound No. | Structure |
| 4-O-III | 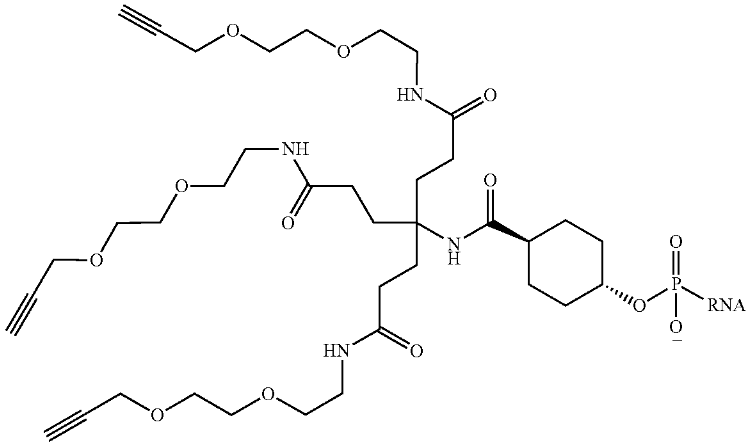 |
| 4-S-III | 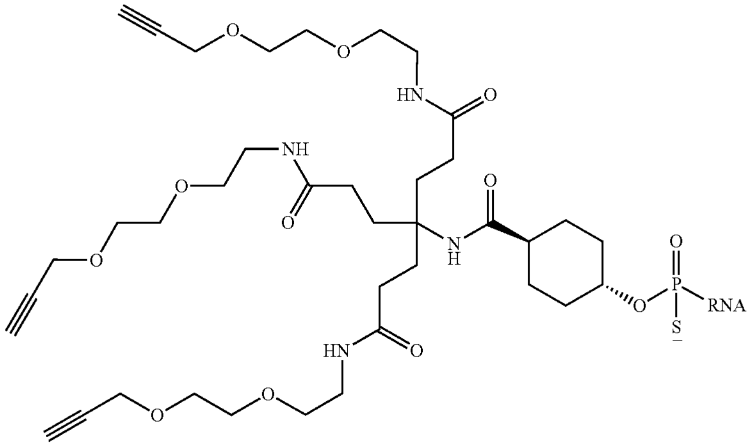 |
| 5-O-III | 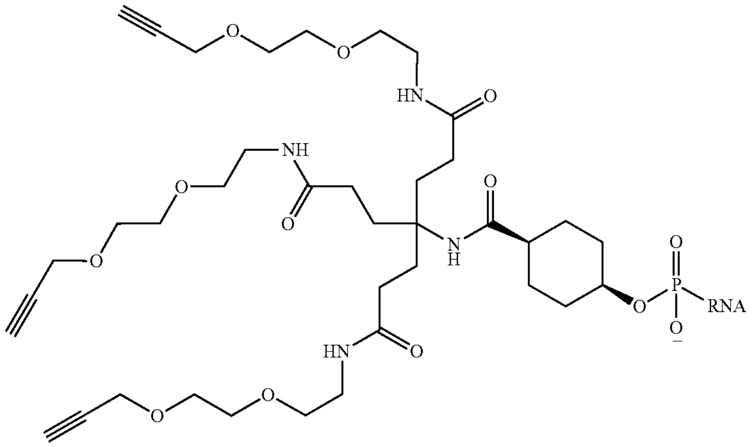 |

TABLE 2-continued
| Compounds of Formula III. | |
|---|---|
| Compound No. | Structure |
| 5-S-III | 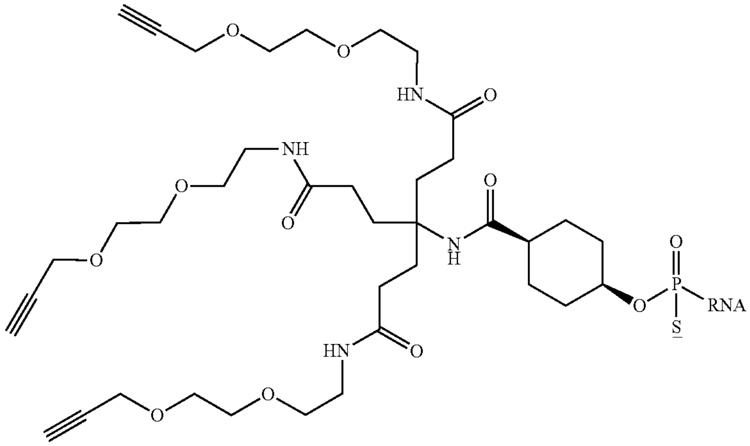 |
| 6-O-III | 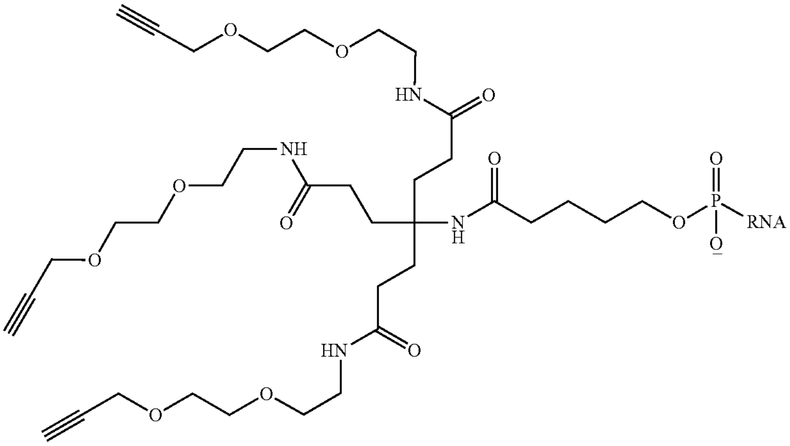 |
| 6-S-III | 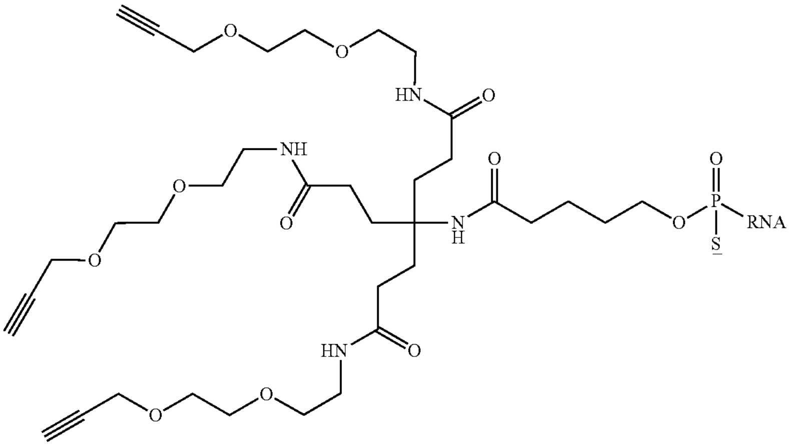 |

TABLE 2-continued
| Compounds of Formula III. | |
|---|---|
| Compound No. | Structure |
| 7-O-III | 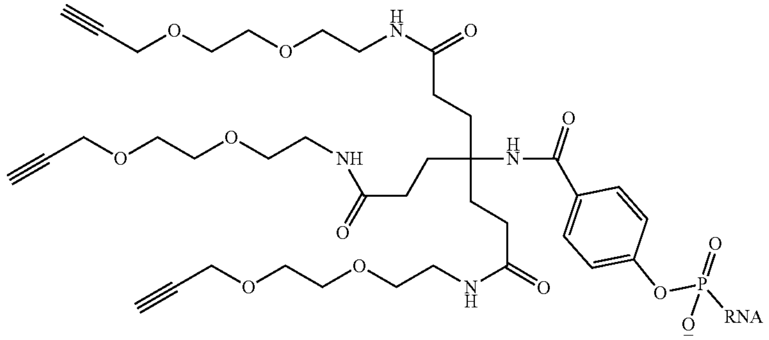 |
| 7-S-III | 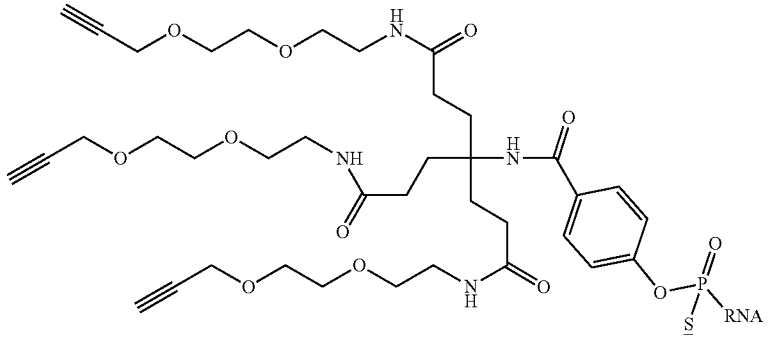 |
| 8-O-III | 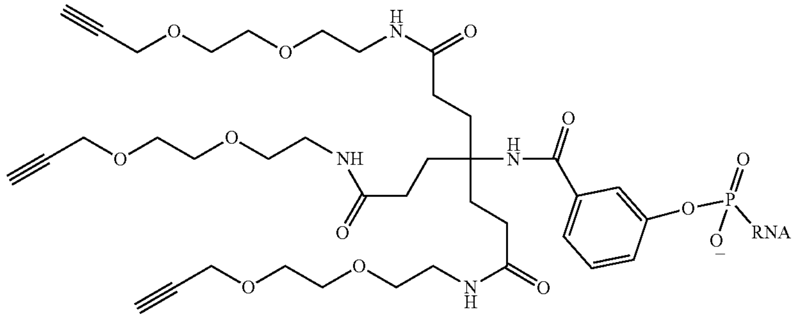 |
| 8-S-III | 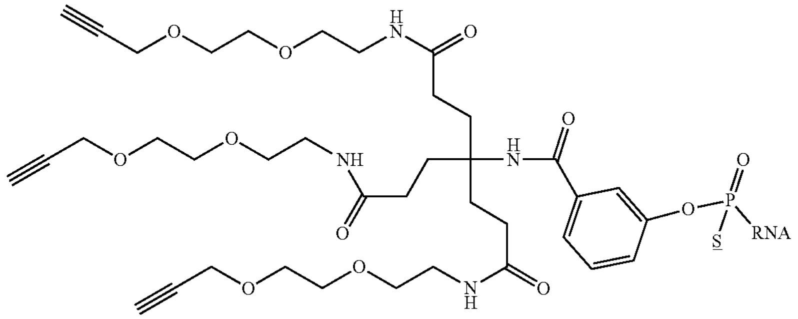 |

TABLE 2-continued
| Compounds of Formula III. | |
|---|---|
| Compound No. | Structure |
| 9-O-III | 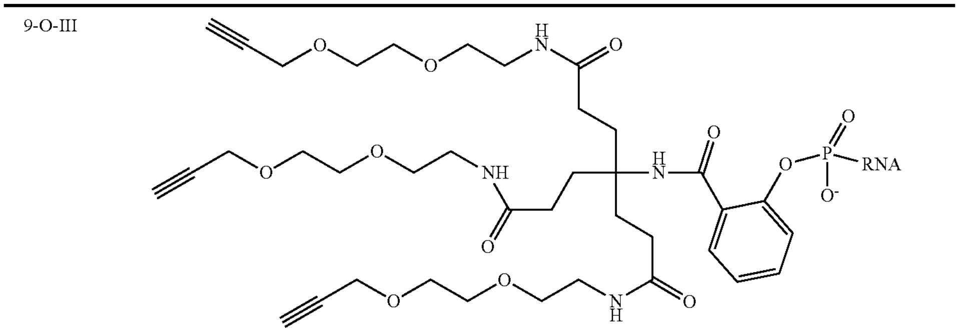 |
| 9-S-III | 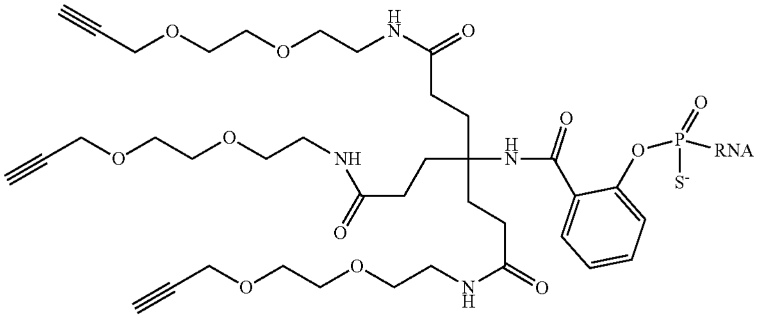 |
| 10-O-III | 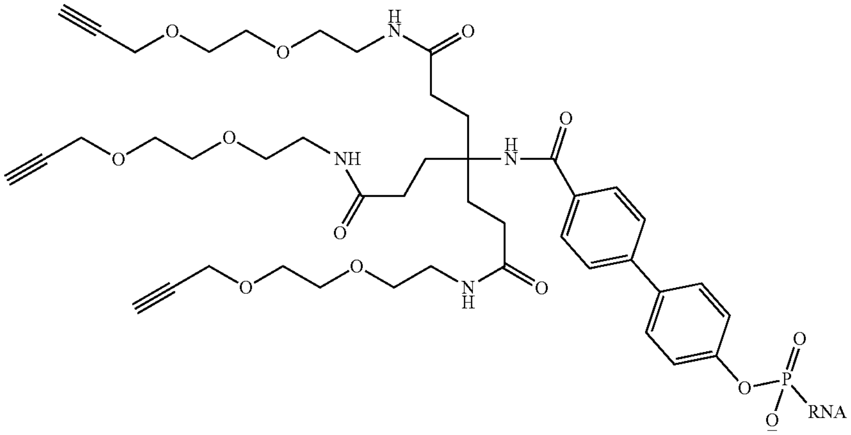 |
| 10-S-III | 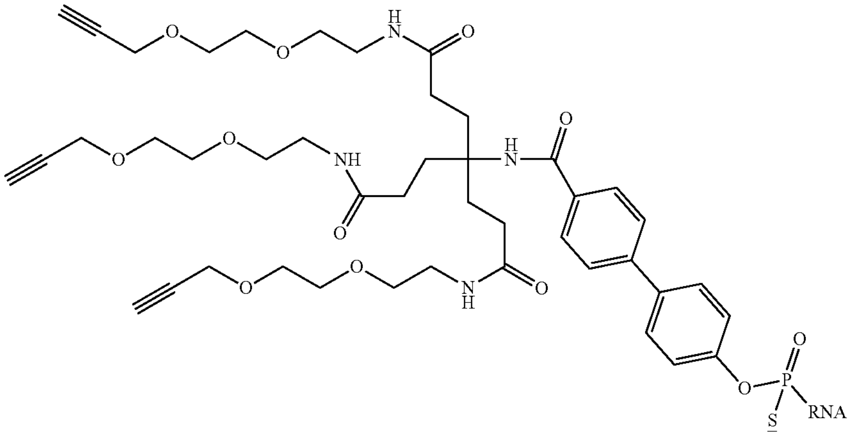 |

TABLE 2-continued
Compounds of Formula III.
| Compound No. | Structure |
| --- | --- |
| 11-O-III | 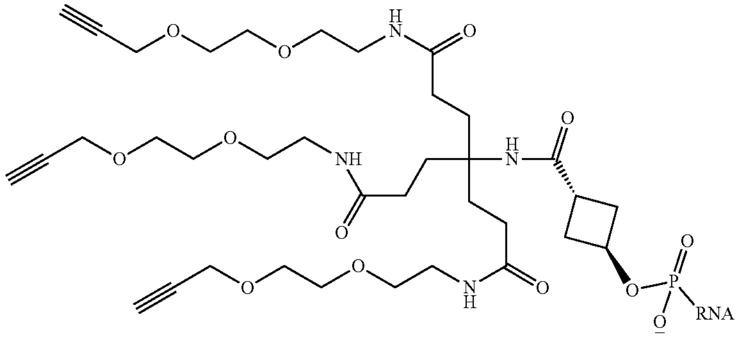 |
| 11-S-III | 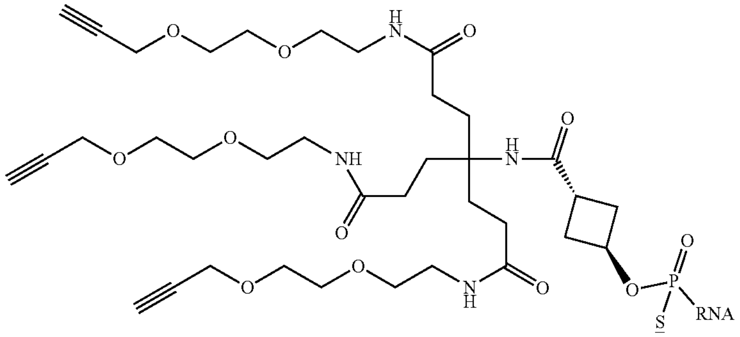 |
| 12-O-III | 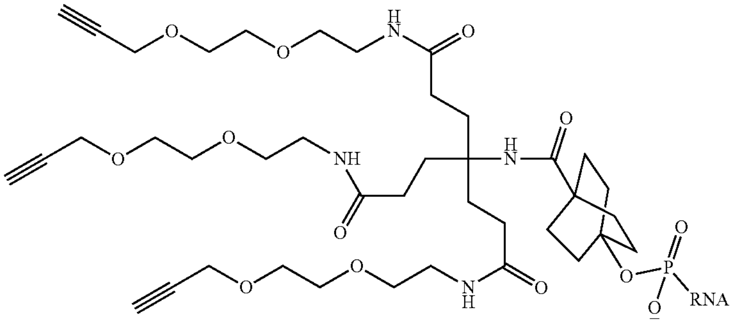 |
| 12-S-III | 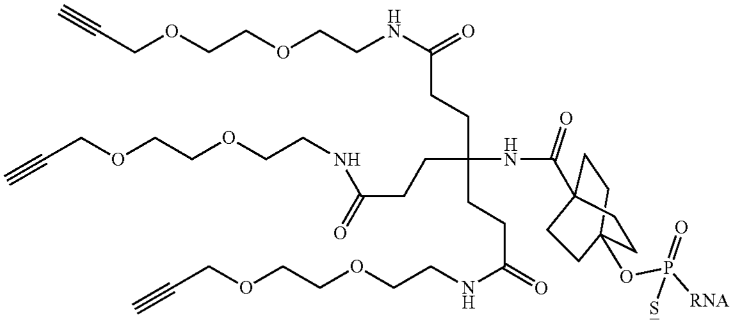 |

TABLE 2-continued
Compounds of Formula III.
| Compound No. | Structure |
|---|---|
| 13-O-III | 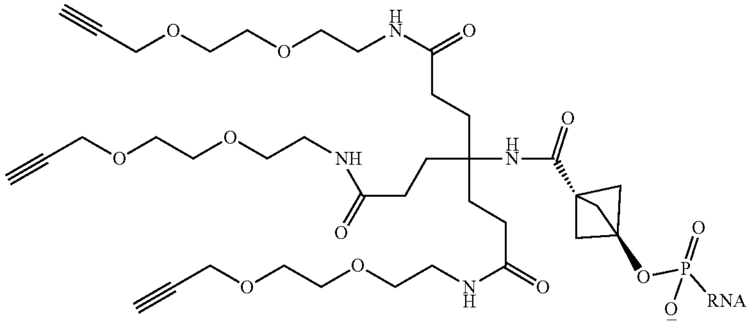 |
| 13-S-III | 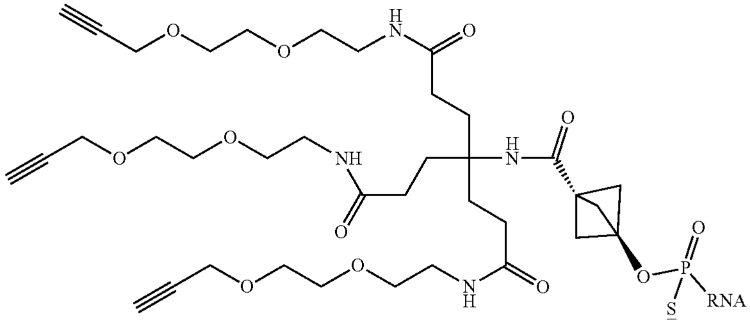 |
| 14-O-III | 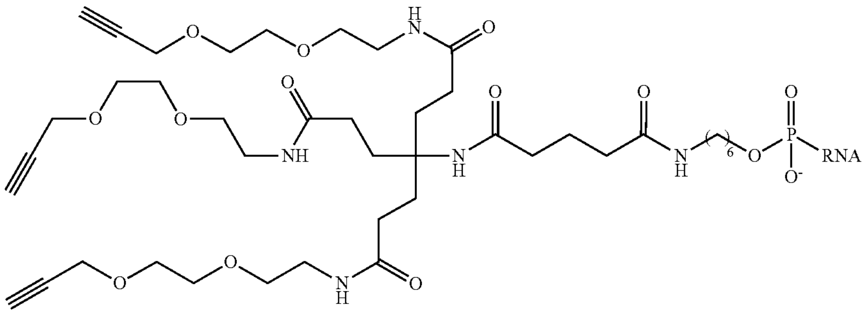 |
| 14-S-III | 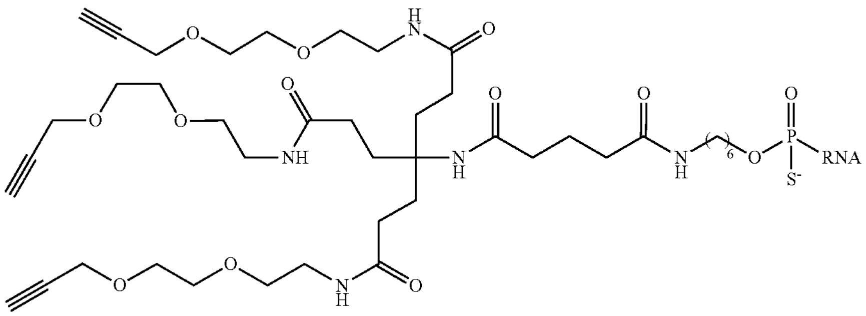 |

Formula IV

Formula IV is represented by the structure:

Formula IV

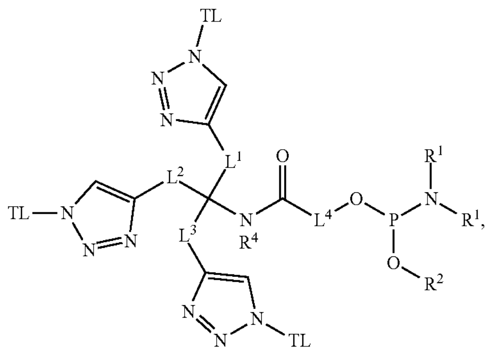

or a pharmaceutically acceptable salt thereof, wherein,

- $L^1$, $L^2$, and $L^3$ are each independently linkers comprising optionally substituted alkylene;
- $L^4$ is a linker comprising optionally substituted alkylene, optionally substituted arylene, and optionally substituted cycloalkylene;
- $R^1$ and $R^2$ are each independently optionally substituted alkyl;
- $R^4$ is H or optionally substituted alkyl; and
- TL is a targeting ligand.

In some embodiments of Formula IV, $L^1$, $L^2$ and $L^3$ are each

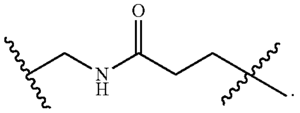 [SMILES: *CCC(=O)NC*]

In some embodiments of Formula IV, $L^1$, $L^2$ and $L^3$ are each

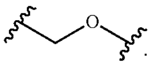 [SMILES: *CO*]

In some embodiments of Formula IV, $L^1$ $L^2$ and $L^3$ are each

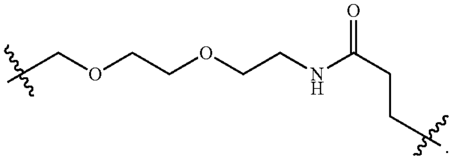 [SMILES: *CCC(=O)NCCOCCOC*]

In some embodiments of Formula IV, $L^4$ is selected from the group consisting of:

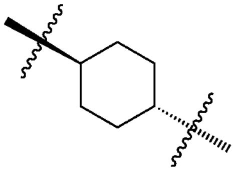,
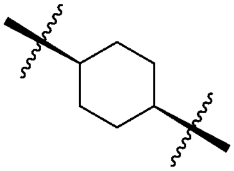,
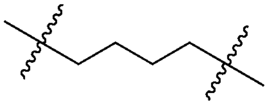,
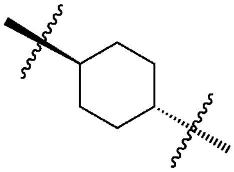,
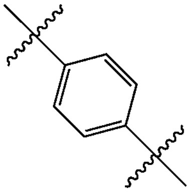,
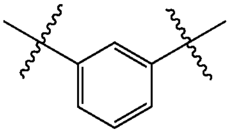,
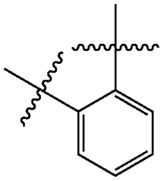,
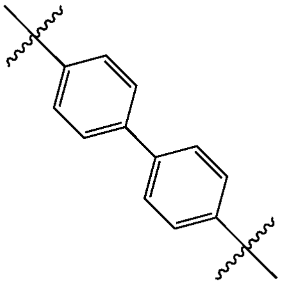,
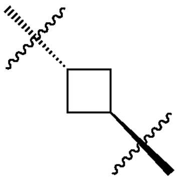,
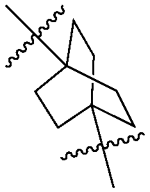,
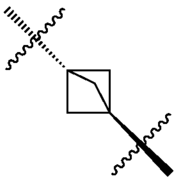, and
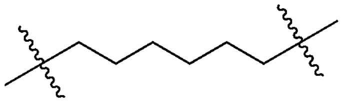, wherein ⌇ indicates the point of attachment.

In some embodiments of Formula IV, each instance of $R^1$ is isopropyl.

In some embodiments of Formula IV, $R^2$ is

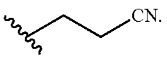

Example compounds of Formula IV are shown in Table 3 below.
TABLE 3
| Example compounds of Formula IV. | |
|---|---|
| Compound No. | Structure |
| 1-IV | 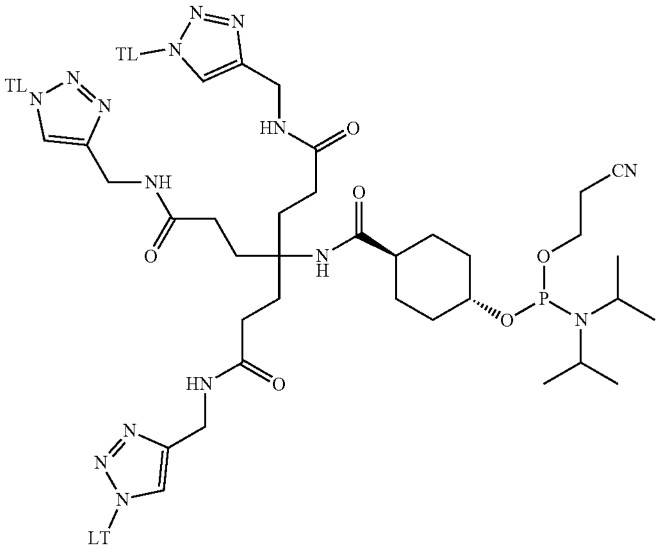 |
| 2-IV | 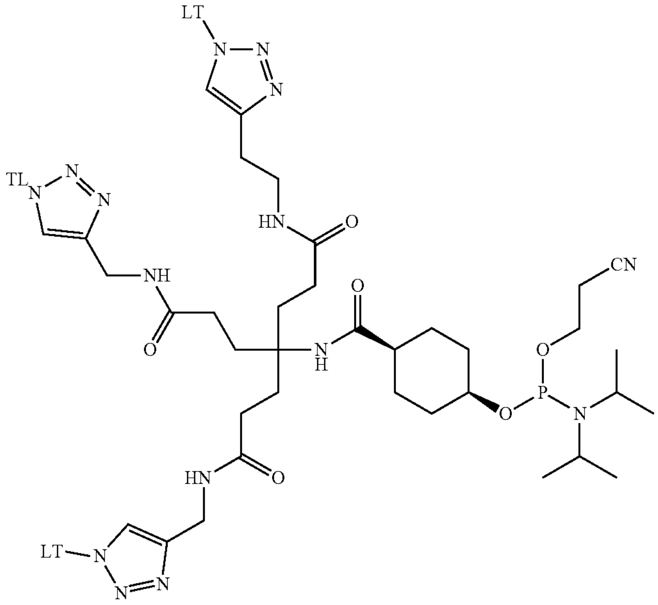 |

TABLE 3-continued
| Example compounds of Formula IV. | |
|---|---|
| Compound No. | Structure |
| 3-IV | 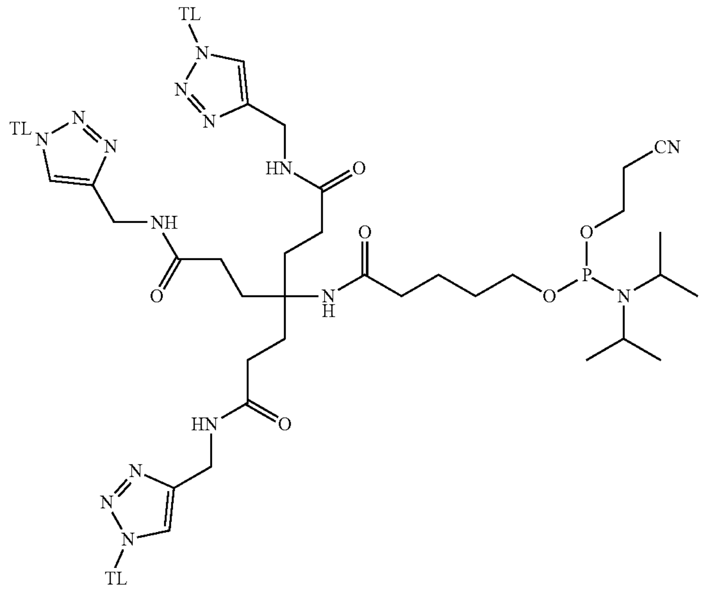 |
| 4-IV | 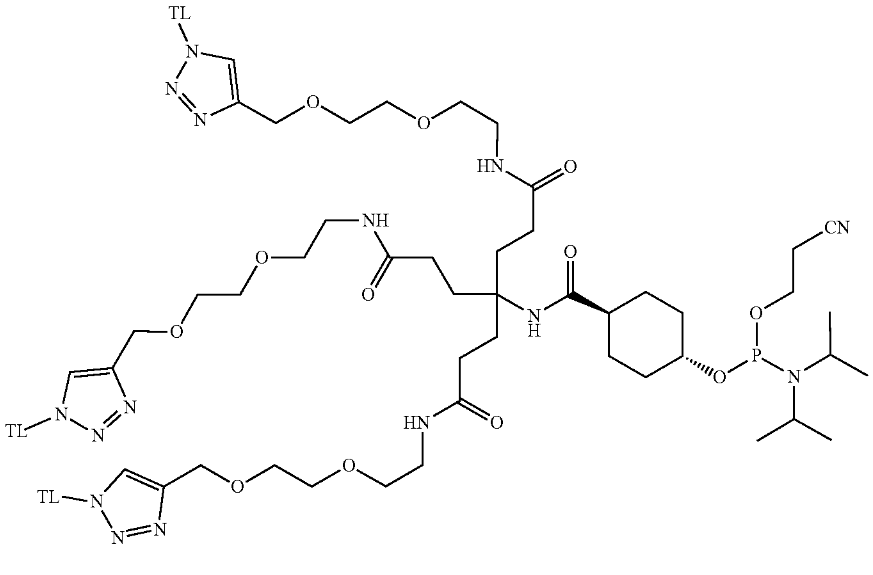 |

TABLE 3-continued
| Example compounds of Formula IV. | |
|---|---|
| Compound No. | Structure |
| 5-IV | 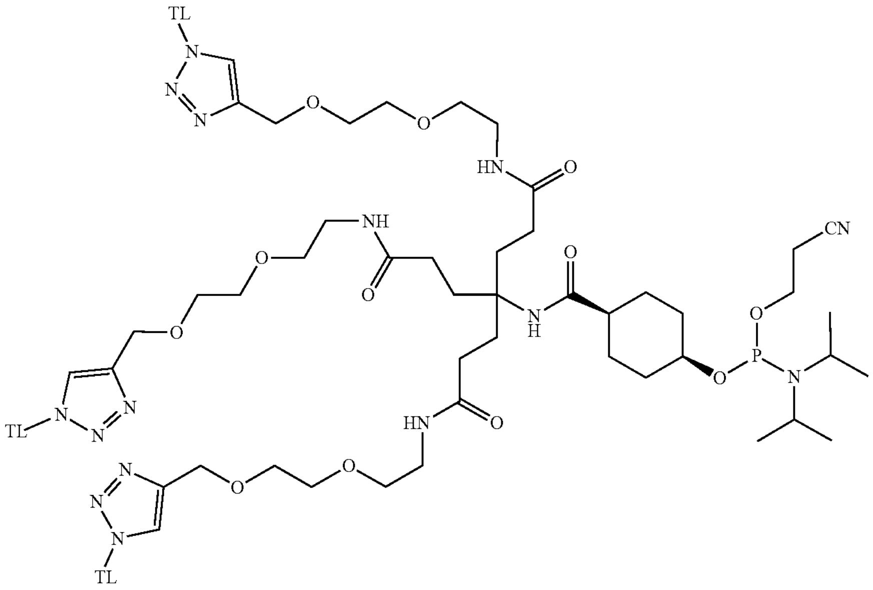 |
| 6-IV | 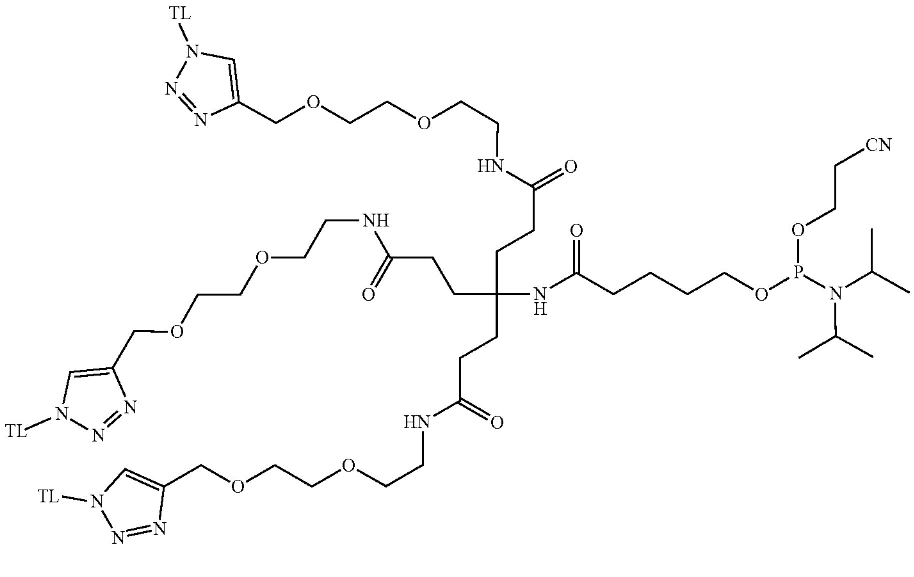 |

TABLE 3-continued
| Example compounds of Formula IV. | |
|---|---|
| Compound No. | Structure |
| 7-IV | 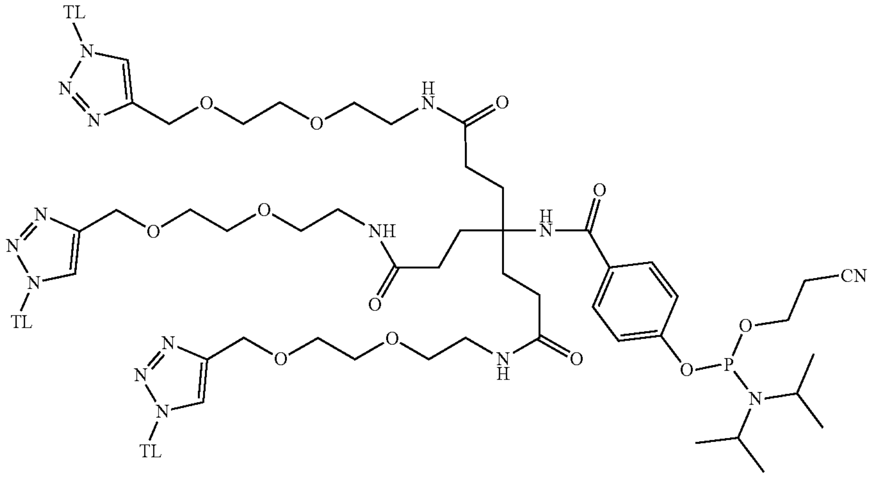 |
| 8-IV | 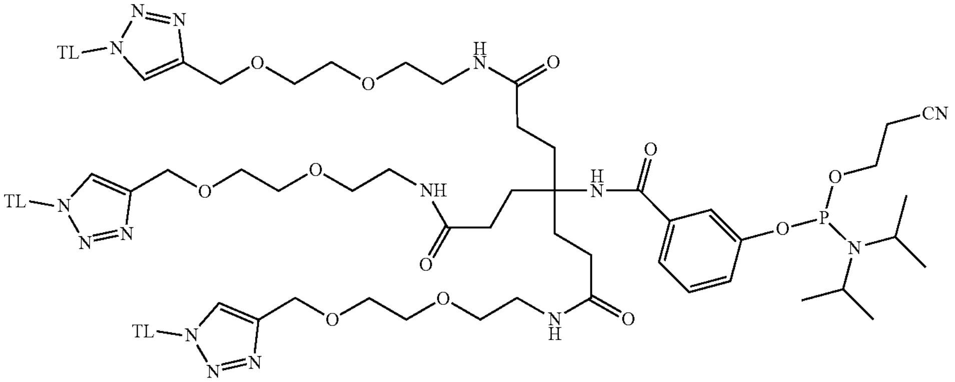 |
| 9-IV | 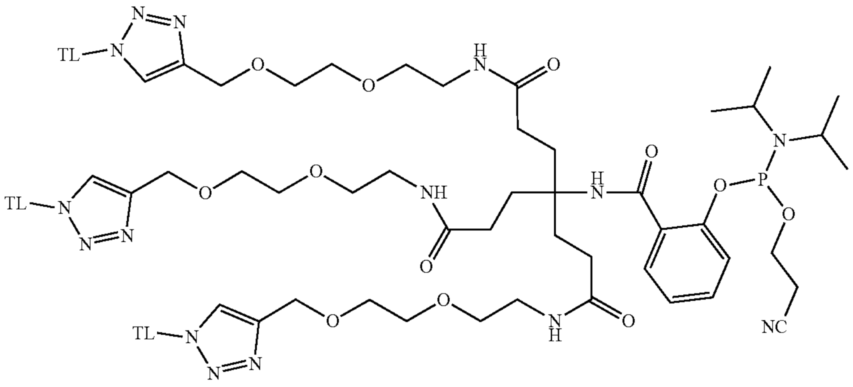 |

TABLE 3-continued
Example compounds of Formula IV.
| Compound No. | Structure |
| --- | --- |
| 10-IV | 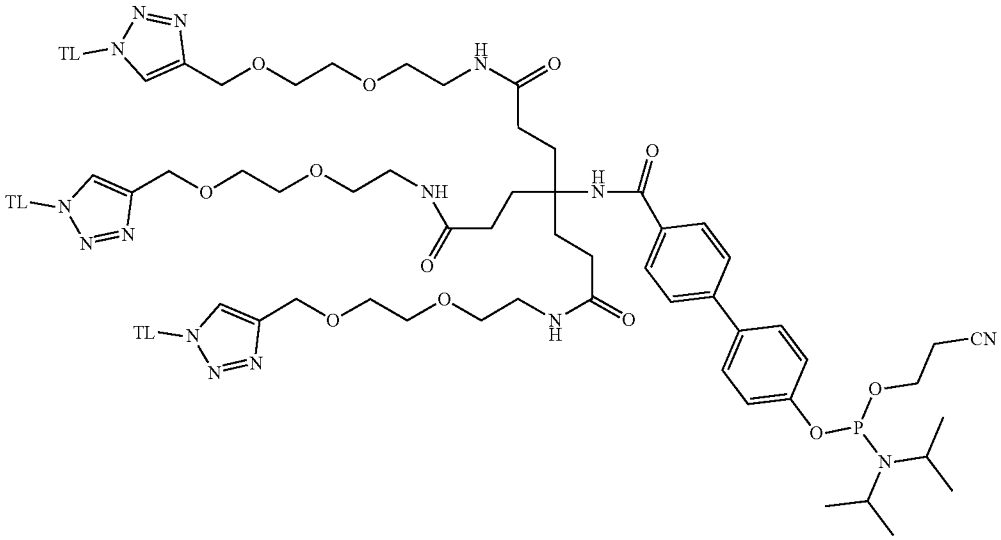 |
| 11-IV | 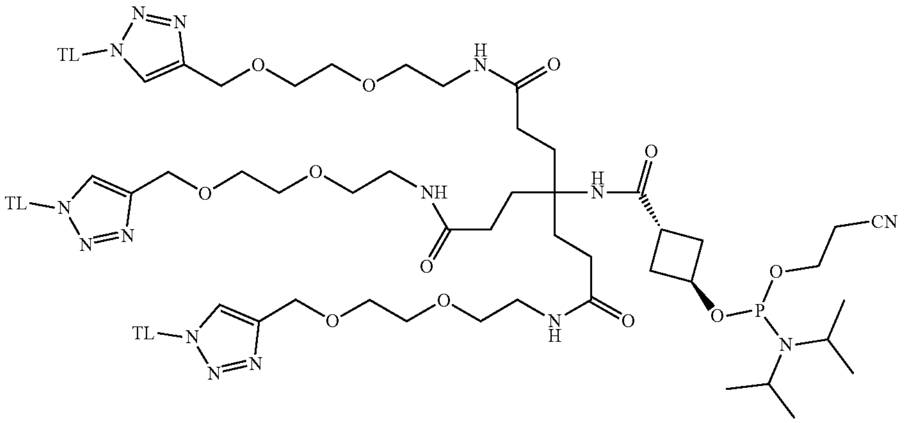 |
| 12-IV | 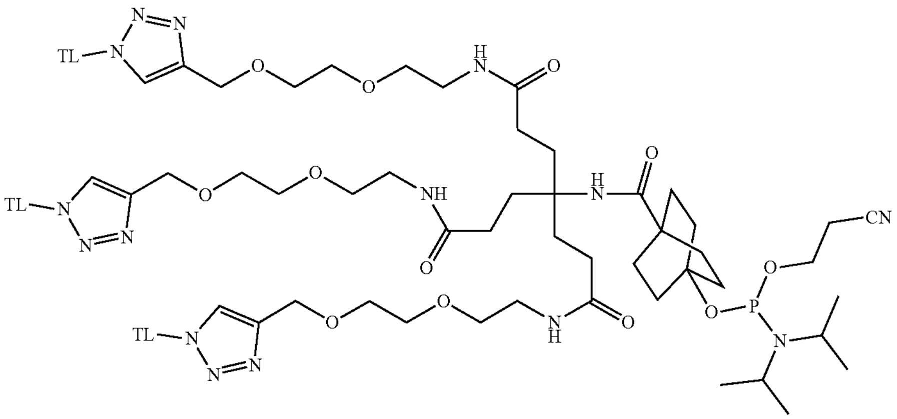 |

TABLE 3-continued

Example compounds of Formula IV.

| Compound No. | Structure |
|---|---|
| 13-IV | 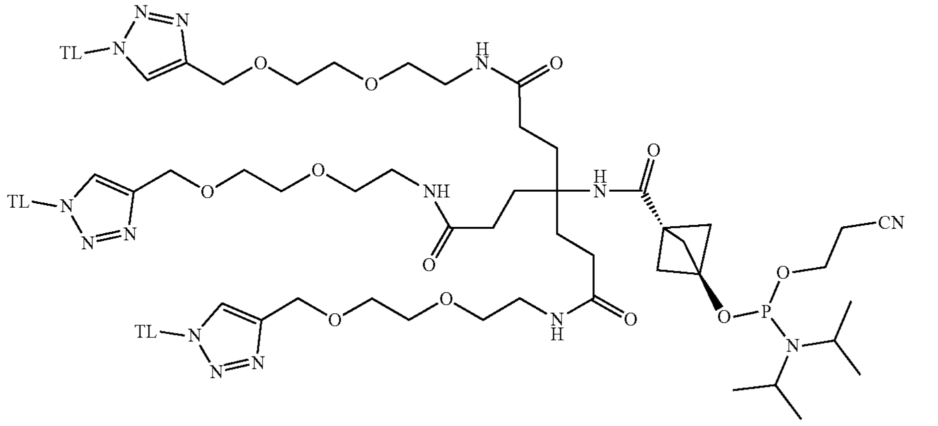 |
| 14-IV | 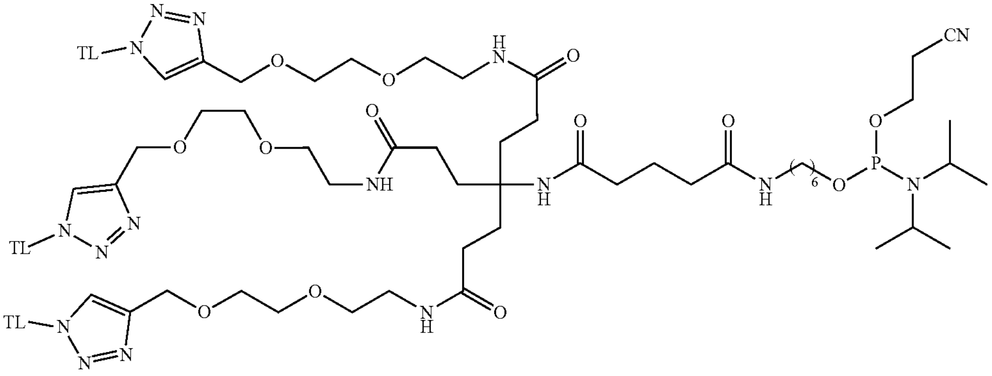 |

Formula V

Formula V is represented by the structure:

Formula V

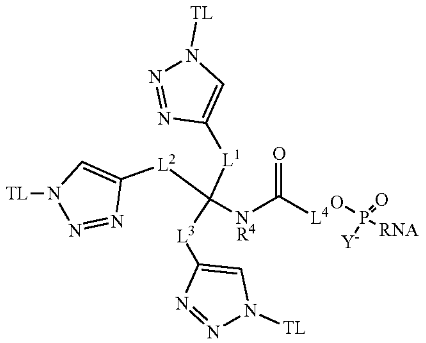

or a pharmaceutically acceptable salt thereof, wherein, $L^1$, $L^2$, and $L^3$ are each independently linkers comprising optionally substituted alkylene;

$L^4$ is a linker comprising optionally substituted alkylene, optionally substituted arylene, or optionally substituted cycloalkylene;

$R^4$ is H or optionally substituted alkyl;

TL is a targeting ligand;

Y is O or S; and

RNA comprises or consists of an RNAi agent.

In some embodiments of Formula V, $L^1$, $L^2$ and $L^3$ are each

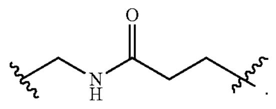 [SMILES: *CCC(=O)NC*]

In some embodiments of Formula IV, $L^1$, $L^2$ and $L^3$ are each

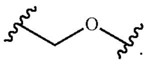 [SMILES: *CO*]

In some embodiments of Formula V, $L^1$, $L^2$ and $L^3$ are each
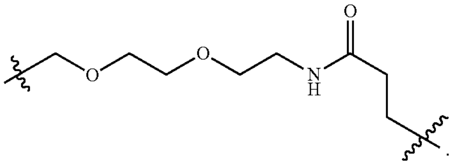 [SMILES: *CCC(=O)NCCOCCOC*]
In some embodiments of Formula V, $L^4$ is selected from the group consisting of:
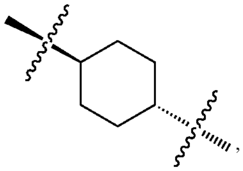
,
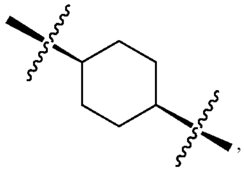
,
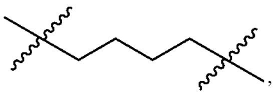
,
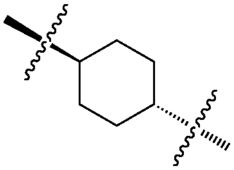
,
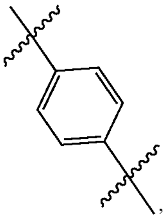
,
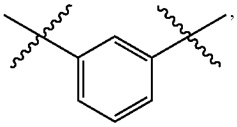
,
-continued
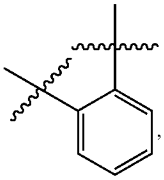
,
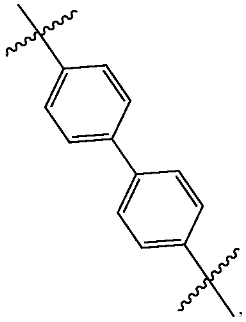
,
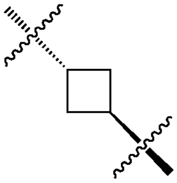
,
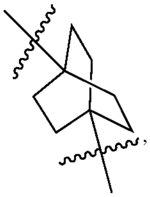
,
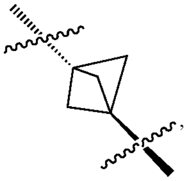
, and
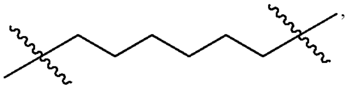
,
wherein ⌇ indicates the point of attachment.
Example compounds of Formula Y are shown in Table 4 below:
TABLE 4
Example compounds of Formula V.
| Compound No. | Structure |
|---|---|
| 1-O-V | 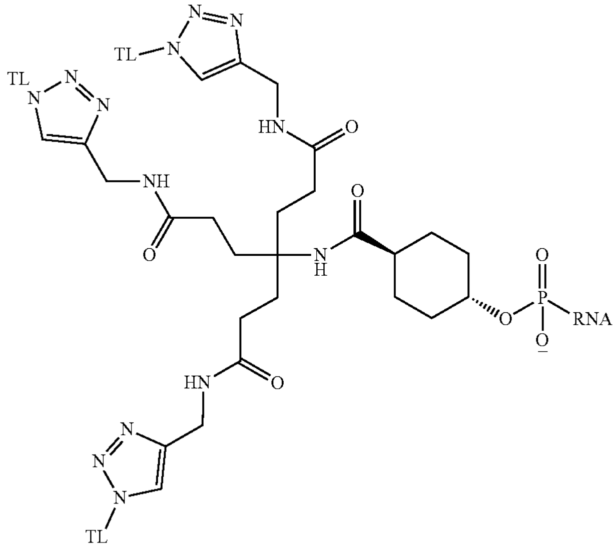 |

TABLE 4-continued
| Example compounds of Formula V. | |
|---|---|
| Compound No. | Structure |
| 1-S-V | 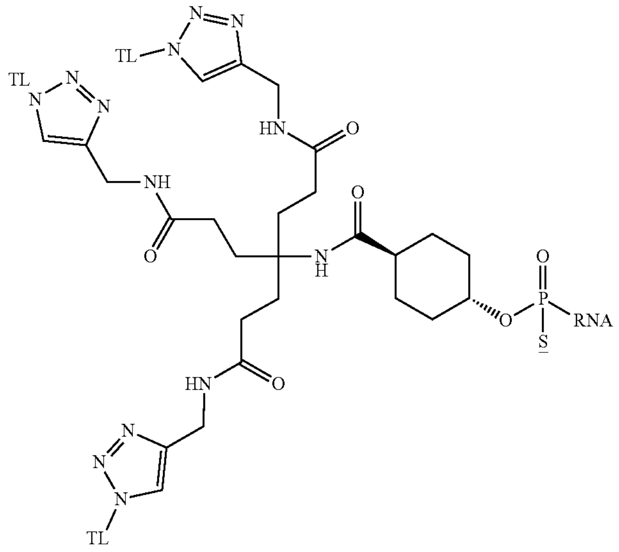 |
| 2-O-V | 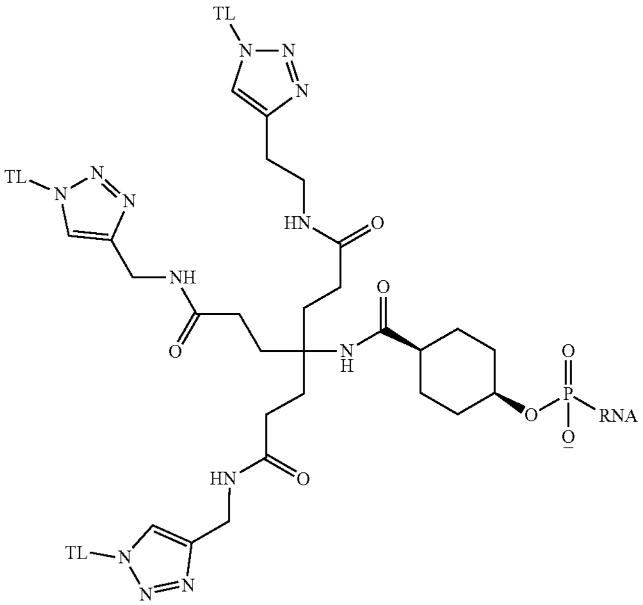 |

TABLE 4-continued
| Example compounds of Formula V. | |
|---|---|
| Compound No. | Structure |
| 2-S-V | 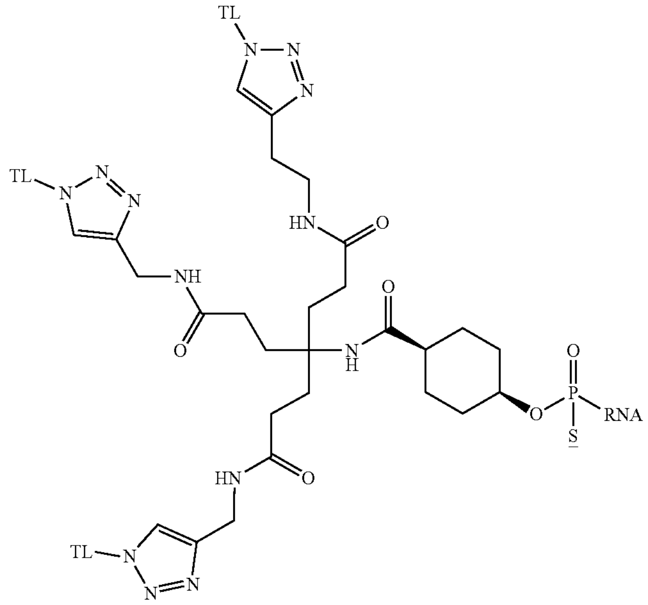 |
| 3-O-V | 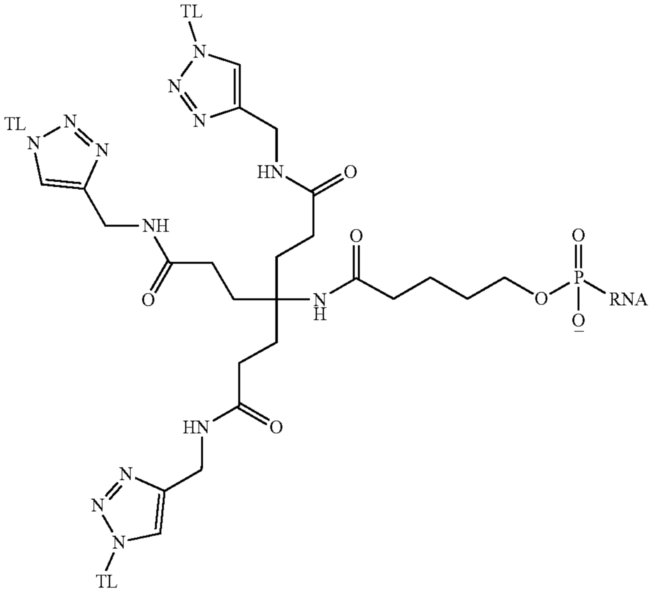 |

TABLE 4-continued
| Example compounds of Formula V. | |
|---|---|
| Compound No. | Structure |
| 3-S-V | 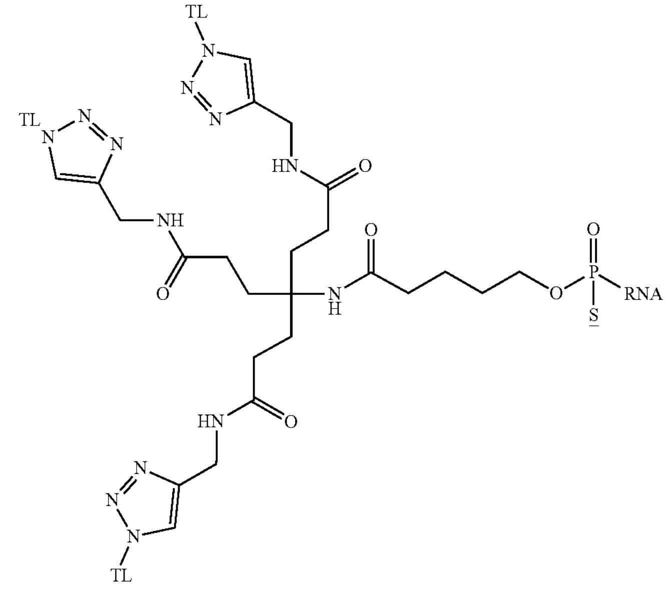 |
| 4-O-V | 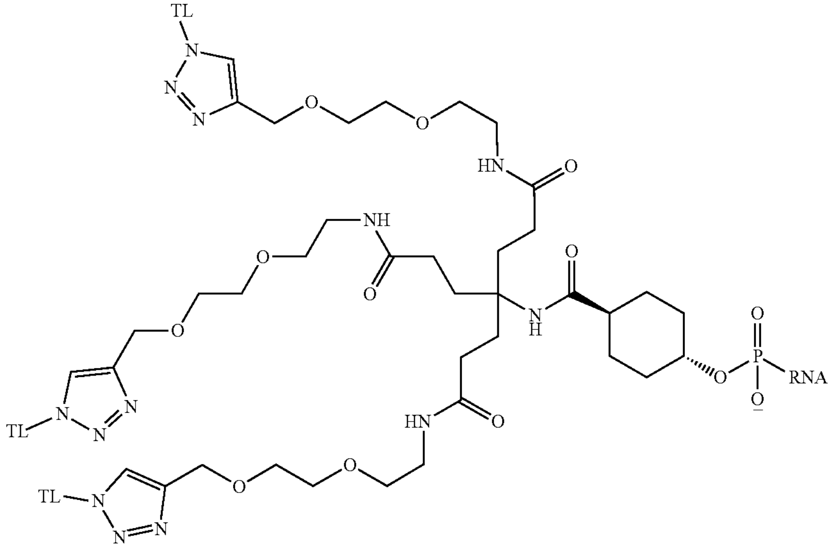 |

TABLE 4-continued
| Example compounds of Formula V. | |
|---|---|
| Compound No. | Structure |
| 4-S-V | 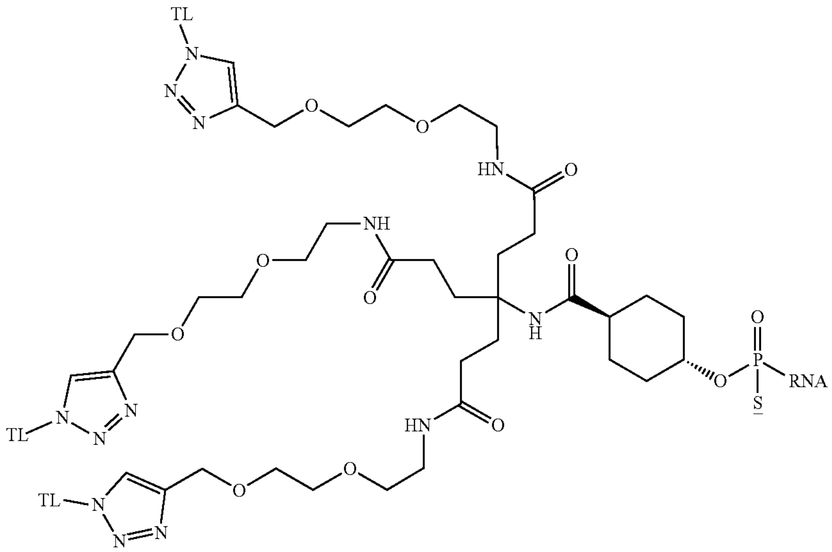 |
| 5-O-V | 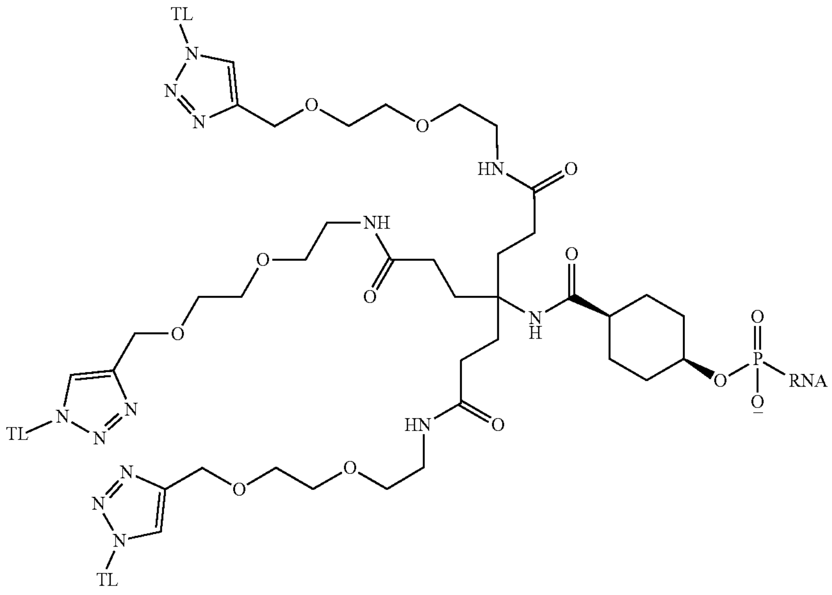 |

TABLE 4-continued
| Compound No. | Structure |
|---|---|
| 5-S-V | 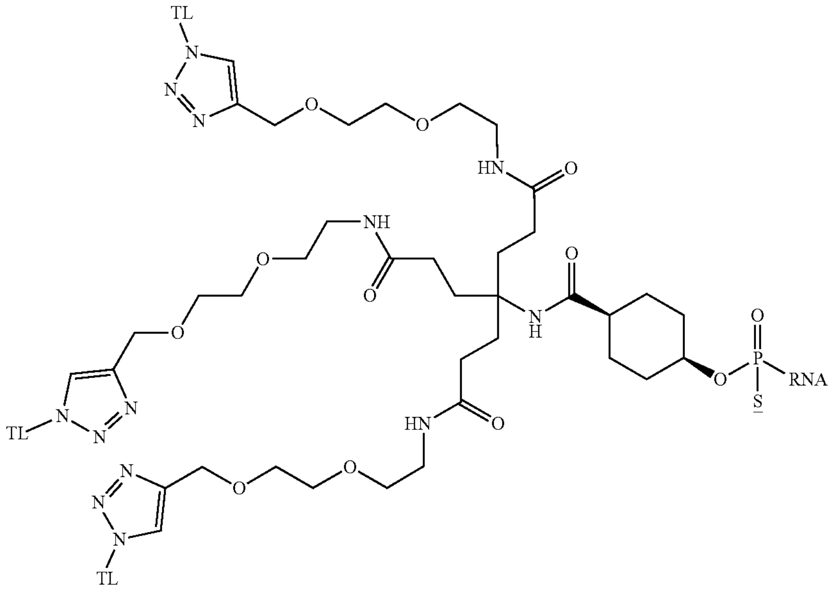 |
| 6-O-V | 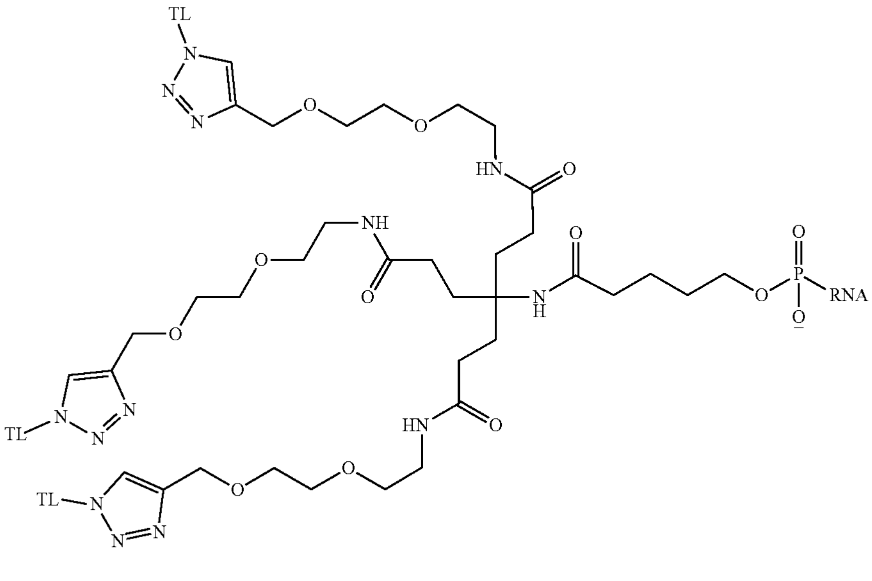 |
Example compounds of Formula V.

TABLE 4-continued
| Example compounds of Formula V. | |
|---|---|
| Compound No. | Structure |
| 6-S-V | 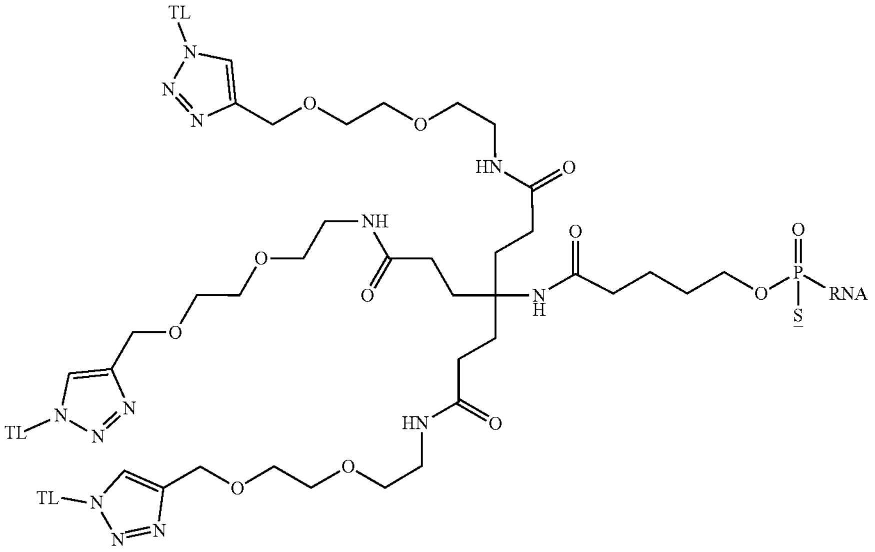 |
| 7-O-V | 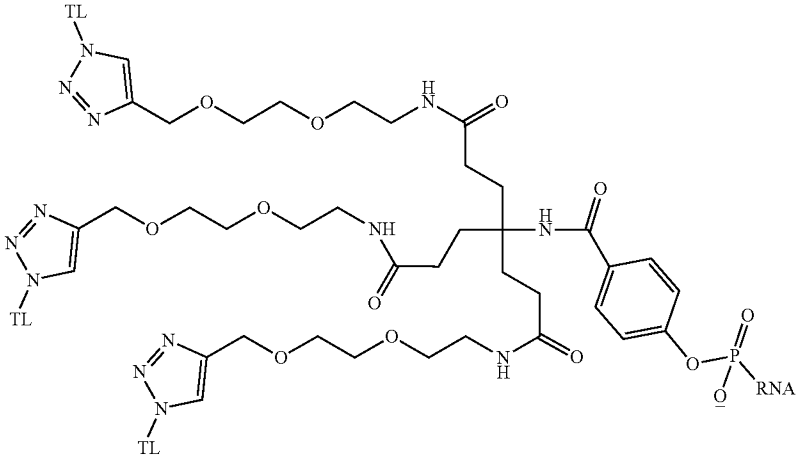 |
| 7-S-V | 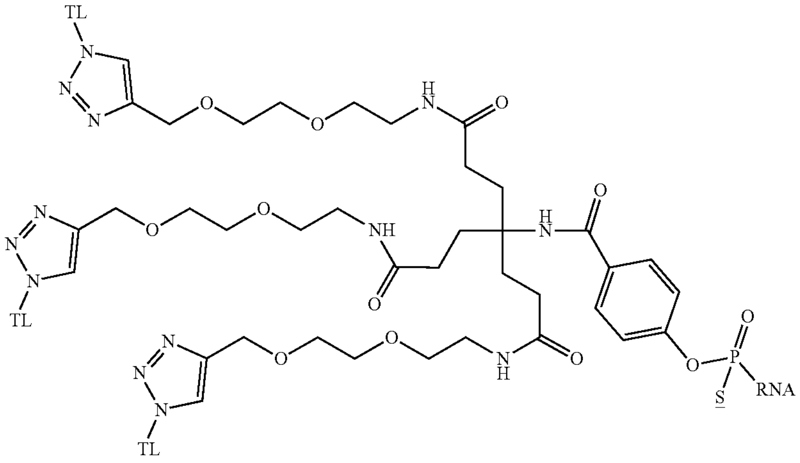 |

TABLE 4-continued
| Example compounds of Formula V. | |
|---|---|
| Compound No. | Structure |
| 8-O-V | 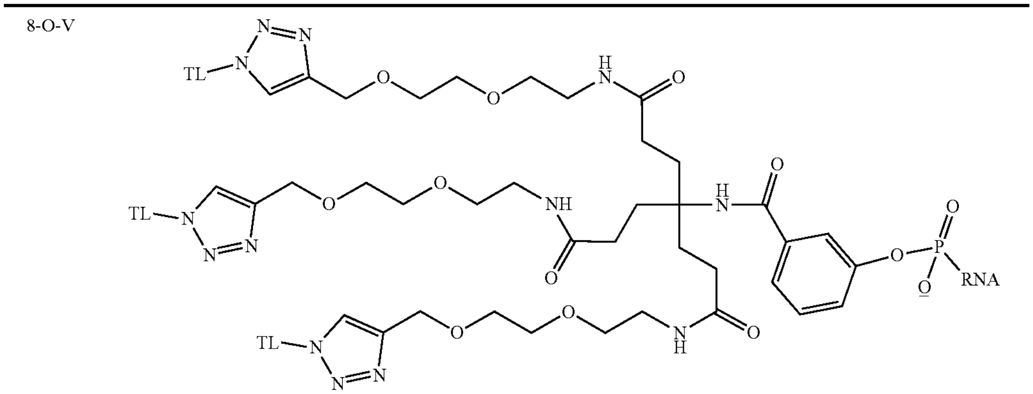 |
| 8-S-V | 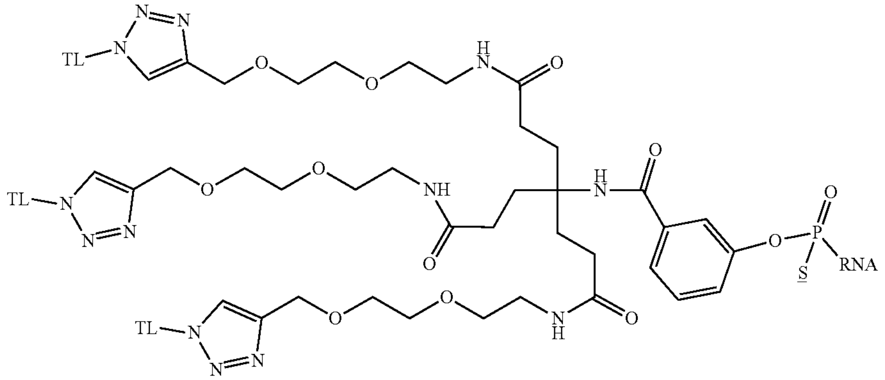 |
| 9-O-V | 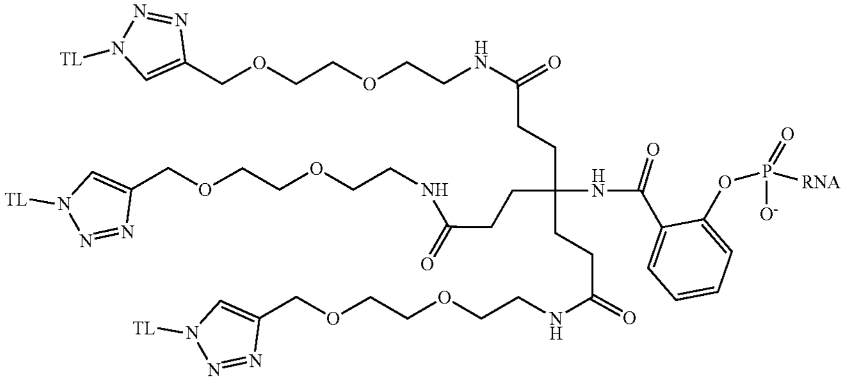 |
| 9-S-V | 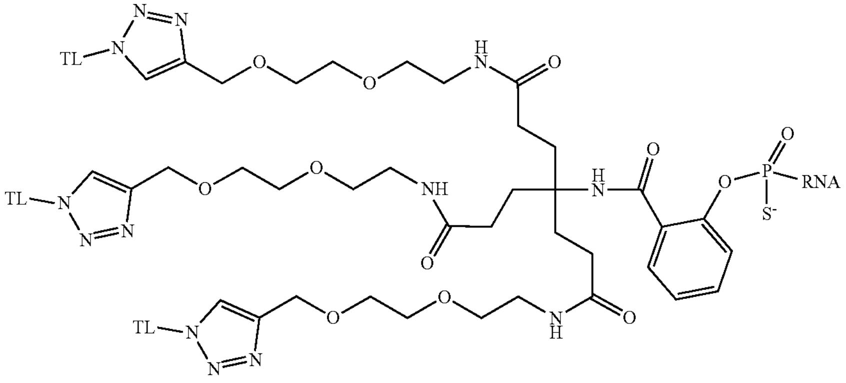 |

TABLE 4-continued
| Example compounds of Formula V. | |
|---|---|
| Compound No. | Structure |
| 10-O-V | 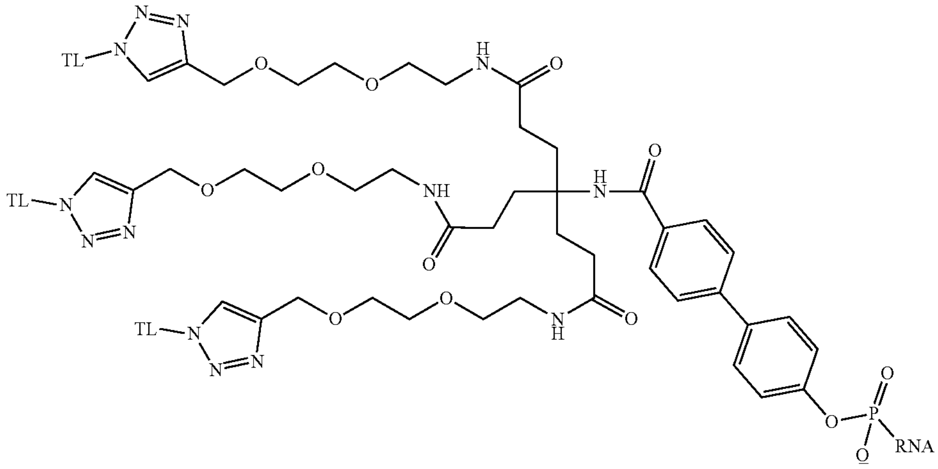 |
| 10-S-V | 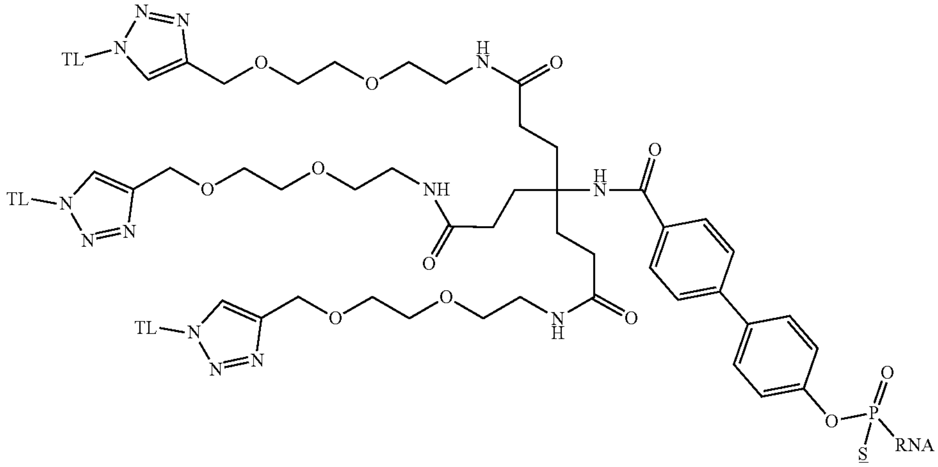 |
| 11-O-V | 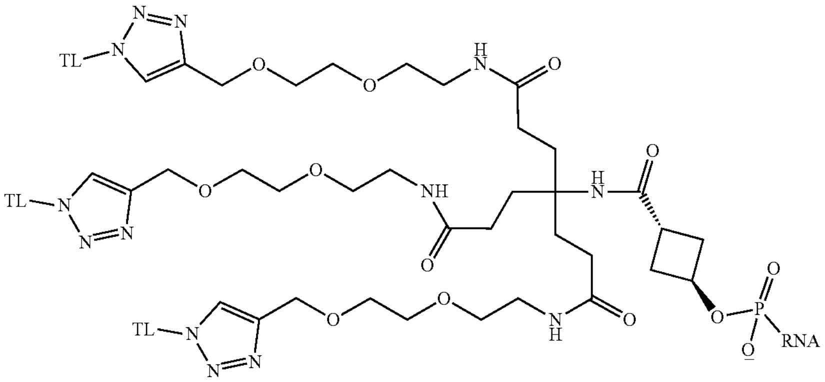 |

TABLE 4-continued
Example compounds of Formula V.
| Compound No. | Structure |
| --- | --- |
| 11-S-V | 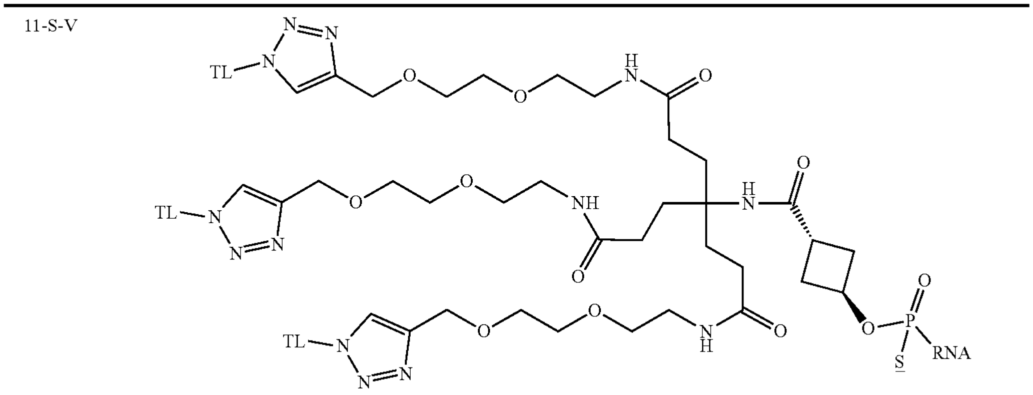 |
| 12-O-V | 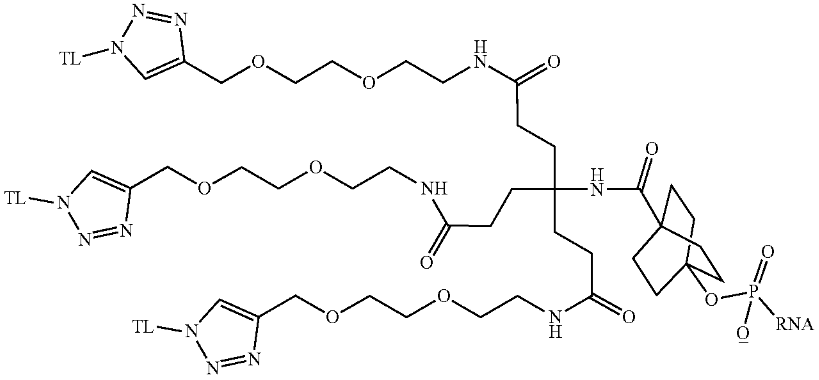 |
| 12-S-V | 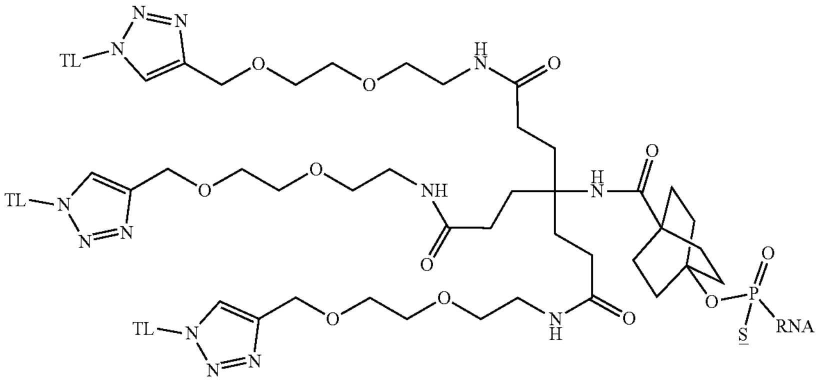 |
| 13-O-V | 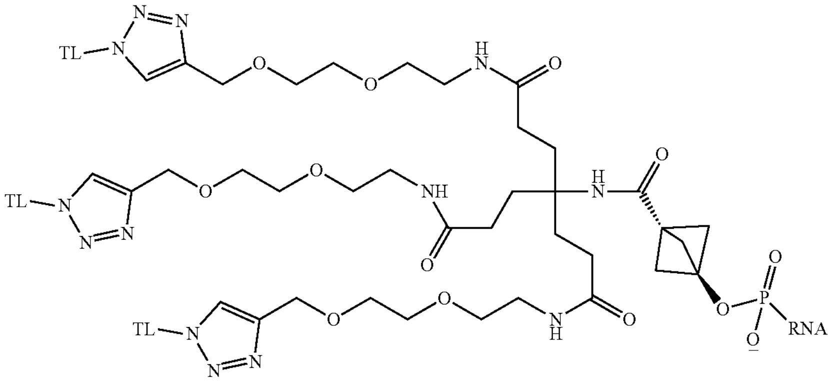 |

TABLE 4-continued
| Example compounds of Formula V. | |
|---|---|
| Compound No. | Structure |
| 13-S-V | 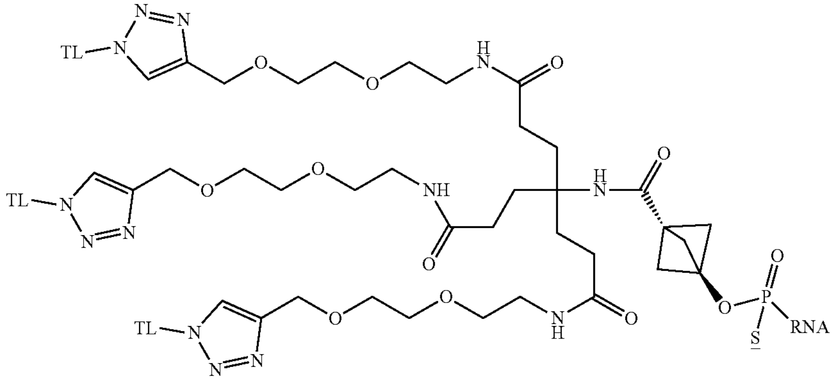 |
| 14-O-V | 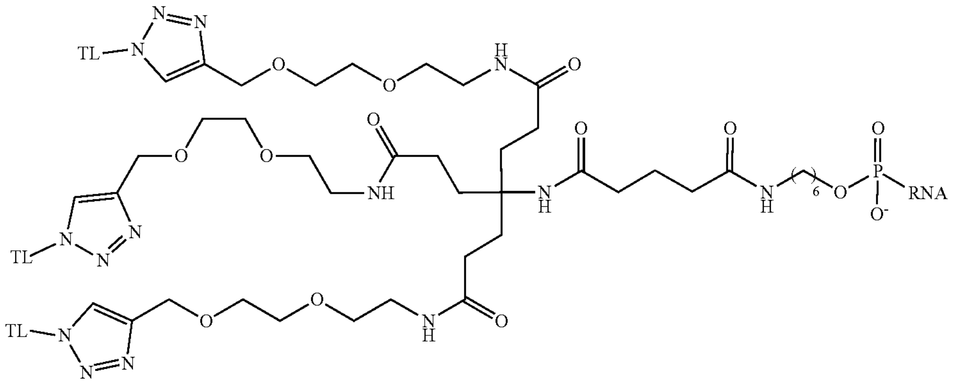 |
| 14-S-V | 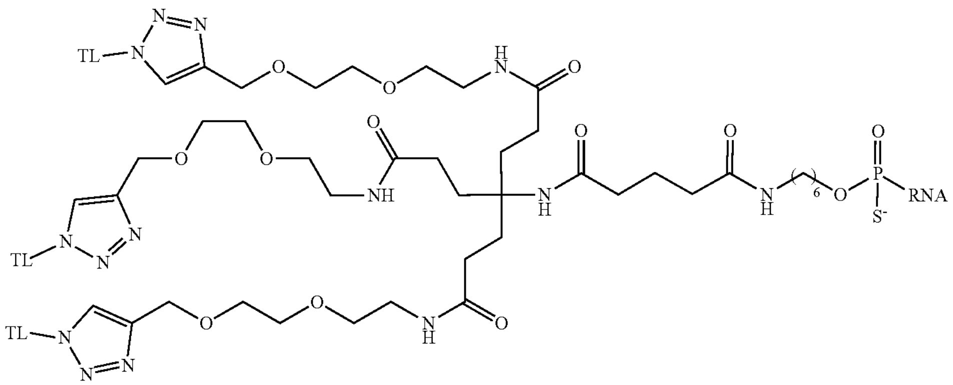 |

Formula VI

Formula VI is represented by the structure

Formula VI

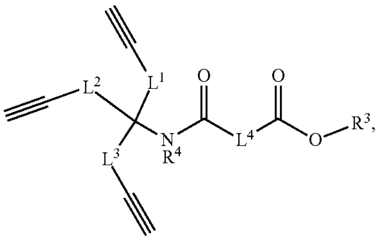

or a pharmaceutically acceptable salt thereof, wherein, $L^1$, $L^2$ and $L^3$ are each independently linkers comprising optionally substituted alkylene;

$L^4$ is a linker comprising optionally substituted alkylene, optionally substituted arylene, or optionally substituted cycloalkylene;

$R^3$ is H, optionally substituted alkyl, or optionally substituted aryl; and $R^4$ is H or optionally substituted alkyl.

In some embodiments of Formula VI, $L^1$, $L^2$ and $L^3$ are each

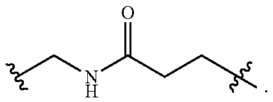 [SMILES: *CCC(=O)NC*]

.

In some embodiments of Formula VI, $L^1$, $L^2$ and $L^3$ are each

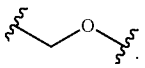 [SMILES: *CO*]

.

In some embodiments of Formula VI, $L^1$ $L^2$ and $L^3$ are each

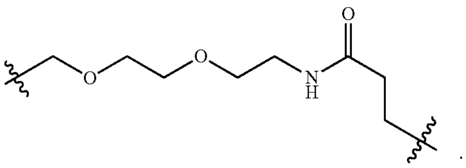 [SMILES: *CCC(=O)NCCOCCOC*]

.

In some embodiments of Formula VI, $L^4$ is selected from the group consisting of:

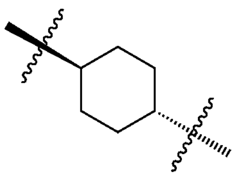

,

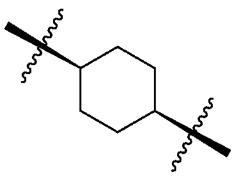

,

-continued

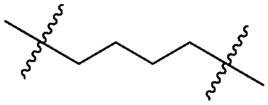

,

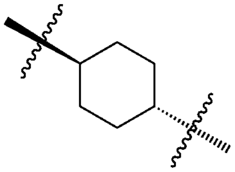

,

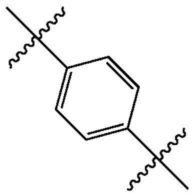

,

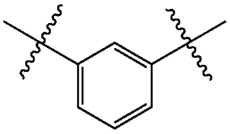

,

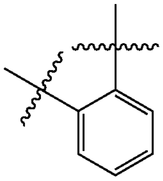

,

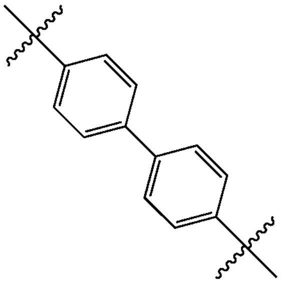

,

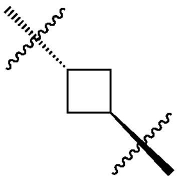

,

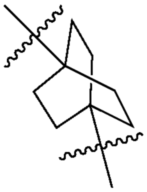

,

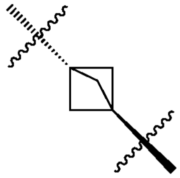

, and

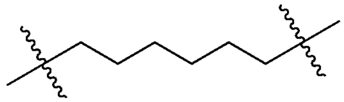

, wherein ⌇ indicates the point of attachment.

In some embodiments of Formula VI, $R^3$ is optionally substituted aryl. In some embodiments of Formula VI, $R^3$ is para-nitrophenyl.

In some embodiments of Formula VI, $R^4$ is H.

Formula VII

Formula VII is represented by the structure:

Formula VII

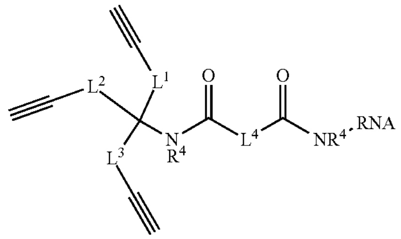

or a pharmaceutically acceptable salt thereof, wherein, $L^1$, $L^2$ and $L^3$ are each independently linkers comprising optionally substituted alkylene;

$L^4$ is a linker comprising optionally substituted alkylene, optionally substituted arylene, or optionally substituted cycloalkylene;

each instance of $R^4$ is H or optionally substituted alkyl; and

RNA comprises or consists of an RNAi agent.

In some embodiments of Formula VII, $L^1$, $L^2$ and $L^3$ are each

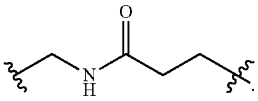 [SMILES: *CCC(=O)NC*]

In some embodiments of Formula VII, $L^1$, $L^2$ and $L^3$ are each

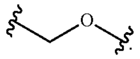

In some embodiments of Formula VII, $L^1$ $L^2$ and $L^3$ are each

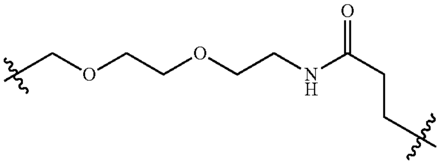

In some embodiments of Formula VII, $L^4$ is selected from the group consisting of:

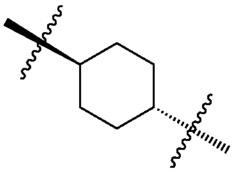
,
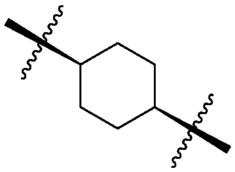
,
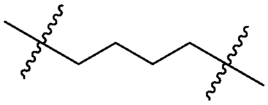
,
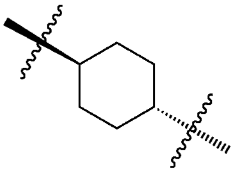
,

-continued

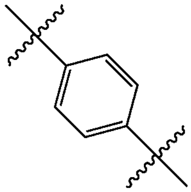
,
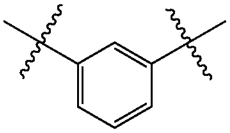
,
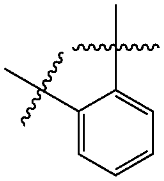
,
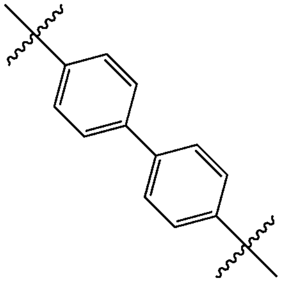
,
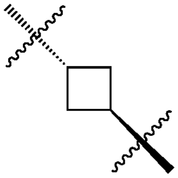
,
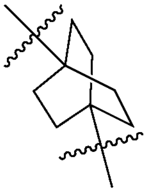
,
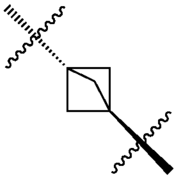
, and
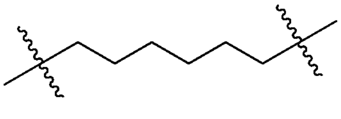
, wherein ⌇ indicates the point of attachment.

Example compounds of Formula VII are shown in Table 5 below.

TABLE 5
| Example compounds of Formula VII. | |
|---|---|
| Compound No. | Structure |
| 15-VII | 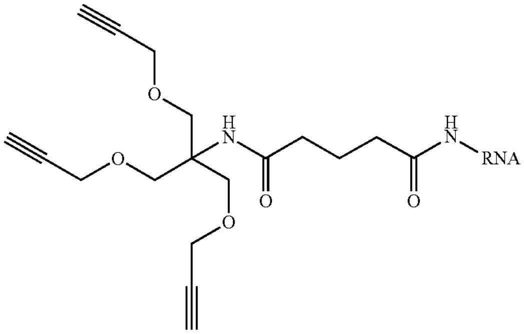 |
| 16-VII | 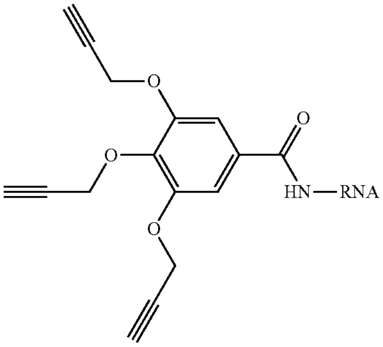 |
| 18-VII | 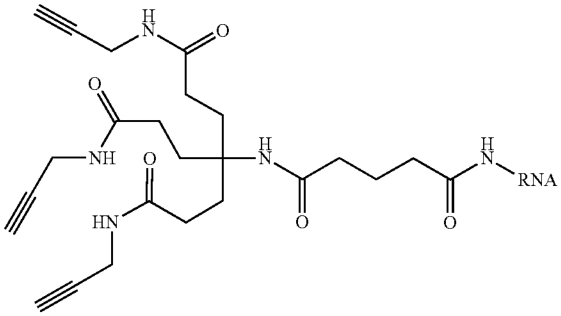 |
| 19-VII | 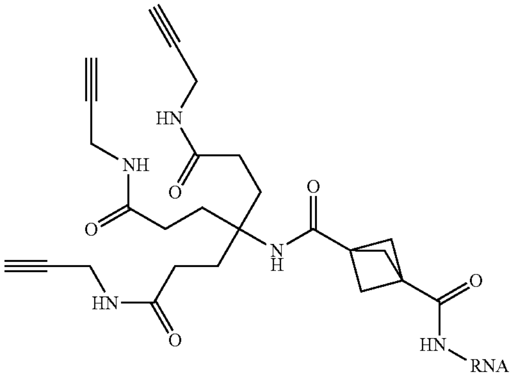 |

TABLE 5-continued
| Example compounds of Formula VII. | |
|---|---|
| Compound No. | Structure |
| 20-VII | 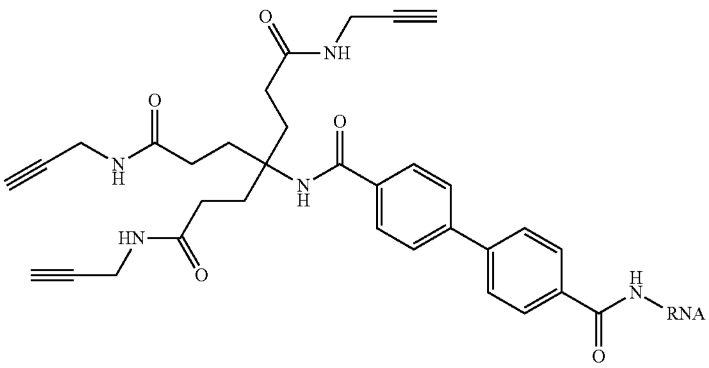 |
| 21-VII | 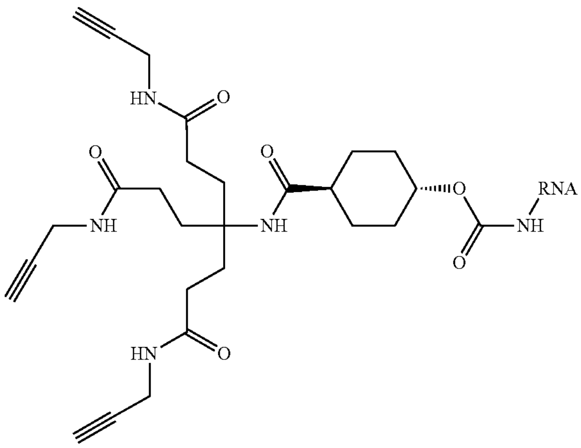 |
| 22-VII | 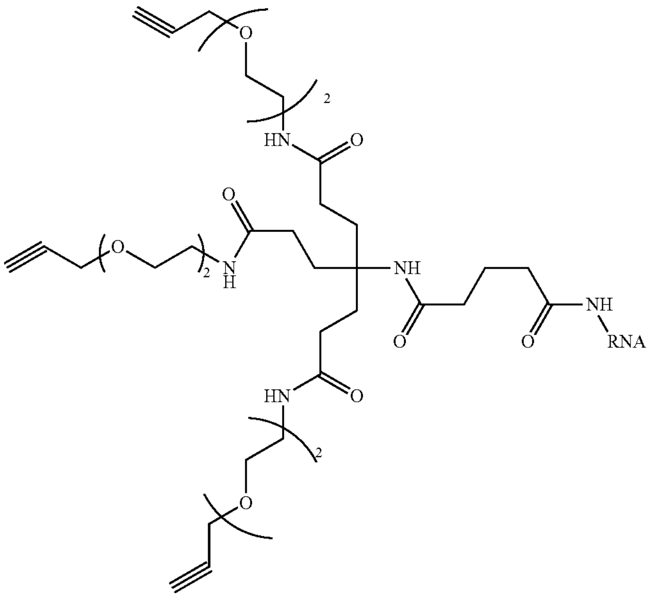 |

Formula VIII

Formula VIII is represented by the structure:

Formula VIII

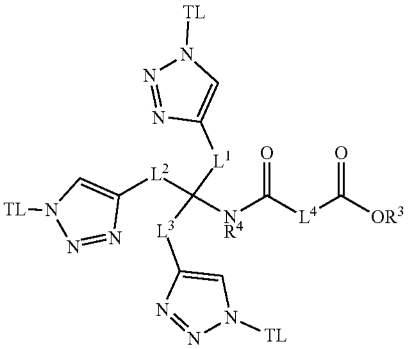

or a pharmaceutically acceptable salt thereof, wherein, $L^1$, $L^2$ and $L^3$ are each independently linkers comprising optionally substituted alkylene;

$L^4$ is a linker comprising optionally substituted alkylene, optionally substituted arylene, or optionally substituted cycloalkylene;

$R^3$ is H, optionally substituted alkyl, and optionally substituted aryl;

$R^4$ is H or optionally substituted alkyl; and

TL is a targeting ligand.

In some embodiments of Formula VIII, $L^1$, $L^2$ and $L^3$ are each

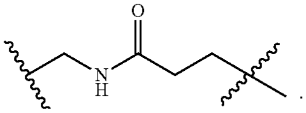 [SMILES: *CCC(=O)NC*]

In some embodiments of Formula VIII, $L^1$, $L^2$ and $L^3$ are each

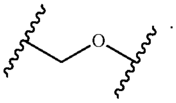 [SMILES: *CO*]

In some embodiments of Formula VIII, $L^1$ $L^2$ and $L^3$ are each

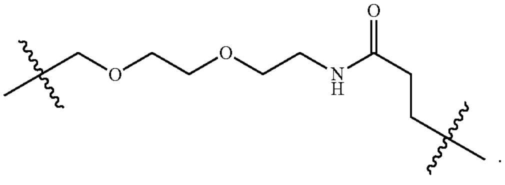 [SMILES: *CCC(=O)NCCOCCOC*]

In some embodiments of Formula VIII, $L^4$ is selected from the group consisting of:

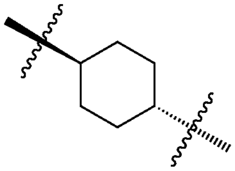,
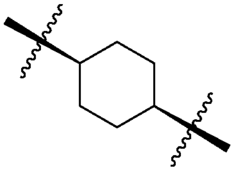,
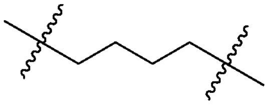,
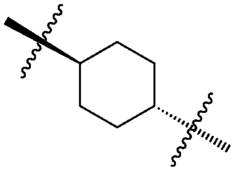,
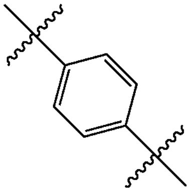,
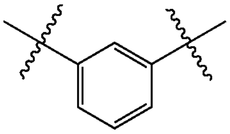,
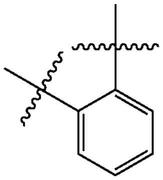,
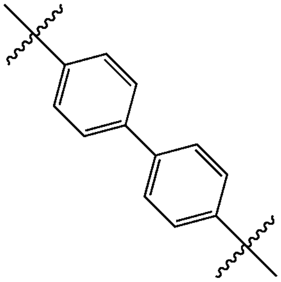,
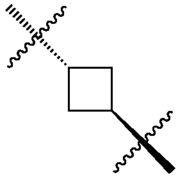,
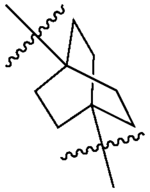,
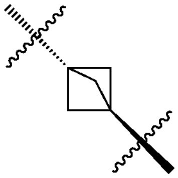, and
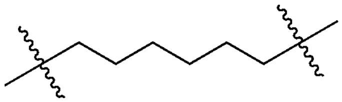, wherein ⌇ indicates the point of attachment.

In some embodiments of Formula VIII, $R^3$ is optionally substituted aryl. In some embodiments of Formula VIII, $R^3$ is para-nitrophenyl.

Example compounds of Formula VIII are shown in Table 6 below.

TABLE 6
| Example compounds of Formula VIII. | |
|---|---|
| Compound No. | Structure |
| 15-VIII | 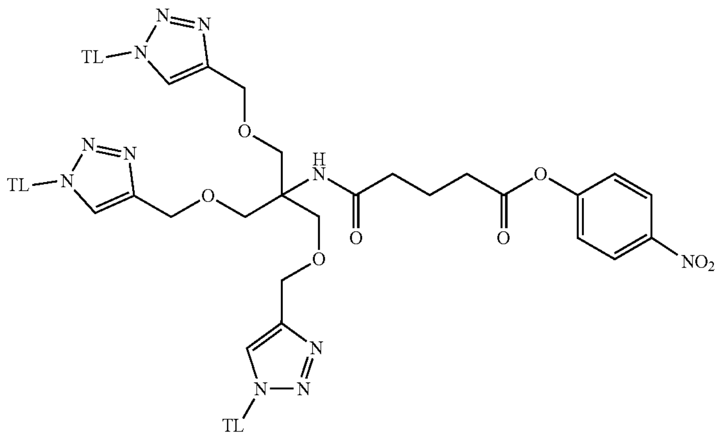 |
| 16-VIII | 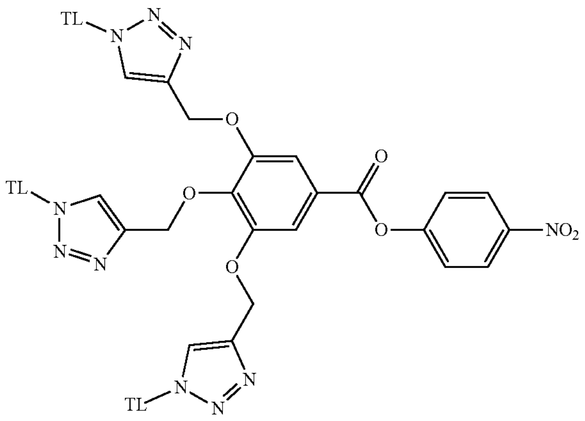 |
| 18-VIII | 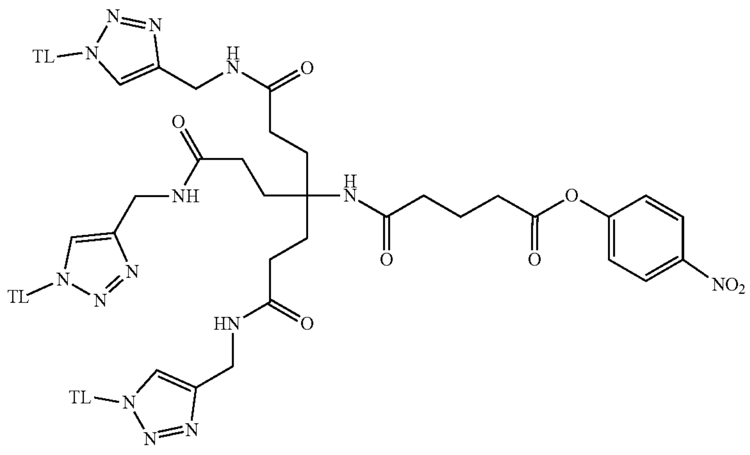 |

TABLE 6-continued
| Example compounds of Formula VIII. | |
|---|---|
| Compound No. | Structure |
| 19-VIII | 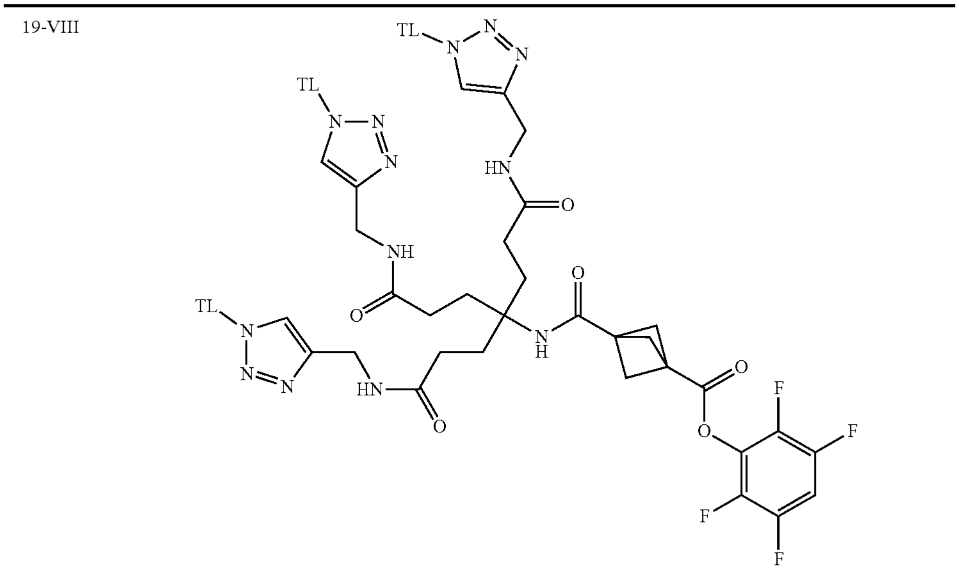 |
| 20-VIII | 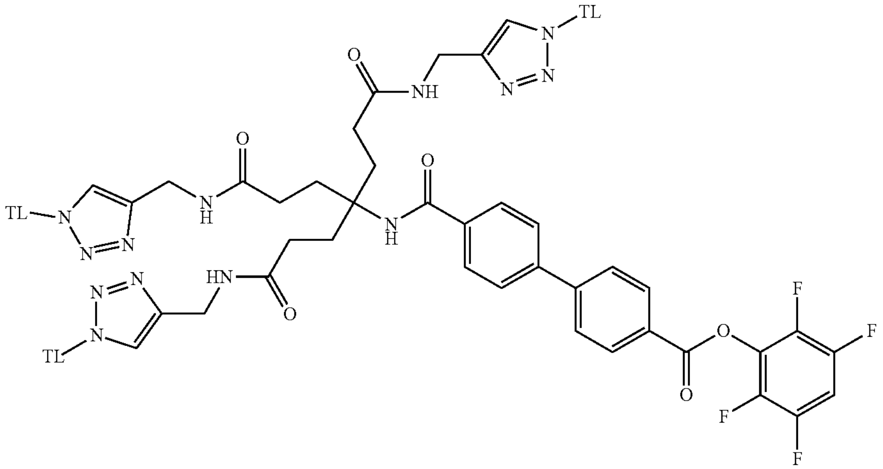 |
| 21-VIII | 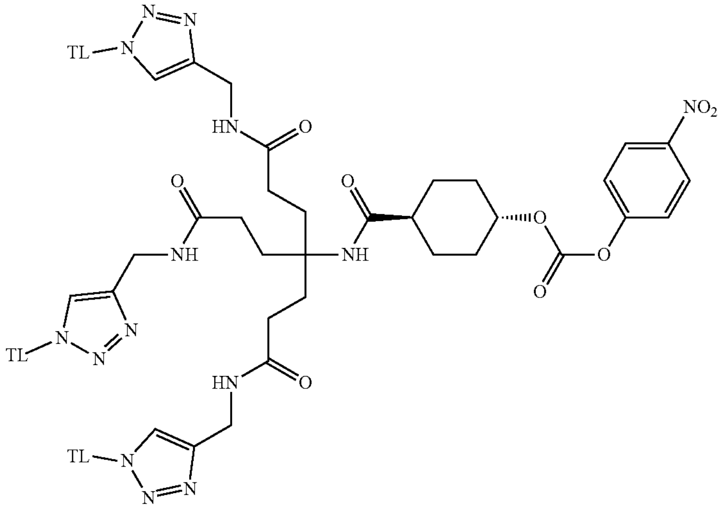 |

TABLE 6-continued

Example compounds of Formula VIII.

| Compound No. | Structure |
| --- | --- |
| 22-VIII | 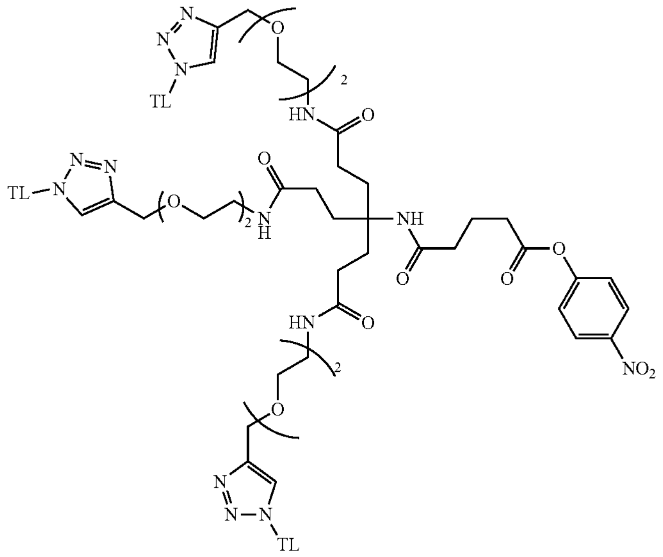 |

Formula IX

Formula IX is represented by the structure:

Formula IX

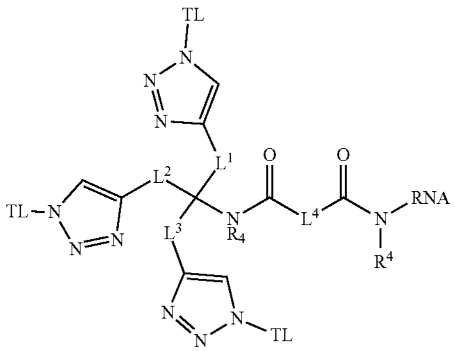

or a pharmaceutically acceptable salt thereof, wherein, $L^1$, $L^2$ and $L^3$ are each independently linkers comprising optionally substituted alkylene;

$L^4$ is a linker comprising optionally substituted alkylene, optionally substituted arylene, or optionally substituted cycloalkylene;

TL is a targeting ligand;

each instance of $R^4$ is H or optionally substituted alkyl; and

RNA comprises or consists of an RNAi agent.

In some embodiments of Formula IX, $L^1$, $L^2$ and $L^3$ are each

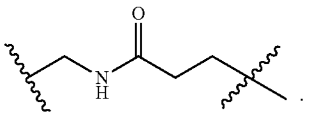 [SMILES: *CCC(=O)NC*]

In some embodiments of Formula IX, $L^1$, $L^2$ and $L^3$ are each

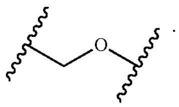 [SMILES: *CO*]

In some embodiments of Formula IX, $L^1$ $L^2$ and $L^3$ are each

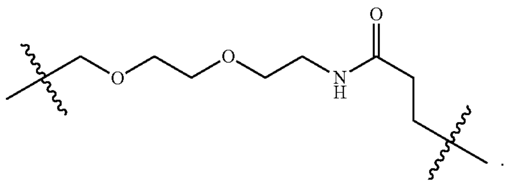 [SMILES: *CCC(=O)NCCOCCOC*]

In some embodiments of Formula IX, $L^4$ is selected from the group consisting of:
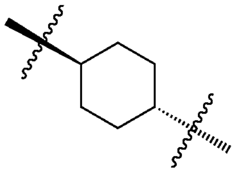,
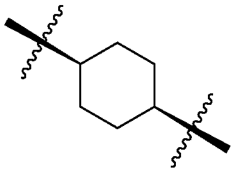,
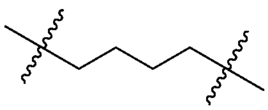,
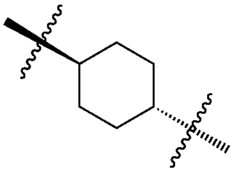,
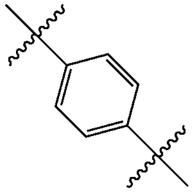,
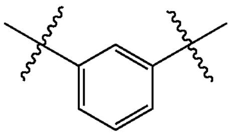,
-continued
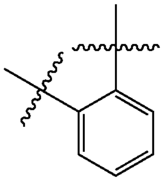,
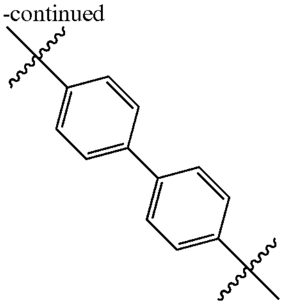,
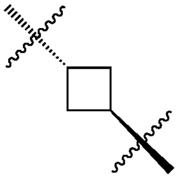,
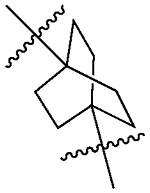,
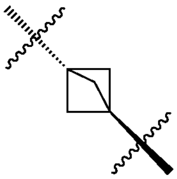, and
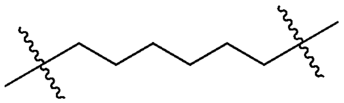,
wherein ⌇ indicates the point of attachment.
Example compounds of Formula IX are shown in Table 7 below.
TABLE 7
| Example compound of Formula IX. | |
|---|---|
| Compound No. | Structure |
| 15-IX | 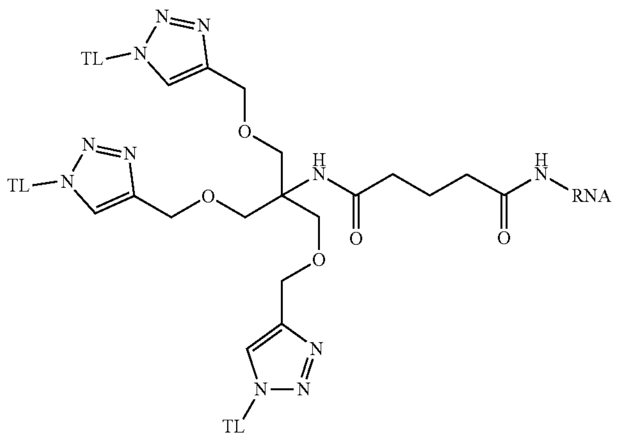 |

TABLE 7-continued
Example compound of Formula IX.
| Compound No. | Structure |
|---|---|
| 16-IX | 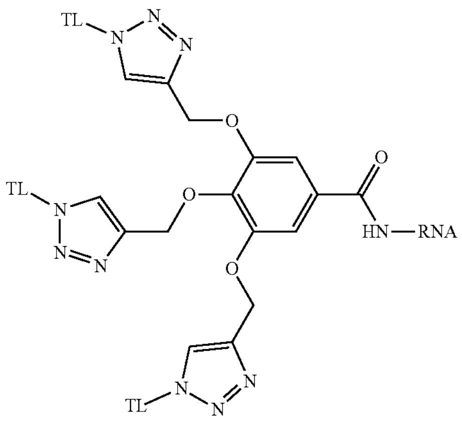 |
| 18-IX | 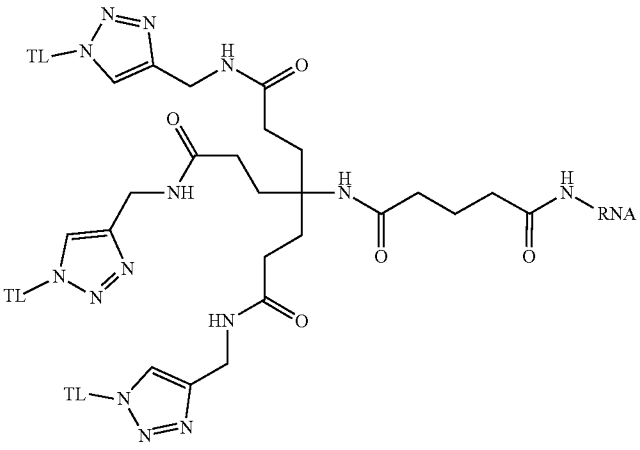 |
| 19-IX | 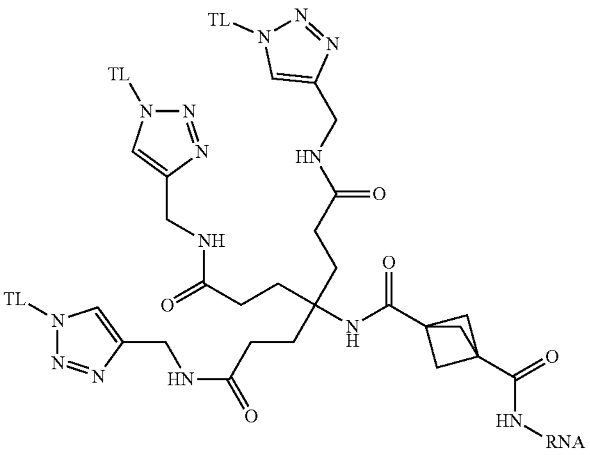 |

TABLE 7-continued
| Example compound of Formula IX. | |
|---|---|
| Compound No. | Structure |
| 20-IX | 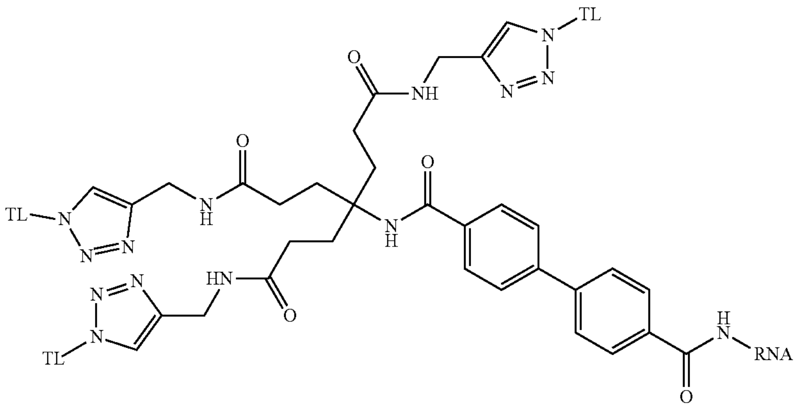 |
| 21-IX | 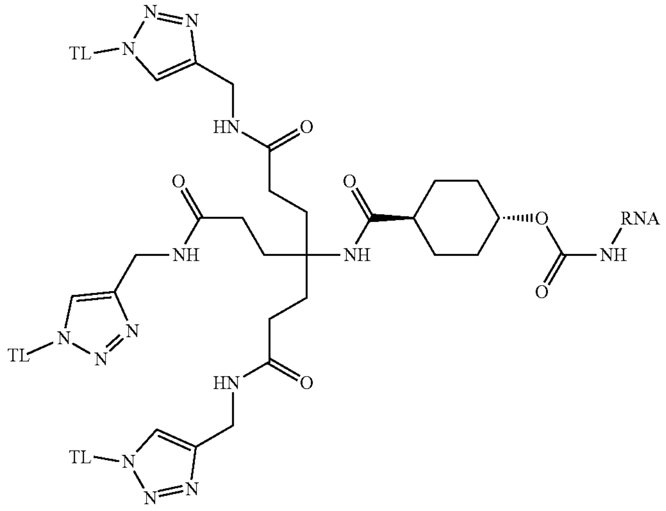 |
| 22-IX | 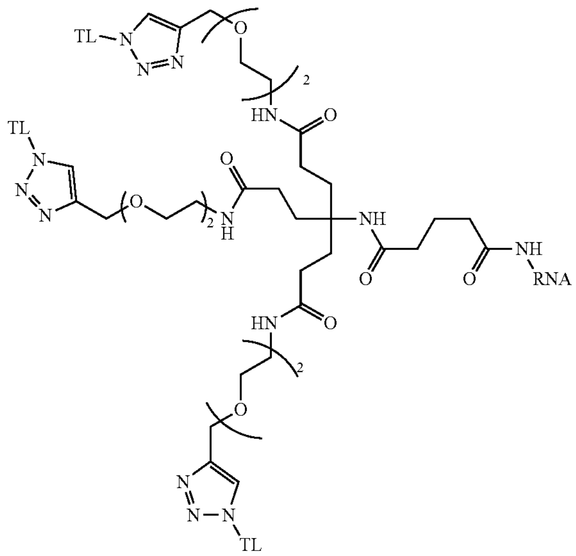 |

wherein TL comprises a targeting ligand and RNA comprises or consists of an RNAi agent.

$L^1$, $L^2$, $L^3$

In embodiments of Formulas I-IX, each instance of $L^1$, $L^2$, or $L^3$ is a linker comprising optionally substituted alkylene. $L^1$, $L^2$, or $L^3$ may include any suitable linking moiety known in the art. In some embodiments, $L^1$, $L^2$, or $L^3$ comprises a chain with a length between 1 and 50 atoms. The length of the chain of $L^1$, $L^2$, or $L^3$ indicates the number of atoms directly between the alkyne and the quaternary carbon, however, there may be further atoms that branch from the atoms in the chain. In some embodiments, the length of $L^1$, $L^2$, or $L^3$ may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 atoms.

In some embodiments, every instance of $L^1$, $L^2$, and $L^3$ is the same. In other embodiments, each of $L^1$, $L^2$, and $L^3$ is a different moiety.

In some embodiments, $L^1$, $L^2$, $L^3$ or $L^4$ may comprise an amide.

In some embodiments, $L^1$, $L^2$, $L^3$ or $L^4$ may comprise a polyethylene glycol (PEG) chain.

In some embodiments, the optionally substituted alkylene of $L^1$, $L^2$, $L^3$ or $L^4$ may be interrupted by an amide, ether, ester, thioether, thione, ketone, amine, sulfone, sulfonamide or a chain of atoms, such as, but not limited to, substituted or unsubstituted alkenyl, arylalkyl, arylalkenyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylheterocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylheteroaryl.

In some embodiments, $L^1$, $L^2$, and $L^3$ may each independently be selected from the group consisting of:

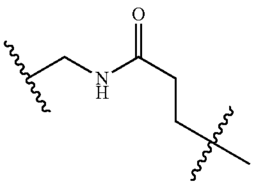

,

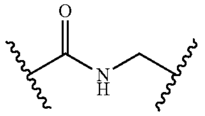

and

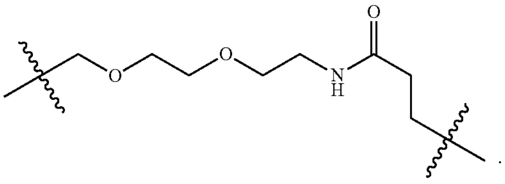

.

In embodiments of Formulas I-IX, $L^4$ is a linker comprising optionally substituted alkylene. $L^4$ may include any suitable linking moiety known in the art. In some embodiments, $L^4$ comprises a chain with a length between 1 and 50 atoms. The length of the chain of $L^2$ indicates the number of atoms directly between the alkyne and the quaternary carbon, however, there may be further atoms that branch from the atoms in the chain. In some embodiments, the length of $L^2$ may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 atoms.

In some embodiments, $L^4$ is selected from the group consisting of:

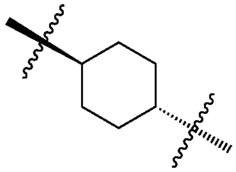

,

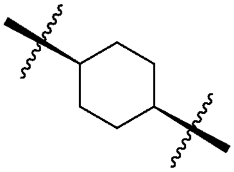

,

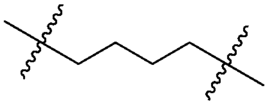

,

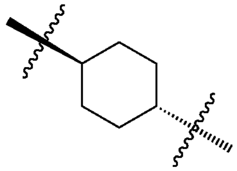

,

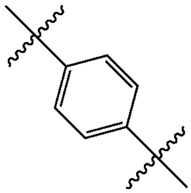

,

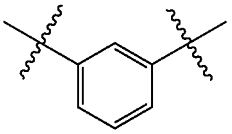

,

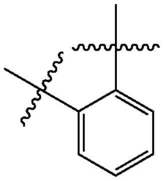

,

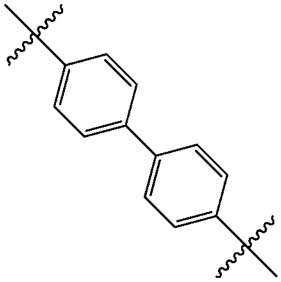

,

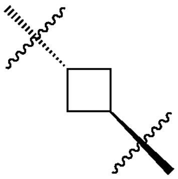

,

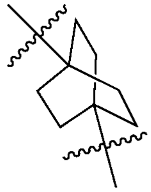

,

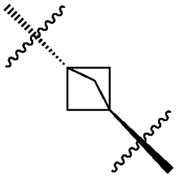

, and

-continued

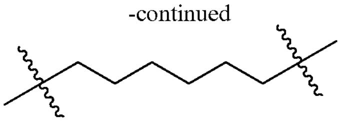

, wherein ⌇ indicates the point of attachment.

R

In embodiments of Formulas I-IX, R comprises a coupling moiety or an RNAi agent. In some embodiments, R comprises a coupling moiety, and the coupling moiety is a phosphoramidite. In other embodiments, R comprises a coupling moiety and the coupling moiety is an ester. In other embodiments, R comprises a coupling moiety and the coupling moiety is a carbonate.

In some embodiments, R comprises an RNAi agent. When R comprises an RNAi agent, R may comprise additional atoms that do not form part of an RNAi sequence. For example, in some embodiments R may be

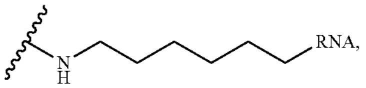

wherein RNA indicates an RNAi agent, and ⌇ indicates the point of attachment. In some embodiments, the RNAi agent is bound to the compounds of Formulas I-IX at the 5' end of the sense strand.

In some embodiments, R is selected from the group consisting of

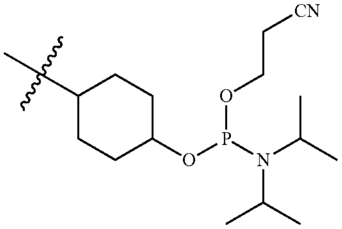

,

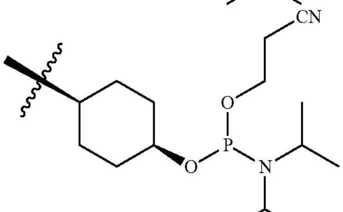

,

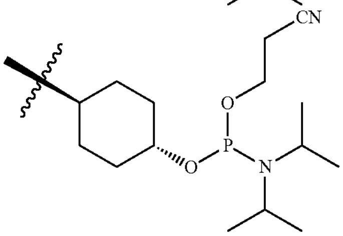

,

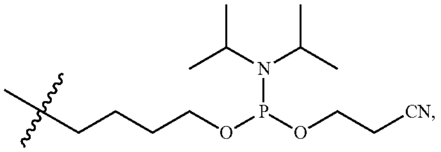

-continued

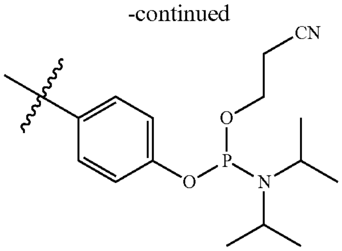

,

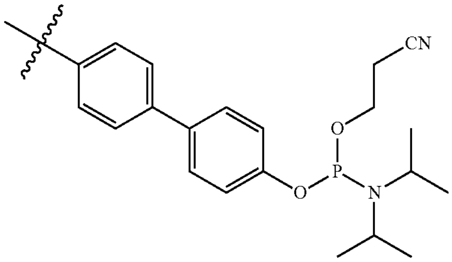

,

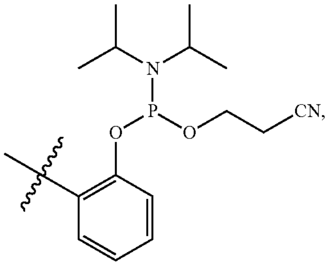

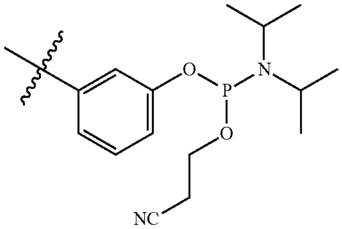

,

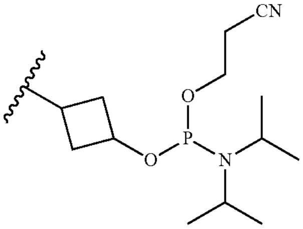

,

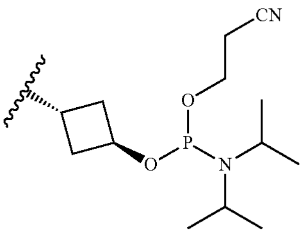

,

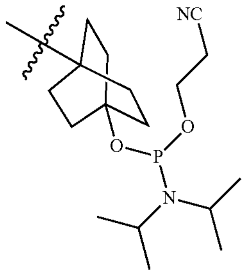

,

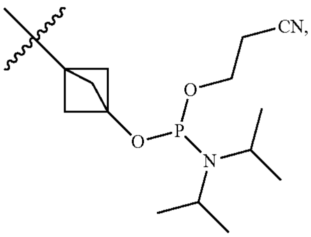

-continued

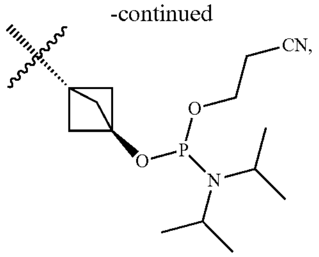

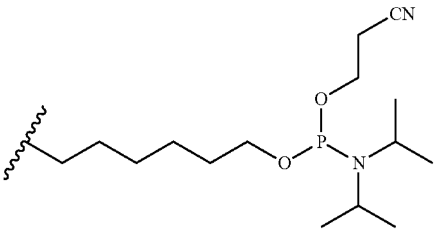

,

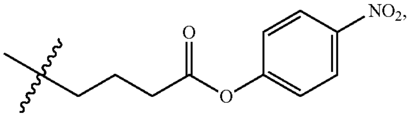

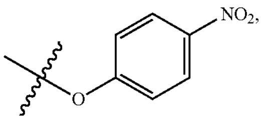

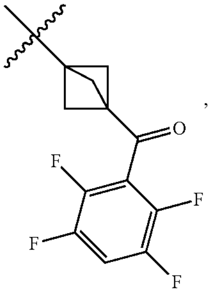

, and

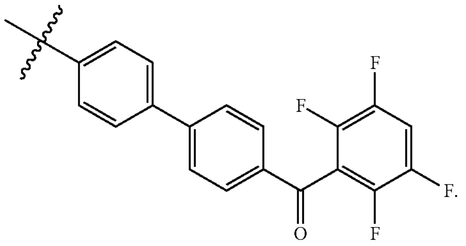

Pharmaceutical Compositions

In some embodiments, the present disclosure provides pharmaceutical compositions that include therapeutic compounds that incorporate one or more of the trialkyne linking agent disclosed herein.

As used herein, a "pharmaceutical composition" comprises a pharmacologically effective amount of an Active Pharmaceutical Ingredient (API), and optionally one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The pharmaceutical compositions described herein can contain other additional components commonly found in pharmaceutical compositions. In some embodiments, the additional component is a pharmaceutically-active material. Pharmaceutically-active materials include, but are not limited to: anti-pruritics, astringents, local anesthetics, or anti-inflammatory agents (e.g., antihistamine, diphenhydramine, etc.), small molecule drug, antibody, antibody fragment, aptamers, and/or vaccine.

The pharmaceutical compositions may also contain preserving agents, solubilizing agents, stabilizing agents, wetting agents, emulsifiers, sweeteners, colorants, odorants, salts for the variation of osmotic pressure, buffers, coating agents, or antioxidants. They may also contain other agents with a known therapeutic benefit.

The pharmaceutical compositions can be administered in a number of ways depending upon whether local or systemic treatment is desired and upon the area to be treated. Administration can be made by any way commonly known in the art, such as, but not limited to, topical (e.g., by a transdermal patch), pulmonary (e.g., by inhalation or insufflation of powders or aerosols, including by nebulizer, intratracheal, intranasal), epidermal, transdermal, oral or parenteral. Parenteral administration includes, but is not limited to, intravenous, intraarterial, subcutaneous, intraperitoneal or intramuscular injection or infusion; subdermal (e.g., via an implanted device), intracranial, intraparenchymal, intrathecal, and intraventricular, administration. In some embodiments, the pharmaceutical compositions described herein are administered by subcutaneous injection. The pharmaceutical compositions may be administered orally, for example in the form of tablets, coated tablets, dragées, hard or soft gelatin capsules, solutions, emulsions or suspensions. Administration can also be carried out rectally, for example using suppositories; locally or percutaneously, for example using ointments, creams, gels, or solutions; or parenterally, for example using injectable solutions.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of any of the ligands described herein that can be in microcrystalline form, for example, in the form of an aqueous microcrystalline suspension. Liposomal formulations or biodegradable polymer systems can also be used to present any of the ligands described herein for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). As used herein, "pharmacologically effective amount," "therapeutically effective amount," or simply "effective amount" refers to that amount of an the pharmaceutically active agent to produce a pharmacological, therapeutic or preventive result.

Medicaments containing a trialkyne linking agent are also an object of the present invention, as are processes for the manufacture of such medicaments, which processes comprise bringing one or more compounds containing a trialkyne linking agent, and, if desired, one or more other substances with a known therapeutic benefit, into a pharmaceutically acceptable form.

The described trialkyne linking agent and pharmaceutical compositions comprising trialkyne linking agents disclosed herein may be packaged or included in a kit, container, pack, or dispenser. The trialkyne linking agents and pharmaceutical compositions comprising the trialkyne linking agents may be packaged in pre-filled syringes or vials.

Targeting Ligands, Pharmacokinetic (PK) Modulators, and Delivery Vehicles

In some embodiments, a trialkyne linking agent is conjugated to one or more non-nucleotide groups including, but not limited to, a targeting ligand, a pharmacokinetic (PK) modulator, a delivery polymer, or a delivery vehicle. The non-nucleotide group can enhance targeting, delivery, or attachment of the cargo molecule. The non-nucleotide group can be covalently linked to the RNAi agent, at the 3' or 5' end of the sense strand. In some embodiments, a non-nucleotide group is linked to the 5' end of an RNAi agent sense strand. In some embodiments, a trialkyne linker of Formula I is linked to an RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

Targeting ligands or targeting moieties enhance the pharmacokinetic or biodistribution properties of a cargo molecule to which they are attached to improve cell-specific (including, in some cases, organ specific) distribution and cell-specific (or organ specific) uptake of the RNAi agent. In some embodiments, a targeting ligand includes a targeting compound and a PK enhancer or modulator. In some embodiments, targeting ligands are directed to cell receptors.

Conjugation to Targeting Ligands

In some embodiments, the trialkyne linkers of formula I may be conjugated to an RNAi agent by way of the coupling agent. An example scheme for conjugating trialkyne linkers of Formula I to RNAi molecules is shown in the reaction scheme below:

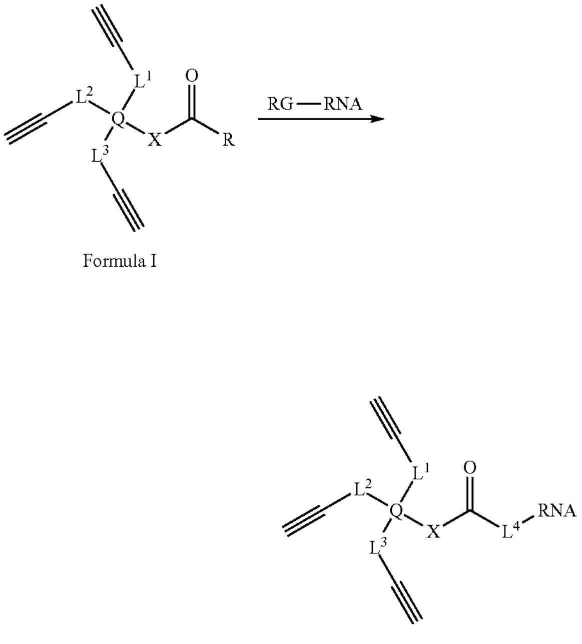

Formula I

Formula I-A wherein $L^1$, $L^2$, $L^3$, Q, and X are all as described in Formula I, R comprises a coupling moiety, RG is a reactive group and $L^4$ is a linker comprising optionally substituted alkylene, optionally substituted arylene, or optionally substituted cycloalkylene.

In some embodiments, targeting ligands (TL) may be conjugated to the trialkyne moieties before conjugation to an RNAi molecule. An example of this reaction is shown in the scheme below:

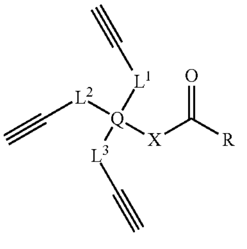

Formula I

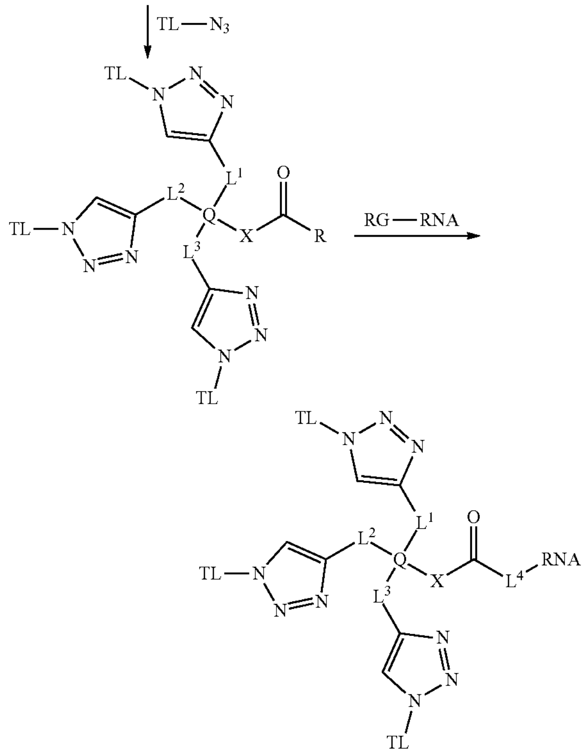

wherein $L^1$, $L^2$, $L^3$, Q, and X are all as described in Formula I, R comprises a coupling moiety and $L^4$ is a linker comprising optionally substituted alkylene, optionally substituted arylene, or optionally substituted cycloalkylene.

RNAi molecules can be synthesized having a reactive group, such as an amino group (also referred to herein as an amine). In some embodiments, the reactive group may be linked at the 5'-terminus and/or the 3'-terminus of the RNAi agent. In some embodiments, the RNAi agent may be double-stranded. In embodiments where the RNAi agent is double-stranded, the reactive group may be on the sense strand or the anti-sense strand of the RNAi agent.

For example, in some embodiments, an RNAi agent is synthesized having an $NH_2$—$C_6H_{12}$ (hexyleneamine) group at the 5'-terminus of the sense strand of the RNAi agent. The terminal amino group subsequently can be reacted to form a conjugate with, for example, the coupling moiety of a compound of Formula I. In some embodiments, the coupling moiety is an ester, and the reactive group on the RNAi agent is a primary amine, and an amide linkage is formed between the RNAi agent and the trialkyne linker. An example of this reaction is shown in the scheme below using a compound of Formula VI:

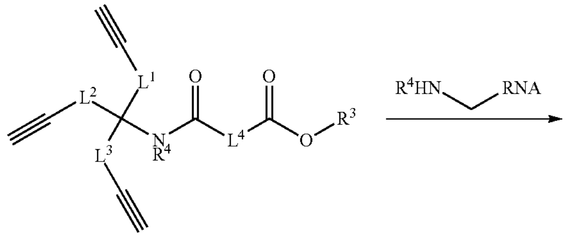

Formula VI

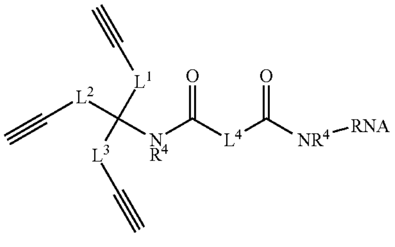

Formula VII wherein $L^1$, $L^2$, $L^3$, $L^4$, $R^3$, $R^4$ and RNA are all as defined in Formulas VI and VII.

In other embodiments, an RNAi agent is synthesized with a terminal —$CH_2OH$ group. In some embodiments, the coupling agent in R of Formula I comprises a phosphoramidite. An RNAi agent comprising a terminal alcohol may be reacted with a trialkyne of Formula II to form a phosphate as shown in the reaction scheme below:

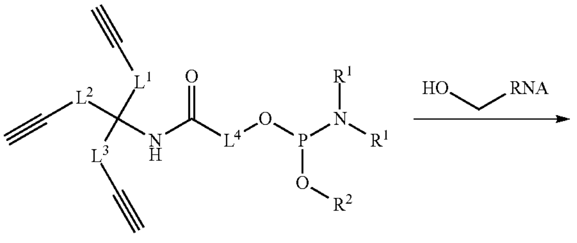

Formula II

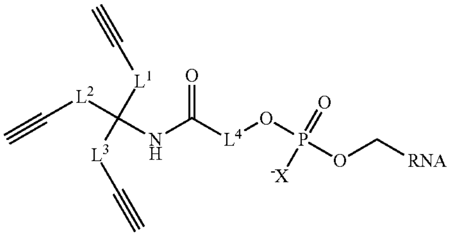

In some embodiments, targeting ligands (TL) may be conjugated to a trialkyne linking agent as described herein after the trialkyne linking agent has been conjugated to an RNAi agent. An example of this reaction is shown in the scheme below:

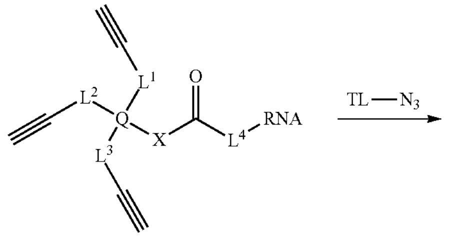

Formula I-A

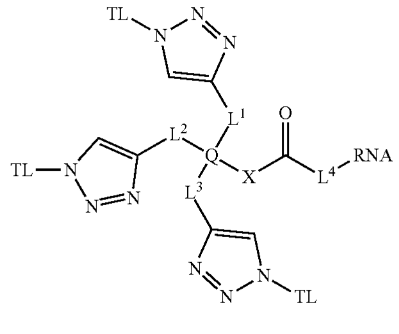

EXAMPLES

Example 1. Synthesis of Compound 1 (2-cyanoethyl ((1r,4r)-4-((1,7-dioxo-4-(3-oxo-3-(prop-2-yn-1-ylamino)propyl)-1,7-bis(prop-2-yn-1-ylamino)heptan-4-yl)carbamoyl)cyclohexyl) diisopropylphosphoramidite

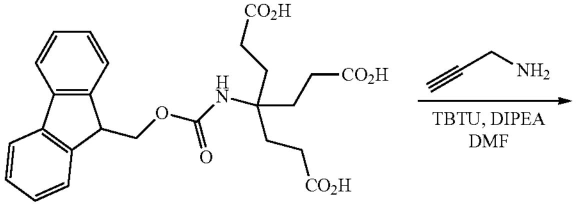

1

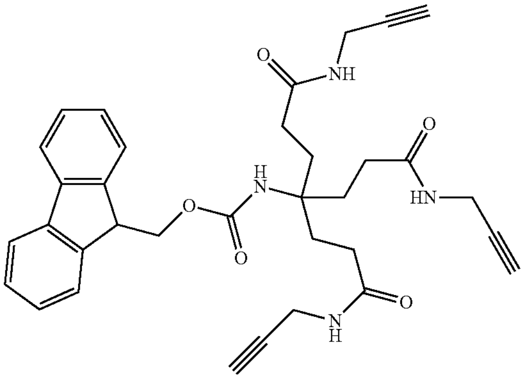

2

To a solution of 1 (12.00 g, 25.6 mmol) and DIPEA (12.22 g, 16.47 mL, 94.6 mmol) in DMF (50 mL) was added TBTU (28.72 g, 89.5 mmol) at 0° C. The internal temperature increased from 0° C. to 16° C. Propargylamine (4.93 g, 5.73 mL, 89.5 mmol) was added dropwise while maintaining an internal temperature of less than 20° C. The cooling bath was removed, and the reaction mixture was stirred overnight at room temperature. The reaction mixture was diluted with DCM (100 mL) and washed with 1 N HCl (2×100 mL) and sat. aq. $NaHCO_3$ (2×100 mL). The organic layer became hazy and was set stirring at room temperature. After 1.5 h, the precipitate was collected by filtration, rinsed with DCM (100 mL), and dried. Yield of 2: 10.4 g (70%). [M+H] calculated for $C_{34}H_{36}N_4O_5$: 581.70, found: 581.79.

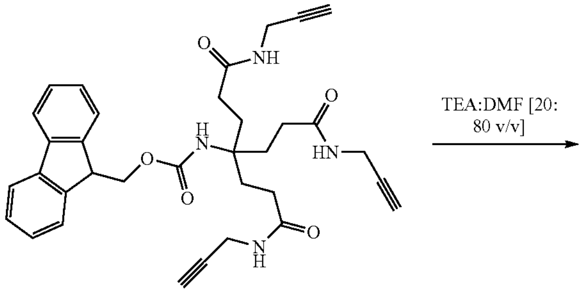

2

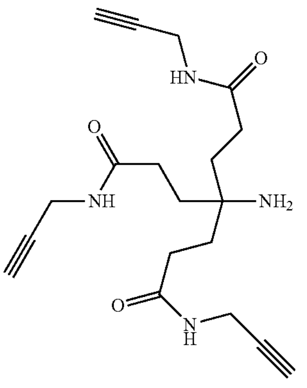

3

To a solution of 2 (12.17 g, 21.0 mmol) in DMF (60 mL) was added triethylamine (10.6 g, 14.7 mL, 105 mmol) at room temperature. The reaction mixture was stirred overnight. The reaction mixture was then concentrated and purified by CombiFlash® using silica gel as the stationary phase and was eluted with a gradient of MeOH in DCM (0-13%) containing 1% triethylamine. Yield of 3: 6.08 g (81%). [M+H] calculated for $C_{19}H_{26}N_4O_3$: 359.45, found: 359.35.

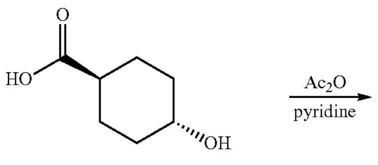

4

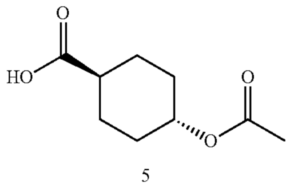

5

4 (2.55 g, 17.69 mmol) in pyridine (26 mL) was treated with acetic anhydride (12.8 mL, 135 mmol) and was stirred at room temperature for 4 hours. Upon completion all volatiles were removed and 5 was isolated by separation over silica eluting a gradient of ethyl acetate in hexanes containing 1% acetic acid. Yield: 2.56 g (78%). $^{1}H$ NMR (400 MHz, DMSO-d6): δ 12.11 (s, br, 1H) 4.56 (m, 1H), 2.21 (m, 1H), 1.97 (s, 3H), 1.90 (m, 4H), 1.38 (m, 4H).

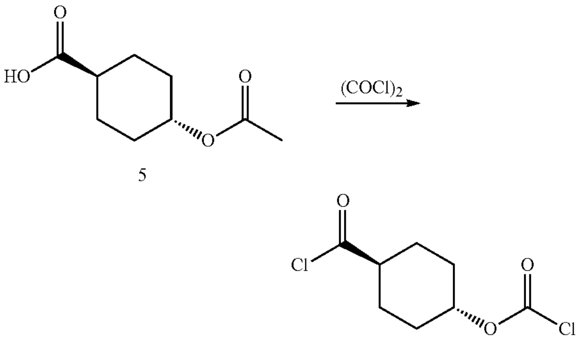

5

6

To a solution of 5 (400 mg, 2.15 mmol) in DCM (5 mL) was added DMF (16 mg, 17 μL, 0.215 mmol) and oxalyl chloride (1.36 g, 922 μL, 10.74 mmol) at 0° C. After 30 m, the cooling bath was removed, and the reaction mixture was stirred at room temperature overnight. The reaction mixture was concentrated, and product was used in the next step without further purification.

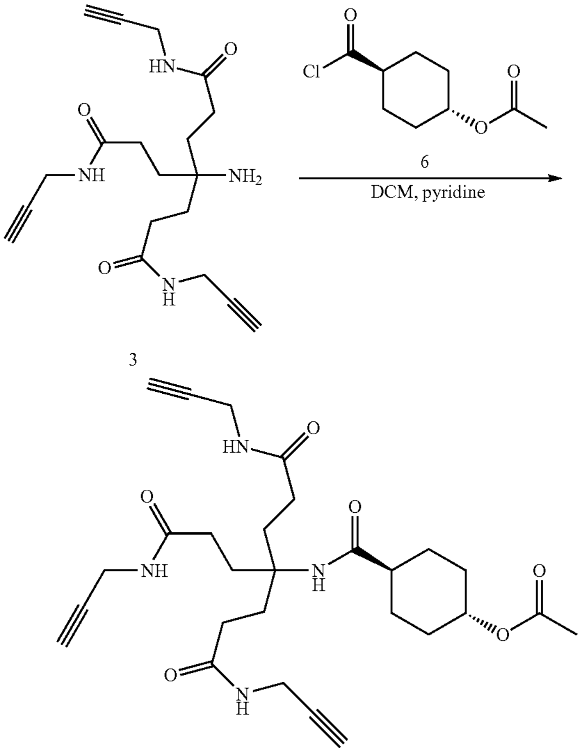

3

7

To a solution of 3 (1000 mg, 2.79 mmol) in DCM (10 mL) was added pyridine (1.88 g, 1.92 mL, 23.7 mmol). The reaction mixture was cooled to 0° C. and a solution of 6 (398 mg, 1.95 mmol) in DCM (5 mL) was added dropwise. The cooling bath was removed, and the mixture was stirred overnight at room temperature. Water (10 mL) was added to quench the reaction. The mixture was diluted with DCM (30 mL) and washed with sat. aq. $NH_4Cl$ (20 mL) and brine (10 mL). The organic phase was dried over $Na_2SO_4$, filtered, and concentrated. The residue was purified by CombiFlash® using silica gel as the stationary phase and was eluted with a gradient of MeOH in DCM (0-7%). Yield of 7: 630 mg (43%). [M+H] calculated for $C_{28}H_{38}N_4O_6$: 527.64, found: 527.69.

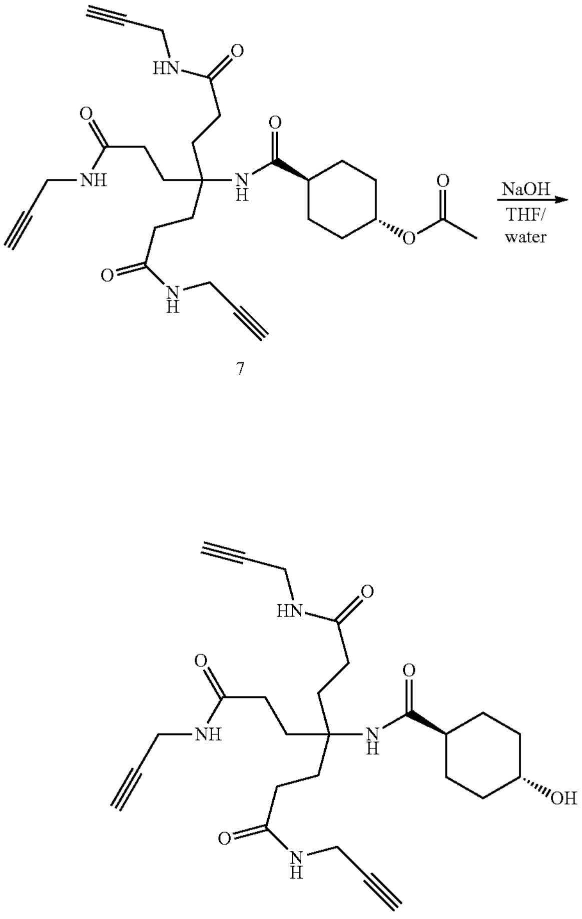

7

8

To a solution of 7 (288 mg, 0.55 mmol) in THF (1.75 mL) was added 1 M NaOH solution (2.73 mL, 2.73 mmol) at room temperature. The reaction mixture was stirred at room temperature for 1.5 h then heated to 35° C. for an additional 30 m. Upon consumption of starting material, the reaction mixture was acidified to pH=5 using 2 M HCl and concentrated. The residue was co-evaporated with ACN (20 mL). After drying, the residue was purified by CombiFlash® using silica gel as the stationary phase and was eluted with a gradient of MeOH in DCM (0-10%). Yield of 8: 216 mg (81%). [M+H] calculated for $C_{26}H_{36}N_4O_5$: 485.61, found: 485.56.

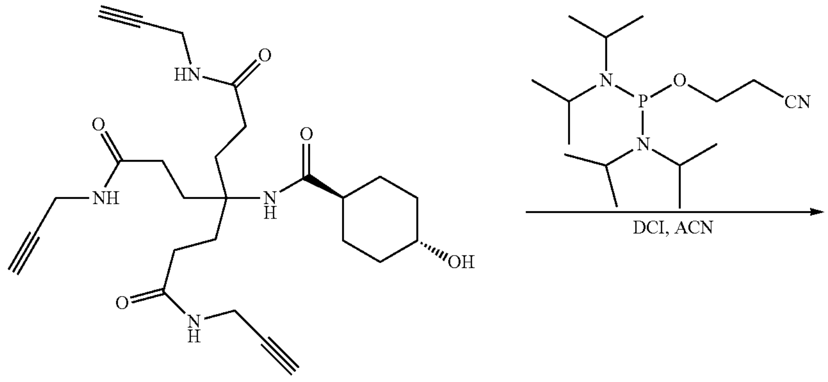

8

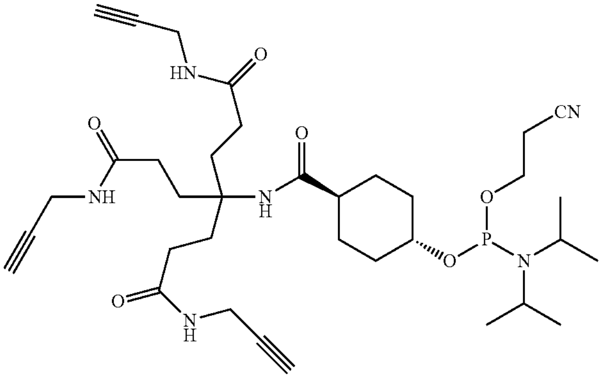

9

8 (213 mg, 0.44 mmol) was dried azeotropically from anhydrous ACN (2×10 mL) then dissolved in ACN (4 mL). The reaction mixture was cooled to 0° C. 4,5-Dicyanoimidazole (26 mg, 0.22 mmol) was added followed by 2-cyanoethyl N,N,N',N'-tetraisopropylphosphorodiamidite (199 mg, 0.66 mmol). The reaction mixture was stirred at 0° C. for 30 m. Upon consumption of starting material, triethylamine (44 mg, 61 µL, 0.44 mmol) was added, and the reaction mixture was concentrated to an oil. The oil was purified by CombiFlash® using silica gel as the stationary phase and was eluted with a gradient of EtOAc in DCM (50-100%) containing 1% triethylamine. Yield of 9 (Compound 1): 174 mg (58%). [M+H] calculated for $C_{35}H_{53}N_6O_6P$: 685.83, found: 685.94.

Example 2. Synthesis of Compound 2 (2-cyanoethyl ((1s,4s)-4-((1,7-dioxo-4-(3-oxo-3-(prop-2-yn-1-ylamino)propyl)-1,7-bis(prop-2-yn-1-ylamino)heptan-4-yl)carbamoyl)cyclohexyl) diisopropylphosphoramidite

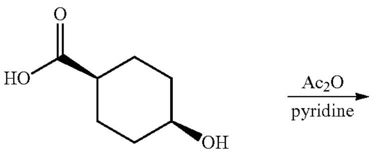

10

-continued

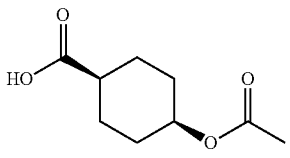

11

To a solution of 10 (cis-4-hydroxycyclohexanecarboxylic acid, 2.00 g, 13.87 mmol) in pyridine (19.75 g, 20.20 mL, 250 mmol) was added acetic anhydride (10.83 g, 10.03 mL, 106 mmol) at 0° C. The cooling bath was removed and the reaction mixture was stirred overnight at room temperature. The reaction mixture was concentrated, and the residue was purified by CombiFlash® using silica gel as the stationary phase and was eluted with a gradient of EtOAc in hexanes (0-30%). Yield of 11: 1.75 g (68%). [M−H] calculated for $C_9H_{14}O_4$: 185.20, found: 185.35.

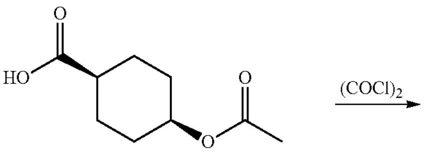

11

-continued

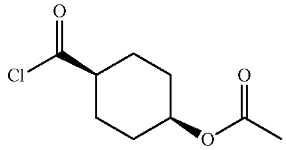

12

To a solution of 11 (420 mg, 2.26 mmol) in DCM (5 mL) was added DMF (16.5 mg, 17.4 μL, 0.226 mmol) and oxalyl chloride (1.43 g, 0.97 mL, 11.3 mmol) at 0° C. After 30 m, the cooling bath was removed, and the reaction mixture was stirred at room temperature for 2 h. The reaction mixture was concentrated, co-evaporated with toluene, and the product 12 was used in the next step without further purification.

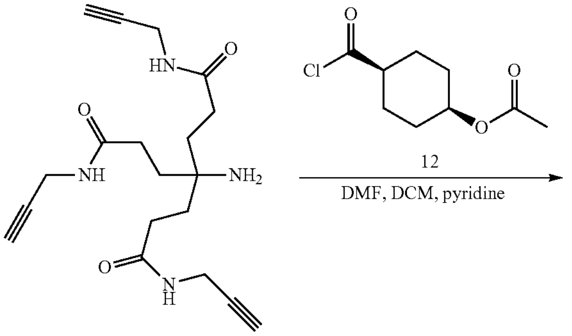

3

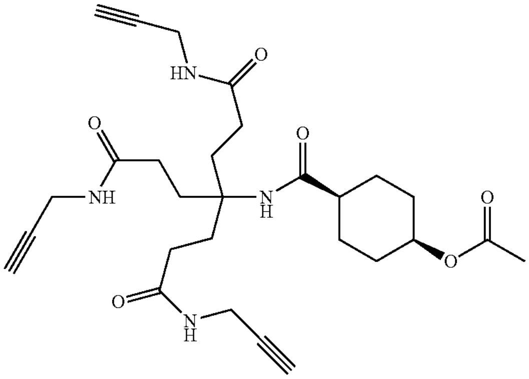

13

To a solution of 3 (400 mg, 1.12 mmol) in DMF (2 mL) was added pyridine (750 mg, 767 μL, 9.50 mmol). The reaction mixture was cooled to 0° C. and a solution of 12 (457 mg, 2.23 mmol) in DCM (2 mL) was added dropwise. The cooling bath was removed, and the mixture was stirred for 1.5 h at room temperature. The mixture was diluted with DCM (20 mL) and quenched with sat. aq. $NH_4Cl$ (10 mL). The organic phase was washed with brine, dried over $Na_2SO_4$, filtered, and concentrated. The residue was purified by CombiFlash® using silica gel as the stationary phase and was eluted with a gradient of MeOH in DCM (0-10%). Yield of 13: 365 mg (62%). $^1$H NMR (400 MHz, DMSO-d6): δ 8.21 (t, 3H), 7.07 (s, 1H), 4.84 (m, 1H), 3.81 (dd, 6H), 3.07 (t, 3H), 2.18 (m, 1H), 1.99 (m, 9H), 1.80-1.72 (m, 8H), 1.64-1.42 (m, 6H).

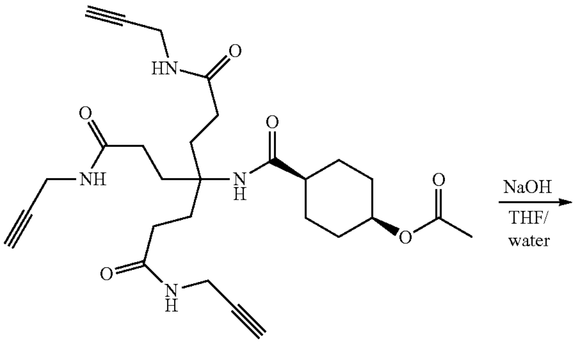

13

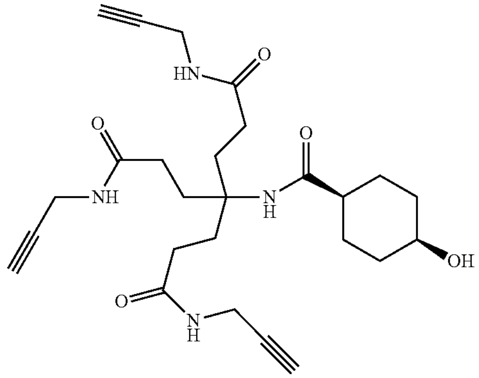

14

To a solution of 13 (360 mg, 0.68 mmol) in THF (2.2 mL) was added 1 M NaOH solution (3.42 mL, 3.42 mmol) at room temperature. The reaction mixture was stirred at room temperature for 2 h then heated to 35° C. for an additional 1.5 h. Upon consumption of starting material, the reaction mixture was acidified to pH=5 using 2 M HCl and concentrated. The residue was co-evaporated with ACN (20 mL). After drying, the residue was purified by CombiFlash® using silica gel as the stationary phase and was eluted with a gradient of MeOH in DCM (0-12%). Yield of 8: 250 mg (75%). $^1$H NMR (400 MHz, DMSO-d6): δ 8.22 (t, 3H), 6.96 (s, 1H), 4.24 (d, 1H), 3.81 (dd, 6H), 3.75 (s, br, 1H), 3.07 (t, 3H), 2.10 (m, 1H), 1.99 (m, 6H), 1.82-1.58 (m, 10H), 1.36 (m, 4H).

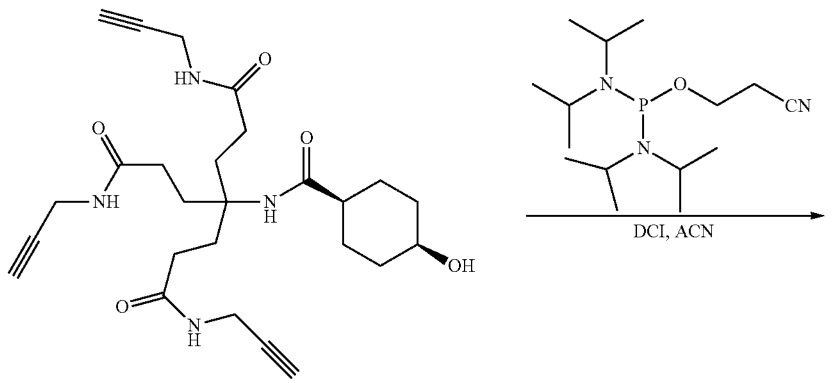
14
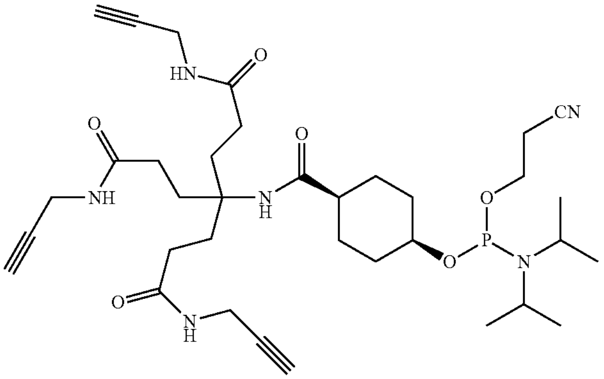
15

14 (245 mg, 0.51 mmol) was dried azeotropically from anhydrous ACN (2×10 mL) then dissolved in ACN (4 mL). The reaction mixture was cooled to 0° C. 4,5-Dicyanoimidazole (30 mg, 0.25 mmol) was added followed by 2-cyanoethyl N,N,N',N'-tetraisopropylphosphorodiamidite (229 mg, 0.76 mmol). The reaction mixture was stirred at 0° C. for 30 m then rt for 1.5 h. The reaction mixture was concentrated to an oil then dissolved in DCM (15 mL). The mixture was washed with sat. aq. $NaHCO_3$ (2×5 mL) and brine (5 mL). The organic phase was dried over $Na_2SO_4$, filtered, and concentrated. The residue was purified by CombiFlash® using silica gel as the stationary phase and was eluted with a gradient of EtOAc in DCM (50-100%) containing 1% triethylamine. Yield of 15 (Compound 2): 204 mg (59%). [M−H] calculated for $C_{35}H_{53}N_6O_6P$: 683.81, found: 684.14.

Example 3. Synthesis of Compound 3 (2-cyanoethyl (5-((1,7-dioxo-4-(3-oxo-3-(prop-2-yn-1-ylamino)propyl)-1,7-bis(prop-2-yn-1-ylamino)heptan-4-yl)amino)-5-oxopentyl) diisopropylphosphoramidite

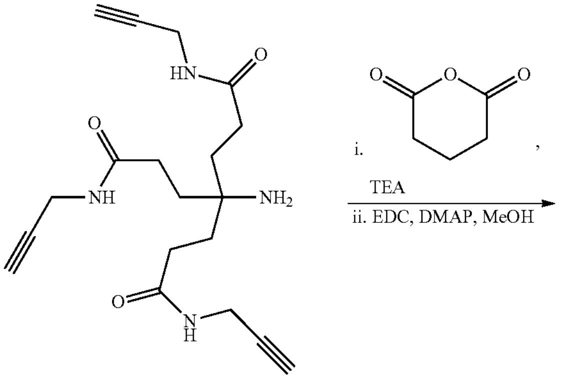

3

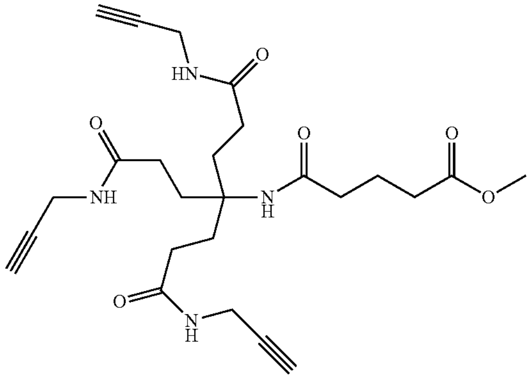

16

To a solution of 3 (475 mg, 1.33 mmol) in DMF (5 mL) was added triethylamine (402 mg, 555 μL, 3.98 mmol) and glutaric anhydride (190 mg, 1.65 mmol) at room temperature. The reaction mixture was stirred for 1 h then DMAP (8.1 mg, 0.066 mmol), MeOH (424 mg, 536 μL, 13.25 mmol), and N-(3-dimethylaminopropyl)-N'-ethylcarbodiimide hydrochloride (508 mg, 2.65 mmol) were added at room temperature. The mixture was stirred overnight at room temperature. The reaction mixture was diluted with DCM (20 mL) and washed with sat. aq. $NaHCO_3$ (10 mL). The aqueous layer was back-extracted with DCM (2×5 mL). The combined organic phase was dried over $Na_2SO_4$, filtered, and concentrated. The residue was purified by CombiFlash® using silica gel as the stationary phase and was eluted with a gradient of MeOH in DCM (0-7.5%). Yield of 16: 273 mg (42%). [M+H] calculated for $C_{25}H_{34}N_4O_6$: 487.58, found: 487.61.

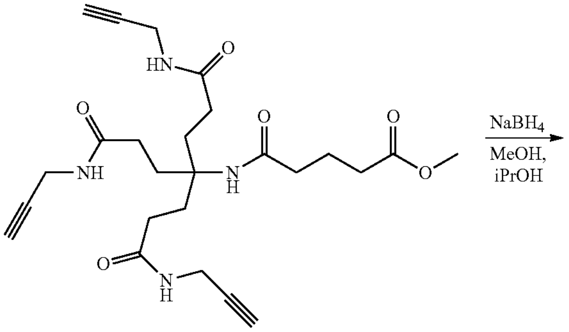

16

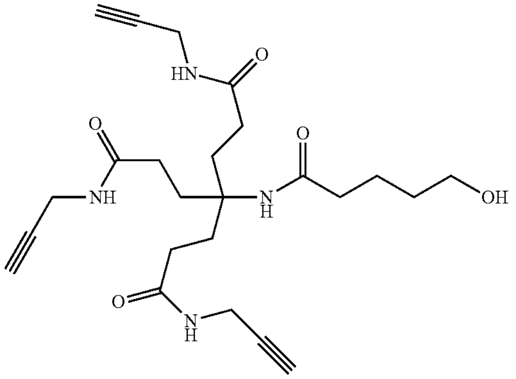

17

To a solution of 16 (173 mg, 0.36 mmol) in MeOH (0.87 mL) and iPrOH (1.74 mL) was added sodium borohydride (54 mg, 1.42 mmol) at 0° C. After 30 m, the cooling bath was removed and lithium chloride (10 mg) was added. The reaction mixture was stirred at room temperature overnight. The next day, an additional portion of sodium borohydride (27 mg, 0.71 mmol) was added, and the reaction was continued for 1 h. The reaction mixture was concentrated and purified by CombiFlash® using silica gel as the stationary phase and eluting with a gradient of MeOH in DCM (0-12%). Yield of 17: 93 mg. [M+H] calculated for $C_{24}H_{34}N_4O_5$: 459.57, found: 459.63.

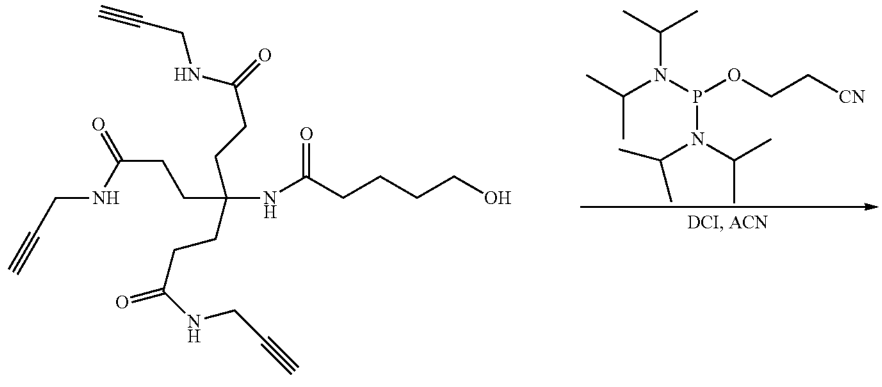

17

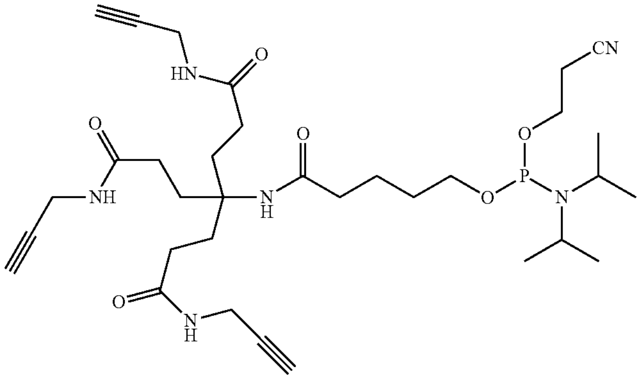

18

Compound 17 (175 mg, 0.38 mmol) was dried azeotropically from anhydrous ACN (2×5 mL) then dissolved in ACN (3 mL). The reaction mixture was cooled to 0° C. 4,5-Dicyanoimidazole (22.5 mg, 0.19 mmol) was added followed by 2-cyanoethyl N,N,N',N'-tetraisopropylphosphorodiamidite (173 mg, 0.57 mmol). The reaction mixture was stirred at 0° C. for 30 m then rt for 30 m. The reaction mixture was concentrated to an oil then dissolved in DCM (15 mL). The mixture was washed with sat. aq. $NaHCO_3$ (5 mL). The organic phase was dried over $Na_2SO_4$, filtered, and concentrated. The residue was purified by CombiFlash® using silica gel as the stationary phase and was eluted with a gradient of EtOAc in DCM (50-100%) containing 1% triethylamine. Yield of 18 (Compound 3): 132 mg (53%). [M+H] calculated for $C_{33}H_{51}N_6O_6P$: 659.79, found: 659.93.

Example 4. Synthesis of Compound 4 (2-cyanoethyl ((1r,4r)-4-((11,17-dioxo-14-(3-oxo-3-((2-(2-(prop-2-yn-1-yloxy)ethoxy)ethyl)amino)propyl)-4,7,21,24-tetraoxa-10,18-diazaheptacosa-1,26-diyn-14-yl)carbamoyl)cyclohexyl) diisopropylphosphoramidite

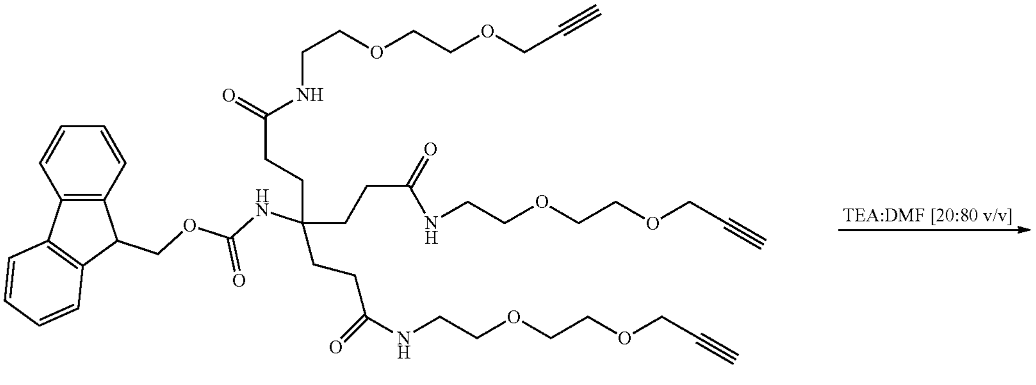

19

-continued
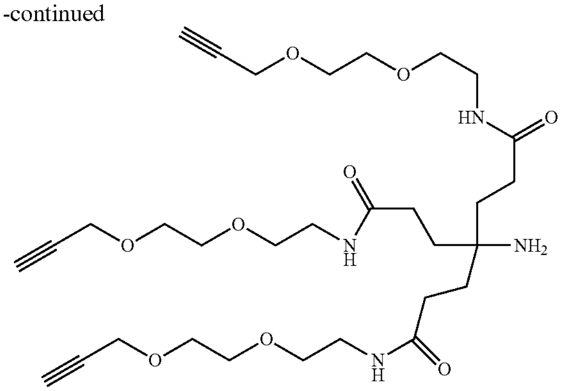
20
To a solution of 19 (4.42 g, 5.23 mmol) in DMF (25 mL) was added triethylamine (3.63 g, 5.00 mL. 35.9 mmol) at room temperature. The reaction mixture was stirred overnight. The reaction mixture was then concentrated and purified by CombiFlash® using silica gel as the stationary phase and was eluted with a gradient of MeOH in DCM (0-20%). Yield of 20: 3.08 g (95%). $^1$H NMR (400 MHz, DMSO-d6): δ 7.82 (t, 3H), 4.14 (d, 6H), 3.58-3.49 (m, 12H), 3.42-3.36 (m, 9H), 3.17 (q, 6H), 2.05 (m, 6H), 1.41 (m, 6H).
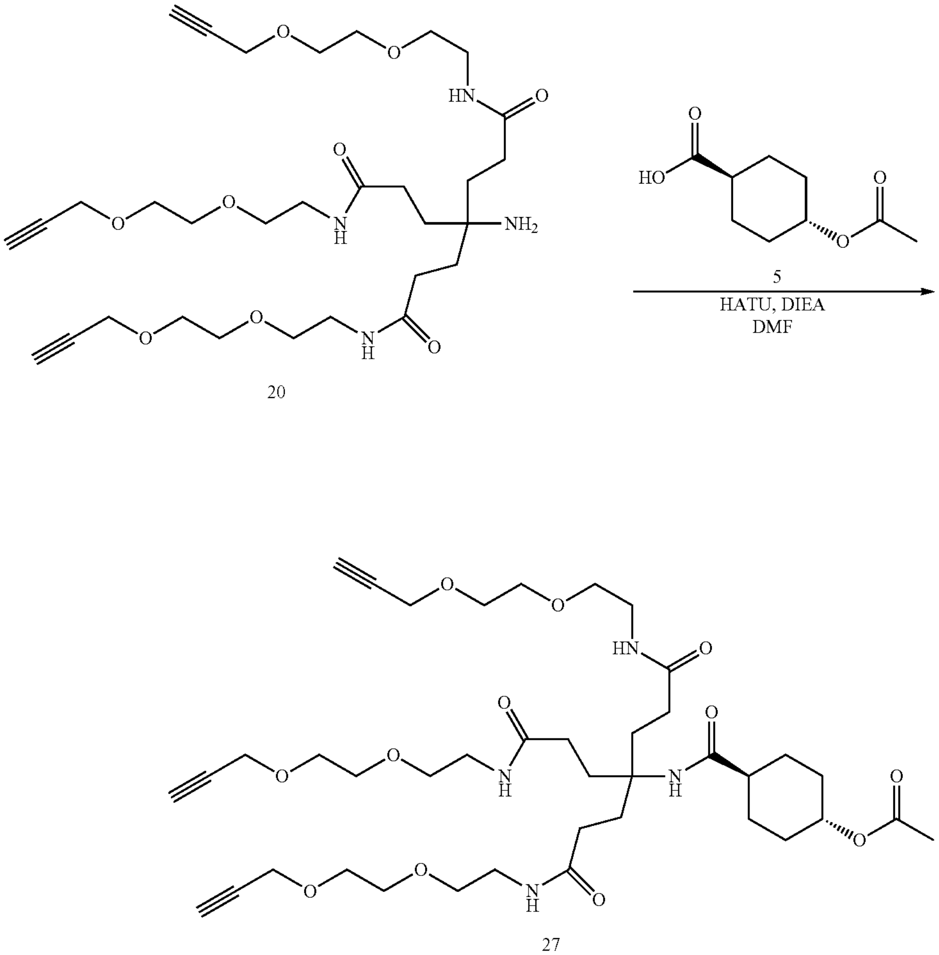
20
5
27

To a solution of 20 (900 mg, 1.45 mmol) and compound 5 (404 mg, 2.17 mmol) in DMF (7 mL) was added O-(7-azabenzotriazol-1-yl)-N,N,N',N'-tetramethyluronium hexafluorophosphate (HATU, 550 mg, 2.17 mmol) followed by DIEA (374 mg, 503 μL, 2.90 mmol) at 0° C. The cooling bath was removed, and the reaction mixture was stirred at room temperature overnight. The reaction mixture was concentrated to an orange oil that was dissolved in DCM (25 mL). The mixture was washed with 1 M HCl (2×10 mL) and sat. aq. $NaHCO_3$ (10 mL). The organic phase was dried over $Na_2SO_4$, filtered, and concentrated. The residue was purified by CombiFlash® using silica gel as the stationary phase and was eluted with a gradient of MeOH in DCM (0-8%). Yield of compound 27: 880 mg (77%). [M+H] calculated for $C_{40}H_{62}N_4O_{12}$: 791.96, found: 792.08.

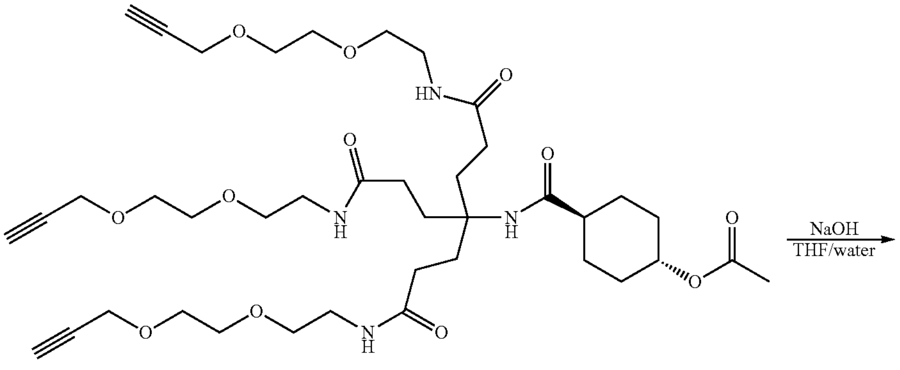

27

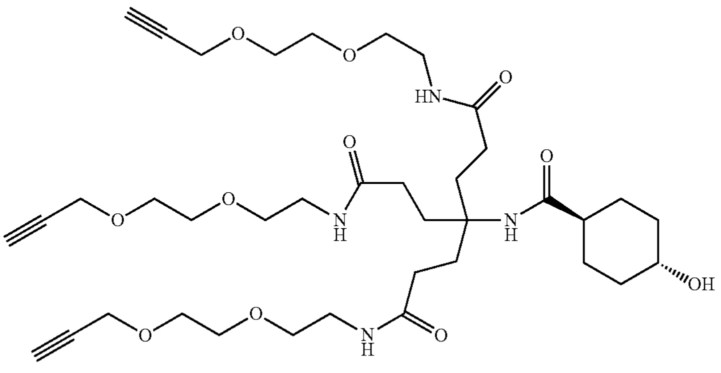

28

To a solution of compound 27 (925 mg, 1.17 mmol) in THF (6 mL) was added 1 M NaOH (5.85 mL, 5.85 mmol) at room temperature. The mixture was heated to 35° C. for 2 h. The reaction mixture was neutralized to pH=6 using 2 M HCl. Sodium chloride (approx. 3 g) was added to the aqueous phase, and the mixture was extracted with DCM (3×40 mL). The combined organic phase was dried over $Na_2SO_4$, filtered, and concentrated. The residue was purified by CombiFlash® using silica gel as the stationary phase and was eluted with a gradient of MeOH in DCM (0-12%). Yield of compound 28: 580 mg (66%). $^1H$ NMR (400 MHz, DMSO-d6): δ 7.82 (t, 3H), 7.04 (s, 1H), 4.51 (d, 1H), 4.14 (d, 6H), 3.58-3.49 (m, 12H), 3.42-3.36 (m, 9H), 3.18 (q, 6H), 2.06-1.92 (m, 7H), 1.88-1.62 (m, 10H), 1.35 (m, 2H), 1.10 (m, 2H).

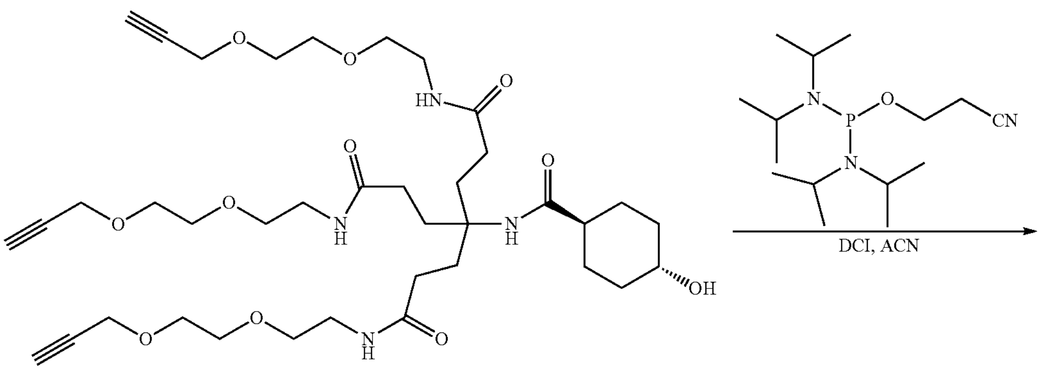

28

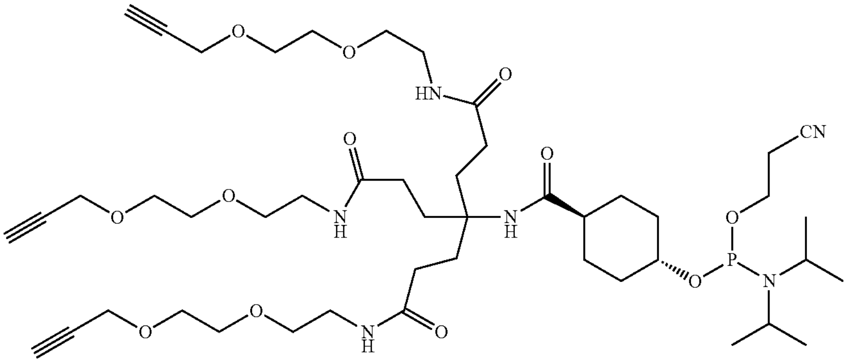

29

Compound 28 (577 mg, 0.77 mmol) was dried azeotropically from anhydrous ACN (2×20 mL) then dissolved in ACN (10 mL). The reaction mixture was cooled to 0° C. 4,5-Dicyanoimidazole (45.5 mg, 0.39 mmol) was added followed by 2-cyanoethyl N,N,N',N'-tetraisopropylphosphorodiamidite (348 mg, 1.12 mmol). The cooling bath was removed, and the reaction mixture was stirred for 1 h at room temperature. The reaction mixture was concentrated to an oil then dissolved in DCM (30 mL). The mixture was washed with sat. aq. $NaHCO_3$ (2×10 mL). The organic phase was dried over $Na_2SO_4$, filtered, and concentrated. The residue was purified by CombiFlash® using silica gel as the stationary phase and was eluted with a gradient of MeOH in DCM (0-2%) containing 1% triethylamine. Yield of 29 (Compound 4): 610 mg (83%). $^1$H NMR (400 MHz, DMSO-d6): δ 7.82 (t, 3H), 7.07 (s, 1H), 4.14 (d, 6H), 3.76-3.60 (m, 2H), 3.58-3.48 (m, 14H), 3.42-3.36 (m, 9H), 3.18 (q, 6H), 2.74 (t, 2H), 2.12-2.04 (m, 1H), 2.02-1.89 (m, 8H), 1.83-1.67 (m, 8H), 1.45-1.31 (m, 2H), 1.30-1.21 (m, 2H), 1.13 (dd, 12H). $^{31}$P NMR (400 MHz, DMSO-d6): δ 144.6.

Example 5. Synthesis of Compound 5 (2-cyanoethyl ((1s,4s)-4-((11,17-dioxo-14-(3-oxo-3-((2-(2-(prop-2-yn-1-yloxy)ethoxy)ethyl)amino)propyl)-4,7,21,24-tetraoxa-10,18-diazaheptacosa-1,26-diyn-14-yl)carbamoyl)cyclohexyl) diisopropylphosphoramidite

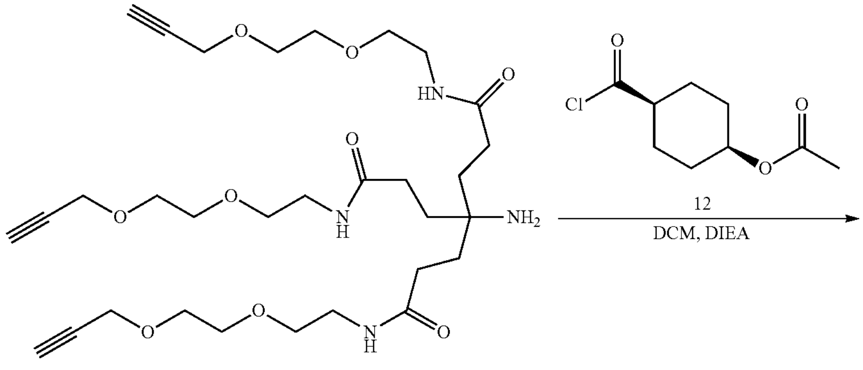

20

-continued

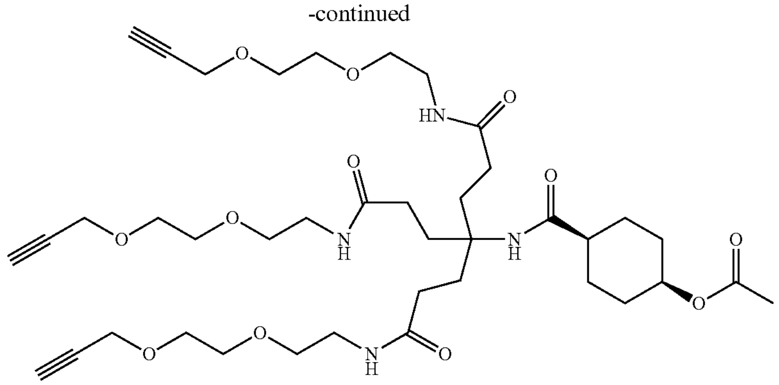

24

To a solution of 20 (1070 mg, 1.72 mmol) in DCM (7 mL) was added pyridine (1.22 g, 1.25 mL, 15.5 mmol). The reaction mixture was cooled to 0° C. and a solution of 12 (1.06 g, 5.15 mmol) in DCM (3.5 mL) was added dropwise. The cooling bath was removed, and the mixture was stirred for 2 h at room temperature. The mixture was diluted with DCM (20 mL) and quenched with sat. aq. $NH_4Cl$ (10 mL). The layers were separated, and the organic phase was washed with sat. aq. $NaHCO_3$ (10 mL) and brine (10 mL). The organic phase was dried over $Na_2SO_4$, filtered, and concentrated. The residue was purified by CombiFlash® using silica gel as the stationary phase and was eluted with a gradient of MeOH in DCM (0-7%). Yield of compound 24: 295 mg (22%). [M+H] calculated for $C_{40}H_{62}N_4O_{12}$: 791.96, found: 792.08.

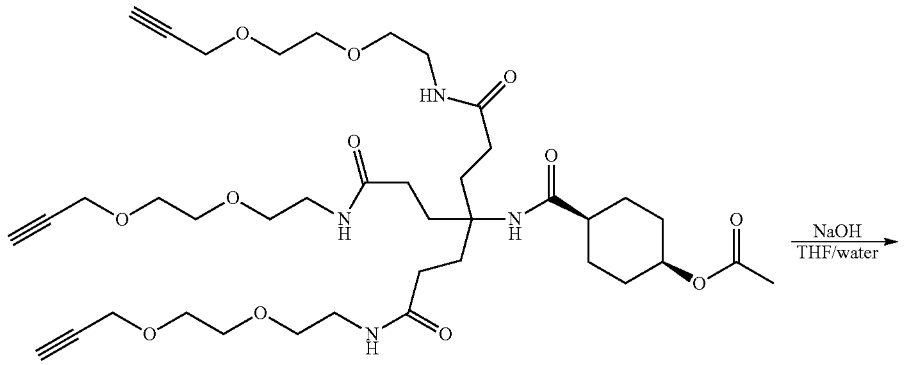

24

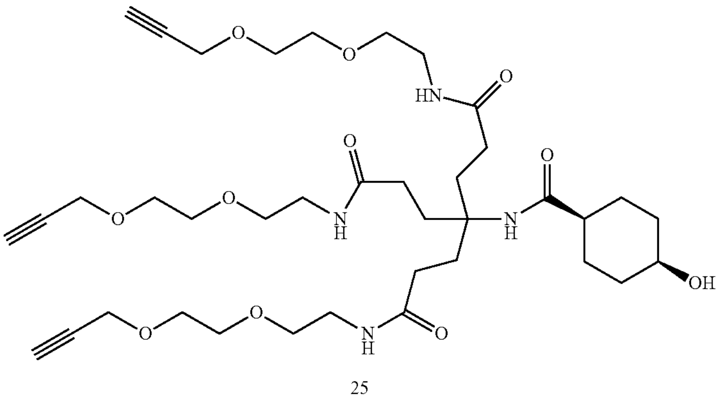

25

To a solution of compound 24 (290 mg, 0.37 mmol) in THF (2 mL) was added 1 M NaOH (1.83 mL, 1.83 mmol) at room temperature. The mixture was heated to 35° C. for 3 h. The reaction mixture was quenched with sat. aq. $NH_4Cl$ (8 mL) and further acidified to pH=6 using 2 M HCl. The mixture was extracted with DCM (3×15 mL). The combined organic phase was dried over $Na_2SO_4$, filtered, and concentrated. The residue was purified by CombiFlash using silica gel as the stationary phase and was eluted with a gradient of MeOH in DCM (0-12%). Yield of compound 25: 183 mg (67%). $^1$H NMR (400 MHz, DMSO-d6): δ 7.83 (t, 3H), 6.97 (s, 1H), 4.24 (d, 1H), 4.14 (d, 6H), 3.75 (s, br, 1H), 3.58-3.49 (m, 12H), 3.42-3.36 (m, 9H), 3.18 (q, 6H), 2.10 (m, 1H), 1.97 (m, 6H), 1.82-1.60 (m, 10H), 1.38 (m, 4H).

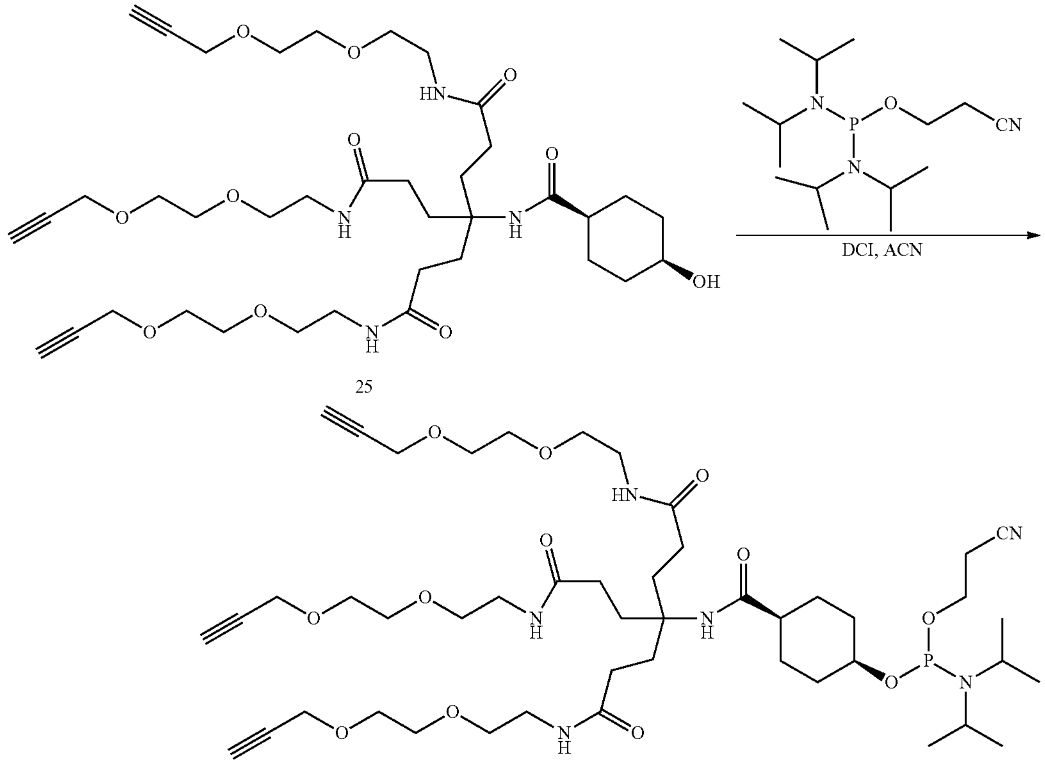

25

26

Compound 25 (180 mg, 0.24 mmol) was dried azeotropically from anhydrous ACN (2×5 mL) then dissolved in ACN (2 mL). The reaction mixture was cooled to 0° C. 4,5-Dicyanoimidazole (14.2 mg, 0.12 mmol) was added followed by 2-cyanoethyl N,N,N',N'-tetraisopropylphosphorodiamidite (109 mg, 0.36 mmol). The reaction mixture was stirred at 0° C. for 30 m then rt for 1.5 h. An additional portion of 2-cyanoethyl N,N,N',N'-tetraisopropylphosphorodiamidite (36 mg, 0.12 mmol) was added, and the reaction mixture was stirred an additional 3 h. The reaction mixture was concentrated to an oil then dissolved in DCM (15 mL). The mixture was washed with a mixture sat. aq. $NaHCO_3$ (2.5 mL) and water (2.5 mL). The organic phase was dried over $Na_2SO_4$, filtered, and concentrated. The residue was purified by CombiFlash® using silica gel as the stationary phase and was eluted with a gradient of MeOH in DCM (0-2%) containing 1% triethylamine. Yield of 26 (Compound 5): 116 mg (51%). [M+H] calculated for $C_{47}H_{77}N_6O_{12}P$: 950.15, found: 950.18.

Example 6. Synthesis of Compound 6 (2-cyanoethyl (11,16-dioxo-14,14-bis(3-oxo-3-((2-(2-(prop-2-yn-1-yloxy)ethoxy)ethyl)amino)propyl)-4,7-dioxa-10,15-diazaicos-1-yn-20-yl) diisopropylphosphoramidite

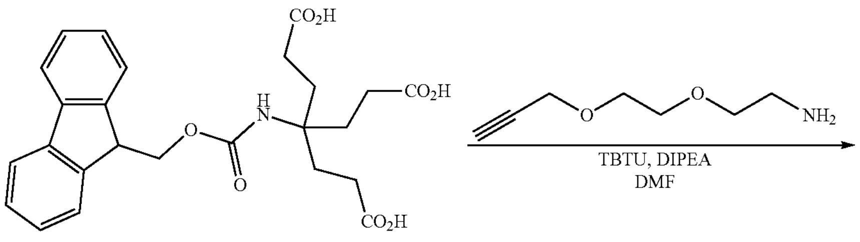

1

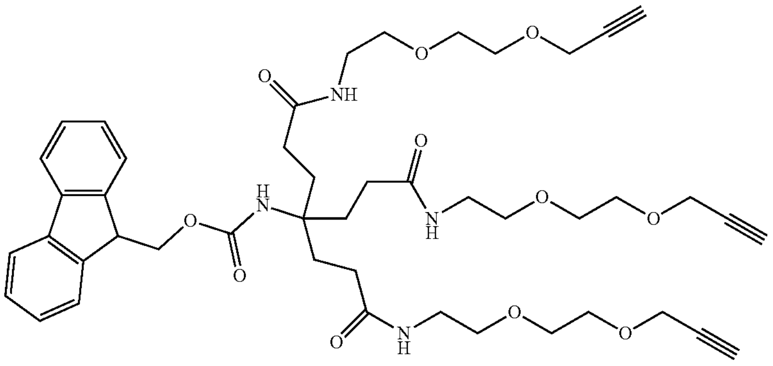

19

To a solution of 1 (3.00 g, 6.39 mmol) and DIPEA (2.89 g, 3.89 mL 16.47 mL, 22.4 mmol) in DMF (50 mL) was added TBTU (6.77 g, 21.1 mmol) at 0° C. A solution of propargyl-PEG2-amine (3.02 g, 21.1 mmol) in DMF (5 mL) was then added dropwise. The cooling bath was removed, and the reaction mixture was stirred for 2 h at room temperature. The reaction mixture was diluted with DCM (30 mL) and washed with 1 N HCl (2×30 mL) and sat. aq. $NaHCO_3$ (2×30 mL). The organic phase was dried over $Na_2SO_4$, filtered, and concentrated. The residue was purified by CombiFlash® using silica gel as the stationary phase and was eluted with a gradient of MeOH in DCM (0-10%). Yield of 19: 4.42 g (82%).

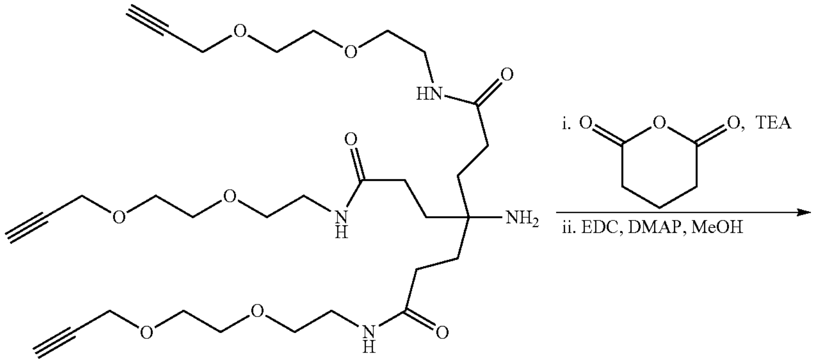

20

-continued

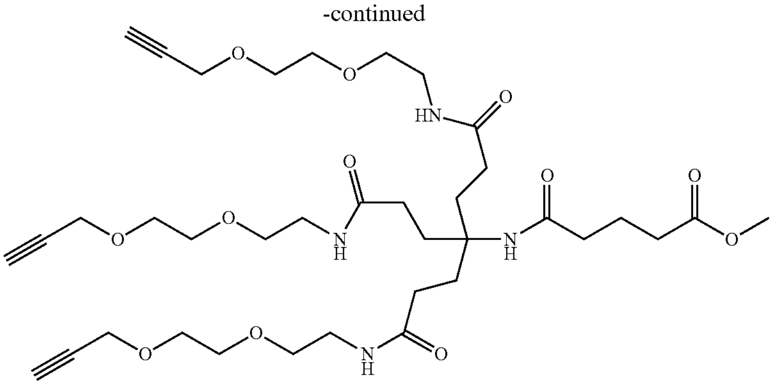

21

To a solution of 20 (960 mg, 1.54 mmol) in DCM (8 mL) was added triethylamine (468 mg, 645 μL, 4.62 mmol) and glutaric anhydride (220 mg, 1.93 mmol). The reaction mixture was stirred overnight at room temperature. The next day, DMAP (9.4 mg, 0.077 mmol), MeOH (494 mg, 624 μL, 15.42 mmol), and N-(3-dimethylaminopropyl)-N'-ethylcarbodiimide hydrochloride (591 mg, 3.08 mmol) were added at room temperature. The reaction mixture was stirred for 5 h. The reaction mixture was concentrated to an oil which was dissolved in DCM (45 mL) then washed with sat. aq. $NaHCO_3$ (10 mL) and sat aq. $NH_4Cl$ (10 mL). The organic phase was dried over $Na_2SO_4$, filtered, and concentrated. The residue was purified by CombiFlash® using silica gel as the stationary phase and was eluted with a gradient of MeOH in DCM (0-7.5%). Yield of 21: 880 mg (76%). [M+H] calculated for $C_{37}H_{58}N_4O_{12}$: 751.90, found: 751.90.

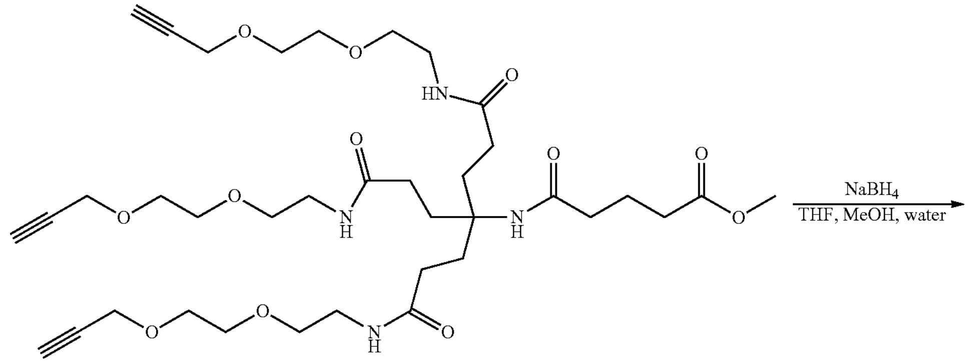

21

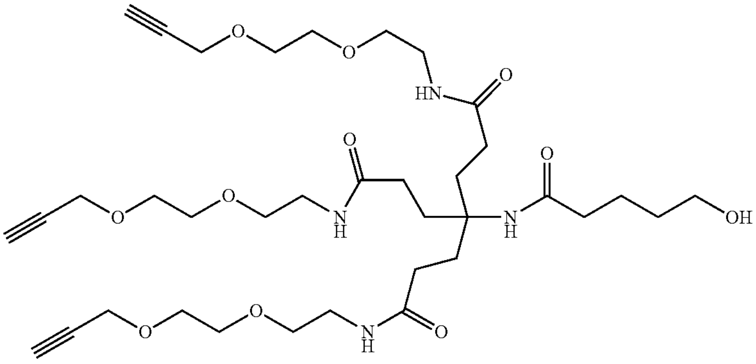

22

To a solution of 21 (877 mg, 1.17 mmol) in THF (4 mL) and MeOH (1.75 mL) was added a solution of lithium chloride (25 mg, 0.58 mmol) in water (1.75 mL). The mixture was cooled to 0° C. and sodium borohydride (265 mg, 7.01 mmol) was added in one portion. The cooling bath was removed, and the reaction mixture was stirred at room temperature overnight. The reaction mixture was quenched by addition of sat. aq. $NH_4Cl$ (5 mL). After stirring for 10 m, the mixture was concentrated to remove THF and MeOH. The residual aqueous phase was diluted with water (5 mL) and extracted with DCM (3×20 mL). The combined organic phase was dried over $Na_2SO_4$, filtered, and concentrated. The residue was purified by CombiFlash® using silica gel as the stationary phase and was eluted with a gradient of MeOH in DCM (0-12%). Yield of 22: 562 mg (66%). [M+H] calculated for $C_{36}H_{58}N_4O_{11}$: 723.19, found: 723.81.

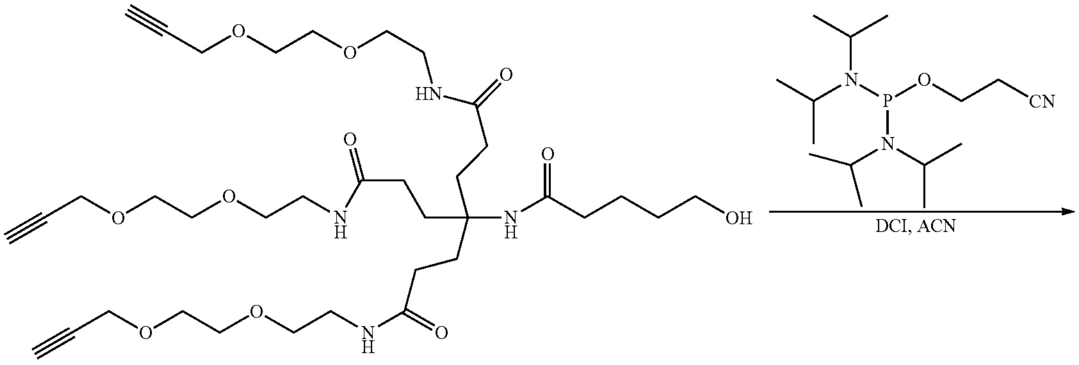

22

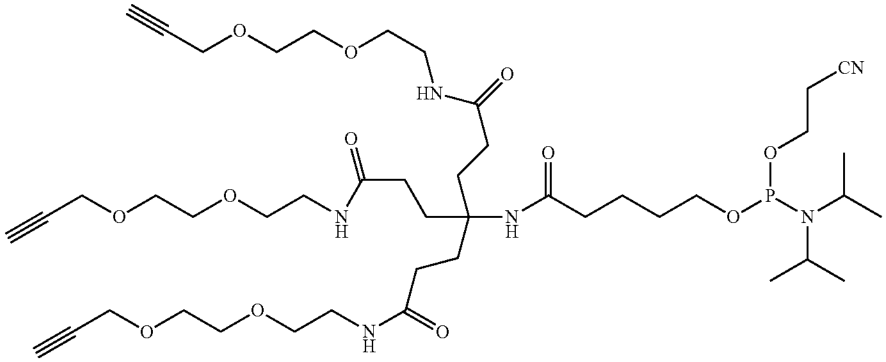

Compound 6

22 (560 mg, 0.77 mmol) was dried azeotropically from anhydrous ACN (2×10 mL) then dissolved in ACN (5 mL). The reaction mixture was cooled to 0° C. 4,5-Dicyanoimidazole (45.7 mg, 0.39 mmol) was added followed by 2-cyanoethyl N,N,N',N'-tetraisopropylphosphorodiamidite (350 mg, 1.16 mmol). The reaction mixture was stirred at 0° C. for 30 m then rt for 30 m. The reaction mixture was concentrated to an oil then dissolved in DCM (30 mL). The mixture was washed with sat. aq. $NaHCO_3$ (2×10 mL) and brine (10 mL). The organic phase was dried over $Na_2SO_4$, filtered, and concentrated. The residue was purified by CombiFlash® using silica gel as the stationary phase and was eluted with a gradient of MeOH in DCM (0-2%) containing 1% triethylamine. Yield of Compound 6: 434 mg (61%). $^1$H NMR (400 MHz, DMSO-d6): δ 7.82 (t, 3H), 7.13 (s, 1H), 4.14 (d, 6H), 3.72-3.65 (m, 2H), 3.58-3.48 (m, 16H), 3.42-3.36 (m, 9H), 3.17 (q, 6H), 2.75 (t, 2H), 2.09-1.92 (m, 8H), 1.83-1.72 (m, 6H), 1.52 (m, 4H), 1.13 (dd, 12H). $^{31}$P NMR (400 MHz, DMSO-d6): δ 146.3.

Example 7. Synthesis of Compound 7 (2-cyanoethyl (4-((11,17-dioxo-14-(3-oxo-3-((2-(2-(prop-2-yn-1-yloxy)ethoxy)ethyl)amino)propyl)-4,7,21,24-tetraoxa-10,18-diazaheptacosa-1,26-diyn-14-yl) carbamoyl)phenyl) diisopropylphosphoramidite

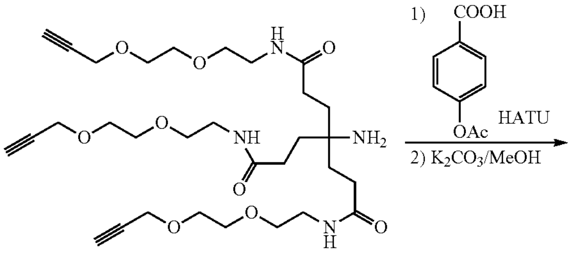

1

-continued

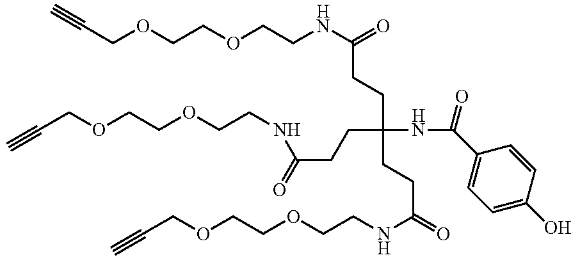

2

Step 1. To a solution of 1 (200 mg, 0.32 mmol), 4-acetoxybenzoic acid (86.4 mg, 0.48 mmol), N,N-diisopropylethylamine (123.8 mg, 0.17 mL, d=0.742 g/mL, 0.96 mmol) in DMF (2 mL) was added HATU (243.2 mg, 0.64 mmol). The reaction mixture was stirred at room temperature. After confirming all starting material was consumed by LC-MS, the reaction mixture was quenched by 2 mL of saturated $NaHCO_3$ aqueous solution and extracted with ethyl acetate (10 mL×3). The combined organic layer was washed with HCl (aq) and brine sequentially. The organic layer was dried over $Na_2SO_4$ and concentrated under high vacuum. The crude was loaded on to a silica column and purified (MPA: DCM, MPB: 20% MeOH in DCM, 0-50% ramp in 30 min) to afford the product. Yield: 133 mg.

Step 2. The amide product from Step 1 was dissolved in 2 mL of MeOH and 100 mg of $K_2CO_3$ was added into the reaction. After stirring at room temperature overnight, the reaction mixture was filtered thought a short pad of silica gel. The filtrate was collected and concentrated under reduced pressure. Yield: 115 mg, 48% for two steps. MS (ESI) m/z calculated for $C_{38}H_{53}N_4O_{11}$ [M−H] 741.37, found: 741.67.

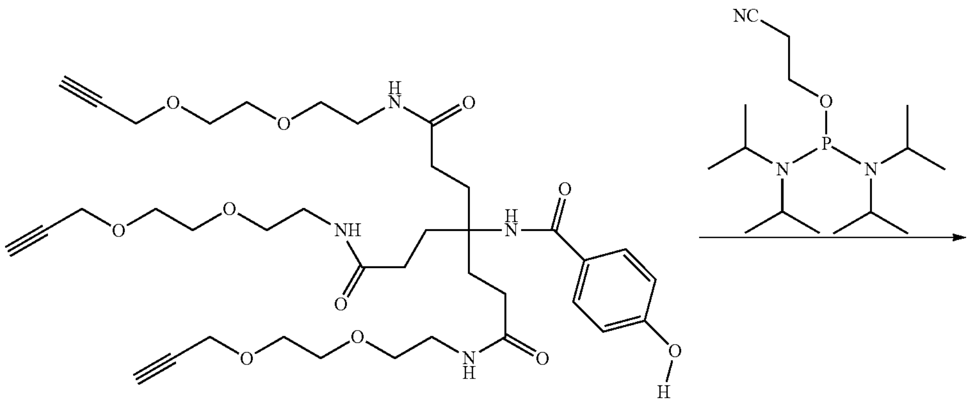

2

-continued

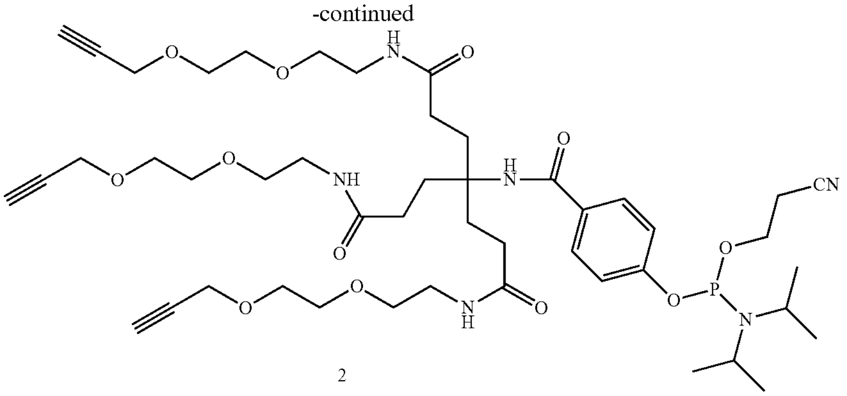

2

Compound 7

To a solution of 2 (100 mg, 0.1346 mmol)), diisopropylammonium tetrazolide (11.5 mg, 0.0673 mmol) and 3 Å molecule sieves (20 mg) in DCM (2 mL) was added 2-cyanoethyl N,N,N',N'-tetraisopropylphosphorodiamidite (60.9 mg, 0.064 mL, 0.2019 mmol, 1.5 eq). The reaction mixture was stirred at room temperature. After confirming by LC-MS that all starting material was consumed, the reaction mixture was quenched by 2 mL of saturated $NaHCO_3$ aqueous solution and extracted with ethyl acetate (10 mL×3). The organic layer was dried over $Na_2SO_4$ and concentrated under high vacuum. The crude was loaded on to a silica column and purified (MPA: 1% TEA in DCM, MPB: 1% TEA and 4% MeOH in DCM, 0-50% ramp in 30 min) to afford Compound 7. Yield: 105 mg (83%). MS (ESI) m/z calculated for $C_{47}H_{70}N_6O_{12}P$ [M−H] 941.48, found 941.88.

Example 8. Synthesis of Compound 8 (2-cyanoethyl (3-((11,17-dioxo-14-(3-oxo-3-((2-(2-(prop-2-yn-1-yloxy)ethoxy)ethyl)amino)propyl)-4,7,21,24-tetraoxa-10,18-diazaheptacosa-1,26-diyn-14-yl)carbamoyl)phenyl) diisopropylphosphoramidite

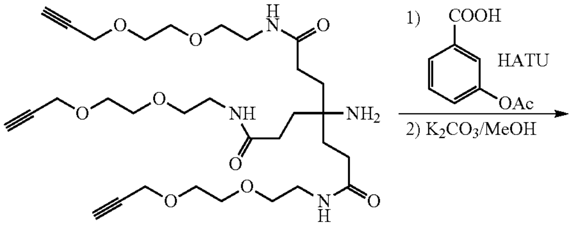

1

-continued

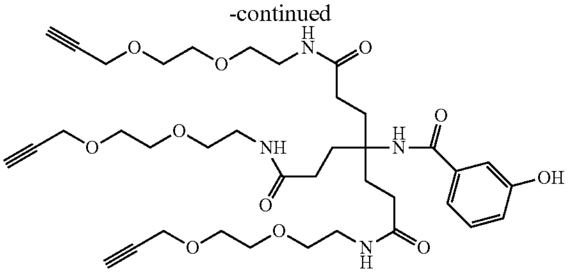

3

Step 1. To a solution of 1 (200 mg, 0.32 mmol), 3-acetoxybenzoic acid (86.7 mg, 0.48 mmol), N,N-diisopropylethylamine (123.8 mg, 0.17 mL, d=0.742 g/mL, 0.96 mmol) in DMF (2 mL) was added HATU (243.2 mg, 0.64 mmol). The reaction mixture was stirred at room temperature. After confirming all starting material was consumed by LC-MS, the reaction mixture was quenched by 2 mL of saturated $NaHCO_3$ aqueous solution and extracted with ethyl acetate (10 mL×3). The combined organic layer was washed with HCl (aq) and brine sequentially. The organic layer was dried over $Na_2SO_4$ and concentrated under high vacuum. The crude was loaded on to a silica column and purified (MPA: DCM, MPB: 10% MeOH in DCM, 0-40% ramp in 30 min) to afford the product. Yield: 148 mg.

Step 2. The amide product from Step 1 was dissolved in 2 mL of MeOH and 100 mg of $K_2CO_3$ was added into the reaction. After stirring at room temperature overnight, the reaction mixture was filtered thought a short pad of silica gel. The filtrate was collected and concentrated under reduced pressure. Yield: 126 mg, 53% for two steps. MS (ESI) m/z calculated for $C_{38}H_{55}N_4O_{11}$ [M+H] 743.39, found: 743.65.

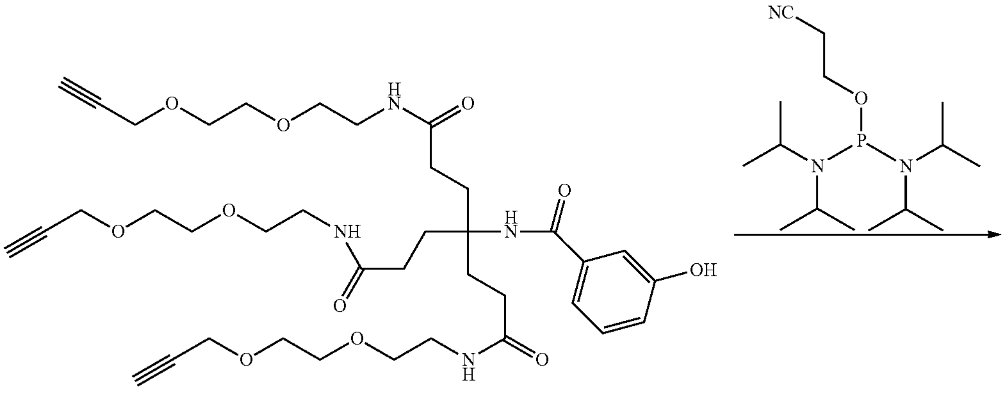

3

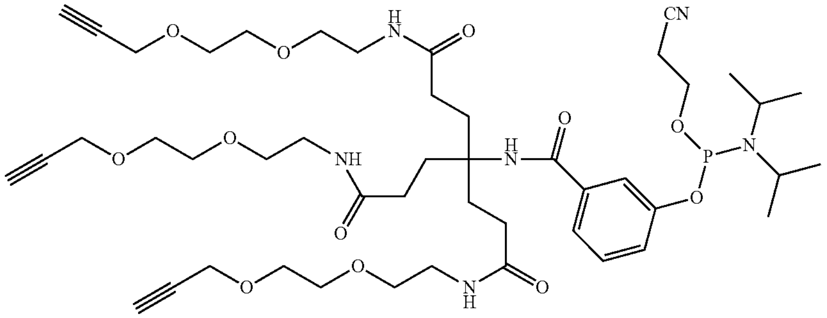

Compound 8

To a solution of 3 (125 mg, 0.1683 mmol)), diisopropylammonium tetrazolide (14.4 mg, 0.0841 mmol) and 3 Å molecule sieves (20 mg) in DCM (2 mL) was added 2-cyanoethyl N,N,N',N'-tetraisopropylphosphorodiamidite (76.1 mg, 0.08 mL, 0.2524 mmol, 1.5 eq). The reaction mixture was stirred at room temperature. After confirming all starting material was consumed monitored by LC-MS, the reaction mixture was quenched by 2 mL of saturated $NaHCO_3$ aqueous solution and extracted with ethyl acetate (10 mL×3). The organic layer was dried over $Na_2SO_4$ and concentrated under high vacuum. The crude was loaded on to a silica column and purified (MPA: 1% TEA in DCM, MPB: 1% TEA and 4% MeOH in DCM, 0-50% ramp in 30 min) to afford Compound 8. Yield: 130 mg (82%). MS (ESI) m/z calculated for $C_{47}H_{70}N_6O_{12}P$ [M−H] 941.48, found 941.79.

Example 9. Synthesis of Compound 9 (2-cyanoethyl (2-((11,17-dioxo-14-(3-oxo-3-((2-(2-(prop-2-yn-1-yloxy)ethoxy)ethyl)amino)propyl)-4,7,21,24-tetraoxa-10,18-diazaheptacosa-1,26-diyn-14-yl)carbamoyl)phenyl) diisopropylphosphoramidite

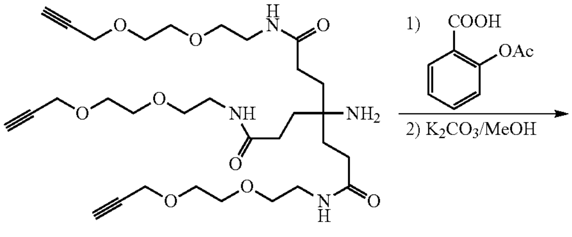

1

-continued

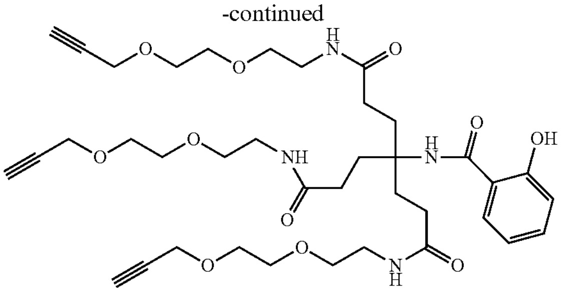

4

Step 1. To a solution of 1 (200 mg, 0.32 mmol), triethyl amine (97.3 mg, 0.134 mL, d=0.726 g/mL, 0.96 mmol) in DCM (2 mL) was added O-acetylsalicyloyl chloride (127.6 mg, 0.6423 mmol, 1.2 eq, CAS Registry Number: 5538-51-2). The reaction mixture was stirred at room temperature. After confirming all starting material was consumed by LC-MS, the reaction mixture was quenched by 2 mL of saturated $NaHCO_3$ aqueous solution and extracted with ethyl acetate (10 mL×3). The combined organic layer was washed with HCl (aq) and brine sequentially. The organic layer was dried over $Na_2SO_4$ and concentrated under high vacuum. The crude was loaded on to a silica column and purified (MPA: DCM, MPB: 10% MeOH in DCM, 0-50% ramp in 30 min) to afford the product. Yield: 177.8 mg.

Step 2. The amide product from Step 1 was dissolved in 2 mL of MeOH and 100 mg of $K_2CO_3$ was added into the reaction. After stirring at room temperature overnight, the reaction mixture was filtered thought a short pad of silica gel. The filtrate was collected and concentrated under reduced pressure. Yield: 126 mg, 53% for two steps. MS (ESI) m/z calculated for $C_{38}H_{53}N4O_{11}$ [M−H] 741.39, found: 741.67.

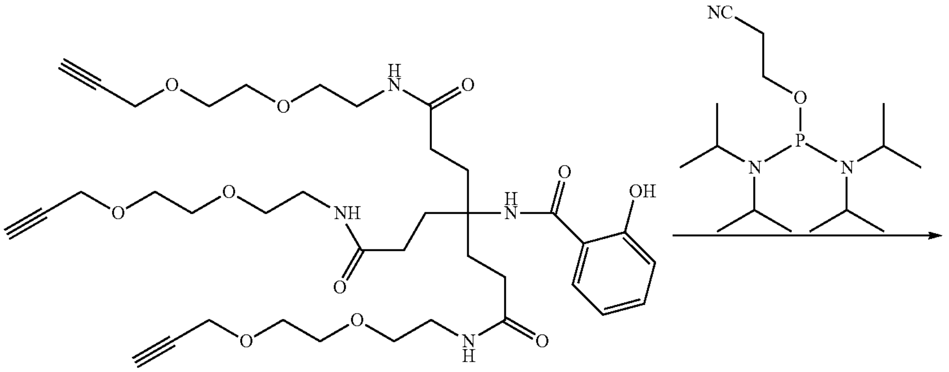

4

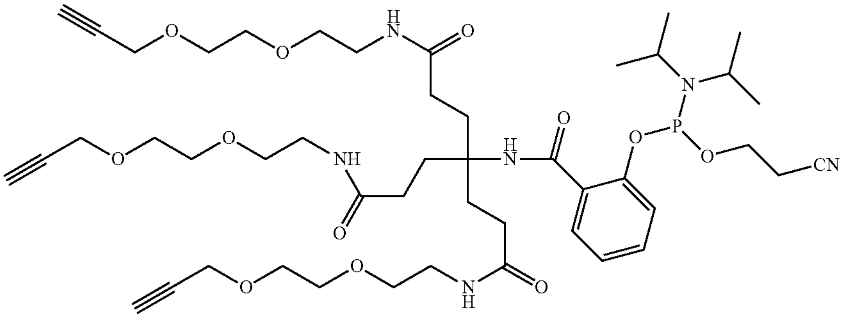

Compound 9

To a solution of 4 (105 mg, 0.1457 mmol)), diisopropylammonium tetrazolide (12.5 mg, 0.0728 mmol) and 3 Å molecule sieves (20 mg) in DCM (2 mL) was added 2-cyanoethyl N,N,N',N'-tetraisopropylphosphorodiamidite (66 mg, 0.069 mL, 0.2185 mmol, 1.5 eq). The reaction mixture was stirred at room temperature. After confirming all starting material was consumed monitored by LC-MS, the reaction mixture was quenched by 2 mL of saturated $NaHCO_3$ aqueous solution and extracted with ethyl acetate (10 mL×3). The organic layer was dried over $Na_2SO_4$ and concentrated under high vacuum. The crude was loaded on to a silica column and purified (MPA: 1% TEA in DCM, MPB: 1% TEA and 4% MeOH in DCM, 0-50% ramp in 30 min) to afford Compound 9. Yield: 181 mg (83%). MS (ESI) m/z calculated for $C_{47}H_{70}N_6O_{12}P$ [M−H] 941.48, found 941.79.

Example 10. Synthesis of Compound 10 (2-cyanoethyl (4'-((11,17-dioxo-14-(3-oxo-3-((2-(2-(prop-2-yn-1-yloxy)ethoxy)ethyl)amino)propyl)-4,7,21,24-tetraoxa-10,18-diazaheptacosa-1,26-diyn-14-yl) carbamoyl)-[1,1'-biphenyl]-4-yl) diisopropylphosphoramidite

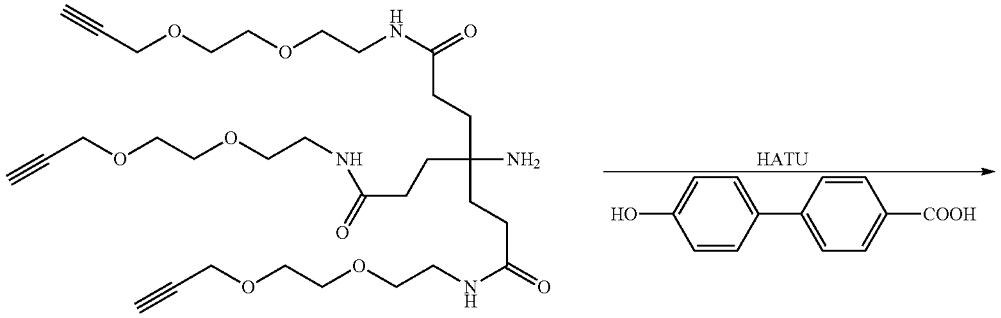

1

-continued

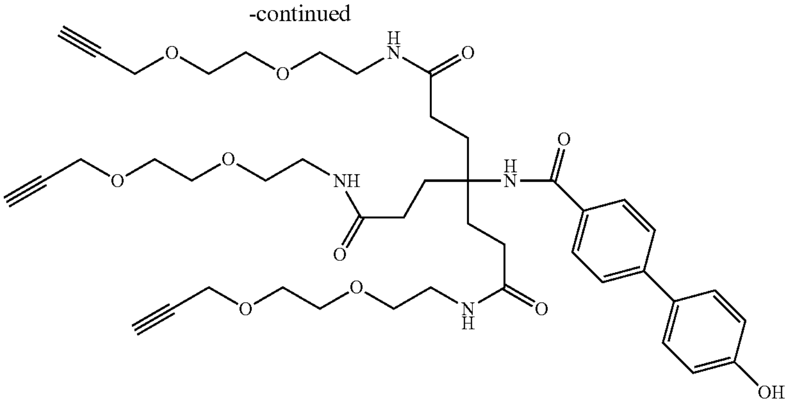

5

To a solution of 1 (200 mg, 0.3212 mmol), 4'-Hydroxy-4-biphenylcarboxylic acid (103.2 mg, 0.4817 mmol), and N,N-diisopropylethylamine (124.5 mg, 0.17 mL, d=0.742 g/mL, 0.96 mmol) in DMF (2 mL) was added HATU (244.2 mg, 0.64 mmol). The reaction mixture was stirred at room temperature. After confirming by LC-MS that all starting material was consumed, the reaction mixture was quenched by 2 mL of saturated $NaHCO_3$ aqueous solution and extracted with ethyl acetate (10 mL×3). The combined organic layer was washed with HCl (aq) and brine sequentially. The organic layer was dried over $Na_2SO_4$ and concentrated under high vacuum. The crude was loaded on to a silica column and purified (MPA: DCM, MPB: 10% MeOH in DCM, 0-50% ramp in 30 min) to afford the product. Yield: 138 mg, 52%. MS (ESI) m/z calculated for $C_{44}H_{59}N_4O_{11}$ [M+H] 819.42, found: 819.90.

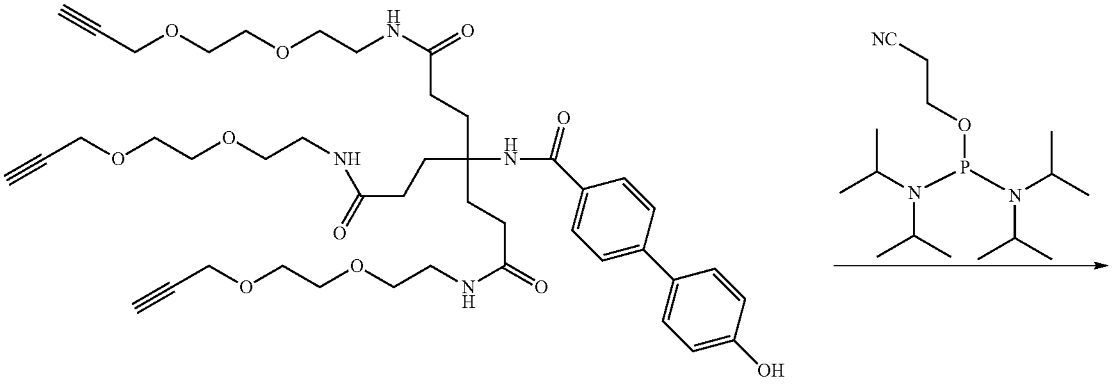

5

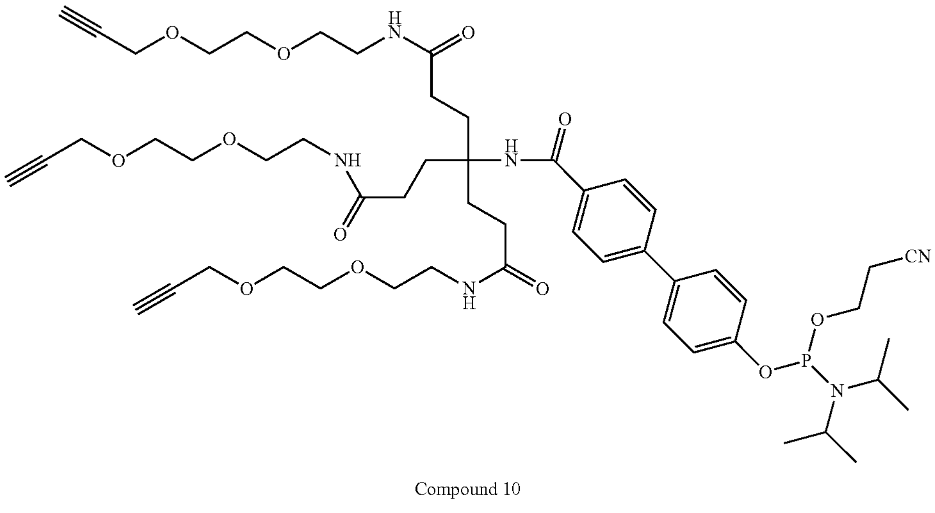

Compound 10

To a solution of 5 (138 mg, 0.1685 mmol)), diisopropylammonium tetrazolide (14.4 mg, 0.0843 mmol) and 3 Å molecule sieves (20 mg) in DCM (2 mL) was added 2-cyanoethyl N,N,N',N'-tetraisopropylphosphorodiamidite (76.2 mg, 0.08 mL, 0.2528 mmol, 1.5 eq). The reaction mixture was stirred at room temperature. After confirming by LC-MS that all starting material was consumed, the reaction mixture was quenched by 2 mL of saturated $NaHCO_3$ aqueous solution and extracted with ethyl acetate (10 mL×3). Dry over $Na_2SO_4$ and concentrate under high vacuum. The crude was loaded on to a silica column and purified (MPA: 1% TEA in DCM, MPB: 1% TEA and 4% MeOH in DCM, 0-50% ramp in 30 min) to afford Compound 10. Yield: 171 mg (99%). MS (ESI) m/z calculated for $C_{53}H_{74}N_6O_{12}P$ [M−H] 1017.51, found 1017.99.

Example 11. Synthesis of Compound 11 (2-cyanoethyl ((1r,3r)-3-((11,17-dioxo-14-(3-oxo-3-((2-(2-(prop-2-yn-1-yloxy)ethoxy)ethyl)amino)propyl)-4,7,21,24-tetraoxa-10,18-diazaheptacosa-1,26-diyn-14-yl)carbamoyl)cyclobutyl) diisopropylphosphoramidite

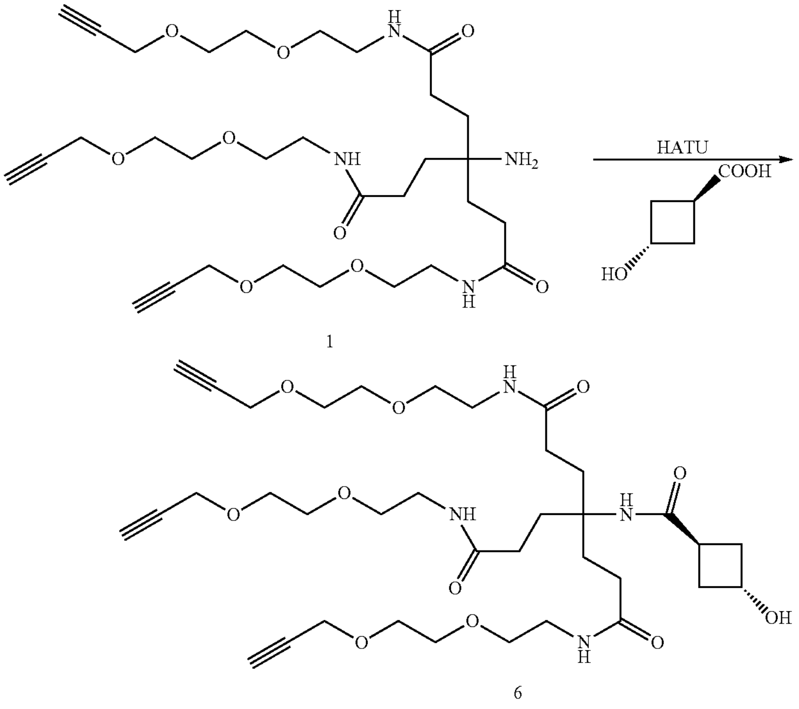

1

6

To a solution of 1 (300 mg, 0.4817 mmol), trans-3-hydroxycyclobutanecarboxylic acid (83.9 mg, 0.7226 mmol, CAS number: 1268521-85-2), and N,N-diisopropylethylamine (186.8 mg, 0.252 mL, d=0.742 g/mL, 1.4452 mmol) in DMF (3 mL) was added HATU (366.3 mg, 0.9635 mmol). The reaction mixture was stirred at room temperature. After confirming by LC-MS that all starting material was consumed, the reaction mixture was quenched with 2 mL of saturated $NaHCO_3$ aqueous solution and extracted with ethyl acetate (10 mL×3). The combined organic layer was washed with HCl (aq) and brine sequentially. The organic layer was dried over $Na_2SO_4$ and concentrated under high vacuum. The crude was loaded on to a silica column and purified (MPA: DCM, MPB: 10% MeOH in DCM, 0-100% ramp in 30 min) to afford the product. Yield: 333.2 mg, 88%. MS (ESI) m/z calculated for $C_{36}H_{57}N_4O_{11}$ [M+H] 721.40, found 721.96.

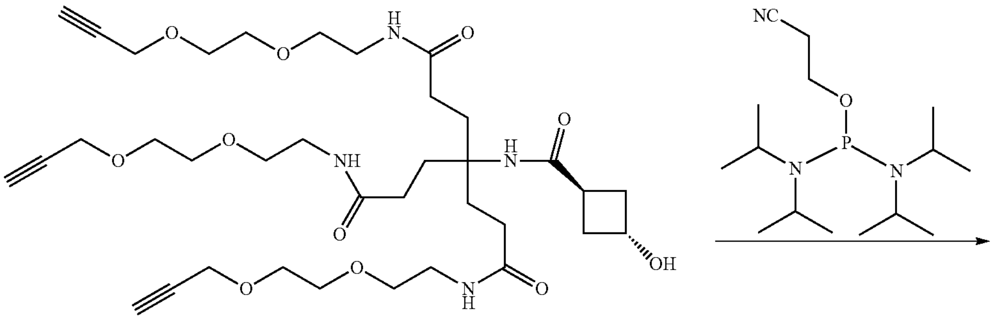

6

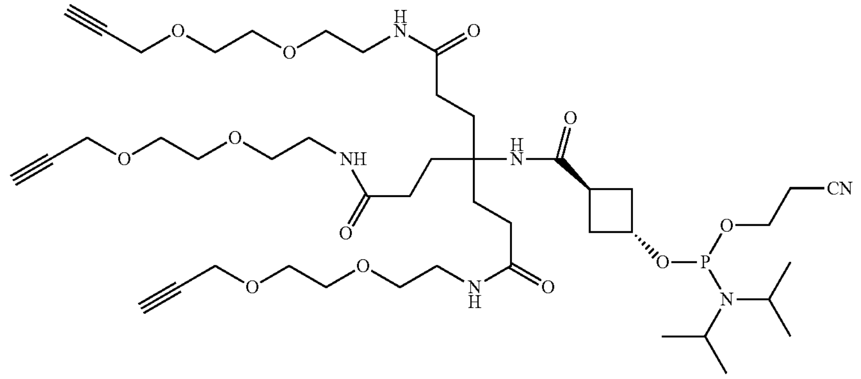

Compound 11

To a solution of 6 (166.5 mg, 0.2310 mmol)), diisopropylammonium tetrazolide (19.8 mg, 0.1155 mmol) and 3 Å molecule sieves (20 mg) in DCM (2 mL) was added 2-cyanoethyl N,N,N',N'-tetraisopropylphosphorodiamidite (104.4 mg, 0.11 mL, 0.3465 mmol, 1.5 eq). The reaction mixture was stirred at room temperature. After confirming by LC-MS that all starting material was consumed, the reaction mixture was quenched with 2 mL of saturated $NaHCO_3$ aqueous solution and extracted with ethyl acetate (10 mL×3). The organic layer was dried over $Na_2SO_4$ and concentrated under high vacuum. The crude was loaded on to a silica column and purified (MPA: 1% TEA in DCM, MPB: 1% TEA and 4% MeOH in DCM, 0-50% ramp in 30 min) to afford Compound 11. Yield: 200 mg (94%). MS (ESI) m/z calcd for $C_{45}H_{72}N_6O_{12}P$ [M−H] 919.50, found: 919.73.

Example 12. Synthesis of Compound 12 (2-cyanoethyl (4-((11,17-dioxo-14-(3-oxo-3-((2-(2-(prop-2-yn-1-yloxy)ethoxy)ethyl)amino)propyl)-4,7,21,24-tetraoxa-10,18-diazakeptacosa-1,26-diyn-14-yl) carbamoyl)bicyclo[2.2.2]octan-1-yl) diisopropylphosphoramidite -continued

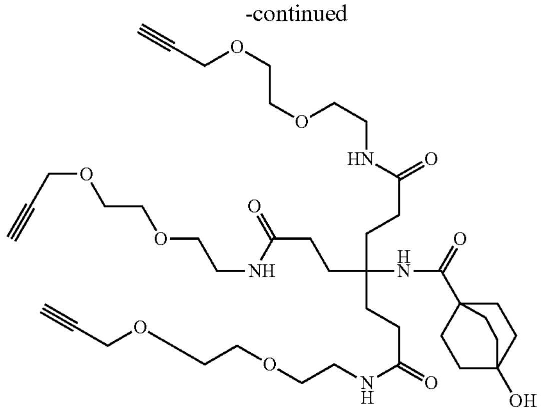

7

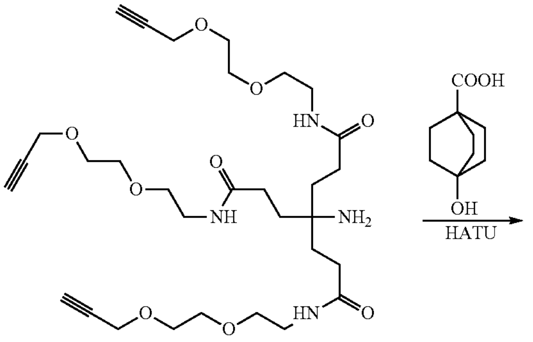

1

To a solution of 1 (600 mg, 0.9635 mmol), 4-Hydroxybicyclo[2.2.2]octane-1-carboxylic acid (245.1 mg, 0.1561 mmol, CAS number: 1127-13-5), and N,N-diisopropylethylamine (373.6 mg, 0.503 mL, d=0.742 g/mL, 2.8904 mmol) in DMF (5 mL) was added HATU (732.7 mg, 1.9269 mmol). The reaction mixture was stirred at room temperature. After confirming by LC-MS that all starting material was consumed, the reaction mixture was quenched with 2 mL of saturated $NaHCO_3$ aqueous solution and extracted with ethyl acetate (10 mL×3). The combined organic layer was washed with HCl (aq) and brine sequentially. The organic layer was dried over $Na_2SO_4$ and concentrated under high vacuum. The crude was loaded on to a silica column and purified (MPA: DCM, MPB: 10% MeOH in DCM, 0-100% ramp in 30 min) to afford the product. Yield: 398 mg, 54%. MS (ESI) m/z calcd for $C_{40}H_{61}N_4O_{11}$ [M−H] 773.45, found: 773.80.

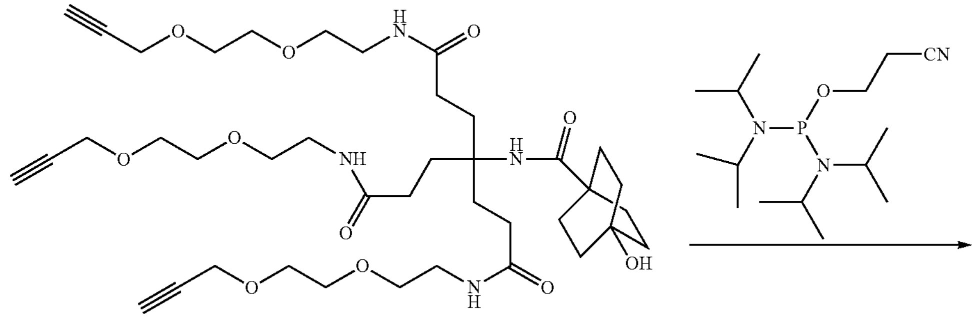

7

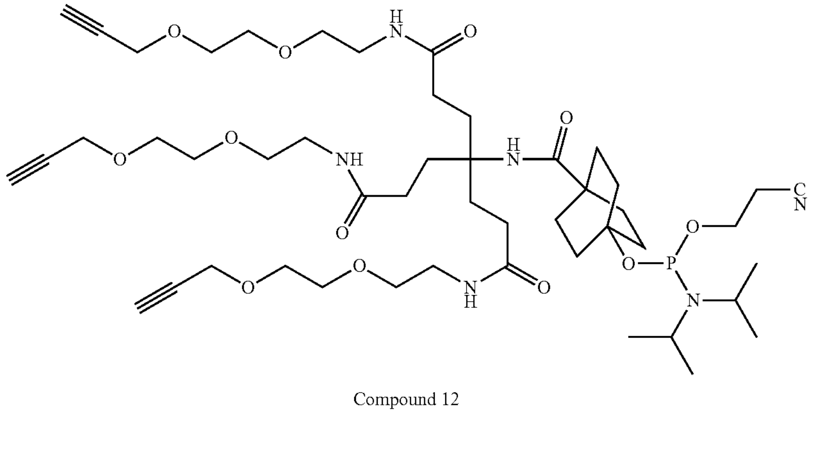

Compound 12

To a solution of 7 (200 mg, 0.2581 mmol)), diisopropylammonium tetrazolide (22.1 mg, 0.1290 mmol) and 3 Å molecule sieves (20 mg) in DCM (2 mL) was added 2-cyanoethyl N,N,N',N'-tetraisopropylphosphorodiamidite (116.7 mg, 0.123 mL, 0.3871 mmol, 1.5 eq). The reaction mixture was stirred at room temperature. After confirming by LC-MS that all starting material was consumed, the reaction mixture was quenched with 2 mL of saturated $NaHCO_3$ aqueous solution and extracted with ethyl acetate (10 mL×3). The organic layer was dried over $Na_2SO_4$ and concentrated under high vacuum. The crude was loaded on to a silica column and purified (MPA: 1% TEA in DCM, MPB: 1% TEA and 4% MeOH in DCM, 0-50% ramp in 30 min) to afford Compound 12. Yield: 40 mg (16%). MS (ESI) m/z calcd for $C_{49}H_{78}N_6O_{12}P$ [M−H] 973.54, found 973.75.

Example 13. Synthesis of Compound 13 (2-cyanoethyl (3-((11,17-dioxo-14-(3-oxo-3-((2-(2-(prop-2-yn-1-yloxy)ethoxy)ethyl)amino)propyl)-4,7,21,24-tetraoxa-10,18-diazaheptacosa-1,26-diyn-14-yl)carbamoyl)bicyclo[1.1.1]pentan-1-yl) diisopropylphosphoramidite

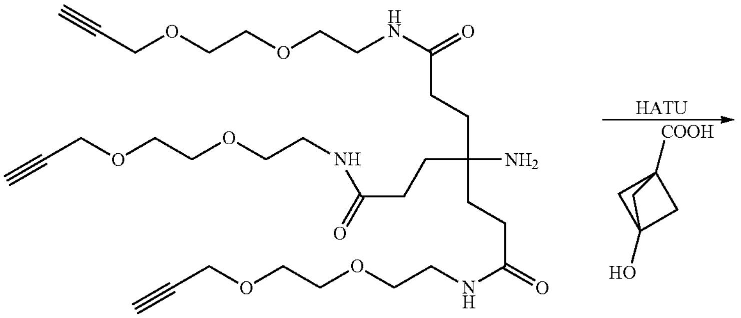

1

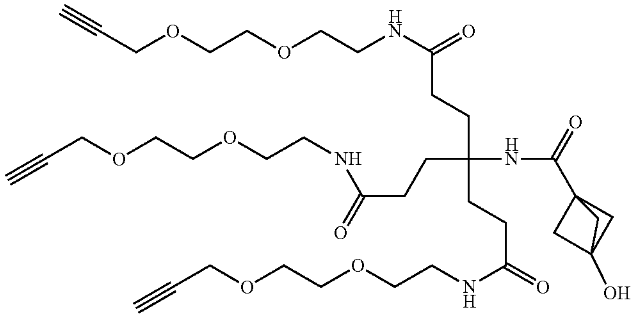

8

To a solution of 1 (400 mg, 0.6423 mmol), 3-hydroxybicyclo[1.1.1]pentane-1-carboxylic acid (98.7 mg, 0.7708 mmol, CAS number: 83249-08-5), and N,N-diisopropylethylamine (249.1 mg, 0.336 mL, d=0.742 g/mL, 1.9269 mmol) in DMF/DCM (10 mL, 1:1 v/v) was added HATU (488.4 mg, 1.2846 mmol). The reaction mixture was stirred at room temperature. After confirming by LC-MS that all starting material was consumed, the reaction mixture was quenched by 2 mL of saturated $NaHCO_3$ aqueous solution and extracted with ethyl acetate (10 mL×3). The combined organic layer was washed with HCl (aq) and brine sequentially. The organic layer was dried over $Na_2SO_4$ and concentrated under high vacuum. The crude was loaded on to a silica column and purified (MPA: DCM, MPB: 10% MeOH in DCM, 0-100% ramp in 30 min) to afford 8. Yield: 387.6 mg, 82%. MS (ESI) m/z calcd for $C_{37}H_{57}N_4O_{11}$ [M+H] 733.40, found: 733.66.

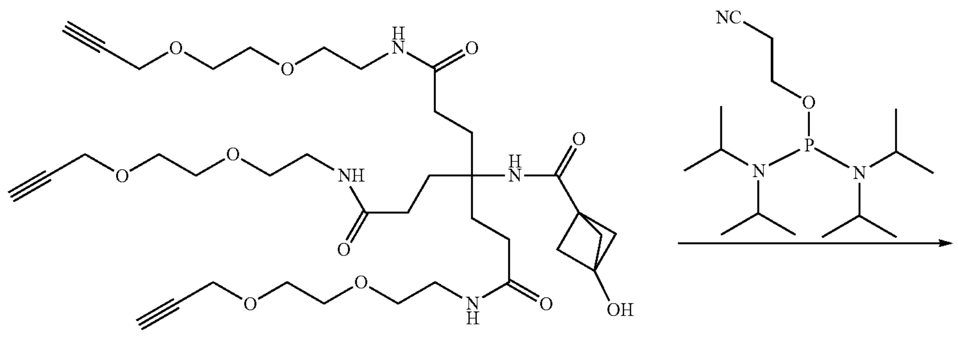

8

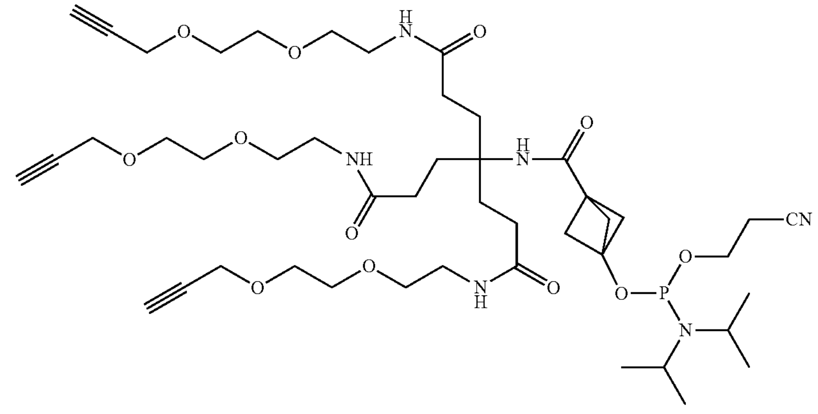

Compound 13

To a solution of 8 (387.6 mg, 0.5289 mmol)), diisopropylammonium tetrazolide (45.3 mg, 0.2644 mmol) and 3 Å molecule sieves (20 mg) in DCM (2 mL) was added 2-cyanoethyl N,N,N',N'-tetraisopropylphosphorodiamidite (239.1 mg, 0.252 mL, 0.7933 mmol, 1.5 eq). The reaction mixture was stirred at room temperature. After confirming by LC-MS that all starting material was consumed, the reaction mixture was quenched with 2 mL of saturated $NaHCO_3$ aqueous solution and extracted with ethyl acetate (10 mL×3). The organic layer was dried over $Na_2SO_4$ and concentrate under high vacuum. The crude was loaded on to a silica column and purified (MPA: 1% TEA in DCM, MPB: 1% TEA and 4% MeOH in DCM, 0-50% ramp in 30 min) to afford the pure phosphoramidite product. Yield: 206.7 mg (42%). MS (ESI) m/z calcd for $C_{46}H_{72}N_6O_{12}P$ [M−H] 931.50, found 931.71.

Example 14. Synthesis of Compound 14 (2-cyanoethyl (11,16,20-trioxo-14,14-bis(3-oxo-3-((2-(2-(prop-2-yn-1-yloxy)ethoxy)ethyl)amino)propyl)-4,7-dioxa-10,15,21-triazaheptacos-1-yn-27-yl) diisopropylphosphoramidite) and Compound 22 (4-nitrophenyl 11,16-dioxo-14,14-bis(3-oxo-3-((2-(2-(prop-2-yn-1-yloxy)ethoxy)ethyl)amino)propyl)-4,7-dioxa-10,15-diazaicos-1-yn-20-oate

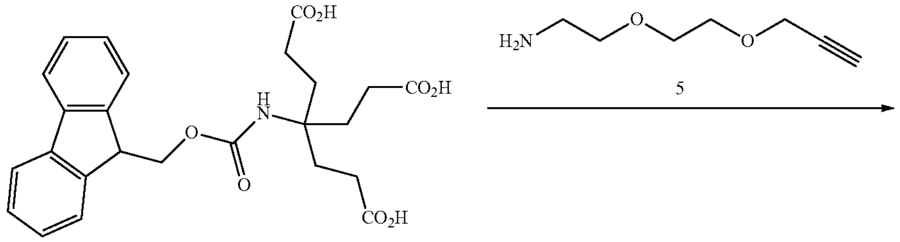

5

4

-continued

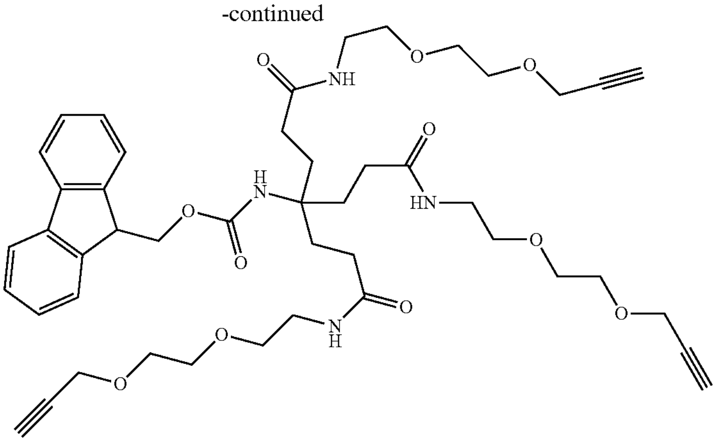

6

To a 3-L jacketed reactor was added 500 mL DCM and 4 (75.0 g, 0.16 mol). The internal temperature of the reaction was cooled to 0° C. and TBTU (170.0 g, 0.53 mol) was added. The suspension was then treated with the amine 5 (75.5 g, 0.53 mol) dropwise keeping the internal temperature less than 5° C. The reaction was then treated with DIPEA (72.3 g, 0.56 mol) slowly, keeping the internal temperature less than 5° C. After the addition was complete, the reaction was warmed up to 23° C. over 1 hour, and allowed to stir for 3 hours. A 10% kicker charge of all three reagents were added and allowed to stir an additional 3 hours. The reaction was deemed complete when <1% of 4 remained. The reaction mixture was washed with saturated ammonium chloride solution (2×500 mL) and once with saturated sodium bicarbonate solution (500 mL). The organic layer was then dried over sodium sulfate and concentrated to an oil. The mass of the crude oil was 188 g which contained 72% 6 by QNMR. The crude oil was carried to the next step. Calculated mass for $C_{46}H_{60}N_4O_{11}$=845.0 m/z. Found [M+H]=846.0.

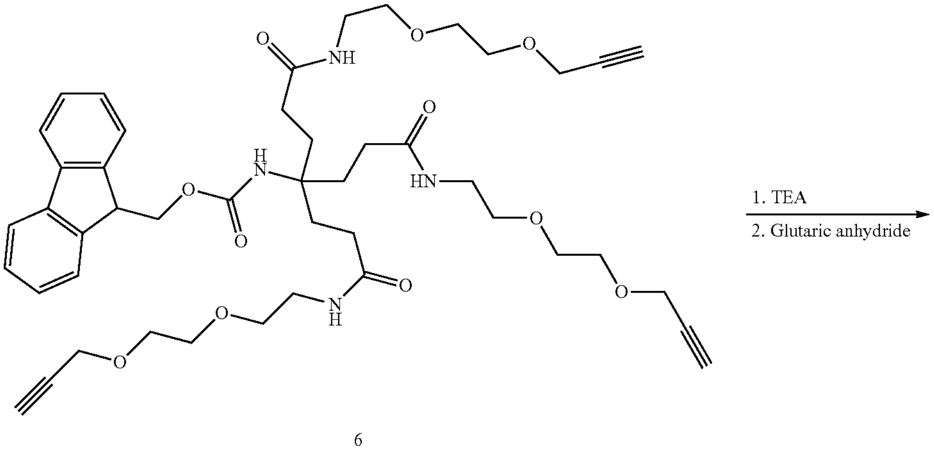

6

-continued

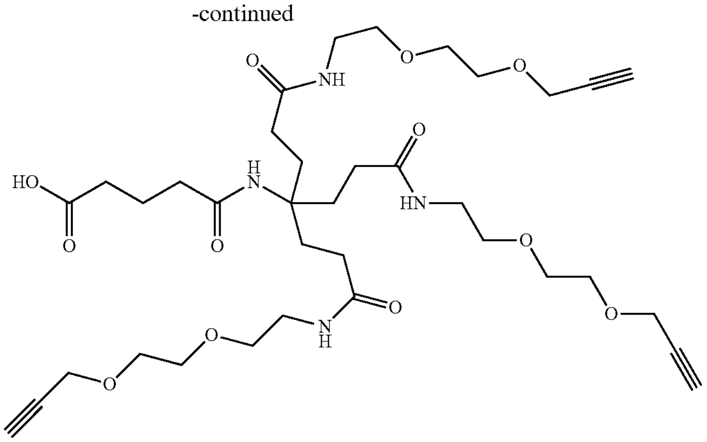

8

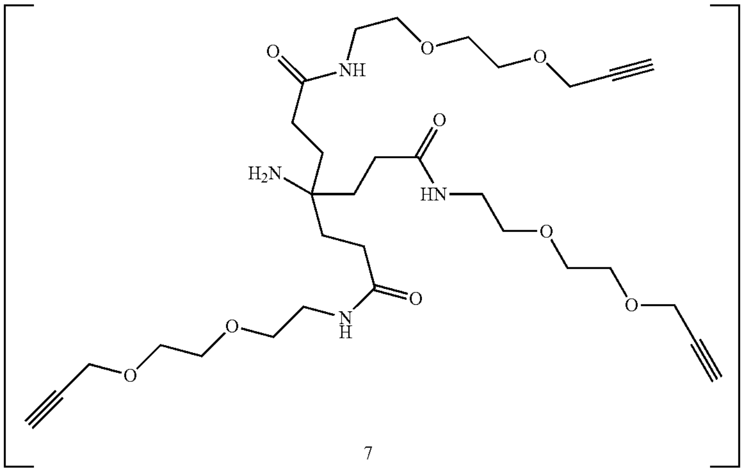

7

The 121.2 g of crude oil containing 72 wt % compound 6 (86.0 g, 0.10 mol) was dissolved in DMF (344 mL) and treated with TEA (86 mL, 20 v/v %), keeping the internal temperature below 23° C. The formation of dibenzofulvene (DBF) relative to the consumption of Fmoc-amine 6 was monitored via HPLC method 1 (FIG. 2) and the reaction was complete within 10 hours. To the solution was added glutaric anhydride (12.8 g, 0.11 mol) and the intermediate amine 7 was converted to compound 8 within 2 hours. Upon completion, the DMF and TEA were removed at 30° C. under reduced pressure resulting in 100 g of a crude oil. Due to the high solubility of compound 7 in water, an aqueous workup could not be used, and chromatography is the only way to remove DBF, TMU, and glutaric anhydride. The crude oil (75 g) was purified on a Teledyne ISCO Combi-Flash® purification system in three portions. The crude oil (25 g) was loaded onto a 330 g silica column and eluted from 0-20% methanol/DCM over 30 minutes resulting in 42 g of compound 8 (54% yield over 3 steps). Calculated mass for $C_{36}H_{55}N_4O_{12}$=736.4 m/z. Found [M+H]=737.0.

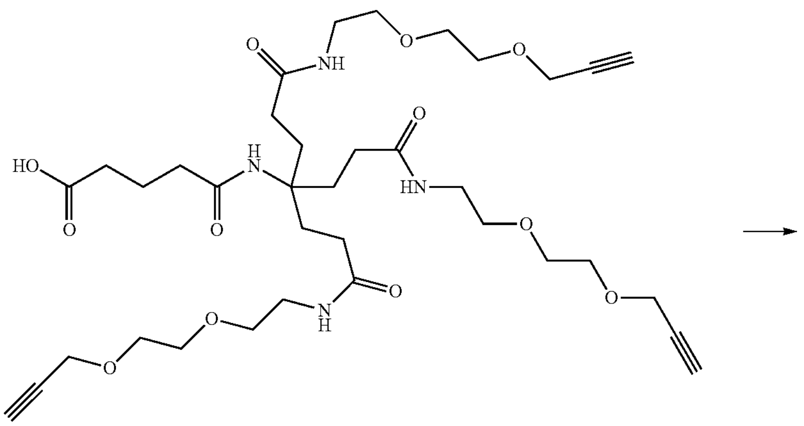

8

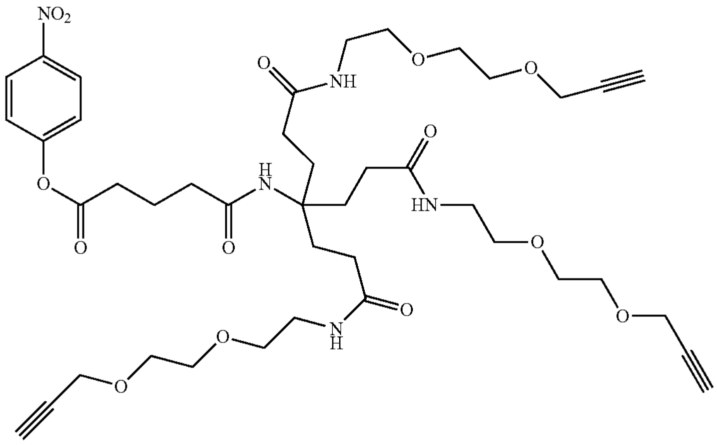

9
Compound 22

Compound 8 (42.0 g, 0.057 mol) was co-stripped with 10 volumes of acetonitrile prior to use to remove any residual methanol from chromatography solvents. The oil was redissolved in DMF (210 mL) and cooled to 0° C. The solution was treated with 4-nitrophenol (8.7 g, 0.063 moL) followed by EDC-hydrochloride (12.0 g, 0.063 mol) and found to reach completion within 10 hours. The solution was cooled to 0° C. and 10 volumes ethyl acetate was added followed by 10 volumes saturated ammonium chloride solution, keeping the internal temperature below 15° C. The layers were allowed to separate and the ethyl acetate layer was washed with brine. The combined aqueous layers were extracted twice with 5 volumes ethyl acetate. The combined organic layers were dried over sodium sulfate and concentrated to an oil. The crude oil (55 g) was purified on a Teledyne ISCO Combi-Flash® purification system in three portions. The crude oil (25 g) was loaded onto a 330 g silica column and eluted from 0-10% methanol/DCM over 30 minutes resulting in 22 g of pure 9 (Compound 22) (50% yield). Calculated mass for $C_{42}H_{59}N_5O_{14}$=857.4 m/z. Found [M+H]=858.0.

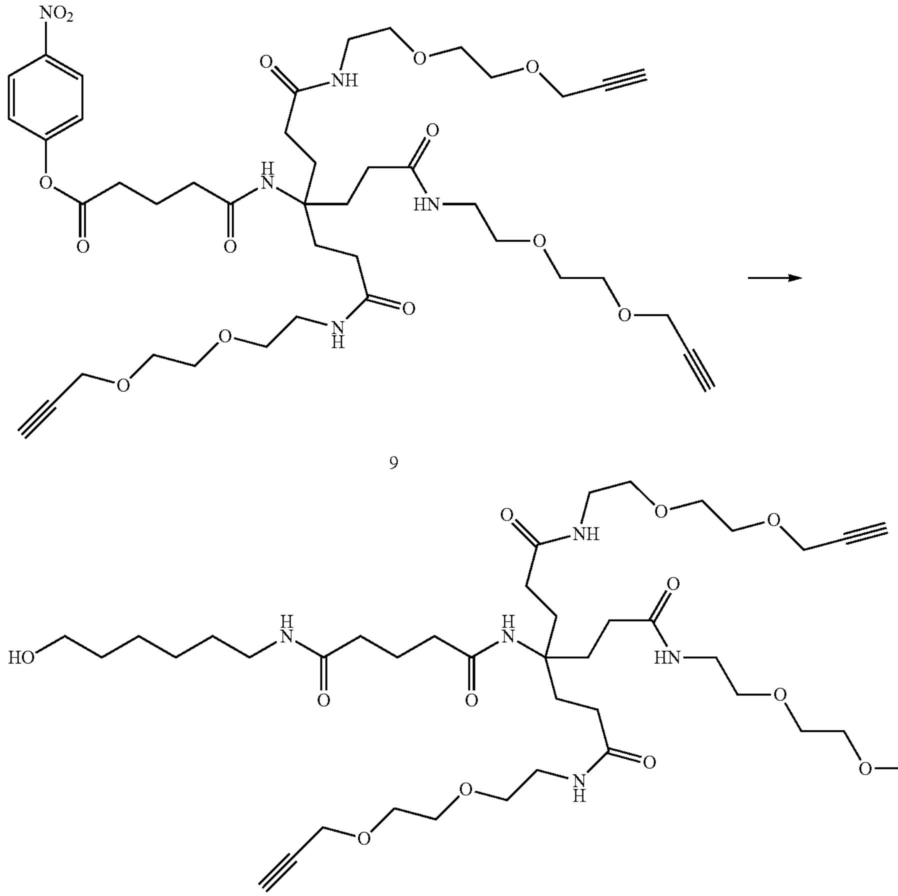

9

10

A solution of ester 9 (49.0 g, 57.1 mmol) and 6-amino-1-hexanol (7.36 g, 6.28 mmol) in dichloromethane (3 volumes) was treated with triethylamine (11.56 g, 111.4 mmol) dropwise. The reaction was monitored by observing the disappearance of compound 9 on HPLC Method 1 and was found to be complete in 10 minutes. The crude reaction mixture was diluted with 5 volumes dichloromethane and washed with saturated ammonium chloride (5 volumes) and brine (5 volumes). The organic layer was dried over sodium sulfate and concentrated to an oil. The crude oil was purified on a Teledyne ISCO Combi-Flash® purification system using a 330 g silica column. The 4-nitrophenol was eluted with 100% ethyl acetate and 10 was flushed from the column using 20% methanol/DCM resulting in a colorless oil (39 g, 81% yield). Calculated mass for $C_{42}H_{69}N_5O_{12}$=836.0 m/z. Found [M+H]=837.0.

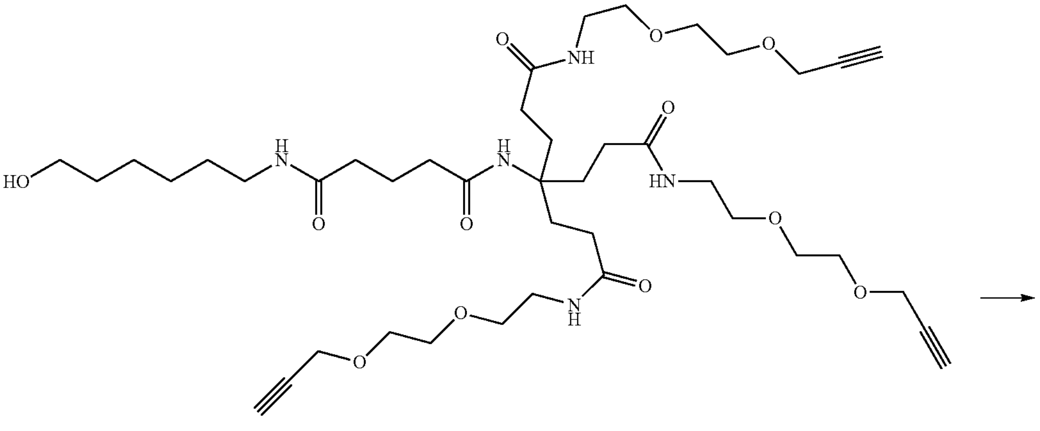

10

-continued

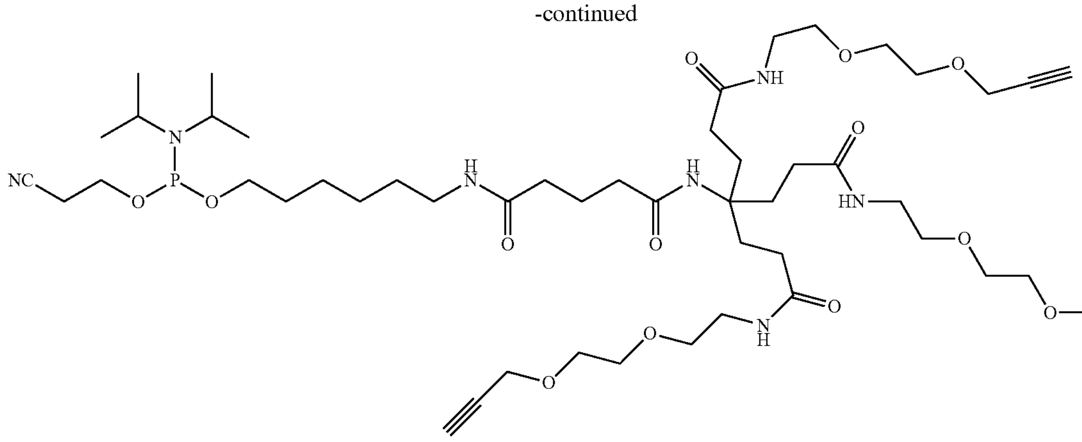

Compound 14

Alcohol 10 was co-stripped twice with 10 volumes of acetonitrile to remove any residual methanol from chromatography solvents and once more with dry dichloromethane (KF<60 ppm) to remove trace water. The alcohol 10 (2.30 g, 2.8 mmol) was dissolved in 5 volumes dry dichloromethane (KF<50 ppm) and treated with diisopropylammonium tetrazolide (188 mg, 1.1 mmol). The solution was cooled to 0° C. and treated with 2-cyanoethyl N,N,N',N'-tetraisopropylphosphoramidite (1.00 g, 3.3 mmol) dropwise. The solution was removed from ice-bath and stirred at 20° C. The reaction was found to be complete within 3-6 hours. The reaction mixture was cooled to 0° C. and treated with 10 volumes of a 1:1 solution of saturated ammonium bicarbonate/brine and then warmed to ambient over 1 minute and allowed to stir an additional 3 minutes at 20° C. The biphasic mixture was transferred to a separatory funnel and 10 volumes of dichloromethane was added. The organic layer was separated, and washed with 10 volumes of saturated sodium bicarbonate solution to hydrolyze unreacted bis-phosphorous reagent. The organic layer was dried over sodium sulfate and concentrated to an oil resulting in 3.08 g of 94 wt % Compound 14. Calculated mass for $C_{51}H_{86}N_7O_{13}P$=1035.6 m/z. Found [M+H]=1036.

Example 15. Synthesis of Compound 15 (4-nitrophenyl 5-((1,3-bis(prop-2-yn-1-yloxy)-2-((prop-2-yn-1-yloxy)methyl)propan-2-yl)amino)-5-oxopentanoate

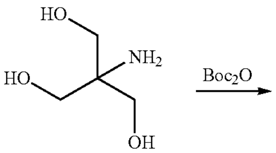

9

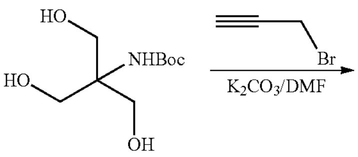

10

-continued

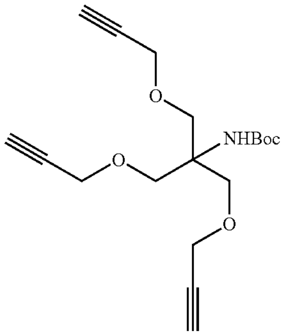

11

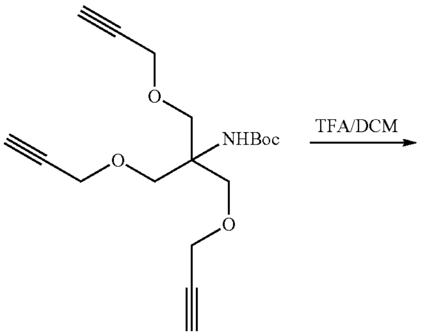

11

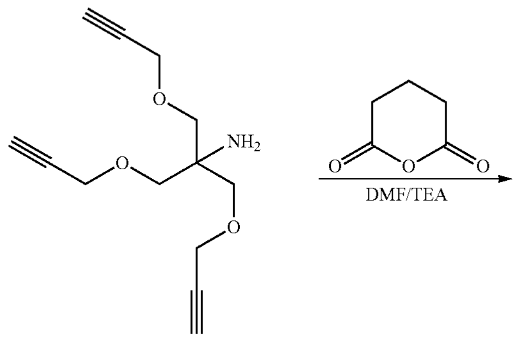

13

-continued

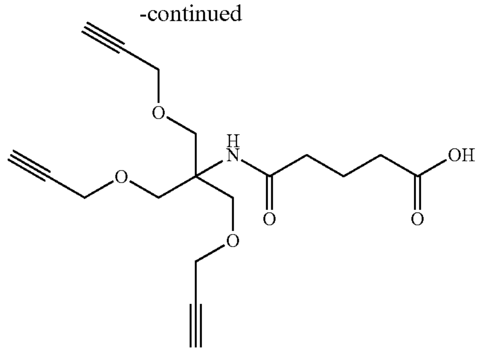

14

Step 1. A solution of di-tert-butyl dicarbonate (2.35 g, 10.7 mmol) in $^{t}$BuOH (10 mL) was added to a suspension of tris(hydroxylmethyl)aminomethane (1.00 g, 8.20 mmol, CAS Number: 77-86-1) in a 1:1 mixture of MeOH/tBuOH (15 mL) and the mixture was stirred at room temperature for 18 h. The solvent was removed at reduced pressure to afford a residue which was purified by precipitation with cold EtOAc. Vacuum filtration afforded the pure compound as a white solid (1.4449, 80% yield). MS (ESI) m/z calcd for $C_9H_{20}NO_5$ [M+H]222.13, found 222.24.

Step 2. A solution of triol-NHBoc 10 (500 mg, 2.26 mmol) in dry DMF (6 mL) was stirred at 0° C. with propargyl bromide (80 wt % in toluene, 1.46 mL, 13.6 mmol). Portions of finely ground KOH (951 mg, 13.6 mmol) were added over a period of 15 min. The mixture was then heated to 35° C. and stirred for 24 h under a nitrogen atmosphere. The reaction mixture was quenched by 2 mL of saturated $NaHCO_3$ aqueous solution and extracted with ethyl acetate (20 mL×3). The organic layer was dried over $Na_2SO_4$ and concentrate under high vacuum. The crude was loaded on to a silica column and purified (MPA: hexanes, MPB: EA, 0-10% ramp in 30 min) to afford the pure product 11. Yield: 483 mg (64%).

Step 3 and 4. To a solution of trialk-NHBoc 11 (483 mg, 1.44 mmol) in dry DCM (5.6 mL) was added dropwise TFA (2.3 mL) at 0° C. The brown mixture was then stirred at room temperature for 2 h. Concentration under high vacuum afford solid without further purification. The crude was dissolved into DMF/TEA (6 mL, 5/1 v/v) at room temperature. Glutaric anhydride (328 mg, 2.877 mmol) was added to the mixture. After overnight, the solvent was removed under reduced pressure. Purification by Combiflash® using silica gel as the stationary phase afforded 0.9357 g of product 14. (MPA: DCM, MPB: 20% MeOH in DCM, 0-50% ramp in 30 min). MS (ESI) m/z calcd. for $C_{18}H_{22}NO_6$ [M−H] 348.15, found 348.28.

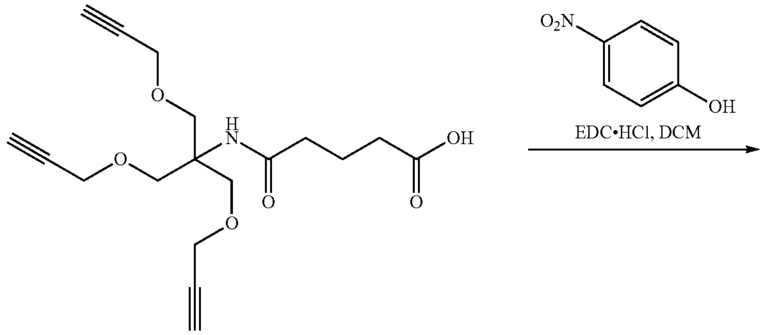

14

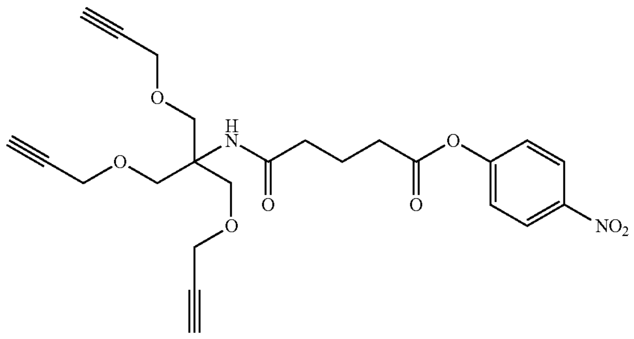

Compound 15

To a solution of 14 (470 mg, 1.3 mmol) and p-nitrophenol (936 mg, 6.7 mmol, 5 eq) in DCM (10 mL) was added EDC HCl salt (1.28 g, 6.7 mmol, 5 eq) at 0° C. The reaction mixture was then stirred at room temperature. After confirming all starting material was consumed by LC-MS, the reaction mixture was quenched by 2 mL of saturated $NaHCO_3$ aqueous solution and extracted with ethyl acetate (10 mL×3). Dry over $Na_2SO_4$ and concentrate under high vacuum. The crude was loaded on to a silica column and purified (MPA: hexanes, MPB: EA, 0-60% ramp in 30 min) to afford the pure product as yellowish oil. Yield: 471 mg (77%). MS (ESI) m/z calcd. for $C_{24}H_{27}N_2O_8$ [M+H] 471.18, found 471.33.

Example 16. Synthesis of Compound 16 (4-nitrophenyl 5-(((S)-1-(((R)-1,5-dioxo-1,5-bis(prop-2-yn-1-ylamino)pentan-2-yl)amino)-1,5-dioxo-5-(prop-2-yn-1-ylamino)pentan-2-yl)amino)-5-oxopentanoate

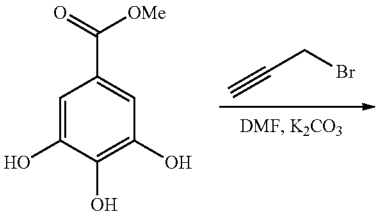

15

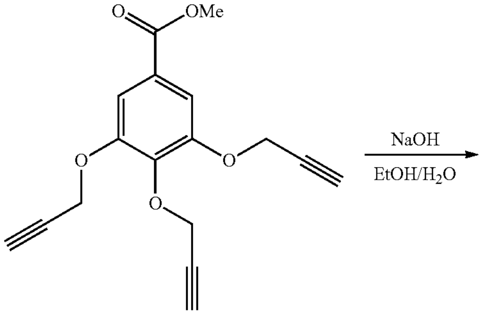

16

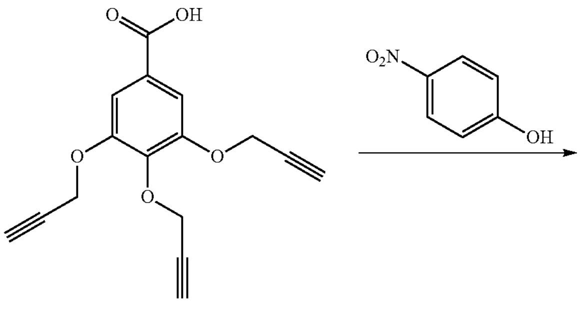

17

-continued

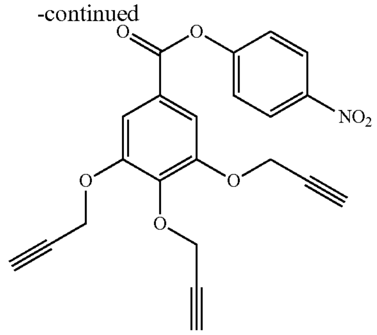

Compound 16

Step 1. To a solution of methyl 3,4,5-trihydroxyl benzoate 15 (4.6 g, 25 mmol, CAS Number 99-24-1) and propargyl bromide (11.9 g, 11.1 mL, d=1.57 g/mL, 100 mmol, 4 eq) in DMF (50 mL) was added $K_2CO_3$ (13.8 g, 100 mmol, 4 eq). The reaction mixture was then stirred at room temperature overnight. After confirming the starting material was consumed by TLC, the reaction mixture was filtered and concentrated under reduced pressure.

Step 2. The above crude was dissolved into EtOH/$H_2O$ (200 mL, 1:1 v/v) and 90 mL of 4 M NaOH aq was then added into the reaction. After confirming all the starting material was consumed by TLC, the reaction mixture was concentrated under reduced pressure to remove EtOH and filtered to afford white solid 17 (6.18 g). The solid was used for the next step without further purification.

Step 3. To a solution of 17 (73 mg, 0.35 mmol) and PNP (139 mg, 1 mmol, 3 eq) in DCM (5 mL) was added EDC HCl salt (191 mg, 1 mmol, 3 eq) at 0° C. The reaction mixture was then stirred at room temperature. After confirming all starting material was consumed by TLC, the reaction mixture was quenched by 2 mL of saturated $NaHCO_3$ aqueous solution and extracted with ethyl acetate (10 mL×3). The organic layer was dried over $Na_2SO_4$ and concentrated under high vacuum. The crude was loaded on to a silica column and purified (MPA: hexanes, MPB: EA, 0-40% ramp in 30 min) to afford Compound 16. MS (ESI) m/z calcd. for $C_{22}H_{14}NO_7$ [M−H] 404.08, found: 404.48.

Example 17. Synthesis of Compound 17 (4-nitrophenyl 5-(((S)-1-(((R)-1,5-dioxo-1,5-bis(prop-2-yn-1-ylamino)pentan-2-yl)amino)-1,5-dioxo-5-(prop-2-yn-1-ylamino)pentan-2-yl)amino)-5-oxopentanoate

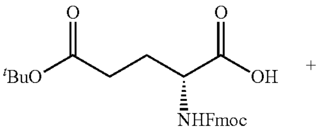

18

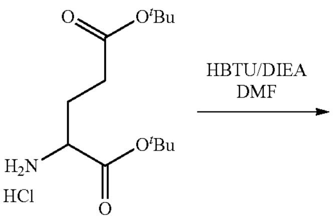

19

-continued

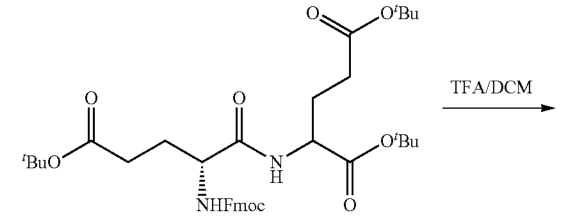

20

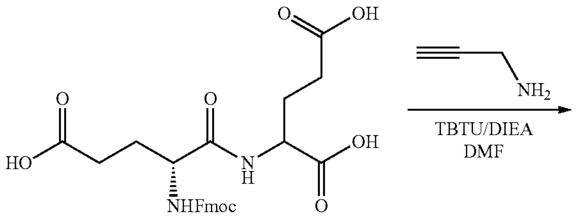

21

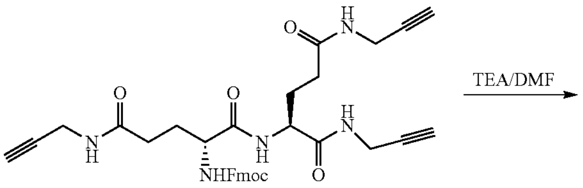

22

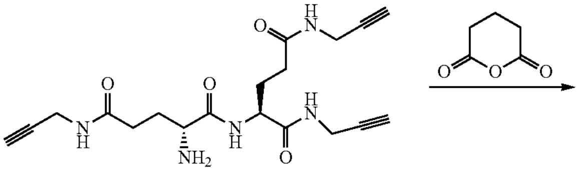

23

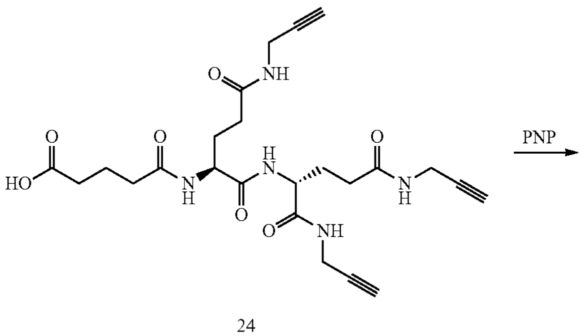

24

-continued

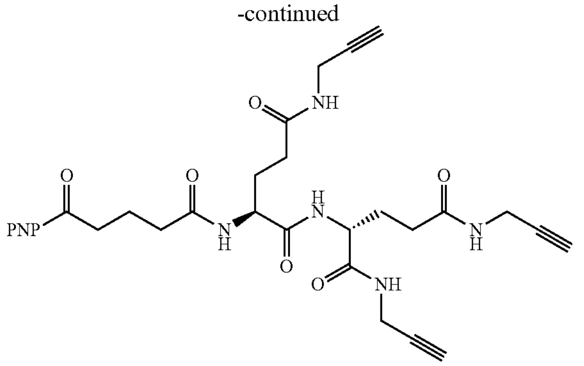

Compound 17

Step 1. To a solution of acid 18 (4.225 g, 10 mmol), amine 19 (2.959 g, 10 mmol), N,N-diisopropylethylamine (3.87 g, 0.52 mL, d=0.742 g/mL, 30 mmol) in DMF (20 mL) was added HBTU (5.685 g, 15 mmol) at 0° C. The reaction mixture was stirred at room temperature. After confirming by LC-MS that all starting material was consumed, the reaction was quenched by 2 mL of saturated $NaHCO_3$ aqueous solution and extracted with ethyl acetate (20 mL×3). The combined organic layer was washed with brine. The organic layer was dried over $Na_2SO_4$ and concentrated under high vacuum. The crude was loaded on to a silica column and purified (MPA: hexanes, MPB: EA, 0-33% ramp in 30 min) to afford the product 20 which was used for the next step. MS (ESI) m/z calculated for $C_{37}H_{51}N_2O_9$ [M+H] 667.36, found: 667.49.

Step 2. The product from step 1 was dissolved in TFA/DCM (20 mL, 1:1 v/v). The reaction was stirred at room temperature for 3 h. After confirming by LC-MS that all starting material was consumed, the mixture was concentrated under reduced pressure overnight. Yield 3.4 g. MS (ESI) m/z calcd for $C_{25}H_{25}N_2O_9$ [M−H] 497.16, found: 497.35.

Step 3. To a flame dried round bottom flask was added tri-acid 21 (1.000 g, 2.008 mmol), DMF (14 mL), propargyl amine (0.3645 g, 0.42 mL, d=0.86 g/mL, 6.6265 mmol), and DIEA (0.9066 g, 1.222 mL, d=0.742 g/mL, 7.0281 mmol). Cool down to 0° C. and TBTU (2.256 g, 7.0281 mmol. 3.5 eq) was added. After confirming by LC-MS that all starting material was consumed, the reaction mixture was concentrated under reduced pressure. The product was obtained through filtration and washed with DCM (5 mL) and $H_2O$ (5 mL). Lyophilization overnight afforded 0.8818 g of white solid 22. MS (ESI) m/z calcd for $C_{34}H_{36}N_5O_6$ [M+H] 610.27, found: 610.41.

Step 4, 5 and 6.22 (100 mg, 0.1642 mmol) in DMF (1 mL) was added to triethylamine (0.1658 g, 0.228 mL, d=0.726 g/mL, 1.6420 mmol) at room temperature. The reaction mixture was stirred overnight. After confirming by LC-MS that all starting material was consumed, glutaric anhydride (28.1 mg, 0.2463 mmol) and DMAP (2.0 mg, 0.0164 mmol) were added. The reaction mixture was stirred overnight. PNP (114.1 mg, 0.821 mmol) and EDC-HCl (156.8 mg, 0.8210 mmol) were added. Upon consumption of starting material, the reaction mixture was concentrated and purified by CombiFlash® using silica gel as the stationary phase and was eluted with a gradient of MeOH in DCM (0-20%). Yield: 34 mg, 34%. MS (ESI) m/z calculated for $C_{30}H_{35}N_6O_9$ [M+H] 623.25, found: 623.38.

Example 18 Synthesis of Compound 18 (4-nitrophenyl 5-((1,7-dioxo-4-(3-oxo-3-(prop-2-yn-1-ylamino)propyl)-1,7-bis(prop-2-yn-1-ylamino)heptan-4-yl)amino)-5-oxopentanoate

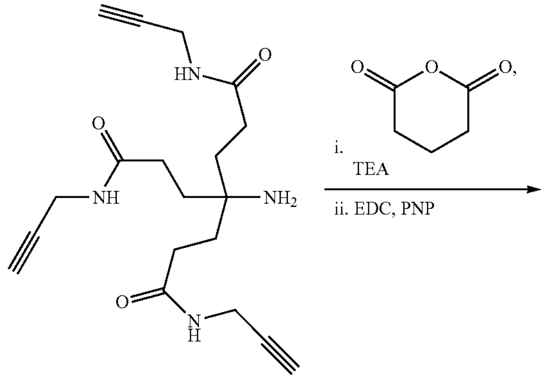

3

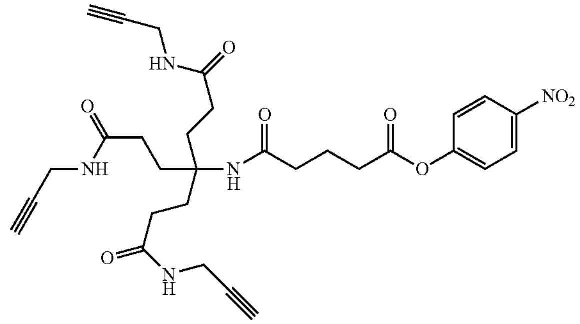

31

To a solution of 3 (1.00 g, 2.79 mmol) in DMF (5 mL) was added triethylamine (0.847 g, 1.17 mL, 8.37 mmol) and glutaric anhydride (493 mg, 4.32 mmol) at room temperature. The reaction mixture was stirred overnight. The next day, 4-nitrophenol (896 mg, 6.44 mmol) and N-(3-dimethylaminopropyl)-N'-ethylcarbodiimide hydrochloride (1.23 g, 6.44 mmol) were added at room temperature and the reaction mixture was stirred overnight. The reaction mixture was concentrated. The residue was purified by Combi-Flash® using silica gel as the stationary phase and was eluted with a gradient of MeOH in DCM (0-6%). Yield of 31 (Compound 18): 1.13 g (74%). [M+H] calculated for $C_{30}H_{35}N_5O_8$: 594.65, found: 594.39.

Example 19. Synthesis of Compound 19 (2,3,5,6-tetrafluorophenyl 3-((1,7-dioxo-4-(3-oxo-3-(prop-2-yn-1-ylamino)propyl)-1,7-bis(prop-2-yn-1-ylamino)heptan-4-yl)carbamoyl)bicyclo[1.1.1]pentane-1-carboxylate

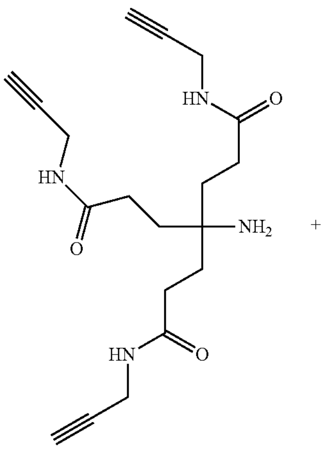

25

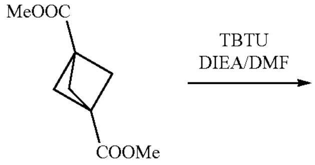

26

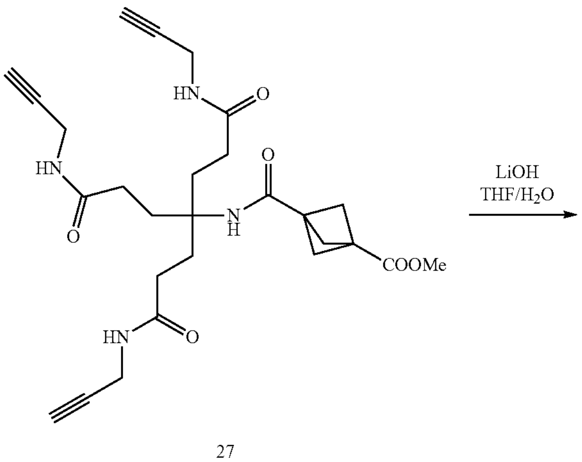

27

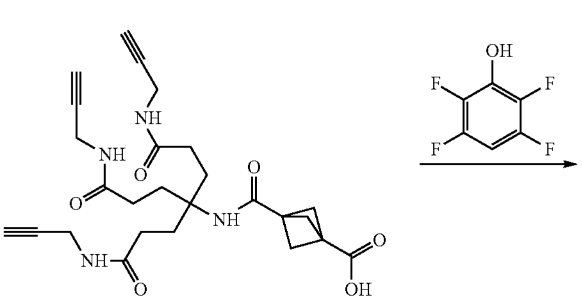

28

-continued

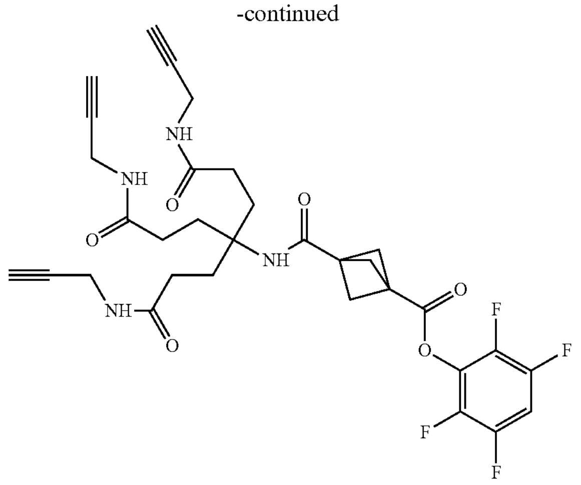

TriAlk19

Step 1. To a solution of acid 26 (52.2 mg, 0.3073 mmol, 1.1 eq), TBTU (134.5 mg, 0.4190 mmol, 1.5 eq), and DIEA (108.1 mg, 0.1457 mL, d=0.742 g/mL, 0.8380 mmol) in DMF (0.5 mL) was added amine 25 (100 mg, 0.2793 mmol). The reaction was stirred at room temperature. After confirming by LC-MS that all starting material was consumed, the reaction mixture was concentrated under reduced pressure. Purification on Combiflash® (MPA: DCM, MPB: 20% MeOH in DCM, 0-50% ramp in 30 min) affords the pure product 27 Yield: 114 mg, 80%. MS (ESI) m/z calcd for $C_{27}H_{35}N_4O_6$ [M+H] 511.26, found: 511.75.

Step 2. The above product was dissolved into THF/$H_2O$ (0.6 mL, 2:1 v/v) and LiOH (16 mg, 0.66 mmol, 3 eq) was then added into the reaction. After confirming by LC-MS that all the starting material was consumed, the reaction mixture was neutralized by adding 0.66 mmol HCl (aq). The mixture was concentrated under reduced pressure and lyophilized over weekend. The crude was used for the next step without further purification.

Step 3. To a solution of 28, TFP (182.6 mg, 1.1 mmol, 5 eq) and DIEA (179.6 mg, 0.242 mL, d=0.742 g/mL, 1.39 mmol) in DCM (5 mL) was added EDC HCl salt (210.1 mg, 1.1 mmol, 5 eq) at 0° C. The reaction mixture was then stirred at room temperature. After confirming by TLC that all starting material was consumed, the reaction mixture was quenched by 2 mL of saturated $NaHCO_3$ aqueous solution and extracted with ethyl acetate (10 mL×3). The organic layer was dried over $Na_2SO_4$ and concentrated under high vacuum. The crude was loaded on to a silica column and purified (MPA: hexanes, MPB: EA, 0-50% ramp in 30 min) to afford Compound 19. Yield: 89 mg (63%). MS (ESI) m/z calcd for $C_{32}H_{33}F_4N_4O_6$ [M+H] 645.23, found: 645.79.

Example 20. Synthesis of Compound 20 (2,3,5,6-tetrafluorophenyl 4'-((1,7-dioxo-4-(3-oxo-3-(prop-2-yn-1-ylamino)propyl)-1,7-bis(prop-2-yn-1-ylamino)heptan-4-yl)carbamoyl)-[1,1'-biphenyl]-4-carboxylate

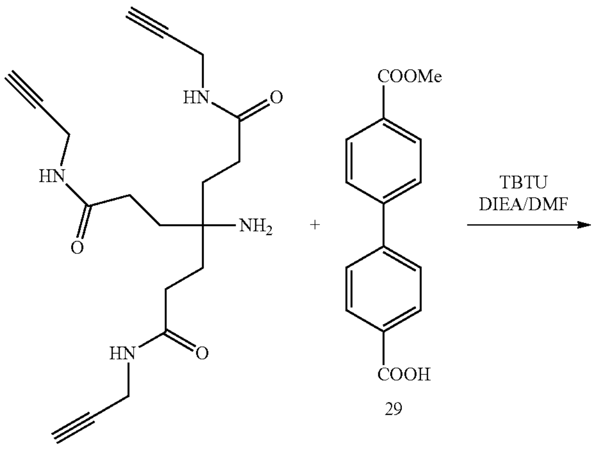

25

29

-continued

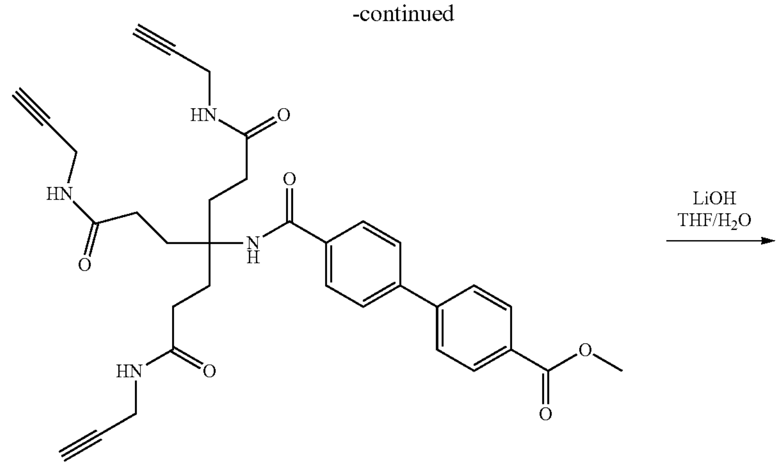

30

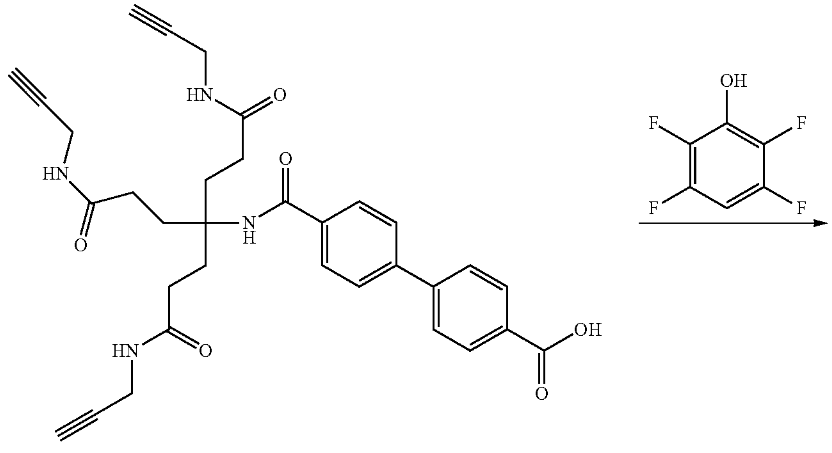

31

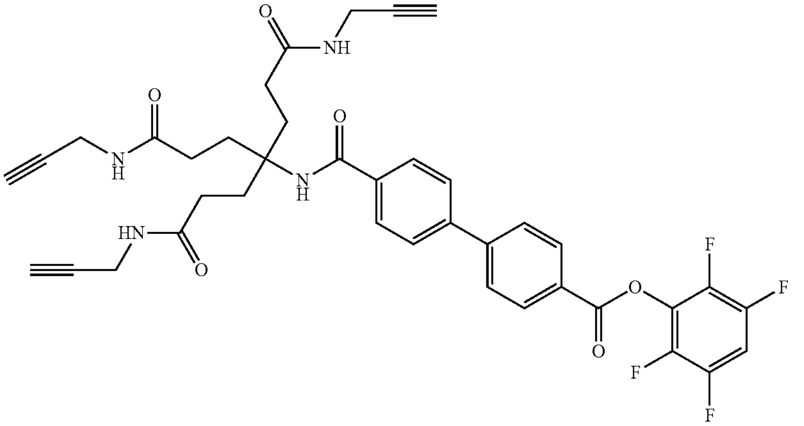

Compound 20

Step 1. To a solution of acid 29 (78.7 mg, 0.3073 mmol, 1.1 eq), TBTU (134.5 mg, 0.4190 mmol, 1.5 eq), and DIEA (108.1 mg, 0.1457 mL, d=0.742 g/mL, 0.8380 mmol) in DMF (0.5 mL) was added 25 (100 mg, 0.2793 mmol). The reaction was stirred at room temperature. After confirming by LC-MS that all starting material was consumed, the reaction mixture was concentrated under reduced pressure. Purification on Combiflash® (MPA: DCM, MPB: 20% MeOH in DCM, 0-50% ramp in 30 min) afforded the pure product 30 Yield: 165 mg, 99%. MS (ESI) m/z calcd for $C_{34}H_{37}N_4O_6$ [M+H] 597.27, found: 597.81.

Step 2. The product from step 1 was dissolved into THF/$H_2O$ (0.6 mL, 2:1 v/v), then LiOH (20 mg, 0.83 mmol, 3 eq) was added. After confirming by LC-MS that all the starting material was consumed, the reaction mixture was neutralized by adding 0.83 mmol HCl (aq). The mixture was concentrated under reduced pressure and lyophilized over the weekend. The crude was used for the next step without further purification.

Step 3. To a solution of 31, TFP (231 mg, 1.39 mmol, 5 eq), and DIEA (179.6 mg, 0.242 mL, d=0.742 g/mL, 1.39 mmol) in DCM (5 mL) was added EDC HCl salt (266 mg, 1.39 mmol, 5 eq) at 0° C. The reaction mixture was then stirred at room temperature. After confirming by TLC that all starting material was consumed, the reaction mixture was quenched by 2 mL of saturated $NaHCO_3$ aqueous solution and extracted with ethyl acetate (10 mL×3). The organic layer was dried over $Na_2SO_4$ and concentrated under high vacuum. The crude was loaded on to a silica column and purified (MPA: hexanes, MPB: EA, 0-50% ramp in 30 min) to afford the pure product Compound 20. Yield: 87 mg (42%). MS (ESI) m/z calcd for $C_{39}H_{35}F_4N_4O_6$ [M+H]+ 731.25, found: 731.85.

Example 21. Synthesis of Compound 21 ((1r,4r)-4-((1,7-dioxo-4-(3-oxo-3-(prop-2-yn-1-ylamino)propyl)-1,7-bis(prop-2-yn-1-ylamino)heptan-4-yl)carbamoyl)cyclohexyl (4-nitrophenyl) carbonate

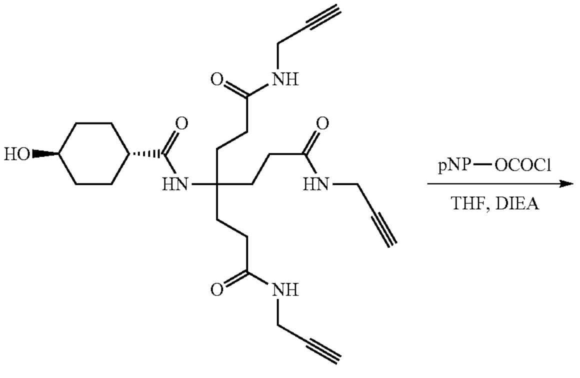

8

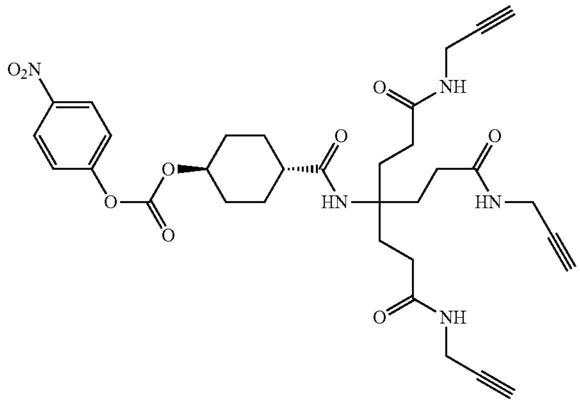

Compound 21

To compound 8 (see Example 1) (0.048 g, 0.10 mmol) and DIEA (0.18 mL, 1.0 mmol) in THF (0.5 mL) was added 4-nitrophenyl chloroformate (0.044 g, 0.22 mmol) and the reaction was stirred at 50° C. Upon completion all volatiles were removed and Compound 21 was isolated by separation over silica eluting a gradient of MeOH in DCM. Yield: 0.035 g (54%).

Example 22. Syntheses of Tridentate Ligands and Conjugation of Targeting Ligands to RNAi Agents The targeting ligands can be conjugated to one or more RNAi agents useful for inhibiting the expression of one or more targeted genes. The targeting ligands facilitate the delivery of the RNAi agents to the targeted cells and/or tissues. Targeting ligands may comprise certain moieties that interact with cell surface receptors resulting in the introduction of the RNAi agent to a cell. The following describes the general procedures for the syntheses of certain targeting ligand-RNAi agent conjugates using the trialkyne linking agent described herein that are illustrated in the non-limiting Examples set forth herein.

A. Synthesis of RNAi Agents

RNAi agents can be synthesized using methods generally known in the art. For the synthesis of the RNAi agents illustrated in the Examples set forth herein, the sense and antisense strands of the RNAi agents were synthesized according to phosphoramidite technology on solid phase used in oligonucleotide synthesis. Depending on the scale, a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the following 2'-O-methyl phosphoramidites were used: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes (Wilmington, MA, USA). The following UNA phosphoramidites were used: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diisopropyl)]-phosphoramidite. TFA aminolink phosphoramidites were also commercially purchased (ThermoFisher).

Alternatively, tri-alkyne moieties were introduced post-solid support synthesis (see section F, below). For this route, the sense strand was functionalized with a 5' and/or 3' terminal nucleotide containing a primary amine. TFA aminolink phosphoramidite was dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' O-Me), and 60 seconds (2' F). In order to introduce phosphorothioate linkages, a 100 mM solution of 3¬phenyl 1,2,4-dithiazoline-5-one (POS, obtained from PolyOrg, Inc., Leominster, MA, USA) in anhydrous acetonitrile was employed.

In some embodiments, compounds of Formula III are synthesized by reacting a compound of Formula II, which can be added at the terminal end of an RNAi agent. In some embodiments, the trialkyne linking agent of Formula II is added to the 5' end of the sense strand of a double-stranded RNAi agent. In some embodiments, the trialkyne linking agent of Formula II is added to the 3' end of the sense strand of a double-stranded RNAi agent. In some embodiments, the compound of Formula II is added to the 5' end of the anti-sense strand of a double-stranded RNAi agent. In some embodiments, the compound of Formula II is added to the 3' end of the anti-sense strand of a double-stranded RNAi agent. An example reaction of this type is shown in the scheme below:

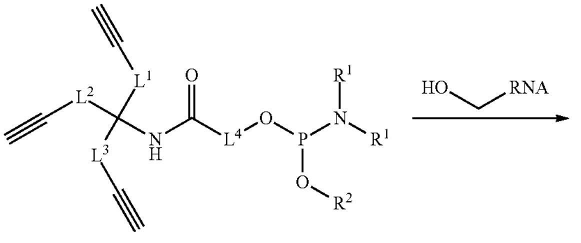

Formula II

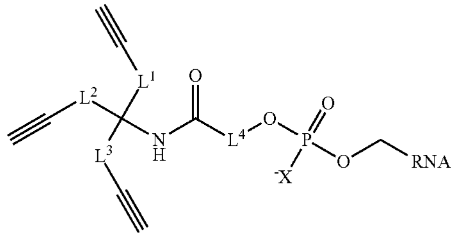

When used in connection with the RNAi agents presented in certain Examples herein, trialkyne-containing phosphoramidites were dissolved in anhydrous dichloromethane or anhydrous acetonitrile (50 mM), while all other amidites were dissolved in anhydrous acetonitrile (50 mM), and molecular sieves (3 Å) were added. 5-Benzylthio-1H-tetrazole (BTT, 250 mM in acetonitrile) or 5-Ethylthio-TH-tetrazole (ETT, 250 mM in acetonitrile) was used as activator solution. Coupling times were 10 min (RNA), 90 sec (2' O-Me), and 60 sec (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

B. Cleavage and Deprotection of Support Bound Oligomer.

After finalization of the solid phase synthesis, the dried solid support was treated with a 1:1 volume solution of 40 wt. % methylamine in water and 28% to 31% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate, pH 6.7 and 20% Acetonitrile or filtered water.

D. Annealing.

Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor and the dilution factor to determine the duplex concentration. The conversion factor used was either 0.037 mg/(mL-cm), or, alternatively for some experiments, a conversion factor was calculated from an experimentally determined extinction coefficient.

E. Conjugation of Targeting Ligands.

Compounds of Formulas IV, V, VIII and IX may be synthesized by conjugating targeting ligands to a trialkyne compound described herein. An example reaction is shown in the scheme:

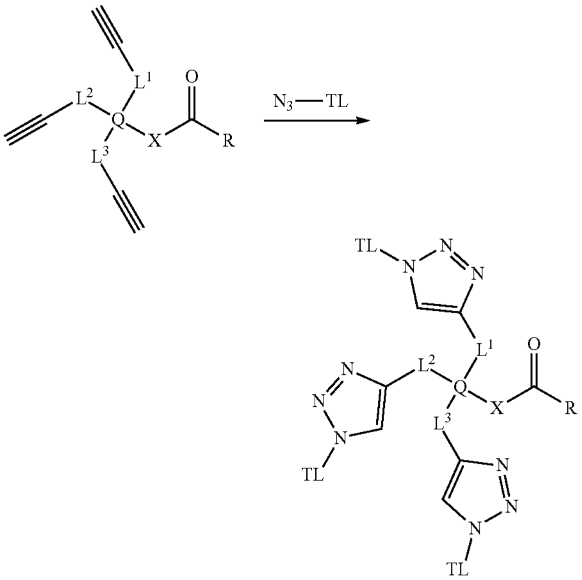

wherein each variable is as described in Formula I, and TL is a targeting ligand.

In some embodiments, targeting ligand conjugation may be carried out using the following procedure. The following procedure describes conjugation of targeting ligands to a compound of Formula I wherein R comprises an RNAi agent, but targeting ligand conjugation may also be carried out on a compound of Formula I where R does not comprise an RNAi agent.

Either prior to or after annealing, the 5' or 3' tridentate alkyne functionalized sense strand is conjugated to the targeting ligands. The following example describes the conjugation of targeting ligands to the annealed duplex: Stock solutions of 0.5M Tris(3-hydroxypropyltriazolylmethyl)amine (THPTA), 0.5M of Cu(II) sulfate pentahydrate ($Cu(II)SO_4.5H_2O$) and 2M solution of sodium ascorbate were prepared in deionized water. A 75 mg/mL solution in DMSO of a targeting ligand was made. In a 1.5 mL centrifuge tube containing trialkyne functionalized duplex (3 mg, 75 μL, 40 mg/mL in deionized water, ~15,000 g/mol), 25 μL of 1M Hepes pH 8.5 buffer is added. After vortexing, 35 μL of DMSO was added and the solution is vortexed. Targeting ligand was added to the reaction (6 eq/duplex, 2 eq/alkyne, ~15 μL) and the solution is vortexed. Using pH paper, pH was checked and confirmed to be pH ~8. In a separate 1.5 mL centrifuge tube, 50 μL of 0.5M THPTA was mixed with 10 uL of 0.5M $Cu(II)SO_4.5H_2O$, vortexed, and incubated at room temp for 5 min. After 5 min, THPTA/Cu solution (7.2 μL, 6 eq 5:1 THPTA:Cu) was added to the reaction vial, and vortexed. Immediately afterwards, 2M ascorbate (5 μL, 50 eq per duplex, 16.7 per alkyne) was added to the reaction vial and vortexed. Once the reaction was complete (typically complete in 0.5-1 h), the reaction was immediately purified by non-denaturing anion exchange chromatography.

F. Post-Solid Support Synthesis Addition of Trialkyne Linking Agents

RNAi molecules can be synthesized having a reactive group, such as an amino group (also referred to herein as an amine). In some embodiments, the reactive group may be linked at the 5'-terminus and/or the 3'-terminus of the RNAi agent. In some embodiments, the RNAi agent may be double-stranded. In embodiments where the RNAi agent is double-stranded, the reactive group may be on the sense strand or the anti-sense strand of the RNAi agent.

For example, in some embodiments, an RNAi agent is synthesized having an $NH_2—C_6H_{12}$ (hexyleneamine) group at the 5'-terminus of the sense strand of the RNAi agent. The terminal amino group subsequently can be reacted to form a conjugate with, for example, the coupling moiety of a compound of Formula I. In some embodiments, the coupling moiety is an ester, and the reactive group on the RNAi agent is a primary amine, and an amide linkage is formed between the RNAi agent and the trialkyne linker. An example of this reaction is shown in the scheme below using a compound of Formula VI:

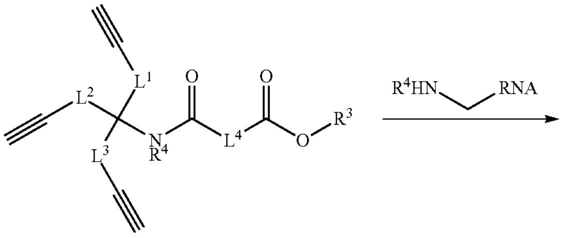

Formula VI

-continued

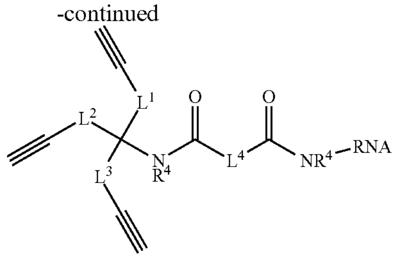

Formula VII wherein $L^1$, $L^2$, $L^3$, $L^4$, $R^3$, $R^4$ and RNA are all as defined in Formulas VI and VII.

When RNAi molecules have been cleaved from the solid support, addition of the trialkyne linking agents described herein may take place as follows. The sense strand was functionalized with a 5' and/or 3' terminal nucleotide containing a primary amine. Amine-functionalized duplex was dissolved in 90% DMSO/10% H2O, at ~50-70 mg/mL. 40 equivalents triethylamine was added, followed by 3 equivalents tri-alkyne-ester of Formula VI. Once complete, the conjugate was precipitated twice in a solvent system of 1× phosphate buffered saline/acetonitrile (1:14 ratio), and dried.

In Vivo Examples

Linkers described herein may be used in conjunction with a variety of RNAi agents. The following examples demonstrate the use of linkers described herein with RNAi agents directed to Alpha-ENaC and HIF2α mRNA sequences and are meant to provide examples of the use of said linkers without limiting the scope of the invention to any specific RNAi agents. The RNAi agents used in the following examples are shown in the following Table 8. Compounds of Table 8 are shown as the structures that were cleaved from the solid support. In some instances, further modifications were made to the compounds before in vivo administration. For AD5614-5617, AD5620, AD5858, AD5860, and AD5919, trialkyne linking agents were added as phosphoramidites of Formula II to the sense strand as part of the synthesis on solid support. In the case of AD04546, AD5347, and AD5453, the sense strand was cleaved from the support in the structure as shown in Table 8. The respective trialkyne linking agents were added as compounds of Formula VI in an amide coupling reaction. Targeting ligands were added following cleavage from the resin, therefore for AD5614-5617, AD5620, AD5858, AD5860, and AD5919, trialkyne linking agents are indicated as compounds of Formula III. In Table 8, below, a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and cPrpu represents a 5'-cyclopropyl phosphonate-2'-O-methyl uridine:

TABLE 8

RNAi agents used in conjunction with Trialkyne linkers.

| Duplex No. - Target | Antisense Sequence (5' → 3') | Sense Sequence (5' → 3') |
|---|---|---|
| AD04546 - HIF2α | usUfsusCfaUfgAfaAfuCfgUfuAfcGfuUfsg (SEQ ID NO: 1) | (NH2-C6)scsaacguaaCfGfAfuuucaugaasa(invAb)(C6-SS-C6) (SEQ ID NO: 4) |
| AD05614 - HIF2α | usUfsusCfaUfgAfaAfuCfgUfuAfcGfuUfsg (SEQ ID NO: 1) | (Compound 1-S-III)csaacguaaCfGfAfuuucaugaasa(invAb)(6-SS-6) (SEQ ID NO: 5) |

TABLE 8-continued

RNAi agents used in conjunction with Trialkyne linkers.

| Duplex No. - Target | Antisense Sequence (5' → 3') | Sense Sequence (5' → 3') |
|---|---|---|
| AD05615 - HIF2α | usUfsusCfaUfgAfaAfuCfgUfuAfcGfuUfsg (SEQ ID NO: 1) | (Compound 2-S-III)csaacguaaCfGfAfuuucaugaasa(invAb) (6-SS-6) (SEQ ID NO: 6) |
| AD05616 - HIF2α | usUfsusCfaUfgAfaAfuCfgUfuAfcGfuUfsg (SEQ ID NO: 1) | (Compound 3-S-III)csaacguaaCfGfAfuuucaugaasa(invAb) (6-SS-6) (SEQ ID NO: 7) |
| AD05617 - HIF2α | usUfsusCfaUfgAfaAfuCfgUfuAfcGfuUfsg (SEQ ID NO: 1) | (Compound 6-S-III)csaacguaaCfGfAfuuucaugaasa(invAb) (6-SS-6) (SEQ ID NO: 8) |
| AD05620 - HIF2α | usUfsusCfaUfgAfaAfuCfgUfuAfcGfuUfsg (SEQ ID NO: 1) | (Compound 4-S-III)csaacguaaCfGfAfuuucaugaasa(invAb) (6-SS-6) (SEQ ID NO: 9) |
| AD05858 - HIF2α | usUfsusCfaUfgAfaAfuCfgUfuAfcGfuUfsg (SEQ ID NO: 1) | (Compound 10-S-III)csaacguaaCfGfAfuuucaugaasa(invAb) (6-SS-6) (SEQ ID NO: 10) |
| AD05860 - HIF2α | usUfsusCfaUfgAfaAfuCfgUfuAfcGfuUfsg (SEQ ID NO: 1) | (Compound 12-S-III)csaacguaaCfGfAfuuucaugaasa(invAb) (6-SS-6) (SEQ ID NO: 11) |
| AD05919 - HIF2α | usUfsusCfaUfgAfaAfuCfgUfuAfcGfuUfsg (SEQ ID NO: 1) | (Compound 13-S-III)csaacguaaCfGfAfuuucaugaasa(invAb) (6-SS-6) (SEQ ID NO: 12) |
| AD05347 - αENaC | cPrpusAfsusUfuGfuUfcUfgGfuUfgCfaCfa Gfsg (SEQ ID NO: 2) | (NH2-C6)cscugugcaAfCfCfagaacaaauas(invAb) (SEQ ID NO: 13) |
| AD05453 - αENaC | usAfsusUfuGfuUfcUfgGfuUfgCfaCfaGfsg (SEQ ID NO: 3) | (NH2-C6)cscugugcaAfCfCfagaacaaauas(invAb) (SEQ ID NO: 13) |

Example 23. Kidney Tumor Bearing Mouse Model (Orthotopic Xenograft

Creation of SEAP-Expressing Clear Cell Renal Cell Carcinoma (ccRCC) A498 Cells

A pCR3.1 expression vector expressing the reporter gene secreted alkaline phosphatase (SEAP) under the CMV promoter was prepared by directional cloning of the SEAP coding sequence PCR amplified from Clontech's pSEAP2-basic vector. Convenient restriction sites were added onto primers used to amplify the SEAP coding sequence for cloning into the pCR3.1 vector (Invitrogen). The resultant construct pCR3-SEAP was used to create a SEAP-expressing A498 ccRCC cell line. Briefly, pCR3-SEAP plasmid was transfected into A498 ccRCC cells by electroporation following manufacturer's recommendation. Stable transfectants were selected by G418 resistance. Selected A498-SEAP clones were evaluated for SEAP expression and integration stability.

Implantation of SEAP-Expressing Clear Cell Renal Cell Carcinoma (ccRCC) A498 Cells.

Female athymic nude mice were anesthetized with ~3% isoflourane and placed in the right lateral decubitus position. A small, 0.5-1 cm, longitudinally abdominal incision in the left flank was made. Using a moist cotton swab, the left kidney was lifted out of the peritoneum and gently stabilized. Just before injection, a 1.0 ml syringe was filled with the cell/Matrigel mixture and a 27 gauge needle catheter was attached to the syringe tip. The filled syringe was then attached to a syringe pump (Harvard Apparatus, model PHD2000) and primed to remove air. The tip of a 27-gauge needle catheter attached to a syringe was inserted just below the renal capsule near the caudal pole and the tip of the needle was then carefully advanced cranially along the capsule 3-4 mm. A 10 μl aliquot of 2:1 (vol:vol) cell/matrigel mixture containing about 300,000 cells was slowly injected into the kidney parenchyma using a syringe pump. The needle was left in the kidney for 15-20 seconds to ensure the injection was complete. The needle was then removed from the kidney and a cotton swab was placed over the injection site for 30 seconds to prevent leakage of the cells or bleeding. The kidney was then gently placed back into the abdomen and the abdominal wall was closed. Serum was collected every 7-14 days after implantation to monitor tumor growth using a commercial SEAP assay kit. For most studies, tumor mice were used 5-6 weeks after implantation, when tumor measurements were typically around 4-8 mm.

Determination of HIF2 mRNA Expression.

For the studies reported in the Examples herein, mice were euthanized the identified day after injection and total RNA was isolated from kidney tumor using Trizol reagent following manufacturer's recommendation. Relative HiF2α mRNA levels were determined by RT-qPCR as described below and compared to mice treated with delivery buffer (isotonic glucose) only.

In preparation for quantitative PCR, total RNA was isolated from tissue samples homogenized in TriReagent (Molecular Research Center, Cincinnati, OH) following the manufacturer's protocol.

Approximately 500 ng RNA was reverse-transcribed using the High Capacity cDNA Reverse Transcription Kit (Life Technologies). For human (tumor) Hif2α (EPAS1) expression, pre-manufactured TaqMan gene expression assays for human Hif2α (Catalog #4331182) and CycA (PPIA) Catalog #: 4326316E) were used in biplex reactions in triplicate using TaqMan Gene Expression Master Mix (Life Technologies) or VeriQuest Probe Master Mix (Affymetrix). Quantitative PCR was performed by using a 7500 Fast or StepOnePlus Real-Time PCR system (Life Technologies). The AACT method was used to calculate relative gene expression.

Example 24. In Vivo Administration of Integrin Targeting Ligands Conjugated to RNAi Agents Targeting HIF-2 Alpha (EPAS1) in Kidney Tumor Bearing Mice RNAi agents that included the sense strand and antisense strand sequences set forth in Table 8 were synthesized according to phosphoramidite technology on solid phase in accordance with general procedures known in the art and commonly used in oligonucleotide synthesis. (See Example 22 herein). The RNAi agents included an antisense strand having a nucleobase sequence at least partially complementary to the HIF-2 alpha (Hif2α or EPAS1) gene. EPAS1 is a member of the HIF (hypoxia inducible factor) gene family and encodes half of a transcription factor involved in the induction of genes regulated by oxygen, and which is induced as oxygen levels fall (a condition known as hypoxia). Hif2α is known to be frequently overexpressed in clear cell renal carcinoma (ccRCC) cells. The Hif2α RNAi agents were designed to be capable of degrading or inhibiting translation of messenger RNA (mRNA) transcripts of Hif2α in a sequence specific manner, thereby inhibiting expression of the EPAS1 gene.

On study day 1, kidney tumor-bearing mice (see Example 23) were dosed via tail vein injection according to dosing regiments that included the following Groups:

TABLE 9

Dosing Groups of Kidney Tumor Bearing Mice in Example 5.

| Group | RNAi Agent and Dose | Dosing Regimen |
|---|---|---|
| 1 | Isotonic glucose (5% dextrose in water (D5W)) (no RNAi agent) | Single injection on day 1 |
| 3 | 7.5 mg/kg of Hif2α RNAi agent (AD04546, comprising trialkyne linker compound 14-S-V) conjugated to a 40 kilodalton (kDa) PEG moiety (with αvβ3 integrin ligand 4.1), formulated in isotonic glucose. | Single injection on day 1 |
| 4 | 7.5 mg/kg of Hif2α RNAi agent (AD05614, comprising trialkyne linker compound 1-S-V) conjugated to a 40 kilodalton (kDa) PEG moiety (with αvβ3 integrin ligand 4.1), formulated in isotonic glucose. | Single injection on day 1 |
| 5 | 7.5 mg/kg of Hif2α RNAi agent (AD05615, comprising trialkyne linker compound 2-S-V) conjugated to a 40 kilodalton (kDa) PEG moiety (with αvβ3 integrin ligand 4.1), formulated in isotonic glucose. | Single injection on day 1 |
| 6 | 7.5 mg/kg of Hif2α RNAi agent (AD05616, comprising trialkyne linker compound 3-S-V) conjugated to a 40 kilodalton (kDa) PEG moiety (with αvβ3 integrin ligand 4.1), formulated in isotonic glucose. | Single injection on day 1 |
| 7 | 7.5 mg/kg of Hif2α RNAi agent (AD05617, comprising trialkyne linker compound 6-S-V) conjugated to a 40 kilodalton (kDa) PEG moiety (with αvβ3 integrin ligand 4.1), formulated in isotonic glucose. | Single injection on day 1 |
| 8 | 7.5 mg/kg of Hif2α RNAi agent (AD05614, comprising trialkyne linker compound 1-S-V) conjugated to a 40 kilodalton (kDa) PEG moiety (with αvβ3 integrin ligand 4.5), formulated in isotonic glucose. | Single injection on day 1 |
| 10 | 7.5 mg/kg of Hif2α RNAi agent (AD05620, comprising trialkyne linker compound 4-S-V) conjugated to a 40 kilodalton (kDa) PEG moiety (with αvβ3 integrin ligand 4.5), formulated in isotonic glucose. | Single injection on day 1 |

The RNAi agents in Example 24 were synthesized having a functionalized amine reactive group ($NH_2$—$C_6$) at the 5' terminal end of the sense strand to facilitate conjugation to the respective trialkyne linker compound indicated. In the case of Groups 4-8 and 10, the trialkyne linkers were added to the RNAi agent by use of phosphoramidite compounds 1, 2, 3, 4 and 6, respectively. The respective integrin targeting ligands were synthesized having an azide reactive group (see, e.g., Example 22), which was then conjugated to the trialkyne component of the linker. A 40 kilodalton (kDa) PEG moiety was attached to serve as a pharmacokinetic (PK) modulator to increase the circulation time of the drug product-conjugate. The structures of Targeting Ligands αvβ3 integrin ligand 4.1 and 4.5 are shown below:

αvβ3 integrin ligand 4.1

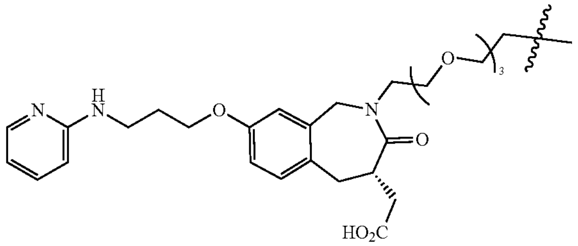

-continued

αvβ3 integrin ligand 4.5

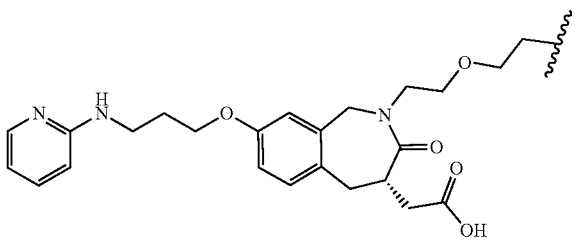

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to Cyclophilin A (PPIA) expression and expressed as fraction of vehicle control group (isotonic glucose) (geometric mean, +/−95% confidence interval), as explained in Example 23.

TABLE 10

Average Relative huHif2α mRNA Expression at Sacrifice in Example 24.

| Group ID | Average Relative huHif2α mRNA Expression | Low (error) | High (error) |
|---|---|---|---|
| Group 1 (isotonic glucose) | 1.000 | 0.069 | 0.074 |
| Group 3 -Compound 14-S-V | 0.377 | 0.071 | 0.087 |
| Group 4-Compound 1-S-V | 0.357 | 0.028 | 0.030 |
| Group 5-Compound 2-S-V | 0.369 | 0.029 | 0.032 |
| Group 6-Compound 3-S-V | 0.290 | 0.035 | 0.039 |
| Group 7-Compound 6-S-V | 0.348 | 0.023 | 0.025 |
| Group 8-Compound 1-S-V | 0.424 | 0.034 | 0.037 |
| Group 10-Compound 4-S-V | 0.307 | 0.053 | 0.064 |

Example 25. In Vivo Administration of Integrin Targeting Ligands Conjugated to RNAi Agents Targeting HIF-2 Alpha (EPAS1) in Kidney Tumor Bearing Mice RNAi agents that included the sense strand and antisense strand sequences set forth in Table 8 were synthesized according to phosphoramidite technology on solid phase in accordance with general procedures known in the art and commonly used in oligonucleotide synthesis. (See Example 22 herein). The RNAi agents included an antisense strand having a nucleobase sequence at least partially complementary to the (Hif2α) (EPAS1) gene.

On study day 1, kidney tumor bearing mice (see Example 23) were dosed via tail vein injection according to the following dosing Groups:

TABLE 11

Dosing Groups of Kidney Tumor Bearing Mice in Example 5.

| Group | RNAi Agent and Dose | Dosing Regimen |
|---|---|---|
| 1 | Isotonic glucose (5% dextrose in water (D5W)) (no RNAi agent) | Single injection on day 1 |
| 2 | 7.5 mg/kg of Hif2α RNAi agent (AD04546, comprising trialkyne linker 14-S-V) conjugated to a C-18 diacid moiety (with αvβ3 integrin ligand 2), formulated in isotonic glucose. | Single injection on day 1 |
| 3 | 7.5 mg/kg of Hif2α RNAi agent (AD04546, comprising trialkyne linker compound 18-IX) conjugated to a C-18 diacid moiety (with αvβ3 integrin ligand 2), formulated in isotonic glucose. | Single injection on day 1 |
| 4 | 7.5 mg/kg of Hif2α RNAi agent (AD04546, comprising trialkyne linker compound 15-IX) conjugated to a C-18 diacid (with αvβ3 integrin ligand 2), formulated in isotonic glucose. | Single injection on day 1 |
| 5 | 7.5 mg/kg of Hif2α RNAi agent (AD04546, comprising trialkyne linker compound 16-IX) conjugated to a C-18 diacid moiety (with αvβ3 integrin ligand 2), formulated in isotonic glucose. | Single injection on day 1 |
| 6 | 7.5 mg/kg of Hif2α RNAi agent (AD04546, comprising trialkyne linker compound 17-IX) conjugated to a C-18 diacid moiety (with αvβ3 integrin ligand 2), formulated in isotonic glucose. | Single injection on day 1 |
| 7 | 7.5 mg/kg of Hif2α RNAi agent (AD05858, comprising trialkyne linker compound 10-S-V) conjugated to a C-18 diacid moiety (with αvβ3 integrin ligand 2), formulated in isotonic glucose. | Single injection on day 1 |
| 8 | 7.5 mg/kg of Hif2α RNAi agent (AD05860, comprising trialkyne linker compound 12-S-V) conjugated to a C-18 diacid moiety (with αvβ3 integrin ligand 2), formulated in isotonic glucose. | Single injection on day 1 |

TABLE 11-continued

| Dosing Groups of Kidney Tumor Bearing Mice in Example 5. | | |
|---|---|---|
| Group | RNAi Agent and Dose | Dosing Regimen |
| 9 | 7.5 mg/kg of Hif2α RNAi agent (AD05919, comprising trialkyne linker compound 13-S-V) conjugated to a C-18 diacid moiety (with αvβ3 integrin ligand 2), formulated in isotonic glucose. | Single injection on day 1 |

The RNAi agents in Example 25 were synthesized having nucleotide sequences directed to target the human Hif2α gene, and, in the case of Groups 3-6, included a functionalized amine reactive group ($NH_2—C_6$) at the 5' terminal end of the sense strand to facilitate conjugation to the trialkyne linker compounds 15-18. In the case of Groups 3 and 7-9, the trialkyne linkers were added to the RNAi agent by use of phosphoramidite compounds 14, 10, 12, and 13, respectively. The respective integrin targeting ligands were synthesized having an azide reactive group (see, e.g., Example 22), which was then conjugated to the trialkyne component of the linker. The 40 kDa PEG moiety and the C-18 diacid moiety were attached to serve as a pharmacokinetic (PK) modulator by increasing the circulation time of the drug product-conjugate. The structure of the C-18 diacid moiety is shown below:

C-18 diacid moiety

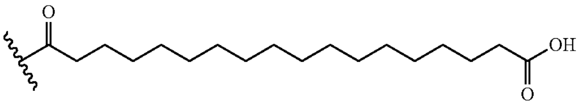

The C-18 diacid moiety was attached via an amide linkage to the 3' end of the sense strand. The structure of Targeting Ligand αvβ3 integrin ligand 2 is shown below:

αvβ3 integrin ligand 2

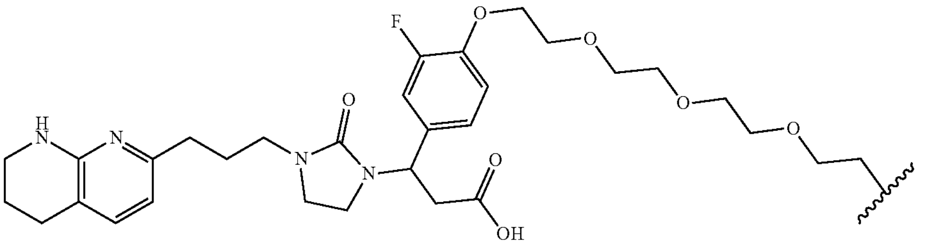

, wherein  indicates the point of attachment to the linking agent.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 23.

TABLE 12

| Average Relative huHif2α mRNA Expression at Sacrifice in Example 25. | | | |
|---|---|---|---|
| Group ID | Average Relative huHif2α mRNA Expression | Low (error) | High (error) |
| Group 1 (isotonic glucose) | 1.000 | 0.093 | 0.103 |
| Group 2 -Compound 14-S-V | 0.585 | 0.095 | 0.113 |
| Group 3-Compound 18-IX | 0.482 | 0.053 | 0.059 |
| Group 4-Compound 15-IX | 0.546 | 0.063 | 0.072 |
| Group 5-Compound 16-IX | 0.572 | 0.030 | 0.031 |
| Group 6-Compound 17-IX | 0.504 | 0.133 | 0.181 |
| Group 7-Compound 10-S-V | 0.484 | 0.107 | 0.138 |
| Group 8-Compound 12-S-V | 0.605 | 0.120 | 0.150 |
| Group 9-Compound 13-S-V | 0.475 | 0.070 | 0.082 |

Example 26. In Vivo Oropharyngeal Aspiration Administration of Alpha-ENaC RNAi Agents Conjugated to Epithelial Cell Targeting Ligands in Rats Trialkyne linking agents may be used in a variety of RNAi constructs. RNAi constructs comprising linking agents of the present invention may be administered in a variety of different dosing methods, as described in this example. Trialkyne linking agents may also be used with a variety of targeting ligands. In this example, targeting ligands conjugated to trialkyne linking agents are αvβ6 targeting ligands.

In this example, a trialkyne linking agent of Compound 22 was added to the sense strand post-solid support synthesis in a method as described in Example 22.

On study day 1, male Sprague Dawley rats were dosed via oropharyngeal aspiration administration (OP) with 200 microliters using a pipette, according to the following dosing groups:

TABLE 13

| Dosing groups of rats in Example 8. | | |
|---|---|---|
| Group | RNAi Agent and Dose | Dosing Regimen |
| 1 | Isotonic saline (no RNAi agent) | Single OP dose on day 1 |
| 2 | 0.5 mg/kg of AD05347 conjugated to a tridentate small molecule αvβ6 epithelial cell targeting ligand (Compound 22-IX, Tri-avB6 SM2) via the amine (NH2-C6) linkage on the 5' terminal end of the sense strand, formulated in isotonic saline. | Single OP dose on day 1 |
| 3 | 0.5 mg/kg of AD05347 conjugated to a tridentate small molecule αvβ6 epithelial cell targeting ligand (Compound 2-IX, Tri-avB6 SM6.1) via the amine (NH2-C6) linkage on the 5' terminal end of the sense strand, formulated in isotonic saline. | Single OP dose on day 1 |
| 4 | 0.5 mg/kg of AD05453 conjugated to a tridentate small molecule αvβ6 epithelial cell targeting ligand (Compound 22-IX, Tri-avB6 SM2) via the amine (NH2-C6) linkage on the 5' terminal end of the sense strand, formulated in isotonic saline. | Single OP dose on day 1 |
| 5 | 0.5 mg/kg of AD05453 conjugated to a tridentate small molecule αvβ6 epithelial cell targeting ligand (Compound 22-IX, Tri-avB6 SM9) via the amine (NH2-C6) linkage on the 5' terminal end of the sense strand, formulated in isotonic saline. | Single OP dose on day 1 |
| 6 | 0.5 mg/kg of AD05453 conjugated to a tridentate small molecule αvβ6 epithelial cell targeting ligand (Compound 22-IX, Tri-avB6 SM6) via the amine (NH2-C6) linkage on the 5' terminal end of the sense strand, formulated in isotonic saline. | Single OP dose on day 1 |
| 7 | 0.5 mg/kg of AD05453 conjugated to a tridentate small molecule αvβ6 epithelial cell targeting ligand (Compound 22-IX, Tri-avB6 SM8) via the amine (NH2-C6) linkage on the 5' terminal end of the sense strand, formulated in isotonic saline. | Single OP dose on day 1 |
| 8 | 0.5 mg/kg of AD05453 conjugated to a tridentate small molecule αvβ6 epithelial cell targeting ligand (Compound 22-IX, Tri-avB6 SM6.1) via the amine (NH2-C6) linkage on the 5' terminal end of the sense strand, formulated in isotonic saline. | Single OP dose on day 1 |
| 9 | 0.5 mg/kg of AD05453 conjugated to a tridentate small molecule αvβ6 epithelial cell targeting ligand (Compound 22-IX, Tri-avB6 SM10) via the amine (NH2-C6) linkage on the 5' terminal end of the sense strand, formulated in isotonic saline. | Single OP dose on day 1 |
| 10 | 0.5 mg/kg of AD05453 conjugated to a tridentate small molecule αvβ6 epithelial cell targeting ligand (Compound 22-IX, Tri-avB6 SM10) via the amine (NH2-C6) linkage on the 5' terminal end of the sense strand, formulated in isotonic saline. | Single OP dose on day 1 |
| 11 | 0.5 mg/kg of AD05453 conjugated to a tridentate peptide-based αvβ6 epithelial cell targeting ligand using Compound 22-IX, via the amine (NH2-C6) linkage on the 5' terminal end of the sense strand, formulated in isotonic saline. | Single OP dose on day 1 |

Compound 22 was reacted with the amine linkage on the 5' terminal end of the sense strand in each group. Structures of the αvβ6 targeting ligands are shown below:

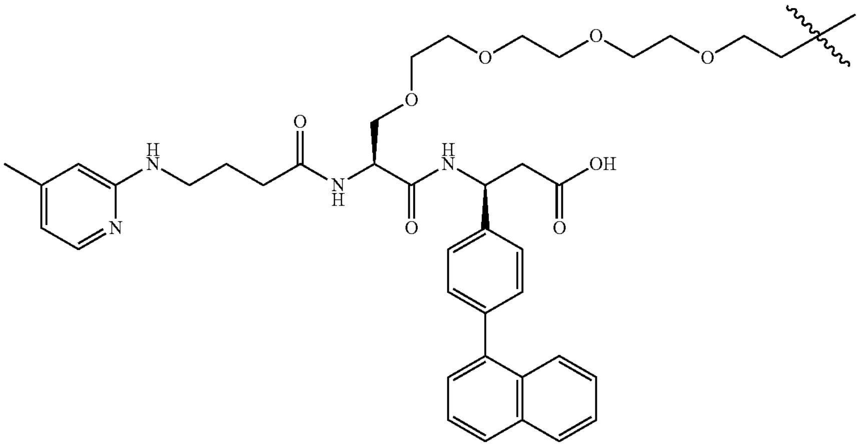

avB6 SM2

-continued
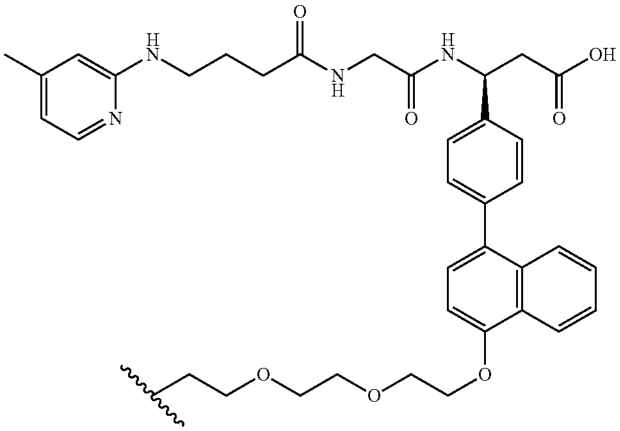
avB6 SM6
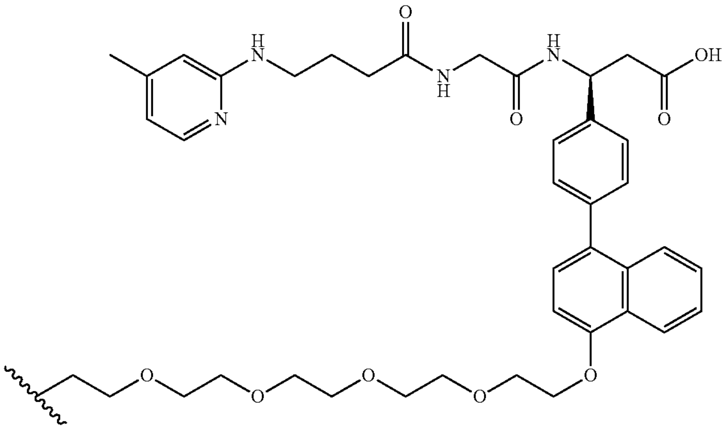
avB6 SM 6.1
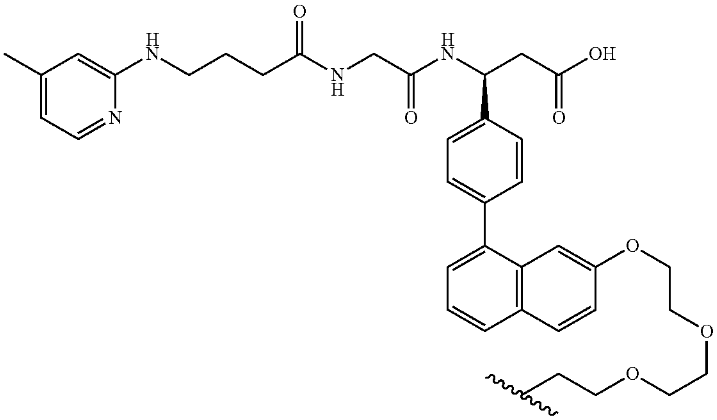
avB6 SM 8

-continued

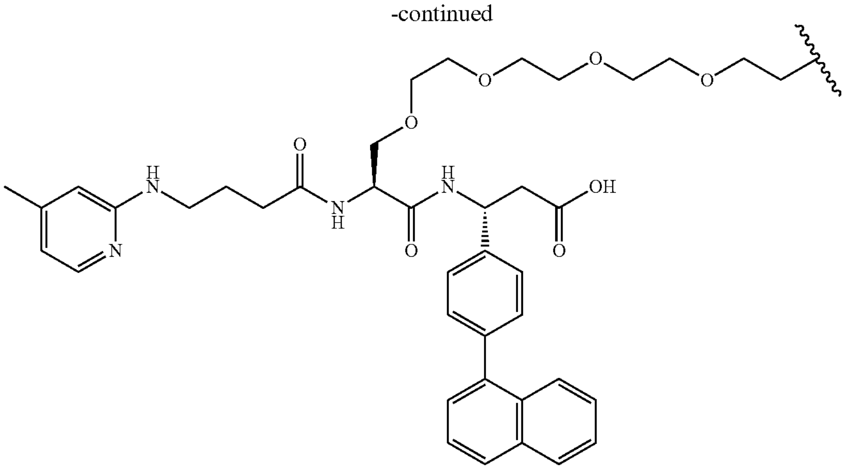

avB6 SM 9

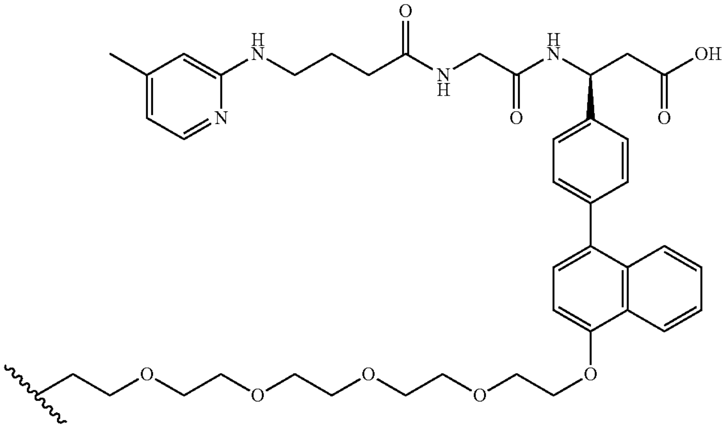

avB6 SM 10 wherein ⌇ indicates the point of attachment to the linking agent.

Four (4) rats were dosed in each Group (n=4). Rats were euthanized on study day 9, and total RNA was isolated from both lungs following collection and homogenization. Alpha-ENaC (SCNN1A) mRNA expression was quantitated by probe-based quantitative PCR, normalized to GAPDH expression and expressed as fraction of vehicle control group (geometric mean, +/−95% confidence interval).

TABLE 14

Average Relative rENaC mRNA expression at sacrifice (day 9) in Example 8.

| Group ID | Average Relative rENaC mRNA expression | Low (error) | High (error) |
|---|---|---|---|
| Group 1 (isotonic saline) | 1.000 | 0.162 | 0.193 |
| Group 2 (0.5 mg/kg AD05347-Compound 22-IX, Tri-SM2) | 0.469 | 0.101 | 0.129 |
| Group 3 (0.5 mg/kg AD05347-Compound 22-IX, Tri-SM6.1) | 0.358 | 0.078 | 0.100 |
| Group 4 (0.5 mg/kg AD05453-Compound 22-IX, Tri-SM2) | 0.562 | 0.086 | 0.102 |
| Group 5 (0.5 mg/kg AD05453-Compound 22-IX, Tri-SM9) | 0.620 | 0.168 | 0.230 |
| Group 6 (0.5 mg/kg AD05453-Compound 22-IX, Tri-SM6) | 0.559 | 0.099 | 0.120 |
| Group 7 (0.5 mg/kg AD05453-Compound 22-IX, Tri-SM8) | 0.691 | 0.072 | 0.081 |
| Group 8 (0.5 mg/kg AD05453-Compound 22-IX, Tri-SM6.1) | 0.454 | 0.055 | 0.063 |
| Group 9 (0.5 mg/kg AD05453-Compound 22-IX, Tri-SM10) | 0.454 | 0.080 | 0.097 |

TABLE 14-continued

| Average Relative rENaC mRNA expression at sacrifice (day 9) in Example 8. | | | |
|---|---|---|---|
| Group ID | Average Relative rENaC mRNA expression | Low (error) | High (error) |
| Group 10 (0.5 mg/kg AD05453-Compound 22-IX, Tri-SM11) | 0.577 | 0.113 | 0.140 |
| Group 11 (0.5 mg/kg AD05453-Compound 22-IX, tridentate peptide ligand) | 0.558 | 0.057 | 0.064 |

As shown in Table 14, above, various different targeting ligand structures linked to the respective RNAi agents using the trialkyne linking compounds disclosed herein showed inhibition of gene expression compared to control.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A compound of Formula III,

Formula III

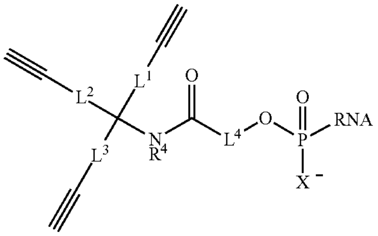

or a pharmaceutically acceptable salt thereof, wherein, $L^1$, $L^2$, and $L^3$ are each linkers of the formula:

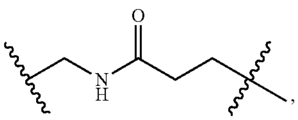, or

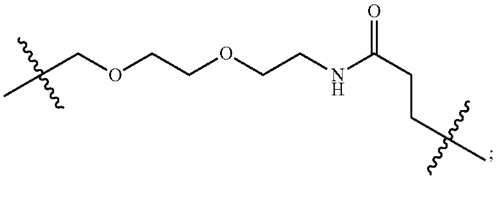;

$L^4$ is selected from the group consisting of:

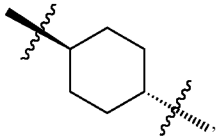, 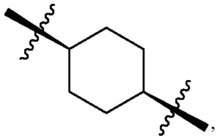,

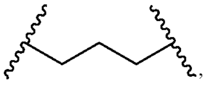, 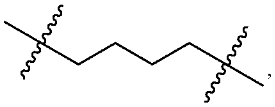,

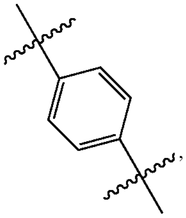, 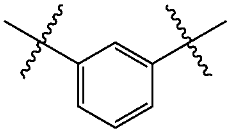,

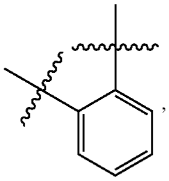, 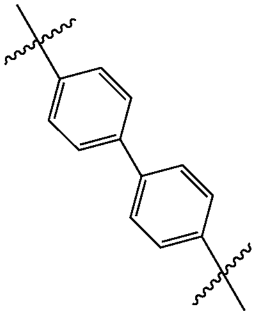,

-continued

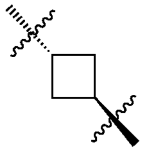, 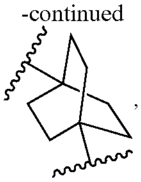, 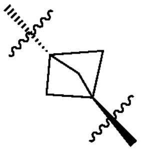,

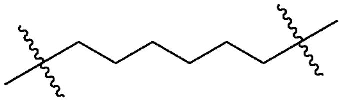, and

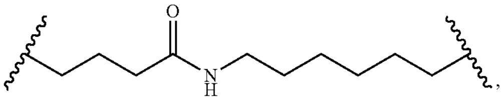, wherein  indicates the point of attachment;

$R^4$ is H or optionally substituted alkyl;

X is O or S; and

RNA comprises or consists of an RNAi agent.

2. The compound or pharmaceutically acceptable salt thereof of claim 1, wherein X is O.

3. The compound or pharmaceutically acceptable salt thereof of claim 1, wherein X is S.

4. The compound or pharmaceutically acceptable salt thereof of claim 1, wherein $L^1$, $L^2$, and $L^3$ are each

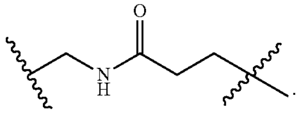 [SMILES: *CCC(=O)NC*].

5. The compound or pharmaceutically acceptable salt thereof of claim 1, wherein $L^1$, $L^2$, and $L^3$ are each

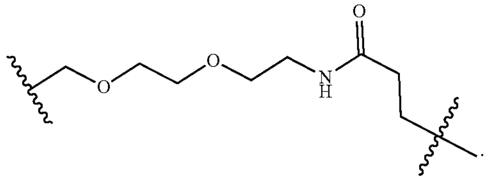 [SMILES: *CCC(=O)NCCOCCOC*].

6. The compound or pharmaceutically acceptable salt thereof of claim 1, wherein the compound is selected from the group consisting of:

| Compound No. | Structure |
|---|---|
| 1-O-III | 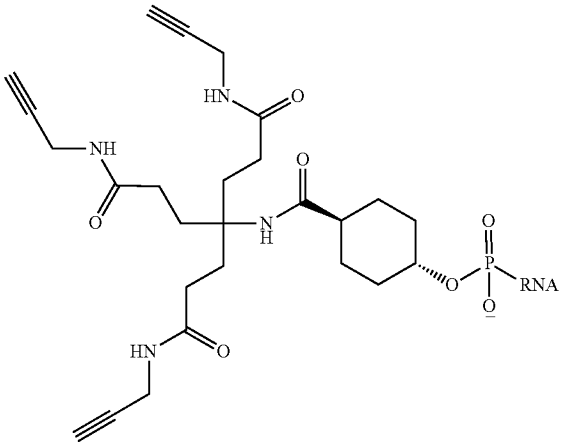 |
| 1-S-III | 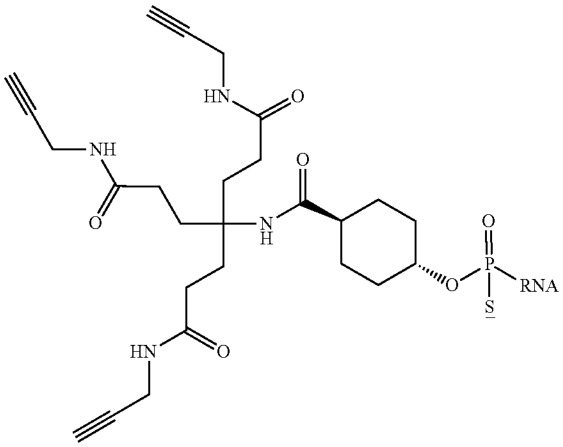 |

-continued
| Compound No. | Structure |
|---|---|
| 2-O-III | 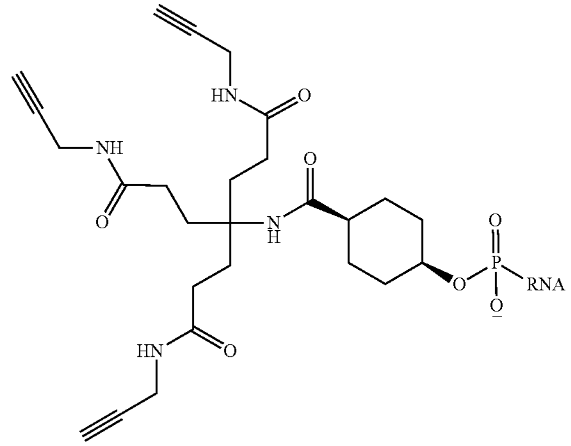 |
| 2-S-III | 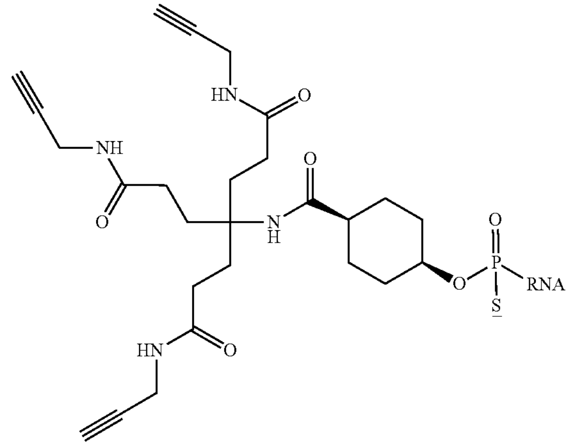 |
| 3-O-III | 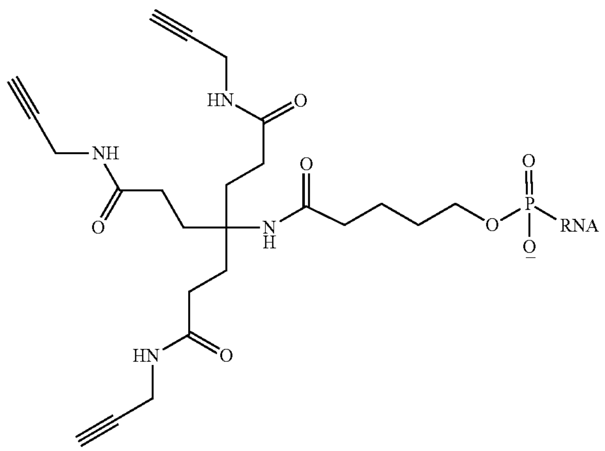 |

-continued
| Compound No. | Structure |
|---|---|
| 3-S-III | 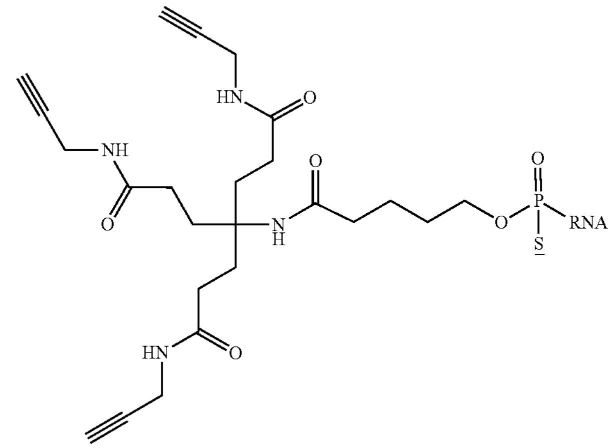 |
| 4-O-III | 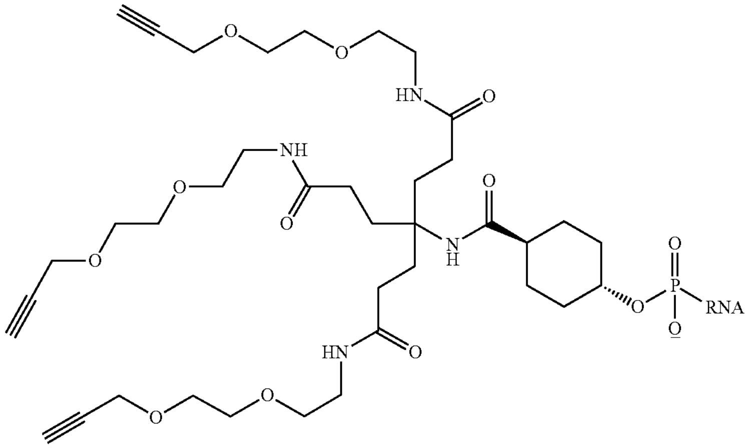 |
| 4-S-III | 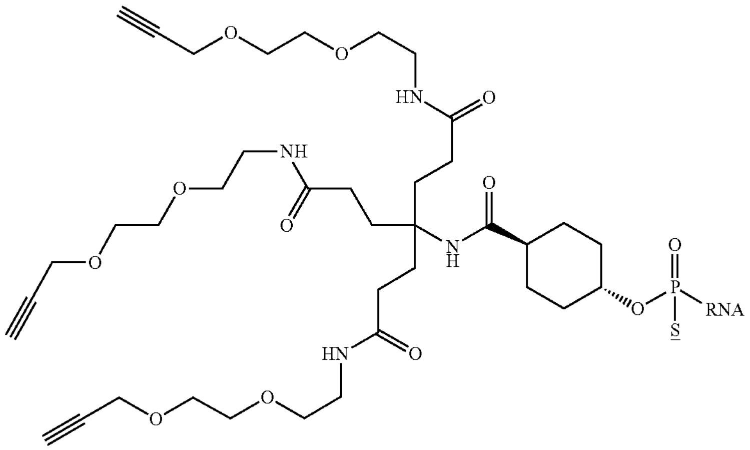 |

-continued
| Compound No. | Structure |
|---|---|
| 5-O-III | 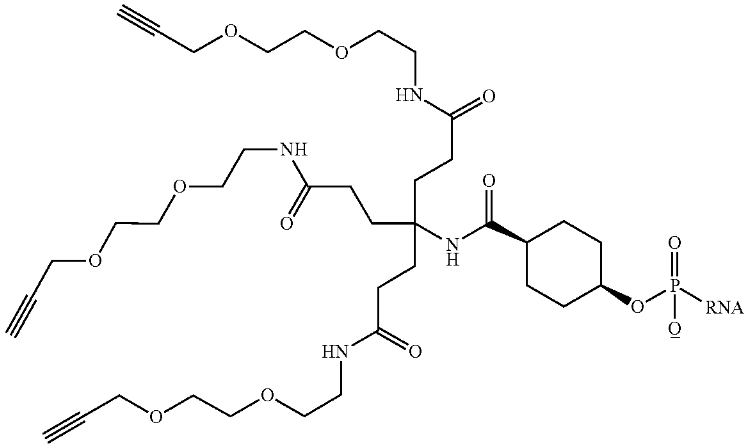 |
| 5-S-III | 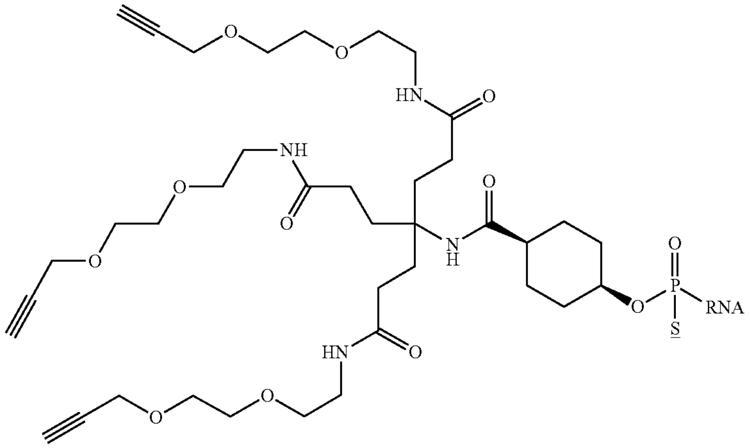 |
| 6-O-III | 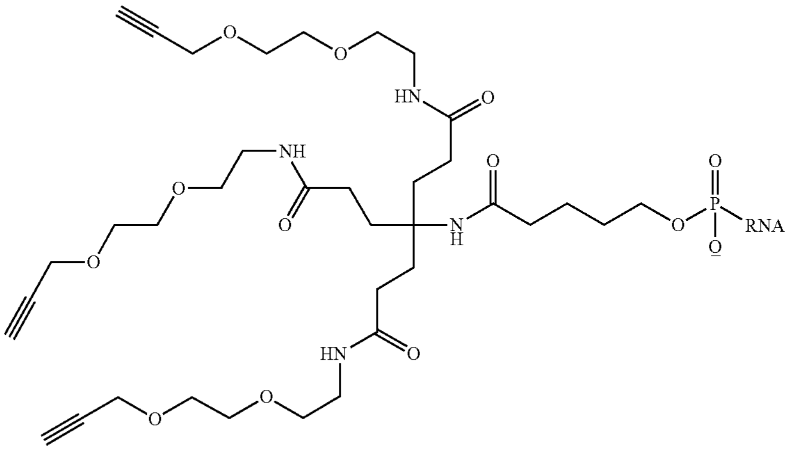 |

-continued
| Compound No. | Structure |
|---|---|
| 6-S-III | 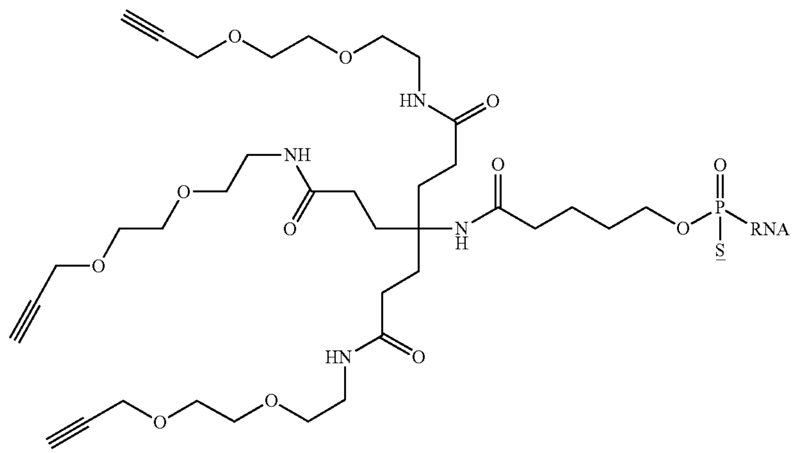 |
| 7-O-III | 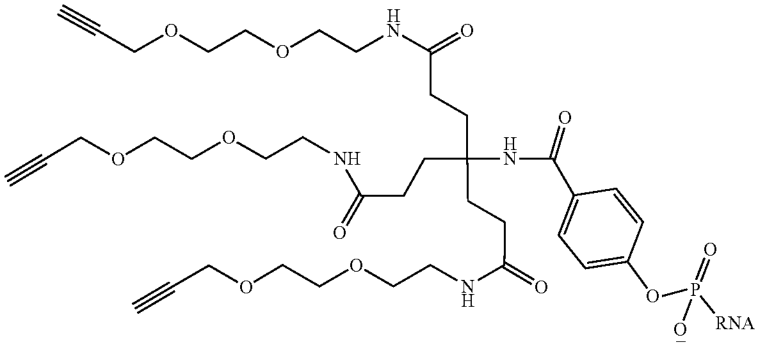 |
| 7-S-III | 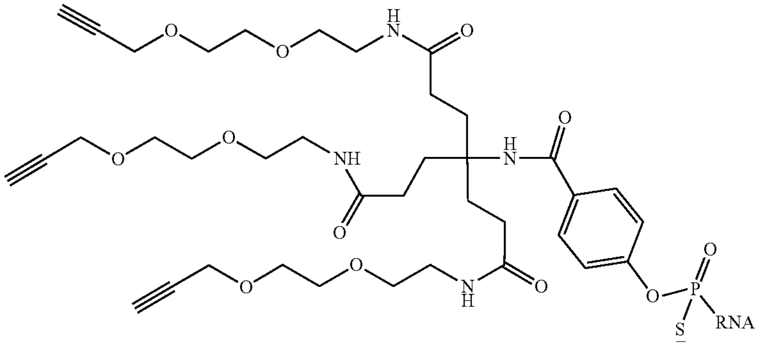 |
| 8-O-III | 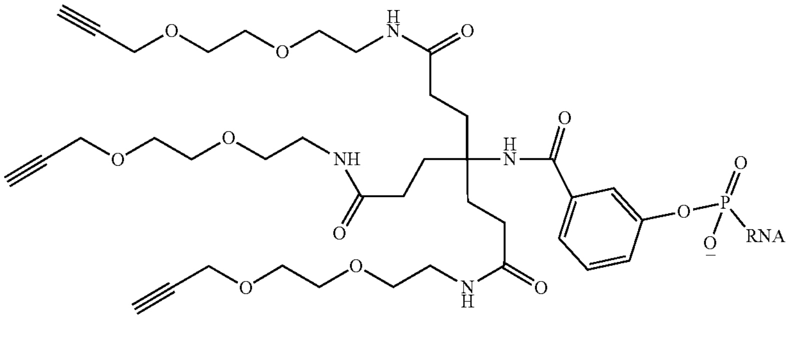 |

-continued
| Compound No. | Structure |
| --- | --- |
| 8-S-III | 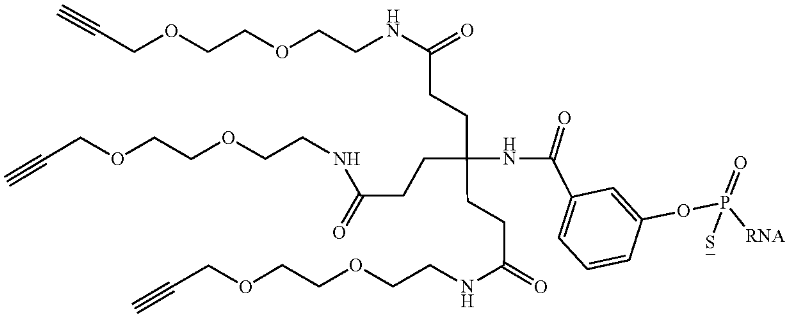 |
| 9-O-III | 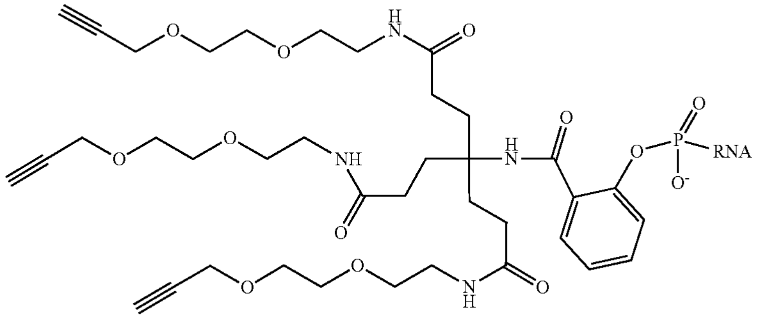 |
| 9-S-III | 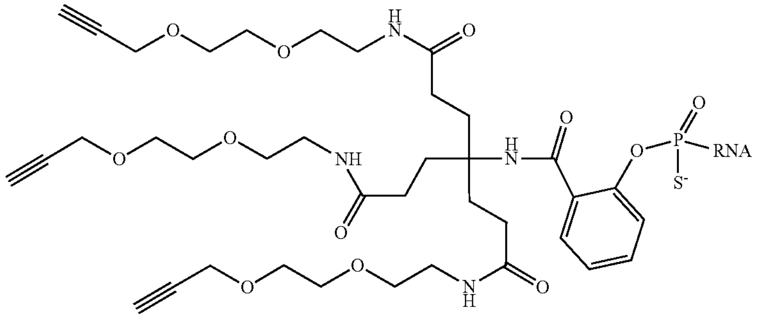 |
| 10-O-III | 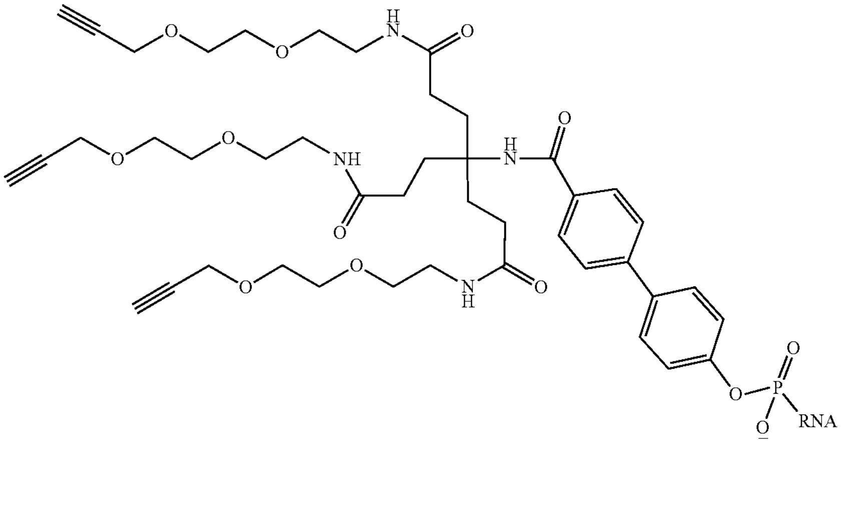 |

-continued
| Compound No. | Structure |
|---|---|
| 10-S-III | 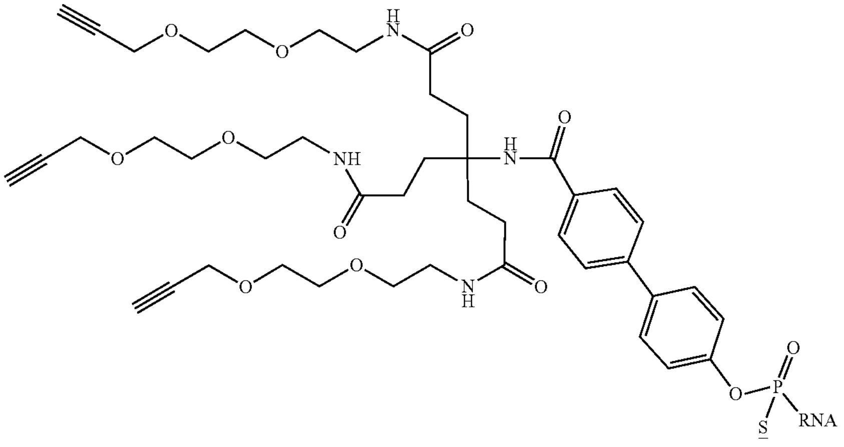 |
| 11-O-III | 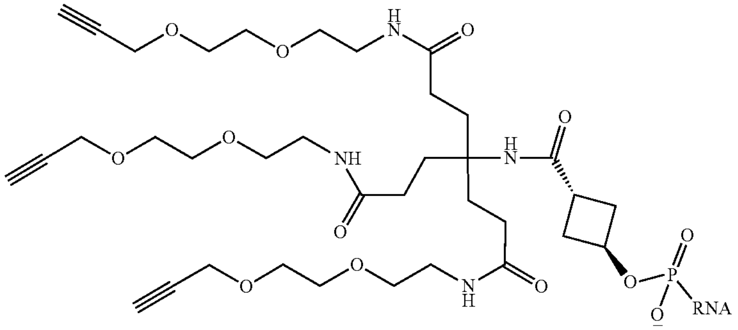 |
| 11-S-III | 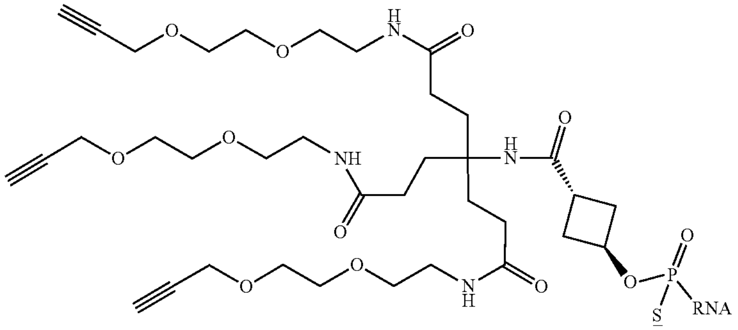 |
| 12-O-III | 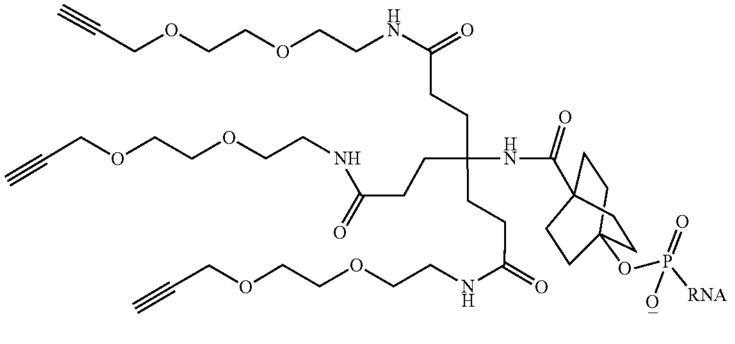 |

-continued
| Compound No. | Structure |
|---|---|
| 12-S-III | 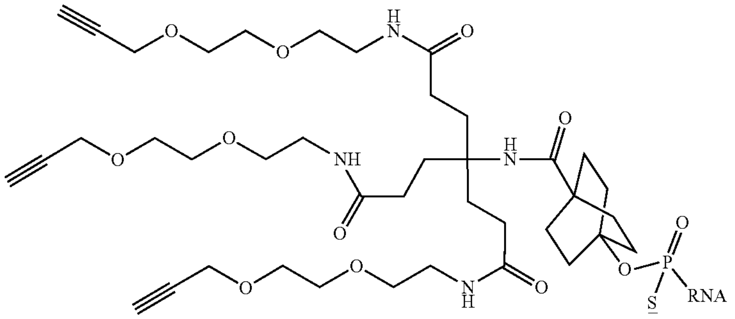 |
| 13-O-III | 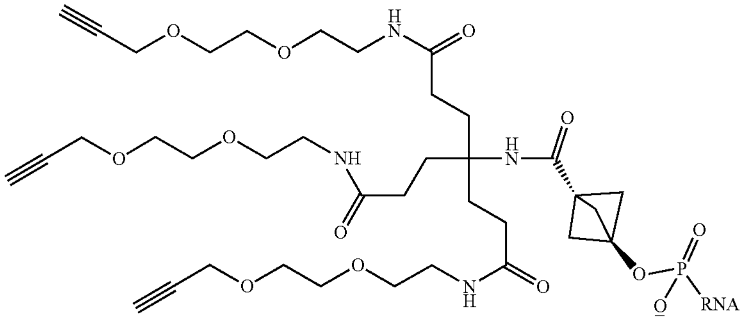 |
| 13-S-III | 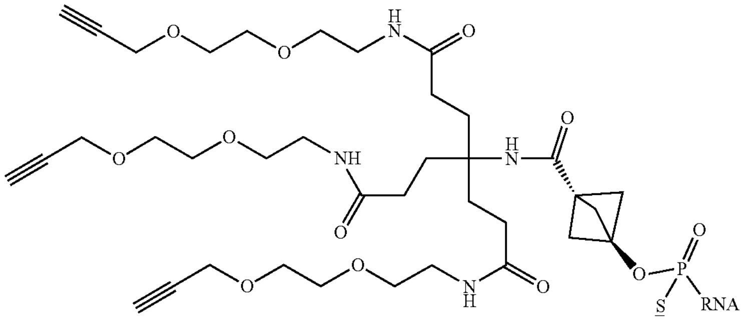 |
| 14-O-III | 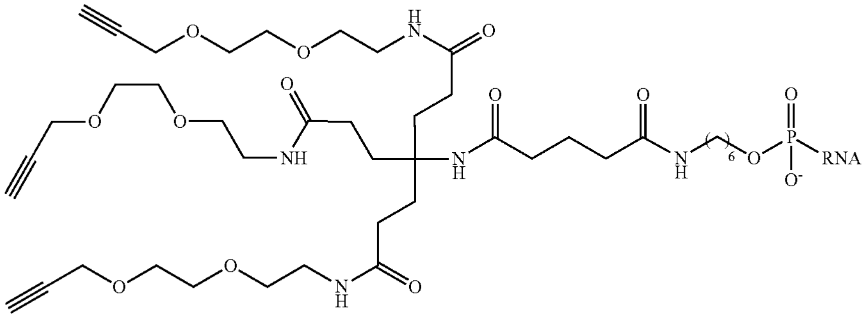 |

-continued

| Compound No. | Structure |
|---|---|
| 14-S-III | 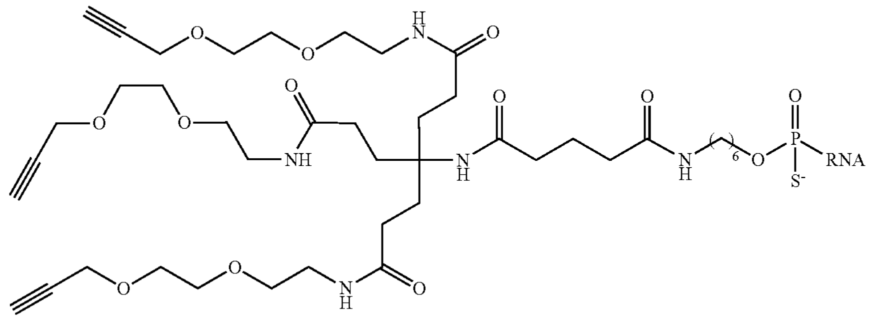 |

or a pharmaceutically acceptable salt thereof, wherein RNA comprises or consists of an RNAi agent.

7. The compound or pharmaceutically acceptable salt thereof of claim 1, wherein $L^4$ is of the formula:

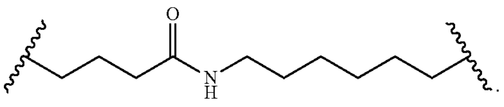 [SMILES: *CCCCCCNC(=O)CCC*]

8. A method of reacting a compound of Formula III

Formula III

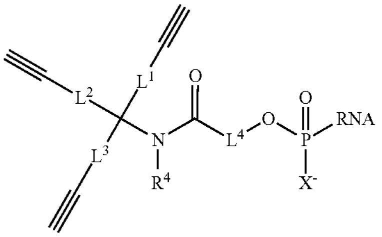

with a targeting ligand (TL) comprising an azide to form a compound of Formula V Formula V

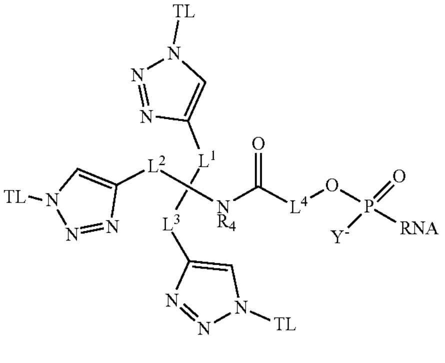

wherein, $L^1$, $L^2$, and $L^3$ are each linkers of the formula:

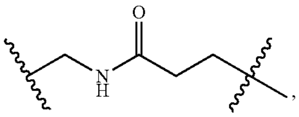

, or

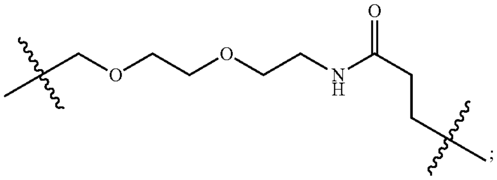

$L^4$ is selected from the group consisting of:

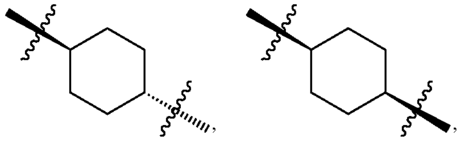

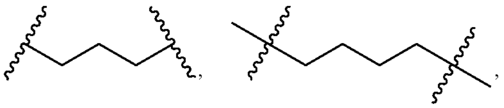

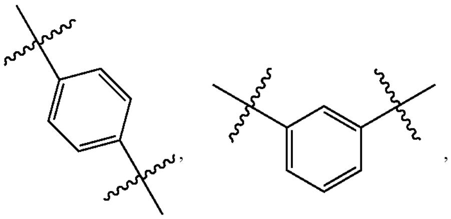

-continued

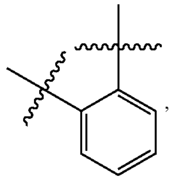,

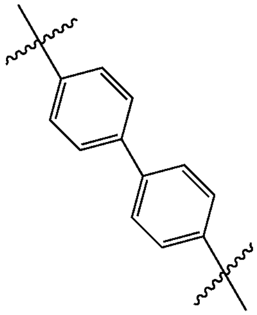,

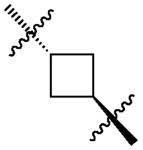,

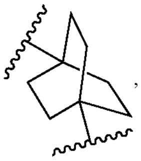,

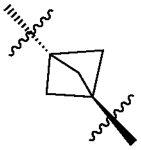,

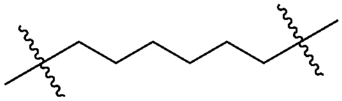, and

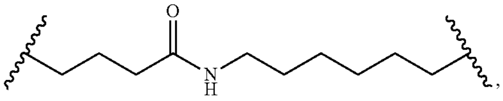, wherein  indicates the point of attachment;

$R^4$ is H or optionally substituted alkyl;

TL is a targeting ligand;

X is O or S;

Y is O or S; and

RNA comprises or consists of an RNAi agent.

9. The method of claim 8, wherein Y is O.

10. The method of claim 8, wherein Y is S.

11. The method of claim 8, wherein $L^1$, $L^2$, and $L^3$ are each

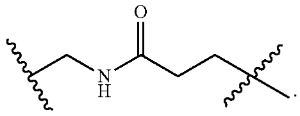 [SMILES: *CCC(=O)NC*].

12. The method of claim 8, wherein $L^1$, $L^2$, and $L^3$ are each

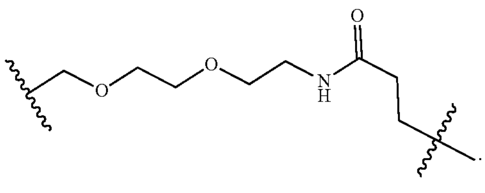 [SMILES: *CCC(=O)NCCOCCOC*].

13. The method of claim 8, wherein $L^4$ is of the formula:

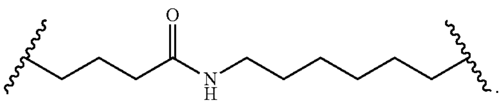 [SMILES: *CCCCCCNC(=O)CCC*].

14. A method of reacting a compound of Formula II:

Formula II

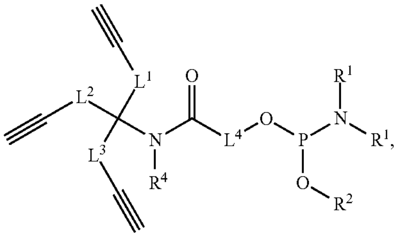, with an RNAi agent to form a compound of Formula III:

Formula III

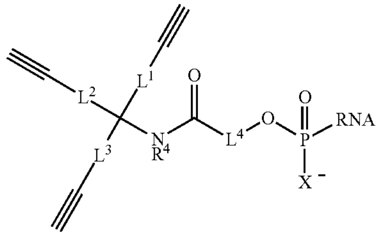

wherein, $L^1$, $L^2$, and $L^3$ are each linkers of the formula of the formula:

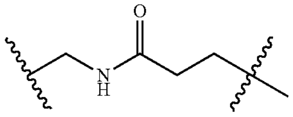, or

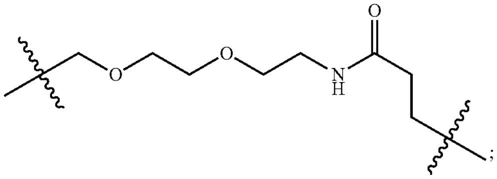;

$L^4$ is selected from the group consisting of:

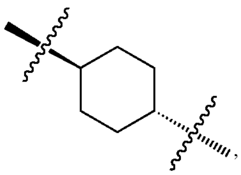,

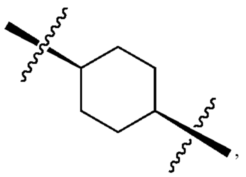,

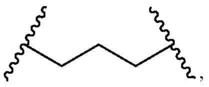,

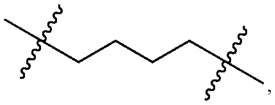,

-continued

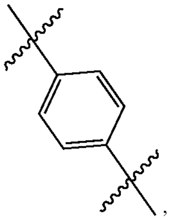
,
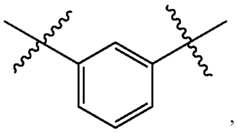
,
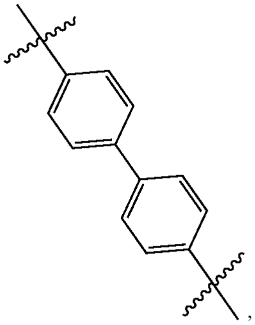
,
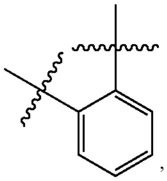
,
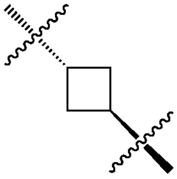
,
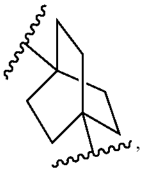
,
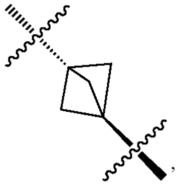
,
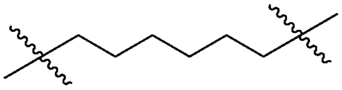
, and
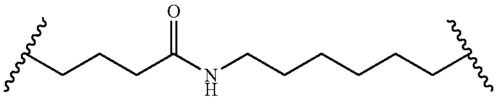
, wherein  indicates the point of attachment;

each instance of $R^1$ is optionally substituted alkyl;

$R^2$ is optionally substituted alkyl; and $R^4$ is H or optionally substituted alkyl X is O or S; and RNA comprises or consists of an RNAi agent.

15. The method of claim 14, wherein X is O.

16. The method of claim 14, wherein X is S.

17. The method of claim 14, wherein $L^1$, $L^2$, and $L^3$ are each

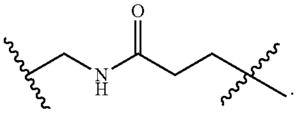 [SMILES: *CCC(=O)NC*]
.

18. The method of claim 14, wherein $L^1$, $L^2$, and $L^3$ are each

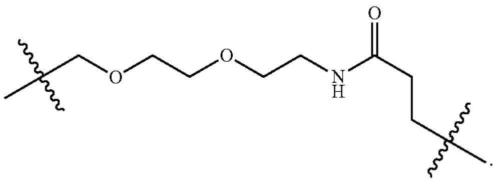 [SMILES: *CCC(=O)NCCOCCOC*]
.

19. The method of claim 14, wherein $L^4$ is of the formula:

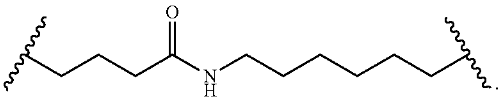 [SMILES: *CCCCCCNC(=O)CCC*]
.

* * * * *